United States Patent
Thompson et al.

(10) Patent No.: US 11,365,191 B2
(45) Date of Patent: Jun. 21, 2022

(54) SUBSTITUTED CYCLOHEXYL COMPOUNDS AS NOP INHIBIIORS

(71) Applicant: Dart NeuroScience, LLC, Dallas, TX (US)

(72) Inventors: Jillian Basinger Thompson, San Diego, CA (US); Brett C. Bookser, San Diego, CA (US); Scott Burley, Oceanside, CA (US); Pablo Garcia-Reynaga, San Diego, CA (US); Andrew Hudson, San Diego, CA (US); Marco Peters, Fallbrook, CA (US); Benjamin Pratt, Encinitas, CA (US); Aaron Thompson, San Diego, CA (US); Joe Tran, San Marcos, CA (US); Lino Valdez, San Diego, CA (US)

(73) Assignee: Dart NeuroScience, LLC, Dallas, TX (US)

( * ) Notice: Subject to any disclaimer, the term of this patent is extended or adjusted under 35 U.S.C. 154(b) by 0 days.

(21) Appl. No.: 16/976,363

(22) PCT Filed: Feb. 26, 2019

(86) PCT No.: PCT/US2019/019650
§ 371 (c)(1),
(2) Date: Aug. 27, 2020

(87) PCT Pub. No.: WO2019/168866
PCT Pub. Date: Sep. 6, 2019

(65) Prior Publication Data
US 2021/0340127 A1   Nov. 4, 2021

Related U.S. Application Data

(60) Provisional application No. 62/636,730, filed on Feb. 28, 2018.

(51) Int. Cl.
| | | |
|---|---|---|
| *C07D 405/12* | (2006.01) | |
| *C07D 213/38* | (2006.01) | |
| *C07C 255/46* | (2006.01) | |
| *C07D 211/76* | (2006.01) | |
| *C07D 207/14* | (2006.01) | |
| *C07D 207/273* | (2006.01) | |
| *C07C 211/40* | (2006.01) | |
| *C07D 211/58* | (2006.01) | |
| *C07D 309/14* | (2006.01) | |
| *C07D 401/12* | (2006.01) | |
| *C07C 237/24* | (2006.01) | |

(Continued)

(52) U.S. Cl.
CPC .......... *C07D 405/12* (2013.01); *A61P 25/28* (2018.01); *C07C 211/40* (2013.01); *C07C 237/24* (2013.01); *C07C 255/46* (2013.01); *C07D 207/14* (2013.01); *C07D 207/273* (2013.01); *C07D 211/58* (2013.01); *C07D 211/76* (2013.01); *C07D 211/96* (2013.01); *C07D 213/38* (2013.01); *C07D 309/14* (2013.01); *C07D 401/12* (2013.01); *C07C 2601/08* (2017.05); *C07C 2601/14* (2017.05); *C07C 2601/16* (2017.05)

(58) Field of Classification Search
CPC .. C07D 405/12; C07D 213/38; C07D 211/76; C07D 207/14; C07D 207/273; C07D 211/58; C07D 309/14; C07D 401/12; C07D 211/96; C07C 255/46; C07C 211/40; C07C 237/24; C07C 2601/14; C07C 2601/16; C07C 2601/08
See application file for complete search history.

(56) References Cited

U.S. PATENT DOCUMENTS

2016/0137653 A1\* 5/2016 Beck ................. A61K 31/4412
                                                    424/133.1
2017/0143649 A1    5/2017 Beck et al.

FOREIGN PATENT DOCUMENTS

| WO | WO 2004/047755 | 6/2004 |
|---|---|---|
| WO | WO 2008/062296 | 5/2008 |

OTHER PUBLICATIONS

International Search Report and Written Opinion dated Apr. 25, 2019 in PCT/US2019/019650, filed Feb. 26, 2019.

\* cited by examiner

*Primary Examiner* — Matthew P Coughlin
(74) *Attorney, Agent, or Firm* — Knobbe, Martens Olson & Bear, LLP

(57) ABSTRACT

Substituted cyclohexyl chemical entities of Formula (I): wherein $R^a$, G, and $R^b$ have any of the values described herein, and compositions comprising such chemical entities; methods of making them; and their use in a wide range of methods, including metabolic and reaction kinetic studies; detection and imaging techniques; radioactive therapies; modulating and treating disorders mediated by nociceptin activity or dopamine signaling; treating neurological disorders, neurodegenerative diseases, depression, and schizophrenia; enhancing the efficiency of cognitive and motor training; and treating peripheral disorders, including renal, respiratory, gastrointestinal, liver, genitourinary, metabolic, and inflammatory disorders.

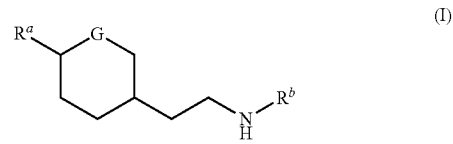

25 Claims, No Drawings

(51) Int. Cl.
*C07D 211/96* (2006.01)
*A61P 25/28* (2006.01)

SUBSTITUTED CYCLOHEXYL COMPOUNDS AS NOP INHIBIIORS

CROSS REFERENCE TO RELATED APPLICATIONS

This application is U.S. National Phase under 35 U.S.C. § 371 of International Application No. PCT/US2019/019650, filed Feb. 26, 2019, designating the U.S. and published in English as International Pub. No. WO 2019/168866, which claims the benefit of U.S. Provisional Application No. 62/636,730, filed Feb. 28, 2018, each of which is incorporated herein by reference in its entirety.

BACKGROUND

Field

The present invention relates to certain substituted cyclohexyl compounds and related chemical entities; compositions containing them; processes for making them; and their use in various methods and therapies, including the enhancement of neuroplasticity and the treatment of neurological, cognitive, pain, cardiovascular, renal, respiratory, gastrointestinal, liver, genitourinary, metabolic, and inflammatory disorders, and other conditions and diseases involving nociceptin receptor signaling.

Description of the Related Technology

Cloning of the classical opioid receptors—delta, kappa, and mu—provided molecular tools to search for additional receptors. For review, see Mogil and Pasternak, 2001, *Pharmacol. Rev.* 53, 381-415; Toll et al., 2016, *Pharmacol Rev.* 68, 419-457. These searches led to the independent isolation of an opioid-receptor like gene in mice, rats, and humans. See, e.g., Pan et al., 1994, *Regul. Pept.* 54, 217-218; Bunzow et al., 1994, *FEBS Lett.* 347, 284-288; Mollerau et al., 1994, *FEBS Lett.* 341, 33-38. The human receptor, which was originally called ORL1, is also known as the human nociceptin receptor, NOP receptor, or NOP. In humans, NOP encodes a typical G-protein coupled receptor (GPCR), comprising seven transmembrane-spanning domains. Chen et al., 1994, *FEBS Lett.* 347, 279-283. The primary amino acid sequence of NOP is highly conserved in mammals, showing about 90% identity in humans, rats, mice, and pigs. Human NOP is distantly related to somatostatin receptors but more closely related to classical opioid receptors. Mollereau et al., 1994, *FEBS Lett.* 341, 33-38.

Shortly after NOP was discovered, its endogenous peptide ligand was isolated by two different laboratories, each giving it a different name: nociceptin, referring to its presumed pronociceptive activity; and orphanin FQ, referring to its affinity for the "orphan" opioid receptor and its first and last amino acids, phenylalanine and glutamine. Meunier et al., 1995, *Nature* 377, 532-535; Reinscheid et al., 1995, *Science* 270, 792-794. Because both names remain in common usage, the peptide is also referred to as nociceptin/orphanin FQ (or N/OFQ). The N/OFQ peptide comprises 17 amino acids, and like classical opioids, is derived from proteolytic processing of a precursor protein, prepronociceptin. N/OFQ shows significant homology to classical opioid peptides but is functionally distinct, showing no significant affinity for the delta, kappa, and mu opioid receptors. Chiou et al., 2007, *Curr. Drug Targets* 8, 117-135.

The NOP and classical opioid GPCRs engage similar signaling pathways. See, e.g., Knoflach et al., 1996, *J. Neurosci.* 16, 6657-6664; Ikeda et al., 1997, *Mol. Brain Res.* 45, 117-126; Moran et al. 2000, *Peptides* 21, 969-976. In each case, agonist binding to the GPCR activates the pertussis toxin (PTX)-sensitive class of Gi and Go proteins, which can trigger several effector functions: (1) reducing cAMP levels by inhibiting adenylate cyclase; (2) increasing potassium currents by activating inward rectifying K+ channels; and (3) reducing calcium currents by mainly inhibiting voltage-dependent, N-type channels.

NOP and N/OFQ are widely expressed in the brain, spinal cord, and peripheral nervous system, as well as other tissues. See, e.g., Houtani et al., 2000, *J. Comp. Neurol.* 424, 489-508; Mollereau and Mouledous, 2000, *Peptides* 21, 907-917; O'Donnell et al., 2001, *J. Comp. Neurol.* 430, 1-11; Clarke et al., 2002, *Eur. J. Neurosci.* 16, 1705-1712. In the brain, for example, each is found in the brainstem, hypothalamus, amygdala, hippocampus, cerebral cortex, and forebrain. NOP is also expressed in peripheral tissues, such as the GI tract, smooth muscles, and immune system. Such expression supports a wide array of physiological roles for the NOP-N/OFQ system. In the CNS, these include learning and memory; synaptic plasticity; pain and sensory perception; emotion and stress responses; locomotor control; reward and motivation pathways; and circadian rhythmicity. The NOP-N/OFQ system is also implicated in peripheral functions, including renal, respiratory, gastrointestinal, metabolic, and inflammatory roles. See, e.g., Reinscheid et al., 1995, *Science* 270, 792-794; Meunier, 1997, *Eur. J. Pharmacol.* 340, 1-15; Civellio et al., 1998, *Crit. Rev. Neurobiol.* 12, 163-176; Witkin et al., 2014, *Pharmacol Ther.* 141, 283-289.

These and other studies highlight the interest in NOP as a target for treating numerous disorders and modulating physiological processes in the CNS and peripheral tissues. See, e.g., Zaveri, 2016, *J. Med. Chem.* 59, 7011-7028. There is a substantial need for NOP modulators, with desirable pharmacological and therapeutic properties, such as effective potency, absorption, selectivity, and safety. The present invention addresses these and other needs in the art by disclosing substituted certain cyclohexyl chemical entities as potent, selective, and well-tolerated NOP inhibitors.

SUMMARY

The present disclosure relates to substituted cyclohexyl chemical entities; compositions including such entities; processes for making them; and their use in various methods, including the treatment of neurological and peripheral disorders associated with NOP, as disclosed herein.

Some embodiments provide a chemical entity of Formula (I), and more specifically, a compound, or pharmaceutically acceptable salt of a compound of Formula (I):

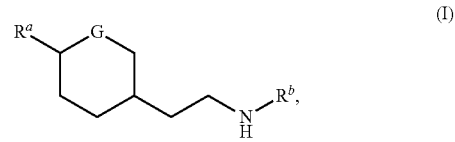

wherein $R^a$, $R^b$, and G have any of the values described herein.

In some embodiments, a chemical entity of Formula (I) is a chemical entity of Formula (Ia), and more specifically, a compound or a pharmaceutically acceptable salt of a compound of Formula (Ia):

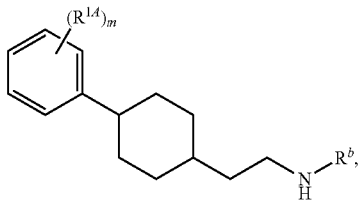

(Ia)

wherein $R^{1A}$, $R^b$, and m have any of the values described herein

In some embodiments, a chemical entity of Formula (I) is a chemical entity of Formula (Ib), and more specifically, a compound or a pharmaceutically acceptable salt of a compound of Formula (Ib):

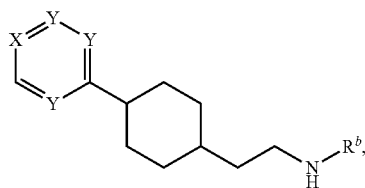

(Ib)

wherein X, Y, and $R^b$ have any of the values described herein.

In some embodiments, a chemical entity of Formula (I) is a chemical entity of Formula (Ic), and more specifically, a compound or a pharmaceutically acceptable salt of a compound of Formula (Ic):

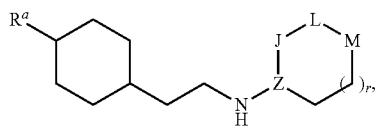

(Ic)

wherein J, L, M, Z, r, and $R^a$ have any of the values described herein.

In some embodiments, a chemical entity of Formula (I) is a chemical entity of Formula (Id), and more specifically, a compound or a pharmaceutically acceptable salt of a compound of Formula (Id):

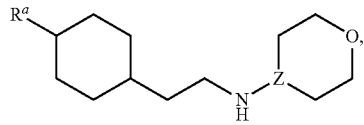

(Id)

wherein Z and $R^a$ have any of the values described herein.

In some embodiments, a chemical entity of Formula (I) is a chemical entity of Formula (Ie), and more specifically, a compound or a pharmaceutically acceptable salt of a compound of Formula (Ie):

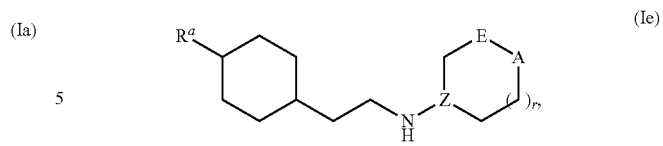

(Ie)

wherein E, A, Z, r, and $R^a$ have any of the values described herein.

In some embodiments, a chemical entity of Formula (I) is a chemical entity of Formula (If), and more specifically, a compound or a pharmaceutically acceptable salt of a compound of Formula (If):

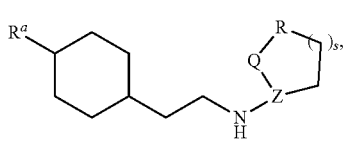

(If)

wherein Q, R, Z, s, and $R^a$ have any of the values described herein.

In some embodiments, the chemical entity is selected from any of the species described or exemplified herein, and more particularly, is a compound, or pharmaceutically acceptable salt thereof.

In some embodiments, the chemical entities, and compositions including such entities, are used in a wide range of methods, as described herein. In some embodiments, the methods include metabolic and reaction kinetic studies, detection and imaging techniques, and radioactive treatments. In some embodiments, the methods include inhibiting NOP, treating disorders that are mediated by NOP or nociceptin, treating disorders characterized by alterations in NOP or nociceptin signaling, enhancing neuronal plasticity, conferring neuroprotection, and promoting neurogenesis. In some embodiments, the methods include treating neurological disorders, particularly CNS disorders, and more particularly, mental and psychiatric disorders, cognitive disorders, movement disorders, psychotic disorders, and neurodegenerative disorders. In some embodiments, the methods are directed to treating peripheral disorders, including cardiovascular, renal, respiratory, gastrointestinal, liver, genitourinary, metabolic, and inflammatory disorders.

In some embodiments, the chemical entities, and compositions including such entities, are useful as augmenting agents to increase the efficiency of cognitive and motor training, including training during post-stroke rehabilitation or post-traumatic brain injury (TBI) rehabilitation; and to increase the efficiency of non-human animal training protocols.

The disclosure is further directed to the general and specific embodiments defined, respectively, and by the independent and dependent claims appended hereto, which are incorporated by reference herein. Additional embodiments, features, and advantages of the disclosure will be apparent from the following detailed description and through practice of the exemplary embodiments.

DETAILED DESCRIPTION

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

Terms and Definitions

The use of headings and subheadings provided in the sections of this specification is solely for convenience of reference and does not limit the various embodiments herein, which are to be construed by reference to the specification as a whole.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. To provide a more concise description, some of the quantitative expressions given herein are not qualified with the term "about." It is understood that, whether the term "about" is used explicitly or not, every quantity given herein is meant to refer to both the actual given value and the approximation of such given value that would reasonably be inferred based on the ordinary skill in the art, including equivalents and approximations due to the experimental and/or measurement conditions for such given value. Accordingly, for any embodiment of the disclosure in which a numerical value is prefaced by "about" or "approximately," the disclosure includes an embodiment in which the exact value is recited. Conversely, for any embodiment of the d in which a numerical value is not prefaced by "about" or "approximately", the disclosure includes an embodiment in which the value is prefaced by "about" or "approximately".

As used herein, the terms "a," "an," and "the" are to be understood as meaning both singular and plural, unless explicitly stated otherwise. Thus, "a," "an," and "the" (and grammatical variations thereof where appropriate) refer to one or more.

Furthermore, although items, elements or components of the embodiments may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof. Adjectives such as "conventional," "normal," "known" and terms of similar meaning should not be construed as limiting the item described to a given time period or to an item available as of a given time, but instead should be read to encompass conventional, or normal technologies that may be available or known now or at any time in the future. Likewise, where this document refers to technologies that would be apparent or known to one of ordinary skill in the art, such technologies encompass those apparent or known to the skilled artisan now or at any time in the future.

As will become apparent to one of ordinary skill in the art after reading this document, the illustrated embodiments and their various alternatives may be implemented without confinement to the illustrated examples.

Chemical Terms

The term "alkyl" refers to a fully saturated aliphatic hydrocarbon group (i.e., contains no double or triple bonds). The alkyl moiety may be a straight- or branched-chain alkyl group having from 1 to 12 carbon atoms in the chain, and more particularly, has 1, 2, 3, 4, 5, 6, 7, 8, 9, 10, 11, or 12 carbons in the chain. Preferably, the alkyl moiety is —$C_{1-6}$ alkyl, and more preferably is $C_{1-4}$alkyl. Examples of alkyl groups include, but are not limited to, methyl (Me, which also may be structurally depicted by the symbol, " ━━ "), ethyl (Et), n-propyl, isopropyl, butyl, isobutyl, sec-butyl, tert-butyl (tBu), pentyl, isopentyl, tert-pentyl, hexyl, and isohexyl. Alkyl groups may be optionally substituted with one or more substituents including, but not limited to, hydroxyl, alkoxy, thioalkoxy, amino, aminoalkyl, and cyano.

The term "alkenyl" refers to unsaturated acyclic aliphatic moieties having at least one carbon-carbon double bond. The term alkenyl includes all possible geometric isomers including E and Z isomers of said alkenyl moiety unless specifically indicated. Examples of alkenyl radicals include ethenyl, propenyl, butenyl, 1,4-butadienyl, and the like.

The term "alkynyl" refers to optionally substituted unsaturated acyclic aliphatic moieties having at least one carbon-carbon triple bond. Examples of alkynyl radicals include ethynyl, propynyl, butynyl and the like.

The term "haloalkyl" refers to a straight- or branched-chain alkyl group having from 1 to 12 carbon atoms in the chain substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, and —$CH_2CF_2CF_3$.

The term "alkoxy" includes a straight chain or branched alkyl group with an oxygen atom linking the alkyl group to the rest of the molecule. Examples of alkoxy groups include, but are not limited to, methoxy, ethoxy, propoxy, isopropoxy, butoxy, t-butoxy, and pentoxy. "Aminoalkyl," "thioalkyl," and "sulfonylalkyl" are analogous to alkoxy, replacing the terminal oxygen atom of alkoxy with, respectively, NH (or NR), S, and $SO_2$ where R is selected from hydrogen, $C_{1-6}$alkyl, $C_{2-6}$alkenyl, $C_{2-6}$alkynyl, $C_{3-7}$cycloalkyl, phenyl, 5-, 6-, 9-, or 10-membered heteroaryl, and 5-10 membered heterocycloalkyl, as defined herein.

The term "haloalkoxy" refers to alkoxy groups substituting one or more hydrogens with halogens. Examples of haloalkoxy groups include, but are not limited to, —$OCF_3$, —$OCHF_2$, —$OCH_2F$, —$OCH_2CF_3$, —$OCH_2CHF_2$, —$OCH_2CH_2Cl$, —$OCH_2CF_2CF_3$, and —$OCH(CH_3)CHF_2$.

The term "amino group" refers to an —$NH_2$ group.

The term "cyano" refers to the group —CN.

The term "aryl" refers to a monocyclic, or fused or spiro polycyclic, aromatic carbocycle (ring structure having ring atoms that are all carbon), having from 3 to 15 ring atoms per ring (carbon atoms in aryl groups are $sp^2$ hybridized). Illustrative examples of aryl groups include the following moieties:

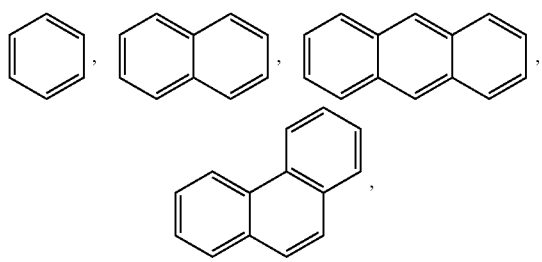

and the like.

The term "phenyl" represents the following moiety:

The term "aryloxy" refers to a group having the formula, —O—R, wherein R is an aryl group.

The term "cycloalkyl" refers to a fully saturated or partially saturated carbocycle, such as monocyclic, fused polycyclic, bridged monocyclic, bridged polycyclic, spirocyclic, or spiro polycyclic carbocycle having from 3 to 15 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

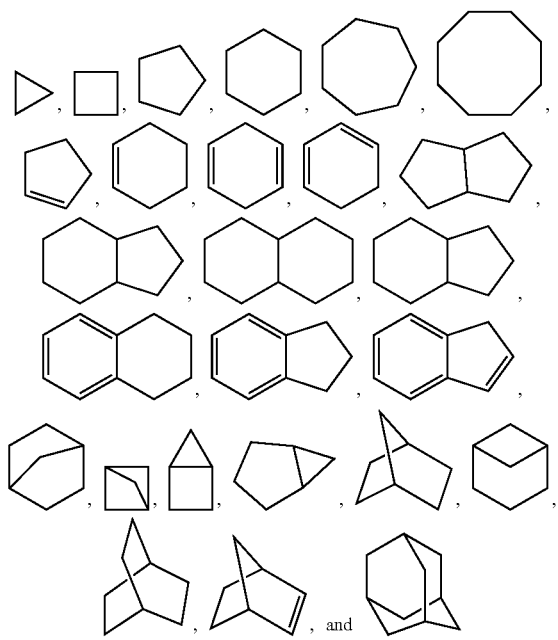

A "heterocycloalkyl" refers to a monocyclic, or fused, bridged, or spiro polycyclic ring structure that is fully saturated or partially saturated and includes at least one heteroatom selected from nitrogen, oxygen, and sulfur in the ring backbone. A heterocycloalkyl may have any degree of saturation provided that at least one ring in a polycyclic ring structure is not aromatic. The heteroatom(s) may be present in either a non-aromatic or aromatic ring in the polycyclic structure. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may be designated as "3-15-membered heterocycloalkyl," "4-10-membered heterocycloalkyl," "3-15-membered $C_{2-14}$heterocycloalkyl," "5-9-membered $C_{4-8}$heterocycloalkyl," "5-10-membered $C_{4-9}$heterocycloalkyl," "5-membered $C_{3-4}$heterocycloalkyl," "6-membered $C_{4-5}$heterocycloalkyl," "7-membered $C_{5-6}$heterocycloalkyl," "bicyclic or tricyclic 9-15-membered $C_{8-14}$heterocycloalkyl," "monocyclic or bicyclic 3-10-membered $C_{2-9}$heterocycloalkyl," "bicyclic 8-10-membered $C_{4-9}$heterocycloalkyl," "bicyclic 8-10-membered $C_{5-9}$heterocycloalkyl," "monocyclic 4-7-membered $C_{3-6}$-heterocycloalkyl," "monocyclic 5-6-membered $C_{3-5}$-heterocycloalkyl," or similar designations. The heterocycloalkyl may be a 5-10 membered ring or ring system comprising one to four heteroatoms each independently selected from nitrogen, oxygen, and sulfur. The heterocycloalkyl may be a monocyclic five-membered ring comprising one to three heteroatoms each independently selected from nitrogen, oxygen, and sulfur. The heterocycloalkyl may be a monocyclic six-membered ring comprising one to three heteroatoms each independently selected from nitrogen, oxygen, and sulfur. The heterocycloalkyl may be a bicyclic nine-membered ring comprising one to three heteroatoms each independently selected from nitrogen, oxygen, and sulfur. The heterocycloalkyl may be a bicyclic ten-membered ring comprising one to three heteroatoms each independently selected from nitrogen, oxygen, and sulfur. The heterocycloalkyl may be optionally substituted. Illustrative unsubstituted heterocycloalkyl entities, in the form of properly bonded moieties, include:

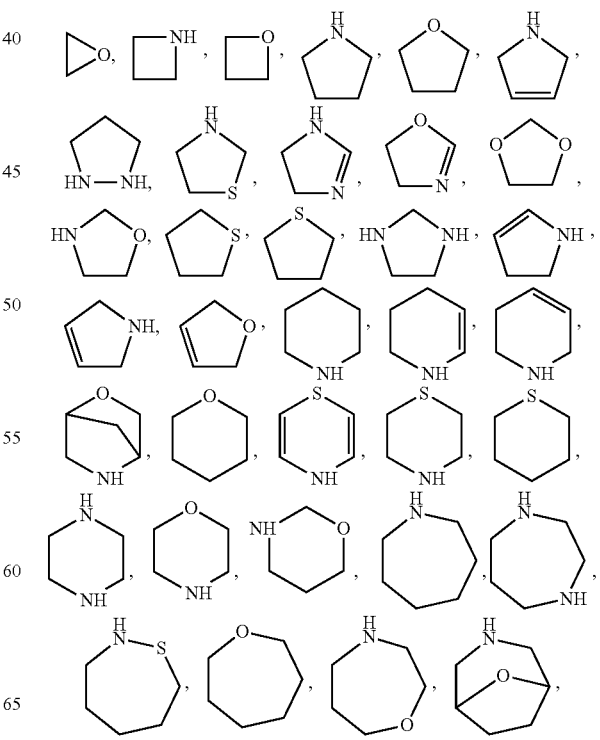

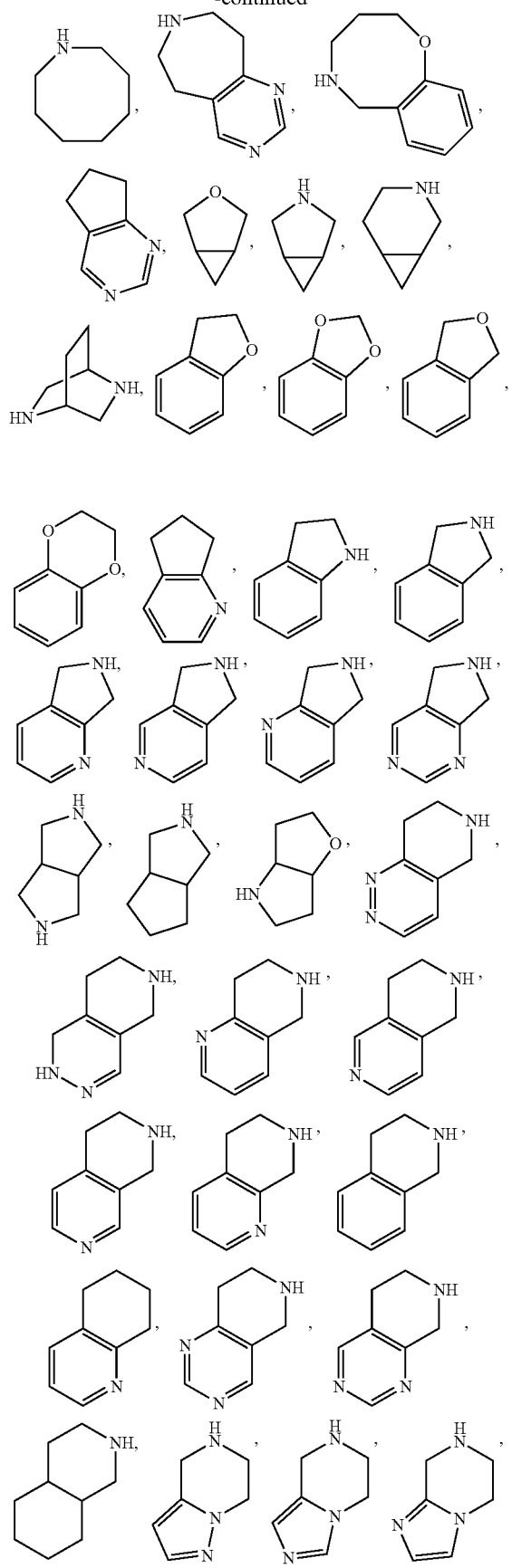
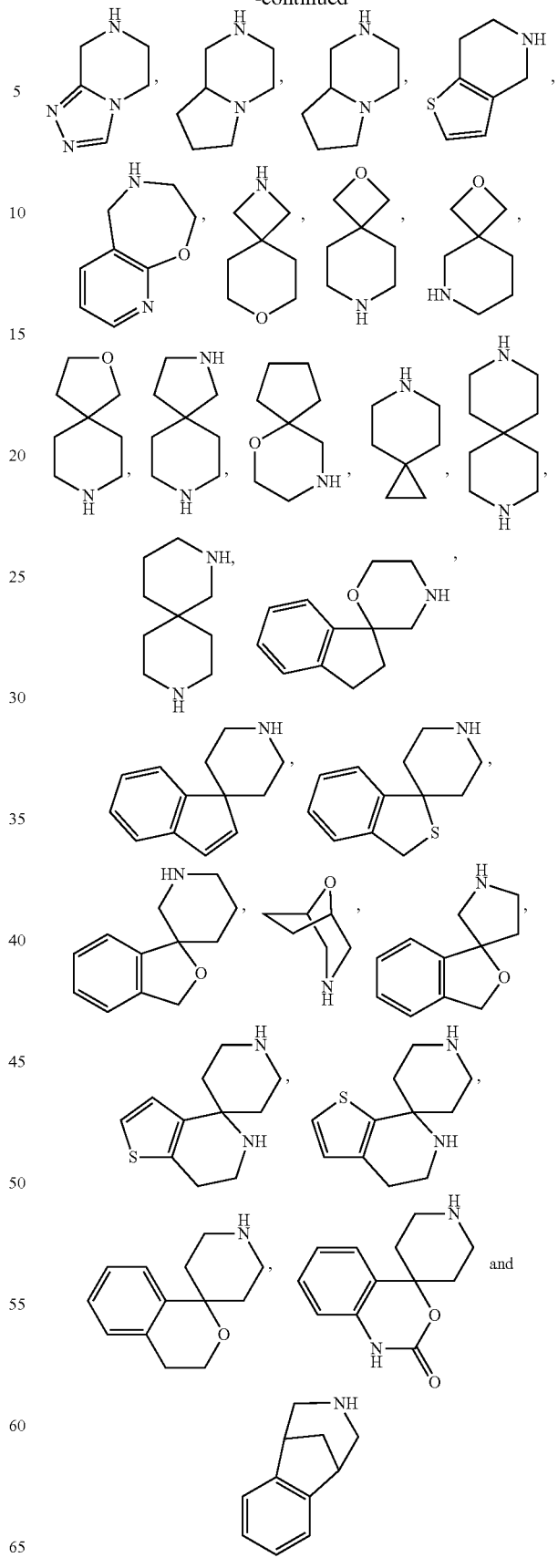

Illustrative carbon or sulfur oxo-substituted heterocycloalkyl entities, in the form of properly bonded moieties, include:

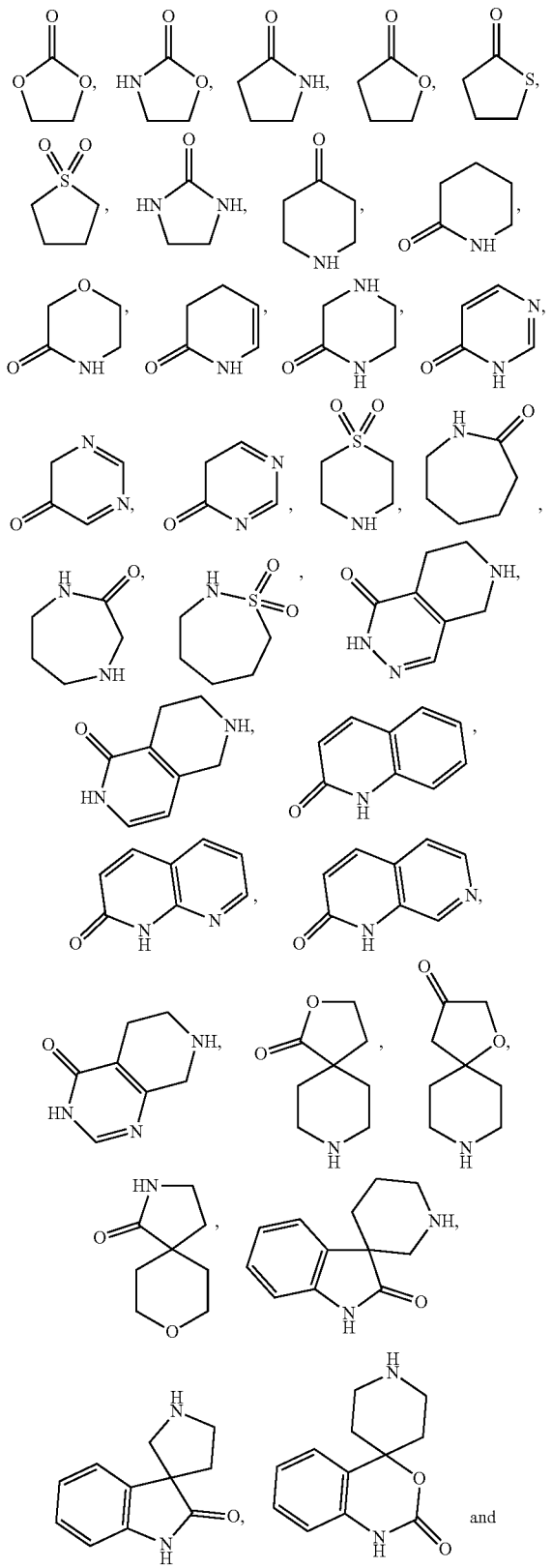

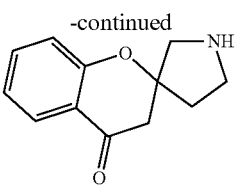

The term "heteroaryl" refers to an aromatic monocyclic, fused bicyclic, or fused polycyclic ring or ring system having one or more heteroatoms selected from nitrogen, oxygen, and sulfur in the ring backbone. When the heteroaryl is a ring system each ring in the ring system is fully unsaturated. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-9-membered heteroaryl," "5-10-membered heteroaryl," "5-9-membered $C_{4-8}$heteroaryl," "5-10-membered $C_{4-9}$heteroaryl," "5-6-membered $C_{3-5}$heteroaryl," "6-membered $C_{4-5}$heteroaryl," "5-membered $C_{3-4}$heteroaryl," or similar designations. The heteroaryl may be a 5-10 membered ring or ring system comprising one to four heteroatoms each independently selected from nitrogen, oxygen, and sulfur. The heteroaryl may be a monocyclic five-membered ring comprising one to four heteroatoms each independently selected from nitrogen, oxygen, and sulfur. The heteroaryl may be a monocyclic six-membered ring comprising one to four heteroatoms each independently selected from nitrogen, oxygen, and sulfur. The heteroaryl may be a bicyclic nine-membered ring comprising one to four heteroatoms each independently selected from nitrogen, oxygen, and sulfur. The heteroaryl may be a bicyclic ten-membered ring comprising one to four heteroatoms each independently selected from nitrogen, oxygen, and sulfur. In some embodiments, the heteroaryl may be a tautomer of a heterocycloalkyl where the heteroaryl is the predominate form under equilibrium conditions. Illustrative examples of heteroaryl groups include the following entities, in the form of properly bonded moieties:

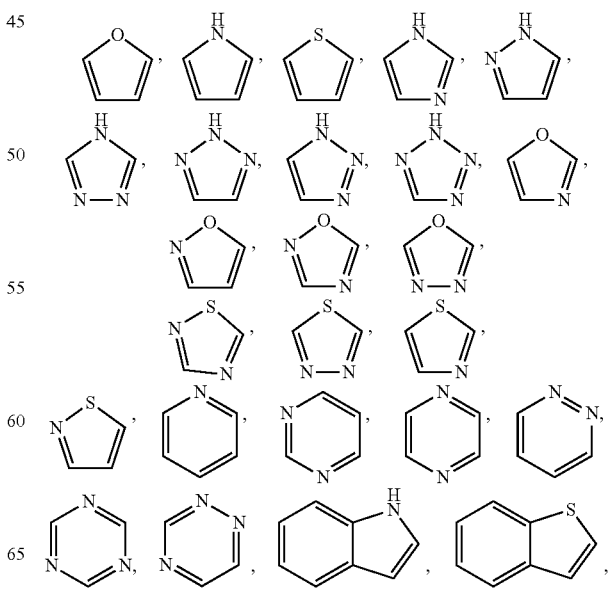

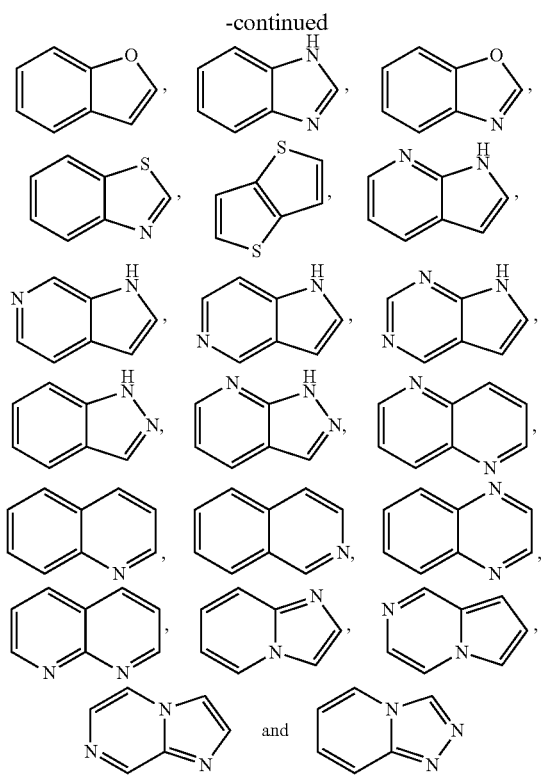

Those skilled in the art will recognize that the species of aryl, cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

By "optional" or "optionally" is meant that the subsequently described event or circumstance may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted" means that the specified group or moiety bears one or more substituents. A substituted group is derived from the unsubstituted parent group in which there has been an exchange of one or more hydrogen atoms for another atom or group or derived from the unsubstituted parent group in which there has been an addition of one or more atoms or group to a carbon, nitrogen or sulfur. Where the term "substituted" is used to describe a structural system, unless specified otherwise, the substitution is meant to occur at any valency-allowed position on the system. The term "unsubstituted" means that the specified group bears no substituents.

For simplicity, groups described herein that are capable of more than one point of attachment (i.e., divalent, trivalent, polyvalent) may be referred to with a common term. For example, the term "$C_{3\text{-}10}$cycloalkyl" can be used to describe a three to ten membered cycloalkyl group ($L^3$) that is monovalent, as in $-L^1-L^3$, wherein $L^3$ has one point of attachment, and that can also be divalent ($L^2$), as in $-L^1-L^2-L^3$, wherein $L^2$ has two points of attachment.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ cycloalkyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-cycloalkyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-cycloalkyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents unless the optional substituents are otherwise specifically identified.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

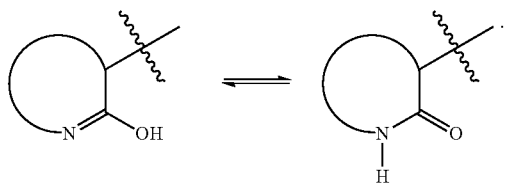 [SMILES: *CC(=N)O ; *CC(N)=O]

The symbols ▬ and ▬ are used as meaning the same spatial arrangement in chemical structures shown herein. Analogously, the symbols ıııııı and ''ıııı are used as meaning the same spatial arrangement in chemical structures shown herein.

Where compounds described herein exist in various tautomeric forms, the term "compound" is intended to include all tautomeric forms (tautomers) of the compound.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

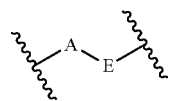

includes the substituent being oriented such that the A is attached at the leftmost attachment point of the molecule as well as the case in which A is attached at the rightmost attachment point of the molecule.

Chemical Entities

As used herein, the term "chemical entity" collectively refers to a compound, along with all pharmaceutically acceptable forms thereof, including pharmaceutically acceptable salts, chelates, solvates, conformers, crystalline forms/polymorphs, tautomers, prodrugs, metabolites, and mixtures thereof. In some embodiments, the chemical entity is selected from the group consisting of a compound and pharmaceutically acceptable salts thereof.

Chelates

The term "chelate" refers to a chemical entity formed by the coordination of a compound to a metal ion at two (or more) points.

Solvates

Additionally, any formula given herein is intended to refer also to solvates, including hydrates, of compounds herein, and mixtures thereof, even if such forms are not listed explicitly. Some embodiments provide a solvate of a compound of Formula (I), and the use of such solvates in methods described herein. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the disclosure with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. Hydrates include a molecule of a compound associated with water molecules.

Conformers and Crystalline Forms/Polymorphs

Some embodiments provide conformer and crystalline forms of a compound of Formula (I), and their use in methods of the present disclosure. A conformer is a structure that is a conformational isomer. Conformational isomerism is the phenomenon of molecules with the same structural formula but different conformations (conformers) of atoms about a rotating bond.

Polymorphs refer to a solid material that can exist in more than one form or crystal structure, where each form or crystal structure is different from the other form(s) or crystal structure(s). Therefore, a single compound may give rise to a variety of polymorphic forms having different and distinct physical properties, such as solubility profiles, melting point temperatures, hygroscopicity, particle shape, density, flowability, compactibility and x-ray diffraction peaks. In certain embodiments, compounds of Formula (I) are obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Compounds

As used herein, a "compound" refers to any one of: (a) the actually recited form of such compound; and (b) any of the forms of such compound in the medium in which the compound is being considered when named. For example, reference herein to a compound such as R—OH encompasses reference to any one of, for example, R—OH(s), R—OH(sol), and R—O-(sol). In this example, R—OH(s) refers to the solid compound, as it could be for example in a tablet or some other solid pharmaceutical composition or preparation; R—OH(sol) refers to the undissociated form of the compound in a solvent; and R—O-(sol) refers to the dissociated form of the compound in a solvent, such as the dissociated form of the compound in an aqueous environment, whether such dissociated form derives from R—OH, from a salt thereof, or from any other entity that yields R—O— upon dissociation in the medium being considered.

In another example, an expression such as "modulate activity of NOP or an associated signaling pathway" refers to the exposure of NOP to the form, or forms, of the compound R—OH that exists, or exist, in the medium in which such exposure takes place. In this regard, if such compound is, for example, in an aqueous environment, it is understood that the compound R—OH is in the same such medium, and therefore NOP is being exposed to the compound as it exists in the medium such as R—OH (aq) and/or R—O-(aq), where the subscript "(aq)" stands for "aqueous" according to its conventional meaning in chemistry and biochemistry. A hydroxyl functional group has been chosen in these nomenclature examples; this choice is not intended, however, as a limitation but is merely an illustration. It is understood that analogous examples can be provided in terms of other functional groups, including, but not limited to, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

Salts

Embodiments of the present disclosure include pharmaceutically acceptable salts of the compounds represented by Formula (I), and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally Paulekuhn et al., 2007, *J. Med. Chem.* 50, 6665-6672; Berge et al., 1977, *J. Pharm. Sci.* 66, 1-19; Stahl and Wermuth (eds), Pharmaceutical Salts: Properties, Selection, and Use: 2nd Revised Edition (2011) Wiley-VCS, Zurich, Switzerland. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form pharmaceutically acceptable salt bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, besylate, mesylate and mandelates.

When a compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When a compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Prodrugs

Some embodiments provide prodrugs of the compounds of Formula (I), and the use of such pharmaceutically acceptable prodrugs in methods of the present disclosure, particularly therapeutic methods.

The term "prodrug" means a precursor of a designated compound that is initially inactive or partially inactive, and that following administration to a subject, yields the compound in vivo via a chemical or physiological process such as solvolysis or enzymatic cleavage, or under physiological conditions (e.g., a prodrug on being brought to physiological pH is converted to an active pharmacological compound of Formula (I)).

A "pharmaceutically acceptable prodrug" is a prodrug that is preferably non-toxic, biologically tolerable, and otherwise biologically suitable for administration to the subject. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug.

Prodrugs may be determined using routine techniques known or available in the art Prodrugs may be produced, for instance, by derivatizing free carboxyl groups, free hydroxy groups, or free amino groups. See, e.g., Bundgaard (ed.), 1985, Design of prodrugs, Elsevier; Krogsgaard-Larsen et al., (eds.), 1991, Design and Application of Prodrugs, Harwood Academic Publishers; Fleisher et al., *Adv. Drug Delivery Rev.* 1996, 19, 115-130; Robinson et al., 1996, *J. Med. Chem.* 39, 10-18.

Tautomers

Some embodiments provide tautomers of compounds of Formula (I), as defined herein, which may also be used in the methods of the disclosure.

Metabolites

Some embodiments provide pharmaceutically active metabolites of the compounds of Formula (I), which may also be used in the methods of the disclosure. A "pharmaceutically active metabolite" means a pharmacologically active product of metabolism in the body of a compound of Formula (I) or salt thereof. Preferably, the metabolite is in an isolated form outside the body.

Active metabolites of a compound may be determined using routine techniques known or available in the art. For example, isolated metabolites can be enzymatically and synthetically produced (e.g., Bertolini et al., 1997, *J. Med. Chem.* 40, 2011-2016; Shan et al., 1997, *J. Pharm. Sci.* 86, 765-767; Bagshawe, 1995, *Drug Dev. Res.* 34, 220-230; and Bodor, 1984, *Adv. Drug Res.* 13, 224-231).

Isotopes

Isotopes may be present in the compounds described. Each chemical element present in a compound either specifically or generically described herein may include any isotope of the element. Any formula given herein is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively.

Compositions

The term "composition," as in pharmaceutical composition, is intended to encompass a product comprising the active ingredient(s) (e.g., one or more of the presently disclosed chemical entities), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a chemical entity of Formula (I) and a pharmaceutically acceptable excipient.

The term "pharmaceutically acceptable," as used in connection with compositions of the disclosure, refers to molecular entities and other ingredients of such compositions that are physiologically tolerable and do not typically produce untoward reactions when administered to an animal (e.g., human). The term "pharmaceutically acceptable" can also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, $21^{st}$ Ed., Lippincott Williams & Wilkins (2005).

A "pharmaceutically acceptable salt" is intended to mean a salt of a free acid or base of a compound represented by Formula (I), as previously defined herein. The term "carrier" refers to an adjuvant, vehicle, or excipients, with which the compound is administered. In preferred embodiments of this disclosure, the carrier is a solid carrier. Suitable pharmaceutical carriers include those described in Remington: The Science and Practice of Pharmacy, $21^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" refers to a sterile, pharmaceutical product produced under good manufacturing practices (GMP) that is prepared and presented in a manner such that the composition is not likely to cause any untoward or deleterious effects when orally administered to a subject. Unless specified otherwise, all of the compositions disclosed herein are suitable for oral administration.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease. Particularly with respect to progressive disease-states or conditions, maintaining the status quo, or arresting the progression of symptoms, is understood to be an amelioration of such symptoms.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the disclosure, "an effective amount" of at least one compound according to the disclosure is administered to a subject (e.g., a mammal). An "effective amount" also means an amount or dose of a compound or composition effective to modulate activity of NOP or an associated signaling pathway. The "effective amount" will vary, depending on the compound, the disease, the type of treatment desired, and its severity, and age, weight, etc.

As used herein, the term "NOP" or "NOP receptor" refers to all translation products encoded by transcripts of any or all genes encoding the nociceptin receptor. The amino acid and nucleotide sequences that encode NOP of various species are known to those skilled in the art and can be found, for example, in GenBank under accession numbers NM_001318919, NM_001318948, NM_001318853.1, NP_001239494.1, NP_113757.1, NP_000904. It is understood that the nomenclature of nociceptin receptors is diverse, and in addition to the term NOP receptor or NOP (Cox et al., 2015, Br. J. Pharmacol. 172, 317-323), includes, but is not limited to, the terms KOR-3 and MOR-C in mice, Pan et al., 1994, Regul. Pept. 54, 217-218; Nishi et al., 1994, Biochem. Biophys. Res. Commun. 205, 1353-1357, the terms LC132, XOR1, Ratxorl, $C_3$, and ROR-C in rats, Bunzow et al., 1994, FEBS Lett. 347, 284-288; Wang et al., 1994, FEBS Lett. 348, 75-79; Chen et al., 1994, FEBS Lett. 347, 279-283; Lachowicz et al., 1995, J. Neurochem. 64, 34-40; Fukuda et al., 1994, FEBS Lett. 343, 42-44; and the term ORL1 in humans, Mollereau et al., 1994, FEBS Lett. 341, 33-38.

The term "nociceptin" refers to the endogenous ligand for the NOP receptor and is interchangeable with the term orphanin FQ and N/OFQ.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present disclosure are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to (or "compared to") the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to embodiments of the present disclosure, examples of which are illustrated by and described in conjunction with the accompanying examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Chemical Entities

Some embodiments provide certain substituted cyclohexyl chemical entities which are useful, for example, as inhibitors of NOP enzymatic activity.

In some embodiments, the chemical entities include the compounds disclosed herein and pharmaceutically acceptable salts, chelates, solvates, conformers, crystalline forms/polymorphs, tautomers, prodrugs, metabolites, and mixtures thereof. In some embodiments, the chemical entities include the compounds disclosed herein and pharmaceutically acceptable salts thereof.

Some embodiments provide a chemical entity of Formula (I):

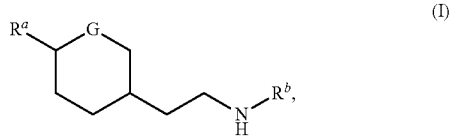

(I)

wherein, G, $R^a$, and $R^b$, have any of the values described herein.

In some embodiments of a chemical entity of Formula (I), G is C(=O), C(=N—OH), CH$_2$, CHR$^{1B}$, or C(R$^{1B}$)$_2$;
$R^a$ is a 6 or 10-membered aryl or 6 or 10-membered heteroaryl, optionally substituted with 1 to 4 $R^{1A}$;
  each $R^{1A}$ is independently selected from the group consisting of: halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, and —C$_{1-6}$haloalkoxy; and
$R^b$ is a —C$_{3-7}$cycloalkyl or 5-10-membered heterocycloalkyl, optionally substituted with 1 to 7 $R^{1B}$; and
  each $R^{1B}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —C(O)C$_{1-4}$alkyl, —C(O)C$_{3-6}$cycloalkyl, —COOC$_{1-4}$alkyl, —C(O)NH$_2$, —OC(O)NH$_2$, —C(O)NH—C$_{1-4}$alkyl, —NHC(O)—C$_{1-4}$alkyl, —C(O)NH—(C$_{1-3}$alkyl-C$_{3-6}$cycloalkyl), 5-6-membered heterocycloalkyl and —C(O)N(C$_{1-4}$alkyl)$_2$.

In certain embodiments, a chemical entity of Formula (I) is a chemical entity of Formula (Ia), and more particularly, is a compound of Formula (Ia), or a pharmaceutically acceptable salt of a compound of Formula (Ia):

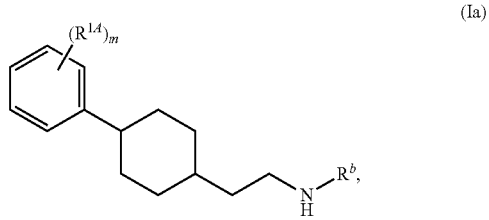

(Ia)

wherein $R^{1A}$, m, and $R^b$ have any of the values described herein.

In certain embodiments of a chemical entity of Formula (Ia),
each $R^{1A}$ is independently selected from the group consisting of: halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, and —C$_{1-6}$haloalkoxy; and
m is 0, 1, 2, or 3;
$R^b$ is a —C$_{5-6}$cycloalkyl or 5-6-membered heterocycloalkyl, optionally substituted with 1 to 4 $R^{1B}$; and
  each $R^{1B}$ is independently selected from the group consisting of: —H, halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —C(O)C$_{1-4}$alkyl, —C(O)C$_{3-6}$cycloalkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), and —C(O)N(C$_{1-4}$alkyl)$_2$.

In certain embodiments, a chemical entity of Formula (I) is a chemical entity of Formula (Ib), and more particularly, is a compound of Formula (Tb), or a pharmaceutically acceptable salt of a compound of Formula (Tb):

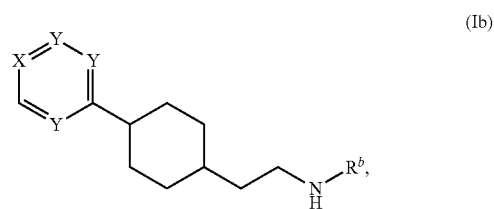

(Ib)

wherein X, Y, and $R^b$ have any of the values described herein.

In certain embodiments of a chemical entity of Formula (Ib),
each Y is independently CH, CR$^{1A}$, or N (nitrogen);
X is CH, CR$^{1A}$, or N (nitrogen);
  each $R^{1A}$ is independently selected from the group consisting of: halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, and —C$_{1-6}$haloalkoxy; and
$R^b$ is a —C$_{5-6}$cycloalkyl or 5-6-membered heterocycloalkyl, optionally substituted with 1 to 4 $R^{1B}$;
  each $R^{1B}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —C(O)C$_{1-4}$alkyl, —C(O)C$_{3-6}$cycloalkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), and —C(O)N(C$_{1-4}$alkyl)$_2$.

In some embodiments of a chemical entity of Formula (Ib) disclosed herein:
X is CH, CR$^{1A}$, or N (nitrogen) where when X is N (nitrogen) and each Y is independently CH, or CR$^{1A}$.

In certain embodiments, a chemical entity of Formula (I) is a chemical entity of Formula (Ic), and more particularly, is a compound of Formula (Ic), or a pharmaceutically acceptable salt of a compound of Formula (Ic):

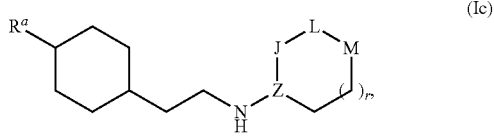

(Ic)

wherein J, L, M, Z, r, and $R^a$ have any of the values described herein.

In certain embodiments of a chemical entity of Formula (Ic),
$R^a$ is a 6-membered aryl or heteroaryl, optionally substituted with 1 to 4 $R^{1A}$;
  each $R^{1A}$ is independently selected from the group consisting of: halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, and —C$_{1-6}$haloalkoxy;

J, L, and M are each independently S(O)$_2$, NH, NR$^{1B}$, C(=O), CH$_2$, CHR$^{1B}$, C(R$^{1B}$)$_2$, or O (oxygen);

Z is —CH or —CR$^{1B}$; and r is 0 or 1.

In some embodiments of a chemical entity of Formula (Ic) disclosed herein:

Z is —CH.

In some embodiments of a chemical entity of Formula (Ic) disclosed herein:

Z is CR$^{1B}$; and

R$^{1B}$ is selected from the group consisting of: —OH, —NH$_2$, —NHC$_{1-4}$alkyl, —N(C$_{1-4}$alkyl)$_2$, —CN, —C$_{1-6}$ alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —C(O)C$_{1-4}$alkyl, —C(O)C$_{3-6}$cycloalkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), and —C(O)N(C$_{1-4}$alkyl)$_2$.

In some embodiments of a chemical entity of Formula (Ic) disclosed herein:

J, L, and M are each independently —NR$^{1B}$, —CHR$^{1B}$, —C(R$^{1B}$)$_2$ where each R$^{1B}$ is independently selected from the group consisting of: halo, —OH, =O, —NH$_2$, —NHC$_{1-4}$ alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C(O)C$_{1-4}$alkyl, —C(O)C$_{3-6}$cycloalkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), and —C(O)N(C$_{1-4}$alkyl)$_2$.

In some embodiments of a chemical entity of Formula (Ic) disclosed herein:

M is —NH, —NR$^{1B}$, —CH$_2$, —CHR$^{1B}$, C(R$^{1B}$)$_2$, or O (oxygen).

In some embodiments of a chemical entity of Formula (Ic) disclosed herein:

M is —NH, —NR$^{1B}$ or O (oxygen).

In some embodiments of a chemical entity of Formula (Ic) disclosed herein:

L is C(=O), CH$_2$, CHR$^{1B}$, or C(R$^{1B}$)$_2$.

In some embodiments of a chemical entity of Formula (Ic) disclosed herein:

J is CH$_2$, CHR$^{1B}$, or C(R$^{1B}$)$_2$.

In certain embodiments, a chemical entity of Formula (I) is a chemical entity of Formula (Id), and more particularly, is a compound of Formula (Id), or a pharmaceutically acceptable salt of a compound of Formula (Id):

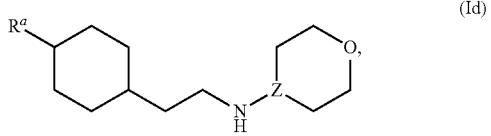

(Id)

wherein Z and R$^a$ have any of the values described herein.

In certain embodiments of a chemical entity of Formula (Id),

Z is —CH or —CR$^{1B}$;

R$^a$ is a 6-membered aryl or heteroaryl, optionally substituted with 1 to 4 R$^{1A}$;

each R$^{1A}$ is independently selected from the group consisting of: halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, and —C$_{1-6}$haloalkoxy; and R$^{1B}$ is selected from the group consisting of: —OH, —NH$_2$, —NHC$_{1-4}$alkyl, —N(C$_{1-4}$alkyl)$_2$, —CN, —C$_{1-6}$alkyl, —C$_{1-6}$ haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —C(O)C$_{1-4}$alkyl, —C(O)C$_{3-6}$cycloalkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), and —C(O)N(C$_{1-4}$alkyl)$_2$.

In certain embodiments, a chemical entity of Formula (I) is a chemical entity of Formula (Ie), and more particularly, is a compound of Formula (Ie), or a pharmaceutically acceptable salt of a compound of Formula (Ie):

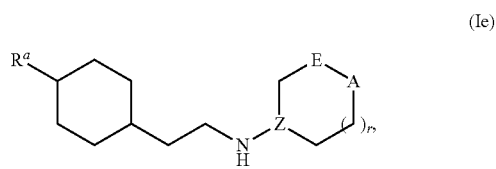

(Ie)

wherein Z, E, A, r, and R$^a$ have any of the values described herein.

In certain embodiments of a chemical entity of Formula (Ie),

R$^a$ is a 6-membered aryl or heteroaryl, optionally substituted with 1 to 4 R$^{1A}$;

each R$^{1A}$ is independently selected from the group consisting of: halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, and —C$_{1-6}$haloalkoxy;

E is —C(=O), —CH$_2$, —CHR$^{1B}$, or —C(R$^{1B}$)$_2$;

A is —NH or —NR$^{1B}$; and each R$^{1B}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C(O)C$_{1-4}$alkyl, —C(O)C$_{3-6}$cycloalkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), and —C(O)N(C$_{1-4}$alkyl)$_2$; and r is 0 or 1.

In some embodiments of a chemical entity of Formula (Ie) disclosed herein:

A is —NH.

In some embodiments of a chemical entity of Formula (Ie) disclosed herein:

E is C(=O) or CH$_2$.

In some embodiments of a chemical entity of Formula (Ie) disclosed herein:

Z is CH.

In certain embodiments, a chemical entity of Formula (I) is a chemical entity of Formula (If), and more particularly, is a compound of Formula (If), or a pharmaceutically acceptable salt of a compound of Formula (If):

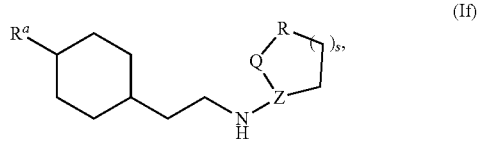

(If)

wherein Q, R, Z, s, and R$^a$ have any of the values described herein.

In certain embodiments of a chemical entity of Formula (If),

Q and R are each independently —$CH_2$, —$CHR^{1B}$, or —$C(R^{1B})_2$;

Z is CH or $CR^{1B}$;

each $R^{1B}$ is independently selected from the group consisting of: halo, —OH, —$NH_2$, —$NHC_{1-4}$alkyl, —$N(C_{1-4}$alkyl$)_2$, —$NO_2$, —$SO_2CH_3$, —CN, —$C_{1-6}$alkyl, —$C_{1-6}$haloalkyl, —$C_{1-4}$alkyl-OH, —$C_{1-6}$alkoxy, —$C_{1-6}$haloalkoxy, —$C_{1-4}$alkyl-O—$C_{1-3}$alkyl, —C(O)$C_{1-4}$alkyl, —C(O)$C_{3-6}$cycloalkyl, —COO$C_{1-4}$alkyl, —C(O)$NH_2$, —C(O)NH—$C_{1-4}$alkyl, —C(O)NH—($C_{1-3}$alkyl-$C_{3-6}$cycloalkyl), and —C(O)N($C_{1-4}$alkyl$)_2$;

$R^a$ is a 6-membered aryl or heteroaryl, optionally substituted with 1 to 4 $R^{1A}$;

each $R^{1A}$ is independently selected from the group consisting of: halo, —OH, —$NH_2$, —$NHC_{1-4}$alkyl, —$N(C_{1-4}$alkyl$)_2$, —CN, —$C_{1-4}$alkyl, —$C_{1-4}$haloalkyl, —$C_{1-6}$alkoxy, and —$C_{1-6}$haloalkoxy; and s is 1 or 2.

In some embodiments of a chemical entity of Formula (I), (Ic), (Id), (Ie), or (If) disclosed herein:
$R^a$ is phenyl.

In some embodiments of a chemical entity of Formula (I), (Ic), (Id), (Ie), or (If) disclosed herein:
$R^a$ is naphthyl.

In some embodiments of a chemical entity of Formula (I), (Ic), (Id), (Ie), or (If) disclosed herein:
$R^a$ is monocyclic or bicyclic 6- or 10-membered $C_{3-9}$heteroaryl, comprising one to three heteroatoms, each independently selected from nitrogen, oxygen, and sulfur.

In some embodiments of a chemical entity of Formula (I), (Ic), (Id), (Ie), or (If) disclosed herein:
$R^a$ is monocyclic 6-membered $C_{3-5}$heteroaryl, comprising one to three heteroatoms, each independently selected from nitrogen, oxygen, and sulfur.

In some embodiments of a chemical entity of Formula (I), (Ic), (Id), (Ie), or (If) disclosed herein:
$R^a$ is a monocyclic 6-membered $C_{4-5}$heteroaryl, comprising one to two heteroatoms, each independently selected from nitrogen, oxygen, and sulfur.

In some embodiments of a chemical entity of Formula (I), (Ic), (Id), (Ie), or (If) disclosed herein:
$R^a$ is a monocyclic 6-membered $C_{4-5}$heteroaryl, comprising one or two nitrogen atoms.

In some embodiments of a chemical entity of Formula (I), (Ic), (Id), (Ie), or (If) disclosed herein:
$R^a$ is a monocyclic 6-membered $C_4$heteroaryl, comprising two nitrogen atoms.

In some embodiments of a chemical entity of Formula (I), (Ic), (Id), (Ie), or (If) disclosed herein:
$R^a$ is a monocyclic 6-membered $C_5$heteroaryl, comprising one nitrogen atom.

In some embodiments of a chemical entity of Formula (I), (Ia), or (Ib) disclosed herein:
$R^b$ is a monocyclic or bicyclic 5-10-membered $C_{4-9}$heterocycloalkyl, comprising one to three heteroatoms, each independently selected from nitrogen, oxygen, and sulfur.

In some embodiments of a chemical entity of Formula (I), (Ia), or (Ib) disclosed herein:
$R^b$ is a monocyclic or bicyclic 3-10-membered $C_{2-9}$heterocycloalkyl, comprising one to four heteroatoms, each independently selected from nitrogen, oxygen, and sulfur.

In some embodiments of a chemical entity of Formula (I), (Ia), or (Ib) disclosed herein:
$R^b$ is a monocyclic 4-7-membered $C_{3-6}$-heterocycloalkyl, comprising one to two heteroatoms, each independently selected from nitrogen, oxygen, and sulfur.

In some embodiments of a chemical entity of Formula (I), (Ia), or (Ib) disclosed herein:
$R^b$ is a monocyclic 5-6-membered $C_{3-5}$-heterocycloalkyl, comprising one to two heteroatoms, each independently selected from nitrogen, oxygen, and sulfur.

In some embodiments of a chemical entity of Formula (I), (Ia), or (Ib) disclosed herein:
$R^b$ is a monocyclic 4-7-membered $C_{3-6}$-heterocycloalkyl, comprising one to two nitrogen atoms.

In some embodiments of a chemical entity of Formula (I), (Ia), or (Ib) disclosed herein:
$R^b$ is a monocyclic 4-7-membered $C_{3-6}$-heterocycloalkyl, comprising one to two oxygen atoms.

In some embodiments of a chemical entity of Formula (I), (Ia), or (Ib) disclosed herein:
$R^b$ is a monocyclic 5-6-membered $C_{3-5}$-heterocycloalkyl, comprising one nitrogen atom.

In some embodiments of a chemical entity of Formula (I), (Ia), or (Ib) disclosed herein:
$R^b$ is a monocyclic 5-6-membered $C_{3-5}$-heterocycloalkyl, comprising one oxygen atom.

In some embodiments of a chemical entity of Formula (I), (Ia), or (Ib) disclosed herein:
$R^b$ is a monocyclic 3-6-membered cycloalkyl.

In some embodiments of a chemical entity of Formula (I), (Ia), or (Ib) disclosed herein:
$R^b$ is a monocyclic 5-6-membered cycloalkyl.

In some embodiments of a chemical entity of Formula (I), (Ia), or (Ib) or (Icc) disclosed herein:
each $R^{1B}$ is a monocyclic 5-6-membered $C_{3-5}$-heterocycloalkyl, comprising one to two heteroatoms, each independently selected from nitrogen, oxygen, and sulfur.

In some embodiments of a chemical entity of Formula (I), (Ia), or (Ib) or (Icc) disclosed herein:
each $R^{1B}$ is a monocyclic 5-6-membered $C_{3-5}$-heterocycloalkyl, comprising one to two nitrogen atoms.

In some embodiments, a chemical entity is selected from compounds of Examples 1-187, and all pharmaceutically acceptable forms thereof, including pharmaceutically acceptable chelates, solvates, conformers, crystalline forms/polymorphs, salts, prodrugs, and pharmaceutically active metabolites. In other embodiments, a chemical entity is selected from compounds of Examples 1-187 and pharmaceutically acceptable salts thereof. In still other embodiments, a chemical entity is a compound selected from Examples 1-187. In still other embodiments, a chemical entity is a compound, or pharmaceutically acceptable salt thereof, selected from Examples 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-105, 106-110, 111-115, 116-120, 121-125, 126-130, 131-135, 136-140, 141-145, 146-150, 151-155, 156-160, 161-165, 166-170, 171-175, 176-180, and 181-187.

Further embodiments are provided by pharmaceutically acceptable salts of compounds of Formula (I), tautomers of compounds of Formula (I), pharmaceutically acceptable prodrugs of compounds of Formula (I), and pharmaceutically active metabolites of compounds of Formula (I).

Isotopically-Labeled Compounds

Compounds of Formula (I) may include any isotope where one or more atoms are replaced by an atom having an atomic mass or mass number different from the atomic mass or mass number usually found in nature. For example, the isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Compounds of the present disclosure (and all forms of such compounds, such as pharmaceutically acceptable salts) that contain the aforementioned isotopes or other isotopes of other atoms are within the scope of the invention. Isotopically-labeled compounds of the present embodiments are useful in binding affinity studies, as well as drug and substrate tissue distribution and target occupancy assays. For example, isotopically labeled compounds are particularly useful in SPECT (single photon emission computed tomography) and in PET (positron emission tomography), as discussed further herein. In addition, isotopically labelled compounds are useful for improving the absorption, distribution, metabolism and/or excretion (ADME) properties of drugs. For instance, replacement of one or more hydrogen atoms with deuterium ($^{2}H$) can modify the metabolism of a drug and improve the metabolic profile by decreasing the metabolic clearance in vivo, extending the half-life, reducing $C_{max}$ or reducing levels of potentially toxic metabolites.

Compositions

In some embodiments, the chemical entities disclosed herein, and more particularly, compounds and pharmaceutically acceptable salts thereof, are used, alone or in combination with one or more additional active ingredients, to formulate pharmaceutical compositions.

In some embodiments, a pharmaceutical composition can comprise: (a) an effective amount of at least one chemical entity of the present disclosure; and (b) a pharmaceutically acceptable carrier.

In some embodiments, a pharmaceutical composition comprises a compound, or pharmaceutically acceptable salt thereof, of any of the embodiments and examples disclosed herein; and a pharmaceutically acceptable carrier. In specific embodiments, a pharmaceutical composition comprises a compound of any one of Examples 1-187; and a pharmaceutically acceptable carrier.

Formulations and Administration

Numerous standard references are available that describe procedures for preparing various formulations suitable for administering the compounds according to the disclosure. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present disclosure is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present disclosure or stabilized form of the compound (e.g., complex with a cyclodextrin derivative or other known complexation agent)) is dissolved in a suitable solvent in the presence of one or more of the excipients described above. The compound of the present disclosure is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Dosage Forms

The chemical entities, and more particularly, compounds and pharmaceutically acceptable salts thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be in a range from 1% to 65% or 2 to 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. These compositions and formulations can be prepared according to ordinary skill in the art.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the chemical entities and compounds (active agents) of the present disclosure can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Effective amounts or doses of the active agents of the present disclosure may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, concomitant medications, and the judgment of the treating physician. An exemplary dose can be in the range from 0.0001 to 200 mg of active agent per day, from 0.001 to 200 mg per day, from 0.05 to 100 mg per day, from 0.1 to 10 mg/day, from 1 to 200 mg/day, or from 5 to 50 mg/day.

In some embodiments, the desired dose may be presented in a unit dosage form; for example, a composition containing from 0.01 to 1000 mg, from 0.1 to 200 mg, from 0.5 to 100 mg, or from 1 to 50 mg, of active ingredient per unit dosage form.

In other embodiments, the desired dose may be presented in divided doses administered at appropriate intervals, for example, as two, three, four, or more sub-doses per day. (e.g., BID, TID, QID). The sub-dose itself may be further divided, e.g., into a number of temporally-distinct administrations used according to the compositions and methods of the present disclosure.

Methods and Uses

Uses of Isotopically-Labeled Compounds

In some embodiments, the present disclosure provides methods of using isotopically labeled compounds of the present disclosure in: (i) metabolic studies (with, for example, $^{14}C$), and reaction kinetic studies (with, for example $^2H$ or $^3H$); (ii) detection or imaging techniques [such as positron emission tomography (PET) or single-photon emission computed tomography (SPECT)] including drug or substrate tissue distribution assays; or (iii) radioactive treatment of patients.

Isotopically labeled compounds and related chemical entities of Formula (I) can generally be prepared by carrying out the procedures disclosed in the schemes or in the examples and preparations described below by substituting a readily available isotopically labeled reagent for a non-isotopically labeled reagent. Compounds labeled with $^{18}F$ or $^{11}C$ may be particularly preferred for PET, and an $^{123}I$-labeled compound may be particularly preferred for SPECT studies. Further substitution of compounds of Formula (I) with heavier isotopes such as deuterium (i.e., $^{2}H$) may afford certain therapeutic advantages resulting from greater metabolic stability, for example increased in vivo half-life or reduced dosage requirements.

Therapeutic Methods

Generally

Chemical entities and compositions of the present disclosure are useful in various therapeutic methods (or in the manufacture of a medicament for use in such methods), comprising administering to a subject in need thereof a chemical entity or composition herein. In a specific aspect, the chemical entity is a compound of Formula (I) or a pharmaceutically acceptable salt thereof. More particularly, the chemical entity is a compound of Formula (Ia), (Ib), (Ic), (Id), (Ie), or (If), or a pharmaceutically acceptable salt thereof.

Such therapeutic methods can be directed to a wide range of indications, as described further herein, including cognitive or motor deficits associated with neurological disorders, neurodegenerative disorders, cognitive disorders, and numerous peripheral disorders.

In some embodiments, chemical entities and compositions herein are useful in methods of inhibiting NOP activity, comprising exposing NOP to an effective amount of a chemical entity or composition of any one of the embodiments disclosed herein. In some embodiments, the NOP is in an animal, and more particularly, is in a human subject.

In some embodiments, chemical entities and compositions herein are useful in methods of treating a subject suffering from or diagnosed with a disorder mediated by NOP activity, comprising administering to a subject in need thereof an effective amount of a chemical entity or composition of any one of the embodiments herein. In one aspect, the subject is diagnosed with a disorder mediated by NOP activity. In another aspect, the subject is suffering from a disorder mediated by NOP activity.

In some embodiments, chemical entities and compositions herein are useful in methods of enhancing neuronal plasticity, an essential property of the brain that can be impaired in numerous CNS disorders and augmented in healthy animals. N/OFQ and its receptor are densely expressed in the hippocampus, amygdala, and cerebral cortex, suggesting a role for this system in learning and memory. Darland and Grandy, 1998, *Br. J. Anaesth.* 81, 29-37; Neal et al., 1999, *J. Comp. Neurol.* 406, 503-547; Neal et al., 1999, *J. Comp. Neurol.* 412, 563-605; Redrobe et al., 2000, *Br. J. Pharmacol.* 131, 1379-1384; Liu et al., *Neurosci. Lett.* 416, 155-159. Moreover, pharmaceutical and genetic manipulations that decrease NOP activity can enhance behavioral and synaptic plasticity. For example, administering the peptide antagonist Ret-Noc-OMe enhances memory retention of mice in a passive avoidance test. Similarly, knocking out either the ORL1 receptor or N/OFQ precursor facilitates long term memory formation and long-term potentiation in mice. Manabe et al., 1998, *Nature* 394, 577-581; Higgins et al., 2002, *Eur. J. Neurosci.* 15, 911-922; Mamiya et al., 2003, *Mol. Psychiatry* 8, 752-765.

Accordingly, in some embodiments, the present disclosure provides methods of enhancing neuronal plasticity, comprising administering to a subject in need thereof an effective amount of a chemical entity or composition of any one of the embodiments herein. In specific embodiments, chemical entities of the present disclosure are useful in methods of enhancing cognitive or motor function, comprising administering to a subject in need thereof an effective amount of a chemical entity or composition of any one of the embodiments disclosed herein. In some embodiments, the cognitive function is memory, and more specifically, is long-term memory.

In some embodiments, chemical entities and compositions herein are used as neuroprotective agents, for example, by enhancing neuronal growth and survival. Accordingly, the present disclosure provides methods of conferring neuroprotection, comprising administering to a subject in need thereof an effective amount of a chemical entity or composition described herein.

In some embodiments, chemical entities and compositions herein are used as treating disorders that include aberrant or dysregulated signaling pathways mediated by NOP. Such NOP-related signaling pathways include, but are not limited to, those involving nociceptin, inward rectifying K+ channels, and voltage-dependent, N-type channels.

In a specific aspect, they are useful in modulating dopaminergic signaling or treating disorders characterized by alterations in dopamine signaling.

In some embodiments, chemical entities and compositions are used as "agents" (or "augmenting agents") to increase the efficiency of training protocols that facilitate functional reorganization in targeted "domains" (or "functions") in the brain.

In some embodiments, chemical entities and compositions are used in combination with other therapies or with other active agents, as described further herein.

Neurological Disorders

In some embodiments the present disclosure provides methods of treating neurological disorders, comprising administering to a subject in need thereof a chemical entity or composition described herein. In a specific aspect, the chemical entity is a compound of Formula (I) or a pharmaceutically acceptable salt thereof. More particularly, the chemical entity is a compound of Formula (Ia), (Ib), (Ic), (Id), (Ie), or (If) or a pharmaceutically acceptable salt thereof.

In some embodiments, the method is directed to a neurological impairment ("neurological deficit") associated with the neurological disorder, including a cognitive impairment ("cognitive deficit") or a motor impairment ("motor deficit") associated with the pathology of the neurological disorder.

A cognitive impairment can manifest, for example, as a deficit in: attention (e.g., sustained attention, divided attention, selective attention, processing speed); executive function (e.g., planning, decision, and working memory); memory (e.g., immediate memory; recent memory, including free recall, cued recall, and recognition memory; and long-term memory, which can be divided into explicit memory (e.g., declarative memory), such as episodic, semantic, and autobiographical memory, and into implicit memory (e.g., procedural memory)); expressive language, including naming, word recall, fluency, grammar, and syntax; understanding speech or writing (e.g., aphasia); perceptual-motor functions (e.g., abilities encompassed under visual perception, visual-constructional, perceptual-motor praxis, and gnosis); and social cognition (e.g., recognition of emotions, theory of mind). In certain embodiments, the cognitive deficit is a deficit in memory and more particularly, a deficit in long-term memory.

A motor impairment can manifest, for example, as weakness or paralysis, deficits in upper and lower extremity function, problems with balance or coordination, impairments of gross motor skills, and deficits in fine motor skills.

A neurological disorder (or condition or disease) is any disorder of the body's nervous system. Neurological disorders can be categorized according to the primary location affected, the primary type of dysfunction involved, and the primary type of cause. The broadest division is between disorders of the central nervous system (CNS), which comprises the nerves in the brain and spinal cord, and disorders of the peripheral nervous system (PNS), which comprises the nerves outside the brain and spinal cord.

Many CNS disorders are amenable for treatment with chemical entities and compositions, including those discussed herein. As used herein, the terms "Neurodevelopment disorders," "Schizophrenia spectrum and other psychotic disorders," "Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep disorders," "Sexual disorders," "Substance-related and addictive disorders," "Personality disorders," "Somatic symptom disorders," "Neurodegenerative disorders," "Neurocognitive disorders," "Delirium," "Dementias," and "Age-associated cognitive deficits, include the diagnosis and classification of these CNS conditions and disorders (and related CNS conditions and disorders) as described in the Diagnostic and Statistical Manual of Mental Disorders (DSM-5; $5^{th}$ ed., 2013, American Psychiatric Association). The skilled artisan will recognize that there are alternative nomenclature and classification systems for these CNS disorders, and that these systems evolve with medical and scientific progress. Thus, these terms in this paragraph are intended to include like disorders that are described in other diagnostic sources.

Mental and Psychiatric Disorders:

In certain embodiments, chemical entities and compositions herein are useful in treating mental or psychiatric disorders, and more particularly, a cognitive impairment associated with the pathology of such disorders. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

Mental and psychiatric disorders are well known in the art, and include, but are not limited to, one or more of the following:

Neurodevelopmental (or "developmental" disorders), such as intellectual disability disorders (e.g., Rubinstein-Taybi syndrome, Down syndrome and Fragile X syndrome); communication disorders; autism-spectrum disorders; attention-deficit/hyperactivity disorders, such as ADHD; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, brief psychotic disorder, schizoaffective disorder, substance/medication-induced psychotic disorder, psychotic disorder due to another medical condition, catatonia, catatonia associated with another mental disorder (catatonia specifier), catatonic disorder due to another medical condition, unspecified catatonia, schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder, persistent depressive disorder (dysthymia), a major depressive episode of the mild, moderate, or severe type, a depressive episode with melancholic features, a depressive episode with catatonic features, seasonal depression (seasonal affective disorder), disruptive mood dysregulation disorder, premenstrual dysphoric disorder, substance/medication-induced depressive disorder, depressive disorder due to another medical condition, mood disorders due to a general medical conditions, and other depressive disorders;

Anxiety disorders, such as specific phobia, agoraphobia, social anxiety disorder (social phobia), panic attack, panic disorder, acute stress disorder, generalized anxiety disorder, posttraumatic stress disorder (PTSD), and other anxiety disorders;

Obsessive-compulsive and related disorders, such as obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified obsessive-compulsive and related disorder and unspecified obsessive-compulsive and related disorder (e.g., body-focused repetitive behavior disorder, obsessional jealousy), and other obsessive-compulsive and related disorders;

Dissociative disorders, such as dissociative identity disorder, dissociative amnesia, depersonalization/derealization disorder, dissociative subtypes (in conjunction with other disorders), and other dissociative disorders;

Disruptive, impulse-control, and conduct disorders, such as conduct disorder, antisocial personality disorder, pyromania, kleptomania, and other disruptive, impulse-control, and conduct disorders;

Trauma- and stressor-related disorders, such as reactive attachment disorder, disinhibited social engagement disorder, posttraumatic stress disorder, acute stress disorder, adjustment disorders, and other trauma- and stressor-related disorders;

Feeding and eating disorders, such as pica, rumination disorder, avoidant/restrictive food intake disorder, anorexia, bulimia, binge-eating disorder, and other feeding and eating disorders;

Sleep disorders, such as sleep-wake disorders, insomnia disorder, hypersomnolence disorder, narcolepsy, breathing-related sleep disorders, sleep apnea, circadian rhythm sleep-wake disorders, non-rapid eye movement (NREM) sleep arousal disorders, nightmare disorder, rapid eye movement (REM) sleep behavior disorder, restless legs syndrome, and substance/medication-induced sleep disorder, parasomnias, and other sleep-wake disorders;

Sexual disorders, such as arousal disorders, desire disorders, dysfunctions, substance- and medication-induced dysfunctions, impotence and other sexual disorders;

Substance-related and addictive disorders, such as those involving alcohol, drugs, stimulants, opioids, tobacco, and non-substance-related addictive disorders;

Personality disorders, such as antisocial personality disorder, borderline personality disorder, histrionic personality disorder, narcissistic personality disorder, avoidant personality disorder, dependent personality disorder, obsessive-compulsive personality disorder, paranoid personality disorder, schizoid personality disorder, schizotypal personality disorder, personality change due to another medical condition, and other personality disorders; and Somatic symptom and related disorders, such as somatic symptom disorder, illness anxiety disorder (hypochondriasis), factitious disorder, factitious disorder imposed on another, pain disorders, conversion disorder, and other somatic symptom and related disorders.

Schizophrenia:

In specific embodiments, the mental or psychiatric disorder is a schizophrenia spectrum or psychotic disorder, and, in particular, is schizophrenia. Schizophrenia is a devastating neurological disorder, characterized by a combination of symptoms, which may include negative, positive, or cognitive symptoms. Negative symptoms can include flat affect (lack or decline in emotional response), alogia (lack or decline in speech), avolition (lack or decline in motivation), anhedonia (the inability to experience pleasure from activities usually found enjoyable), and asociality (lack of motivation to engage in social interaction, or a preference for solitary activities). Positive symptoms include paranoia, hallucinations, and delusions. Cognitive symptoms can include impairments in such functions as attention, memory, reasoning, and processing speed. See, e.g., Keefe and Harvey, 2012, *Handb. Exp. Pharmacol.* 213, 11-23. Intracellular signaling of dopamine D1 and various serotonin receptors, which signal through cyclic nucleotides, is known to be defective in schizophrenia, as well as depression and other cognitive disorders. More particularly, N/OFQ is expressed in corticolimbic circuits, NOP antagonists enhance LTM, and NOP−/− mice show increased NMDA-R dependent LTP and increased binding of MK801 in synaptosomal preparations.

Accordingly, the present disclosure provides a method of treating schizophrenia, comprising administering to a subject in need thereof an effective amount of a chemical entity or composition herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If) or a pharmaceutically acceptable salt thereof. In some embodiments, the treatment is directed to a positive symptom of schizophrenia. In some embodiments, treatment is directed to a negative symptom of schizophrenia. In some embodiments, treatment is directed to cognitive impairment associated with schizophrenia (CIAS). In some embodiments, the treatment also include a cognitive training protocol.

Depressive Disorders:

In specific embodiments, the mental or psychiatric disorder is a depressive disorder. Pharmacological and genetic experiments support antidepressant-like effects mediated by NOP receptor inhibition. See, e.g.: Redrobe et al., 2002, *Naunyn-Schmiedeberg Arch. Pharmacol.* 365, 164-167; Gavioli et al., 2003, *Eur. J. Neurosci.* 17, 1987-1990; Vitale et al., 2009, *Psychopharmacology* 207, 173-189; Gavioli and Calo, 2013, *Pharmacol. Ther.* 140, 10-25; Post et al., 2015, *Neuropsychopharmacology* 41, 1803-1812; Holanda et al., 2016, *Psychopharmacology* 233, 2525-2532.

Anxiety Disorders:

In specific embodiments, the mental or psychiatric disorder is an anxiety disorder. For example, central administration of the NOP antagonist, UFP-101, shows anxiolytic-like effects in rats evaluated using the elevated T maze phase. Duzzioni et al., 2011, *Behav. Brain Res.* 12, 206-211. Similarly, the NOP antagonist, JTC-801, can reverse pain and anxiety symptoms in a rat model of post-traumatic stress disorder. Zhang et al., 2015, *Br. J. Pharmacol.* 172, 751-582.

Accordingly, the present disclosure provides a method of treating an anxiety disorder, comprising administering to a subject in need thereof an effective amount of a chemical entity or composition herein. In a specific embodiment, the chemical entity is a compound of Formula (I), or pharmaceutically acceptable salt thereof. More particularly, the chemical entity is a compound of Formula (Ia), (Ib), (Ic), (Id), (Ie), or (If) or a pharmaceutically acceptable salt thereof. In a specific aspect, the anxiety disorder is a generalized anxiety disorder, panic disorder, post-traumatic stress disorder, acute stress disorder, a phobia including social phobia/social anxiety, or a combination thereof.

Feeding and Eating Disorders:

In specific embodiments, the mental or psychiatric disorder is a feeding or eating disorder. Chronic administration of N/OFQ increases body weight by inducing hyperphagia and decreasing energy expenditure. Matsuhita et al., 2009, *Endocrinology* 150, 2668-2673. In addition, the NOP antagonist LY2940094 inhibits excessive feeding behavior in rodents, and the NOP antagonist SB 612111 decreases high fat diet binge eating. Hardaway et al., 2016, *Behav. Brain. Res.* 307, 25-34.

Accordingly, the present disclosure provides a method of treating a feeding or eating disorder, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof. In specific embodiments, the feeding or eating disorder is a binge eating disorder (BED).

Addictive Disorders:

In specific embodiments, the mental or psychiatric disorder is an addictive disorder. Genetic deletion of NOP confers resilience to drug abuse, supporting the use of NOP antagonists in treating drug addiction. Kallupi et al., 2017, *Neuropsychopharmacology* 42, 695-706. Administering the NOP antagonist, LY2940094, to rats exhibiting excessive ethanol consumption attenuates ethanol self-administration and ethanol-motivated behaviors, stress-induced ethanol seeking, and ethanol-induced stimulation of brain reward pathways. Rorick-Kehn et al., 2016, *Alcohol Clin. Exp. Res.* 40, 945-954.

Accordingly, the present disclosure provides a method of treating an addictive disorder, comprising administering to a subject in need thereof an effective amount of a chemical entity or composition herein. In a specific embodiment, the chemical entity is a compound of Formula (I), or pharmaceutically acceptable salt thereof. More particularly, the chemical entity is a compound of Formula (Ia), (Ib), (Ic), (Id), (Ie), or (If) or a pharmaceutically acceptable salt thereof. In one aspect, the subject is addicted to an addictive agent selected from the group consisting of alcohol, nicotine, marijuana, a marijuana derivative, an opioid agonist (such as morphine, methadone, fentanyl, sufentanil, or heroin), a benzodiazepine, a barbiturate, and a psychostimulant, such as cocaine or amphetamine. More particularly, the addiction is alcohol addiction. In another aspect, the addiction is associated with an obsessive-compulsive disorder. In another aspect, the disorder is associated with a primary impulse-control disorder, such as pathological gambling, addiction to pornography, sex addiction, compulsive spending, anorexia, bulimia, kleptomania, pyromania, trichotillomania, compulsive over-exercising, or compulsive overworking. In another aspect the treatment is directed to withdrawal from alcohol or other addictive agents.

In some embodiments, chemical entities and compositions of the present disclosure are useful in methods of treating tolerance to narcotics and opiates. For example, morphine tolerance is reduced in NOP knockout mice, N/OFQ can induce symptoms resembling withdrawal symptoms observed with morphine addiction, and NOP antagonists can improve morphine tolerance, dependence, and withdrawal-type symptoms. Ueda et al., 1997, *Neurosci. Lett.* 237, 136-138; Malin et al., 2000, *Psychopharmacology* 151, 344-350; Ueda et al., 2000, *J. Neurosci.* 20, 7640-7647.

Accordingly, the present disclosure provides a method of treating tolerance to, dependence on, or withdrawal from a narcotic or opiate, comprising administering to a subject in need thereof an effective amount of a chemical entity or composition herein. In a specific embodiment, the chemical entity is a compound of Formula (I), or pharmaceutically acceptable salt thereof. More particularly, the chemical entity is a compound of Formula (Ia), (Ib), (Ic), (Id), (Ie), or (If) or a pharmaceutically acceptable salt thereof. In one aspect, the narcotic is morphine.

Cognitive Disorders:

In specific embodiments, the present disclosure provides a method of treating a cognitive disorder, and more particularly, a neurological impairment associated with the disorder, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

A "cognitive disorder" (or "neurocognitive disorder") is one in which the primary clinical feature is impaired cognition, i.e., a disorder in which the primary cognitive deficit has not been present since birth or very early life and therefore represents a decline from a previously attained level of functioning. Such disorders, include one or more of the following:

Delirium, such as substance-intoxication (or withdrawal) delirium, medication-induced delirium, and other forms of delirium;

Dementias and other cognitive impairments due to acquired diseases, such as HIV infection, or transmissible encephalopathies; or due to neurodegenerative or progressive nervous system diseases, such as Alzheimer's disease, Parkinson's disease (in particular Parkinson's Disease Dementia (PDD)), Huntington's disease, Lewy body disease, Pick's disease, a prion disease (e.g., Creutzfeldt-Jakob disease), Amyotrophic lateral sclerosis (ALS), multiple sclerosis (MS), frontotemporal lobar degeneration (FTLD), and corticobasal degeneration; dementia due to a vascular disease ("vascular disease"); autoimmune disorders; and other dementias and neurodegenerative diseases.

Age-associated cognitive decline, including age-associated memory impairment (AAMI), also referred to as age-related memory impairment (AMI) (See, e.g., Crook et al., 1986, *Devel. Neuropsychol.* 2, 261-276); and cognitive decline affecting patients in early stages of cognitive decline, as in Mild Cognitive Impairment (MCI) (See, e.g., Arnaiz and Almkvist, 2003, *Acta Neurol. Scand.* Suppl. 179, 34-41);

Trauma-dependent losses of function, including vascular diseases, such as stroke (e.g., ischemic or hemorrhagic stroke) or ischemia; infarction, including cerebral and myocardial; microvascular or macrovascular disease arising from diabetes or arthrosclerosis; traumatic brain injury (TBI), such as brain trauma including subdural hematoma and brain tumor; head trauma (closed and penetrating); head injury; tumors, such as nervous system cancers, including cerebral tumors affecting the thalamic or temporal lobe; hypoxia, and viral, fungal, or bacterial infection (e.g., encephalitis, or meningitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such cognitive disorders can include neurological impairments other than cognitive impairments. For example, trauma-dependent losses of function, such as stroke, traumatic brain injury, head trauma, and head injury, can include impairments in multiple neurological functions, such as impairments in motor functions.

Age Associated Cognitive Decline:

In specific embodiments, the cognitive disorder is age-associated cognitive decline.

In one aspect, the age-related cognitive decline is age-associated memory impairment (AAMI). AAMI is a decline in various cognitive abilities, in particular memory abilities, associated with normal aging. For example, AAMI subjects show a decline in the ability to encode new memories of events or facts, as well as in working memory (Hedden and Gabrieli, 2004, *Nat. Rev. Neurosci.* 5, 87-96). In addition, AAMI subjects, when compared with age-matched controls, appeared to be impaired in tests of executive functions associated with frontal lobe function. These and other studies suggest an important role for frontal lobe dysfunction in the memory loss of elderly people (Nilsson, 2003, *Acta Scand. Suppl.* 179, 7-13). In general, an AAMI diagnosis identifies persons with subjectively and objectively evidenced memory loss without cognitive decline impaired enough to warrant the diagnosis of dementia. For example, the NIH working group has established multiple criteria for a diagnosis of AAMI in a person aged 50 or older, including the presence of subjective memory decline, objective evidence of memory loss, evidence of adequate intellectual function, and the absence of dementia (or other memory-affecting disease) (Crook et al., 1986, *Devel. Neuropsychol.* 2, 261-276). Individuals with AAMI have been shown to have a three-fold greater risk for development of dementia than individuals who do not meet AAMI criteria (Goldman and Morris, 2002, *Alzheimer Dis. Assoc. Disord.* 75, 72-79).

In another aspect, the age-associated cognitive decline is Mild Cognitive Impairment (MCI), which may be diagnosed when an individual's memory declines below the level considered normal for that age group. In other words, MCI is a condition in which people face memory problems more often than that of the average person their age. Symptoms often include misplacing items, forgetting events or appointments, and having trouble thinking of desired words (e.g., Arnaiz and Almkvist, 2003, *Acta Neurol. Scand.* Suppl. 179, 34-41). MCI can represent a transitional state between cognitive changes of normal aging and Alzheimer's disease (AD). Many people who experience mild cognitive impairment are at a high risk of developing Alzheimer's disease.

About 12% of people aged 65 or older diagnosed with MCI go on to develop Alzheimer's disease within a year, and about 40% develop Alzheimer's within three years. This is a much higher rate than in the general population, in which only about 1% of people aged 65 or older develop Alzheimer's each year. Thus, people with MCI are considered at heightened risk to develop Alzheimer's disease. Some patients with MCI, however, never progress to AD.

Accordingly, the disclosure includes methods of treating age-associated cognitive decline, and more particularly, age-related memory impairment or mild cognitive impairment, comprising administering to a subject in need thereof an effective amount of a chemical entity or composition disclosed herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

Trauma-Dependent Loss of Function:

In specific embodiments, the cognitive disorder is a trauma-dependent loss of function, and more particularly, stroke or TBI. For example, post-blast treatment with the NOP receptor antagonist, SB-612111, reduces brain injury-induced hypoxia and signaling proteins in vestibulomotor-related brain regions. Awwad et al., 2018, *Behav. Brain Res.* 340, 183-194.

Appetitive Disorders:

In specific embodiments, the present disclosure provides a method of treating disorders of appetitive behavior. N/OFQ and NOP localize within key nuclei of the hypothalamus involved in the regulation of appetite and metabolism. Florin et al., 2000, *Brain Res.* 880, 11-16; Gehlert et al., 2005, *Neuropeptides* 40, 95-105. Administering N/OFQ into the brain of sated mice or rats or into the CNS of fat-preferring rats stimulates feeding. Olszewski et al., 2002, *Pharmacol. Biochem. Behav.* 73, 529-535; Olszewski et al., 2010, *Am. J. Physiol. Regul. Integr. Comp. Physio.* 299, R655-R663. NOP receptor knockout mice exhibit reduced fasting-induced feeding relative to wild type controls, and in dietary-induced obese rats, a NOP antagonist inhibits feeding and body weight regain induced by 30% caloric restriction and also decreases daily intake of a freely available high-energy diet. Statnick et al., 2016, *J. Pharmacol. Exp. Ther.* 356, 493-502. Moreover, the NOP antagonist SB612111 inhibits fasting-induced feeding, an effect that is absent in mice missing the NOP receptor. Witkin et al., 2014, *Pharmacol. Ther.* 141, 283-299. Similarly, Accordingly, the disclosure includes methods of treating a disorder of appetitive behavior, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof. In some embodiments, the disorder is overeating. In some embodiments, the disorder is obesity. In some embodiments, obesity is associated with binge eating or hyperphagia. In some embodiments, the chemical entities or compositions described herein are useful in methods of maintaining weight (or weight maintenance), including after treatment for obesity.

Movement Disorders:

In certain embodiments, the present disclosure provides methods of treating movement and motor disorders, and more particularly, a movement or motor impairment associated with the pathology of such disorders, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

NOP is widely represented in cortical and subcortical motor areas involved in motor control, and N/OFQ modulates motor behavior and primary motor cortex output through receptors located in substantia nigra reticulata. Marti et al., 2009, *Neuropsychopharm.* 34, 341-355. Injections of the ORL1 antagonist UFP-101 in substantia nigra reticulate enhance locomotor performance on the rotarod test. Marti et al., 2004, *J. Neurosci.* 24, 6659-6666. Similarly, pharmacological blockade (or genetic deletion) of ORL1 does not affect spontaneous locomotion but increases exercise-induced motor activity. ORL1 antagonists have also been shown to reverse motor deficits associated with Parkinson's disease in primate models, showing greatest efficacy against hypokinesia. Viaro et al., 2008, *Neurobio. Dis.* 30, 430-438.

Movement disorders include, but are not limited to, basal ganglia disorders, Parkinson's disease, Post-Encephalitic Parkinsonism, Dopamine-Responsive Dystonia, Hallervorden-Spatz Syndrome (HSS), Restless Leg Syndromes, Wilson's Disease, Shy-Drager Syndrome, Periodic Limb Movement Disorder (PLMD), Periodic Limb Movements in Sleep (PLMS), Tourette's Syndrome, Restless Leg(s) Syndrome (RLS); chorea, such as that in Huntington's disease; myoclonus (including generalized myoclonus and focal myoclonus); tics (including simple tics, complex tics and symptomatic tics); and hyperkinetic, hypokinetic, and dyskinetic disorders; movement disorders induced by drugs, diseases associated with striatal hypofunction; and other movement and motor disorders.

In specific embodiments, the dyskinetic disorder is a drug-induced dyskinesia. More particularly, the dyskinetic disorder is levodopa induced dyskinesia (LID) or tardive dyskinesia (TD), which represent the most common forms of drug-induced dyskinesias. For example, uncontrolled stimulation of supersensitized dopamine D1 receptors in the direct striatonigral pathway are thought to mediate LIDs. In addition, long-term blockade of dopamine D2 receptors in the basal ganglia by dopamine D2 antagonists (e.g., neuroleptics) may produce compensatory supersensitivity of dopamine receptors and TD. Accordingly, in specific embodiments, then present disclosure provides methods of treating LID (or TD), comprising administering to a subject in need therefor an effective amount of a chemical entity of any of the embodiments disclosed herein.

In certain embodiments, the movement disorder is a basal ganglia disorder.

In other embodiments, the movement disorder includes kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor.

In specific embodiments, the movement disorder is Parkinson's disease or Huntington's disease, as discussed further herein.

In some embodiments, the methods are directed to a specific movement abnormality associated with the pathology of a movement or motor disorder. Movement abnormalities include, but are not limited to, tremors, resting tremors, rigidity, bradykinesia, and deficient postural reflexes.

Neurodevelopmental Disorders

In specific embodiments, the disclosure provides methods of treating a neurodevelopmental disorder, comprising administering to a subject in need thereof an effective amount of a chemical entity or composition described herein. More particularly, the learning disorder is a learning disorder or ADHD.

Neurodegenerative Disorders:

In specific embodiments, the disclosure provides methods of treating a neurodegenerative disorder, and more particularly treating a neurological impairment associated with the pathology of a neurodegenerative disorder, comprising administering to a subject in need thereof an effective amount of a chemical entity or composition described herein.

Neurodegenerative disorders can result from a primary nervous system disease or a primary nervous system injury.

Accordingly, in some embodiments, the therapeutic methods are directed to neurodegenerative disorders resulting from a primary nervous system disease. Such diseases include, but are not limited to, Parkinson's disease, Alzheimer's disease, Huntington's disease, Lewy body disease, Pick's disease, a prion disease (e.g., Creutzfeldt-Jakob disease), Amyotrophic lateral sclerosis (ALS), multiple sclerosis (MS), frontotemporal lobar degeneration (FTLD), and corticobasal degeneration.

In other embodiments, the therapeutic methods are directed to a neurodegenerative disorder resulting from a primary nervous system injury. Such primary injuries can include, but are not limited to, stroke, including hemorrhagic stroke and ischemic stroke; a traumatic brain injury (TBI), which can include closed head injuries and blunt trauma, including those caused by participation in sports, and penetrating trauma, such as gunshot wounds; spinal cord injuries; glaucoma, cerebral ischemia, or damages caused by surgery such as tumor excision.

Parkinson's Disease:

In specific embodiments, the present disclosure provides methods of treating Parkinson's disease, comprising administering to a subject in need thereof an effective amount of a chemical entity or composition described herein. Parkinson's disease (PD), also known as Parkinson's, idiopathic Parkinsonism, or primary Parkinsonism, is a degenerative disorder of the CNS estimated to afflict more than 5 million people worldwide. It is a slowly progressive neurological condition, characterized by tremors, stiffness, slowness of movement (bradykinesia) and impaired balance. N/OFQ and NOP are expressed in rodent and human basal ganglia, and brain interstitial levels of N/OFQ are elevated in Parkinson's disease. Marti et al., 2010, *Mov. Disord.* 25, 1723-1732. Moreover, NOP antagonists attenuate dopamine cell loss and motor deficits in rodent and NHP models of PD. See, e.g., Visanji et al., 2008, *Mov. Disord.* 23, 1922-1025; Viaro et al., 2008, *Neurobiol. Dis.* 30, 430-438; Marti et al., 2013, Br. *J. Pharmacol.* 168, 863-879; Arcuri et al., 2016, *Neurobiol. Dis.* 89, 55-64.

While Parkinson's disease has been defined by its motor hallmarks, non-motor features such as cognitive impairment and dementia have been increasingly recognized. For example, MCI is common in a significant fraction (with estimates ranging from 20%-50%) of non-demented PD patients. See, e.g., Broeders et al., 2013, *Neurology* 81, 346-352. While diagnostic criteria are not completely uniform, PD patients with MCI (PD-MCI patients) typically exhibit non-amnestic deficits in cognitive domains such as executive function, attention, and visuospatial function (Litvan et al., 2012, *Mov. Disord.* 27, 349-356). The cognitive phenotype of PD-MCI is heterogeneous, however, with some patients demonstrating amnestic deficits. Certain PD-MCI patients may be at high risk for developing dementia. (e.g., Goldman and Litvan, 2011, *Minerva Med.* 102, 441-459).

Thus, in specific embodiments, chemical entities and compositions herein can be used to treat motor deficits associated with PD, and in other embodiments to treat cognitive impairments associated with PD, including in PD-MCI subjects. In other embodiments, chemical entities and compositions are used as an adjunctive treatment to L-DOPA in the management of motor dysfunction in Parkinson's disease. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

Pain:

In certain embodiments, the present disclosure provides methods of treating pain, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

NOP and the N/OFQ peptide show intense expression in several areas involved in pain processing, including the dorsal horn of the spinal cord, the nucleus raphe magnus, and the periaqueductal gray area. Neal et al., 1999, *J. Comp. Neurol.* 406, 503-547; Neal et al., 1999, *J. Comp. Neurol.* 412, 563-605. In addition, NOP antagonists have been implicated in pain modulation. Zaratin et al., 2004, *J. Pharmacol. Exp. Ther.* 308, 454-461; Shinkai et al., 2000, *J. Med. Chem.* 43, 4667-04677; Zhang et al., 2015, *Br. J. Pharmacol.* 172, 571-582. When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain these mechanisms can be useful, in promoting protective behaviors which may better enable repair processes to take place. In many chronic pain states, the hypersensitivity far outlasts the healing process and is often due to nervous system injury. This injury often leads to abnormalities in sensory nerve fibers associated with maladaptation and aberrant activity (Woolf & Salter, 2000, *Science*, 288, 1765-1768).

In some embodiments, the pain is acute pain. Acute pain begins suddenly and is short-lived (usually in twelve weeks or less). It is usually associated with a specific cause, such as a specific injury resulting from surgery, dental work, a strain or a sprain, and is often sharp and severe. Acute pain does not generally result in any persistent psychological response.

In some embodiments, the pain is chronic pain. In contrast to acute pain, chronic pain is long-term pain, typically persisting for more than three months and leading to significant psychological and emotional problems. Common examples of chronic pain are neuropathic pain (e.g., painful diabetic neuropathy, postherpetic neuralgia), carpal tunnel syndrome, back pain, headache, cancer pain, arthritic pain and chronic post-surgical pain.

In some embodiments, the pain is clinical pain. Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia; see Meyer et al., 1994, *Textbook of Pain*, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

In some embodiments, the pain is neuropathic pain, which is currently defined as pain initiated or caused by a primary lesion or dysfunction in the nervous system. Nerve damage can be caused by trauma and disease and thus the term 'neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency.

In some embodiments, the pain is inflammatory pain. The inflammatory process is a complex series of biochemical and cellular events, activated in response to tissue injury or the presence of foreign substances, which results in swelling and pain (Levine and Taiwo, 1994, *Textbook of Pain*, 45-56). Arthritic pain is the most common inflammatory pain. Rheumatoid disease is one of the commonest chronic inflammatory conditions in developed countries and rheumatoid arthritis is a common cause of disability. Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

In some embodiments, the pain is headache pain, and more particularly, is migraine headache pain or a migraine.

Augmented Training

In some embodiments, chemical entities, and compositions thereof, of the present disclosure are used as augmenting agents in methods to increase the efficiency of training protocols for enhancing a neurological function or treating a neurological impairment associated with a neurological disorder. Such methods are known as "augmented training," and more particularly, in the case of cognitive impairments, "augmented cognitive training," and in the case of motor impairments, "augmented motor training." Augmenting agents can act by shortening the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc.; and a general administration of an augmenting agent of the present disclosure.

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (See, e.g., U.S. Pat. Nos. 7,868,015; 7,947, 731; U.S. 2008-0188525). When administered in combination with training protocols (or "training"), augmenting agents enhance functional reorganization in targeted domains (or "functions") in the brain.

Cognitive domains (or "functions") that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (e.g., declarative memory) memory, such as episodic, semantic, and autobiographical memory, and into implicit memory (e.g., procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols:

Training protocols (or "modules") include cognitive training and motor training protocols. Training protocols are well-known in the art and typically comprise a set of distinct exercises that can be process-specific or skill-based. See, e.g., Kim et al., 2014, *J. Phys. Ther. Sci.* 26, 1-6; Allen et al., 2012, *Parkinson's Dis.* 1-15; Jaeggi et al., 2011, *Proc. Natl. Acad. Sci. USA* 108, 10081-10086; Chein et al., 2010, *Psychon. Bull. Rev.* 17, 193-199; Klingberg, 2010, *Trends Cogn. Sci.* 14, 317-324; Owen et al., 2010, *Nature* 465, 775-778; Tsao et al., 2010, *J. Pain* 11, 1120-1128; Lustig et al., 2009, *Neuropsychol. Rev.* 19, 504-522; Park and Reuter-Lorenz, 2009, *Ann. Rev. Psych.* 60, 173-196; Oujamaa et al., 2009, *Ann. Phys. Rehabil. Med.* 52, 269-293; Frazzitta et al., 2009, *Mov. Disord.* 8, 1139-1143; Jaeggi et al., 2008, *Proc. Natl. Acad. Sci. USA* 105, 6829-6833; Volpe et al., 2008, *Neurorehabil. Neural Repair* 22, 305-310; Fischer et al., 2007, *Top. Stroke Rehab.* 14, 1-12; Jonsdottir et al., 2007, *Neurorehabil. Neural Repair* 21, 191-194; Stewart et al., 2006, *J. Neurol. Sci.* 244, 89-95; Krakauer, 2006, *Curr. Opin. Neurol.* 19, 84-90; Belleville et al., 2006, *Dement. Geriatr. Cogn. Disord.* 22, 486-499; Klingberg et al., 2005, *J. Am. Acad. Child. Adolesc. Psychiatry* 44, 177-186; Dean et al., 2000, *Arch. Phys. Med. Rehabil.* 81, 409-417; Whitall et al., 2000, *Stroke* 31, 2390-2395; Hummelsheim and Eickhof, 1999, *Scand. J. Rehabil. Med.* 31, 250-256; Merzenich et al., 1996, *Science* 271, 77-81; Merzenich et al., 1996, *Cold Spring Harb. Symp. Quant. Biol.* 61, 1-8; Rider and Abdulahad, 1991, *Percept. Mot. Skills* 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of facts, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a NOP inhibitor, and more particularly, is a chemical entity of the present disclosure, and is administered in conjunction with training. The phrase "in conjunction with" means that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a chemical entity or composition of the present disclosure can be used as an augmenting agent in conjunction with any psychotherapeutic approach intended to modulate cognitive function in the brain, thereby enhancing the efficacy of such therapy by reducing the amount of training, e.g., the number of sessions, necessary to attain benefits. In a specific aspect, the chemical entity is a compound of Formula (I), or pharmaceutically acceptable salt thereof. More particularly, the chemical entity is a compound of Formula (Ia), (Ib), (Ic), (Id), (Ie), or (If), or a pharmaceutically acceptable salt thereof.

Accordingly, in some embodiments, the disclosure provides the use of a chemical entity or composition herein in a method of augmented training to treat a neurological disorder, the method comprising: (a) providing training to an animal in need of treatment of a neurological impairment associated with the neurological disorder under conditions sufficient to produce an improvement in performance by said animal of a neurological function whose deficit is associated with said neurological impairment; (b) administering the chemical entity or composition to the animal in conjunction with said training; (c) repeating said providing and administering steps one or more times; and (d) reducing the amount of training sufficient to produce the improvement in performance, relative to the improvement in performance produced by training alone. In specific embodiments, the animal is a human subject. In some aspects, the augmented training is augmented cognitive training. In some aspects, the neurological impairment is a cognitive impairment. In some aspects, the neurological impairment is a motor impairment. In a specific aspect, the neurological disorder is stroke or traumatic brain injury. In some aspects, the augmented training is provided to a stroke patient during post-stroke rehabilitation, as described further herein. In a specific aspect, the chemical entity is a compound of Formula (I), or pharmaceutically acceptable salt thereof. In some embodiments, training comprises spaced training sessions. In other embodiments, training comprises massed training sessions.

Animal Skill Protocols:

In some embodiments, chemical entities of the present disclosure are used to enhance the efficiency of training protocols directed to cognitive and motor skills in an animal. Such augmented training (augmenting agent and training) reduces the time necessary to acquire a cognitive or motor skill, and/or enhance function or cognitive ability beyond what would be possible by training alone in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a specific contraband category by a service animal. In other embodiments, the training protocol may be directed to a complex set of skills, such as those underlying search and rescue training of a service animal; for a complex set of skills, training will therefore comprise more than one tasks.

Accordingly, in some embodiments, the present disclosure provides a method of teaching a non-human animal one or more skills, comprising (a) administering to a non-human animal in need thereof a NOP inhibitor; (b) providing training to the animal under conditions sufficient to improve performance of the one or more skills; and (c) repeating steps (a) and (b) one or more times, whereby the amount of training sufficient to improve the performance is reduced compared to that produced by training alone.

Stroke:

In certain embodiments, chemical entities and compositions of the present disclosure are useful in methods of treating a trauma-dependent loss of function, and more particularly, stroke. Stroke is a leading cause of serious long-term disability in adults and is the second leading cause of death worldwide (e.g., Go et al., 2014, *Circulation* 129, e28-e92). Stroke is comprises two main types: 1) ischemic stroke which occurs when blood vessels supplying the brain are blocked by clot formation (85% of all strokes) and 2) hemorrhagic stroke which occurs when blood vessels rupture within the brain (13-15% of all strokes). Stroke care is a temporal continuum that includes medical intervention during the acute phase of stroke and subsequent rehabilitative therapy directed to restoring function during the post-stroke phase of stroke.

Acute Treatments:

Treatments following the onset of stroke directly target the initial damage triggered by ischemic or hemorrhagic stroke. Acute treatment options for ischemic stroke include pharmacotherapy with intravenous recombinant tissue plasminogen activator (r-tPA) to thrombolyze the clot, or the use of endovascular procedures or mechanical thrombectomy to physically remove the clot. Acute treatment options for hemorrhagic stroke typically involve endovascular or surgical procedures to physically repair the rupture.

Post-Stroke Rehabilitation:

Following the acute phase of stroke—and typically after the patient has been medically stabilized—the focus of stroke treatment shifts to restoring function by rehabilitation. Depending on the severity and location of the stroke as well as the timing and effectiveness of acute interventions, post-stroke symptoms may persist and can include motor deficits (e.g., hemiparesis, apraxia), speech impairment (e.g., aphasia), visual impairments (e.g., visual field loss), emotional and behavioral changes (e.g., depression, anxiety), and mental and cognitive changes (e.g., confusion, apathy, cognitive impairment) (Winstein et al., 2016, Stroke 47, e98-e169). Rehabilitation (also referred to as "stroke rehabilitation" or "post-stroke rehabilitation") is directed to post-stroke deficits, such as cognitive and motor deficits that persist after the initial stroke injury. The goal is to restore and recover neurological functions, e.g., physical, intellectual, psychological, and social functions, as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals, which may include occupational, speech, and physical therapists. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; as problems with balance or coordination; as deficits in gross motor skills such as gait and walking speed; as deficits in fine motor skills or manual dexterity; and as deficits in upper and lower extremity function.

In the United States, more than 700,000 people suffer a stroke each year, two-thirds of these survive and require rehabilitation. Unfortunately, recovery is generally only partial and considerable deficits persist in many patients (e.g., Gordon et al., 2004, Stroke 35, 1230-1240). For example, after standard rehabilitation, approximately 30% to 60% of patients are left without functional use of their paretic/plegic arm (Gowland, 1982, Physiother. Can. 34, 77-84; Kwakkel et al., 1996, Age Ageing 25, 479-489), and despite intensive rehabilitation efforts, only approximately 5% to 20% reach complete functional recovery of their arm (Nakayama et al., 1994, Arch. Phys. Med. Rehabil. 75, 394-398).

As discussed herein, chemical entities, and compositions thereof, of the present disclosure are used as augmenting agents to increase the efficiency of training protocols for treating a neurological impairment, which encompasses impairments due to traumatic events such as stroke. Accordingly, in some embodiments, the present disclosure provides methods of treating a neurological deficit during post-stroke rehabilitation comprising: (a) administering to a subject in need thereof a NOP inhibitor disclosed herein during recovery of the subject from stroke; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In some embodiments, administration can begin during the acute stage. In other embodiments, the NOP inhibitor is administered only after the acute stage, i.e., during post-stroke rehabilitation, which may include sub-acute and chronic stages. In some embodiments, administration occurs during the acute stage and post-stroke stage. In some embodiments, the NOP inhibitor is administered chronically, meaning that it is indicated for long-term use after the acute stage of the stroke has ended and the patient has been medically stabilized.

In other embodiments, the subject is a post-stroke patient, and NOP inhibitors are administered during stroke rehabilitation to treat stroke deficits (or "post-stroke deficits") resulting from impaired neurological functions. In some embodiments, the deficit is a motor deficit, including upper or lower extremity motor deficit. In other embodiments, the deficit is a cognitive deficit, such as such as aphasia, apraxia, and mental and cognitive changes, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Traumatic Brain Injury:

In some embodiments, chemical entities and compositions are useful in methods of treating traumatic brain injury (TBI), and in more specific embodiments, treating motor or cognitive impairments during rehabilitation of TBI after the initial trauma.

TBI, also known as intracranial injury, occurs when an external force injures the brain. TBI can be classified based on severity, mechanism (closed or penetrating head injury), or other features (e.g., occurring in a specific location or over a widespread area). TBI can result in physical, cognitive, social, emotional, and behavioral symptoms. Causes include falls, vehicle collisions, gunshot injuries, and explosives. Outcomes can range from complete recovery to permanent disability or death.

Like stroke care, TBI case is a temporal continuum that includes acute (or sub-acute) treatments directed to the injury itself and subsequent rehabilitative therapy directed to restoring function.

Accordingly, in some embodiments, the chemical entities and compositions of the present disclosure are useful during the acute (or sub-acute) stage of TBI, during which their administration can treat neuroinflammatory and neurodegenerative events following the primary injury.

Some embodiments provide the use of a NOP inhibitor disclosed during TBI rehabilitation to treat TBI deficits (or "post-TBI deficits") resulting from impaired neurological functions. Some embodiments provide methods of treating a neurological deficit during post-TBI rehabilitation comprising: (a) administering to a subject in need thereof a NOP inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the NOP inhibitor is a chemical entity of the present disclosure, and more specifically, is a compound, or pharmaceutically acceptable salt thereof, of Formula (I). More particularly, the chemical entity is a compound of Formula (Ia), (Ib), (Ic), (Id), (Ie), or (If), or a pharmaceutically acceptable salt thereof. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Peripheral Disorders

In some embodiments, the present disclosure provides methods of treating a peripheral disorder (i.e., a disorder other than a primary neurological disorder), comprising administering to a subject in need thereof an effective amount of a chemical entity or composition disclosed herein. In one embodiment of these methods, the chemical entity is a compound, or pharmaceutically acceptable salt thereof, of Formula (I). More particularly, the chemical entity is a compound of Formula (Ia), (Ib), (Ic), (Id), (Ie), or (If), or a pharmaceutically acceptable salt thereof.

Peripheral disorders that can be treated by compounds and compositions of the present disclosure include, but are not limited to, cardiovascular, renal, pulmonary (respiratory), gastrointestinal, liver, genitourinary, metabolic, and inflammatory disorders. Peripheral disorders also include diseases and conditions (other than primary neurological disorders) characterized by altered nociceptin or NOP signaling or by reduced dopaminergic signaling activity.

In specific embodiments, the peripheral disorder is a cardiovascular disorder, including arterial blood pressure disorder, angina pectoris, coronary artery disease, hypertension, congestive heart failure, myocardial infarction, ischemic diseases of the heart, atrial and ventricular arrhythmias, hypertensive vascular diseases, peripheral vascular diseases, pulmonary arterial hypertension, and atherosclerosis. For example, NOP receptors are found on sympathetic and parasympathetic nerve fibers innervating blood vessels and the heart. Notably, these receptors do not seem to be tonically activated but instead appear to play a role in the pathophysiology of inflammation, arterial hypertension, and cardiac or brain circulatory ischemia. Malinowska et al., 2002, *J. Physiol. Pharmacol.* 53, 301-324.

In specific embodiments, the peripheral disorder is a renal disorder, including water excretion, sodium ion excretion, syndrome of inappropriate secretion of antidiuretic hormone (SIADH), renal artery stenosis, pyelonephritis, glomerulonephritis, kidney tumors, polycystic kidney disease, injury to the kidney, damage resulting from radiation of the kidney, and autosomal dominant polycystic kidney disease (ADPKD).

In specific embodiments, the peripheral disorder is a respiratory disorder, including adult respiratory distress syndrome (ARDS), obstructive pulmonary disease, and altered pulmonary function.

In some embodiments, the peripheral disorder is a gastrointestinal disorder, including ulcers, Inflammatory Bowel Disorder (IBD), Irritable Bowel Syndrome (IBS), diarrhea, constipation.

In some embodiments, the peripheral disorder is a liver disorder, including chronic liver disease and cirrhosis with ascites.

In some embodiments, the peripheral disorder is a genitourinary disorder, including overactive bladder, polyuria, urgency, urinary incontinence (UI), urge incontinence, frequency, nocturia, stress incontinence, and mixed urinary incontinence. When given intravenously or intracerebroventricularly in rats, for example, N/OFQ inhibits the micturition reflex. Giuliani et al., 1998, *Br. J. Pharmacol.* 124, 1566-1572; Lecci et al., 2000, *J. Urol.* 163, 638-45; Lecci et al., 2000, *Peptides* 21, 1007-1021. These and other studies suggest that NOP antagonists may increase micturition reflex responses and reduce bladder capacity or reverse conditions of retention due to dysfunction of the micturition reflex.

In some embodiments, the peripheral disorder is a metabolic disorder, such as diabetes, including diabetes mellitus and diabetes insipidus. For example, nociceptin-reactive cells are found in the central and peripheral regions of the islets of both normal and diabetic rat pancreas, and are significantly lower in diabetic rats compared with controls. Tariq et al. 2015, *Pancreas* 44, 602-607.

In some embodiments, the peripheral disorder is an inflammatory or immune-mediated disorder, including sepsis, colitis, Parkinson's disease, or arthritis. Cells from the immune system express NOP, as well as secrete N/OFQ. Within smaller blood vessels (15 to 40 µm) N/OFQ also induces dilation, along with inflammatory responses, such as increased permeability and leukocyte-endothelial interactions within post-capillary venules. Brookes et al., 2007, *Am. J. Physiol. Heart Circ. Physiol.* 293, H2977-H2985. NOP activation can influence leukocyte migration, cytokine and chemokine production, and lymphocyte proliferation. Gavioli et al., 2015, *Vitam. Horm.* 97, 241-266.

Treatment Combinations

Chemical entities and compositions of the present disclosure can be administered as a monotherapy or as part of a combination therapy. "Monotherapy" refers to a treatment regimen based on the delivery of one (e.g., one and only one) therapeutically effective chemical entity or composition thereof.

In a combination therapy, one or more chemical entities or compositions of the present disclosure can be co-administered or used in combination with one or more additional agents (or therapies), such as additional agents (or therapies) known in the art. Such administration may be simultaneous, sequential, or staggered. In certain embodiments, the additional agent (or therapies) is based on a different target or modality (e.g., is not a NOP inhibitor).

In some embodiments, the combination is administered as part of an adjunct (or adjunctive) therapy, in which one agent is given in addition to a primary agent to assist or maximize the effectiveness of the primary agent.

In specific embodiments, the combination is administered to treat schizophrenia, Parkinson's disease, Alzheimer's disease, Huntington's disease, anxiety and depressive disorders, or stroke. In some embodiments, a chemical entity or composition disclosed herein is administered as an adjunct therapy in conjunction with a dopamine precursor, such as levodopa, to treat Parkinson's disease or a related disorder.

Exemplary agents for treating schizophrenia include, but are not limited to, clozapine, aripiprazole, brexpiprazole, cariprazine, lurasidone, paliperidone, quetiapine, risperidone, olanzapine, ziprasidone, and iloperidone.

Exemplary agents for treating Parkinson's disease include, but are not limited to, dopamine preparations (including dopamine precursors such as levodopa), dopamine agonists, or COMT agents (drugs that inhibit the action of catechol-methyl transferase).

Exemplary agents for treating Alzheimer's disease include, but are not limited to, donepezil, rivastigmine, galantamine, marijuana-like cannabinoids, and memantine.

Exemplary agents for treating Huntington's disease (or other motor disorders) may include, but are not limited to, tetrabenazine, as well as antipsychotic drugs such as haloperidol, chlorpromazine, risperidone, and quetiapine, and anti-epileptic drugs such as levetiracetam and clonazepam, which may be beneficial in treating chorea or related motor disorders.

Exemplary agents for treating anxiety or depression include, but are not limited to, benzodiazepines and other anxiolytics; serotonin reuptake inhibitors (SSRIs), such as sertraline, fluoxetine, citalopram, escitalopram, paroxetine, fluvoxamine, and trazodone; serotonin and norepinephrine reuptake inhibitors (SNRIs), such as desvenlafaxine, duloxetine, levomilnacipran, and venlafaxine; tricyclic antidepressants (TCAs), such as amitriptyline, amoxapine, clomipramine, desipramine, doxepin, imipramine, nortriptyline, protriptyline, and trimipramine; monoamine oxidase inhibitors (MAOIs), such as isocarboxazid, phenelzine, selegiline, and tranylcypromine; and other classes of drugs, such as maprotiline, bupropion, vilazodone, nefazodone, trazodone, vortioxetine, and mirtazapine Exemplary agents for treating stroke include, but are not limited to, a thrombolytic agent (e.g., streptokinase, acylated plasminogen-streptokinase activator complex (APSAC), urokinase, single-chain urokinase-plasminogen activator (scu-PA), anti-inflammatory agents, thrombin-like enzymes, tissue plasminogen activator (t-PA); an anticoagulant (e.g., warfarin or heparin); an antiplatelet drug (e.g., aspirin); a glycoprotein IIb/IIIa inhibitor; a glycosaminoglycan; coumarin; GCSF; melatonin; an apoptosis inhibitor (e.g., caspase inhibitor), an anti-oxidant (e.g., NXY-059); and a neuroprotectant (e.g., an NMDA receptor antagonists or a cannabinoid antagonist).

Exemplary agents for treating a migraine headache include alpiropride, dihydroergotamine, dolasetron, ergocomine, ergocominine, ergocryptine, ergot, ergotamine, flumedroxone acetate, fonazine, lisuride, lomerizine, methysergide oxetorone, and pizotyline.

The preceding list of additional active agents is meant to be exemplary rather than fully inclusive. Additional active agents not included in the above list may be administered in combination with a compound of Formula (I) such as those know for treating peripheral disorders described herein. The additional active agent will be dosed according to its approved prescribing information, though in some embodiments the additional active agent may be dosed at less the typically prescribed dose.

EXAMPLES

The present disclosure will be further illustrated by the following non-limiting Examples. These Examples are understood to be exemplary only, and they are not to be construed as limiting the scope of the one or more embodiments, and as defined by the appended claims.

Preparative Examples

Exemplary compounds will now be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −100° C. and the reflux temperature of the solvent. Reactions may be heated employing conventional heating or microwave heating. Reactions may also be conducted in sealed pressure vessels above the normal reflux temperature of the solvent.

Abbreviations

The specification includes numerous abbreviations, whose meanings are listed in the following Table:

TABLE 1

| Abbreviation | Definition |
| --- | --- |
| ACN, MeCN | Acetonitrile |
| AcOH | Acetic acid |
| BCl$_3$ | Boron trichloride |

TABLE 1-continued

| Abbreviation | Definition |
|---|---|
| Boc | tert-Butyloxycarbonyl |
| Boc$_2$O | Di-tert-butyl dicarbonate |
| n-BuLi | n-Butyl Lithium |
| Burgess Reagent | (Methoxycarbonylsulfamoyl)triethylammonium hydroxide, methyl N-(triethylammoniumsulfonyl)carbamate |
| CAS | Chemical abstracts service |
| CDCl$_3$ | Deuterated chloroform |
| Celite ® | Diatomaceous earth |
| CHCl$_3$ | Chloroform |
| Cs$_2$CO$_3$ | Cesium carbonate |
| DCM, CH$_2$Cl$_2$ | Dichloromethane |
| DCE | Dichloroethane |
| DIBAL, DIBAL-H | Diisobutyl aluminum hydride |
| Diglyme | Diethylene glycol dimethyl ether |
| DIPEA, DIEA | N,N-ethyldiisopropylamine or N,N-Diisopropylethyl amine |
| DMA | N,N-Dimethylacetamide |
| DMAP, 4-DMAP | 4-(Dimethylamino)pyridine |
| DME | Dimethyoxyethane |
| DMF | N,N-Dimethylformamide |
| DMP | Dess-Martin Periodinane, 1,1,1-Tris(acetyloxy)-1,1-dihydro-1,2-benziodoxol-3-(1H)-one |
| DMSO | Dimethylsulfoxide |
| dppf | 1,1'-Bis(diphenylphosphino)ferrocene |
| EtOAc, or EA | Ethyl acetate |
| EtOH | Ethanol |
| FCC | Flash column chromatography |
| H$_2$ | Hydrogen |
| HATU | 1-[Bis(dimethylamino)methylene]-1H-1,2,3-triazolo[4,5-b]pyridinium 3-oxid hexafluorophosphate |
| HCl | Hydrochloric acid |
| Hep | Heptanes |
| H$_2$O | Water |
| H$_2$O$_2$ | Hydrogen peroxide |
| HPLC | High-performance liquid chromatography |
| I$_2$ | Iodine |
| IPA | Isopropyl alcohol, 2-propanol |
| K$_2$CO$_3$ | Potassium carbonate |
| KOAc | Potassium acetate |
| LAH, LiAlH$_4$ | Lithium Aluminum Hydride |
| LCMS | Liquid chromatography-mass spectrometry |
| LiHMDS, LHMDS | Lithium hexamethyldisilazane, lithium bis(trimethylsilyl)amide |
| LiOH | Lithium hydroxide |
| MeNH$_2$ | Methyl amine, methanamine |
| MeOH | Methanol |
| 2-MeTHF | 2-Methyltetrahydrofuran |
| MgSO$_4$ | Magnesium sulfate |
| MHz | Megahertz |
| [Mn(dpm)$_3$], | Tris(2,2,6,6-tetramethyl-3,5-heptanedionato)manganese(III), |
| Mn(TMHD)$_3$ | 2,4,8,10-tetra-tert-butyl-1$\lambda^3$,5,7$\lambda^3$,11-tetraoxa-6-manganaspiro[5.5]undeca-1,3,7,9-tetraene, Shenvi hydrogenation catalyst |
| MsCl | Methanesulfonyl chloride, mesyl chloride |
| MTBE | Methyl tert-butyl ether |
| N$_2$ | Nitrogen |
| NaBH$_4$ | Sodium borohydride |
| NaCl | Sodium chloride, brine |
| NaBH$_3$CN | Sodium cyanoborohydride |
| Na$_2$CO$_3$ | Sodium carbonate |
| NaH | Sodium hydride |
| NaHCO$_3$ | Sodium bicarbonate |
| NaI | Sodium iodide |
| NMR | Nuclear magnetic resonance |
| NaOt-Bu | Sodium tert-butoxide |
| NaOH | Sodium hydroxide |
| Na(OAc)$_3$BH, STAB | Sodium triacetoxyborohydride |
| Na$_2$SO$_4$ | Sodium sulfate |
| NH$_4$Cl | Ammonium chloride |
| Pd | Palladium |
| Pd/C | Palladium on carbon, 10% |
| Pd(dppf)Cl$_2$ | [1,1'-Bis(diphenylphosphino)ferrocene]dichloropalladium(II) |
| Pd(dppf)Cl$_2$•CH$_2$Cl$_2$ | [1,1'-Bis(diphenylphosphino)ferrocene]dichloropalladium(II), complex with dichloromethane |
| Pd(OH)$_2$ | Palladium(II) hydroxide |
| Pd(PPh$_3$)$_4$ | Tetrakis(triphenylphosphine)palladium(0), palladium-tetrakis(triphenylphosphine) |
| PE | Petroleum ether |
| PhCH$_2$Br | Benzyl bromide |
| Pin$_2$B$_2$ | Bis(pinacolato)diboron, 4,4,4',4',5,5,5',5'-octamethyl-2,2'-bi-1,3,2-dioxaborolane |

TABLE 1-continued

| Abbreviation | Definition |
|---|---|
| i-PrMgCl | iso-Propyl magnesium chloride |
| psi | Pounds per square inch |
| $PtO_2$ | Platinum(IV) oxide |
| $Pt(OH)_2$ | Platinum(II) hydroxide |
| $R_f$ | Retention factor |
| Rochelle's salt | Potassium sodium tartrate tetrahydrate |
| RT, rt | Room temperature |
| $Rh(PPh_3)_3Cl$ | Tris(triphenylphosphine)ruthenium(II) dichloride |
| L-Selectride | Lithium tri-sec-butylborohydride |
| SFC | Supercritical fluid chromatography |
| $SiO_2$ | Silica |
| TEA, $Et_3N$ | Triethylamine |
| TFA | Trifluoroacetic acid |
| THF | Tetrahydrofuran |
| TLC | Thin layer chromatography |
| TosCl | p-Toluenesulfonyl chloride, tosyl chloride |
| p-TsOH, PTSA | p-Toluenesulfonic acid monohydrate, toluene sulfonic acid |
| UPLC-MS | Ultra performance liquid chromatography - mass spectrometry |

Synthetic Schemes

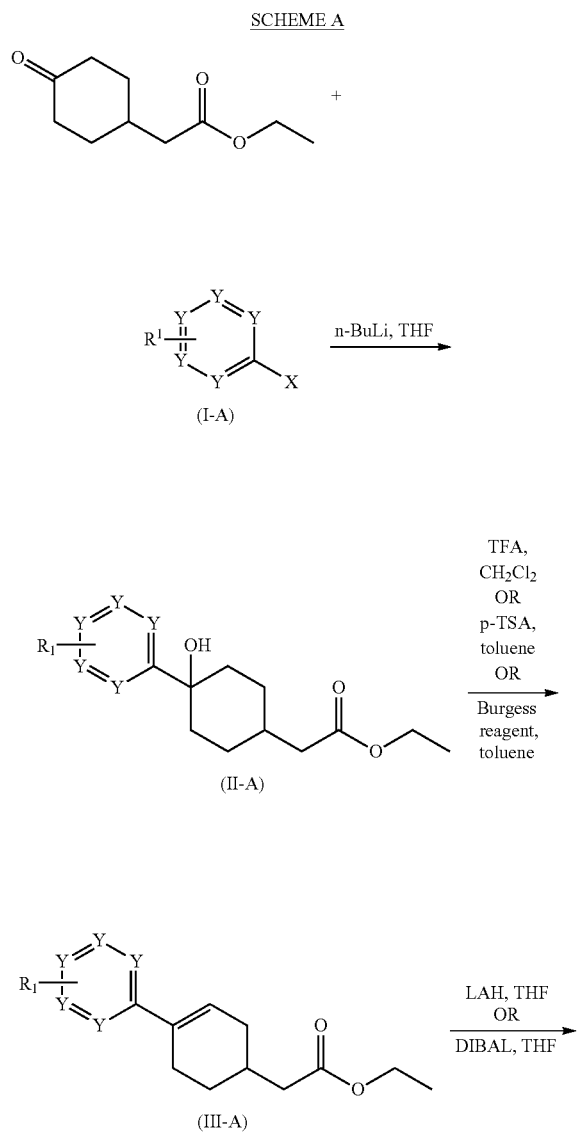

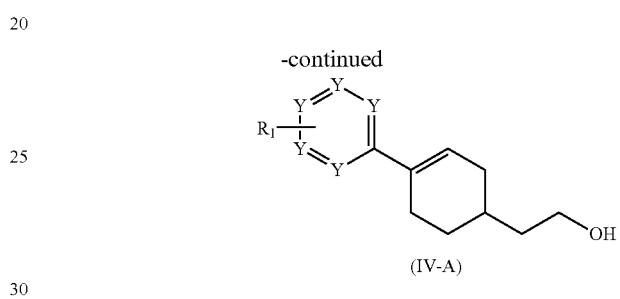

According to Scheme A, optionally substituted 2-(2,3,4,5-tetrahydro-[1,1'-biphenyl]-4-yl)ethan-1-ol (IV-A) can be synthesized in 3 steps from commercially available starting materials. Treatment of ethyl 2-(4-oxocyclohexyl)acetate with a substituted aryl halide of formula (I-A), where X is I, Cl or Br, using a base such as n-butyllithium, in a solvent, such as THF or the like, at a temperature ranging from −78° C. to rt, provides a hydroxy-substituted compound of formula (II-A), where each Y is independently C or N and $R^1$ is independently one or more halo, —OH, —$NH_2$, —$NHC_{1-4}$ alkyl, —$N(C_{1-4}alkyl)_2$, —CN, —$C_{1-4}$alkyl, —$C_{1-4}$haloalkyl, —$C_{1-6}$alkoxy, or —$C_{1-6}$haloalkoxy. Next, treatment with trifluoroacetic acid, in a solvent such as dichloromethane or the like, or treatment with p-toluenesulfonic acid in a solvent such as toluene or the like, provides a cyclohexene compound of formula (III-A). Alternatively, treatment of a compound of formula (II-A) with (methoxycarbonylsulfamoyl)triethylammonium hydroxide (Burgess reagent), in a solvent such as toluene or the like, at a temperature ranging from rt to 100° C., sometimes 80° C., also provides a cyclohexene compound of formula (III-A).

Finally, reduction of the ethyl ester can be achieved by addition of a reducing agent, under standard conditions known to one of skill in the art. For instance, treatment of (III-A) with lithium aluminum hydride, in a solvent such as THF or the like, at a temperature ranging from −78° C. to rt, sometimes ranging from 0° C. to rt provides an alcohol of formula (IV-A), where each Y is independently C or N and $R^1$ is independently one or more halo, —OH, —$NH_2$, —$NHC_{1-4}$alkyl, —$N(C_{1-4}alkyl)_2$, —CN, —$C_{1-4}$alkyl, —$C_{1-4}$ haloalkyl, —$C_{1-6}$alkoxy, or —$C_{1-6}$haloalkoxy. Alternatively, treatment with DIBAL in a solvent such as THF or the like, a temperature of −78° C., provides the primary alcohol product.

SCHEME B

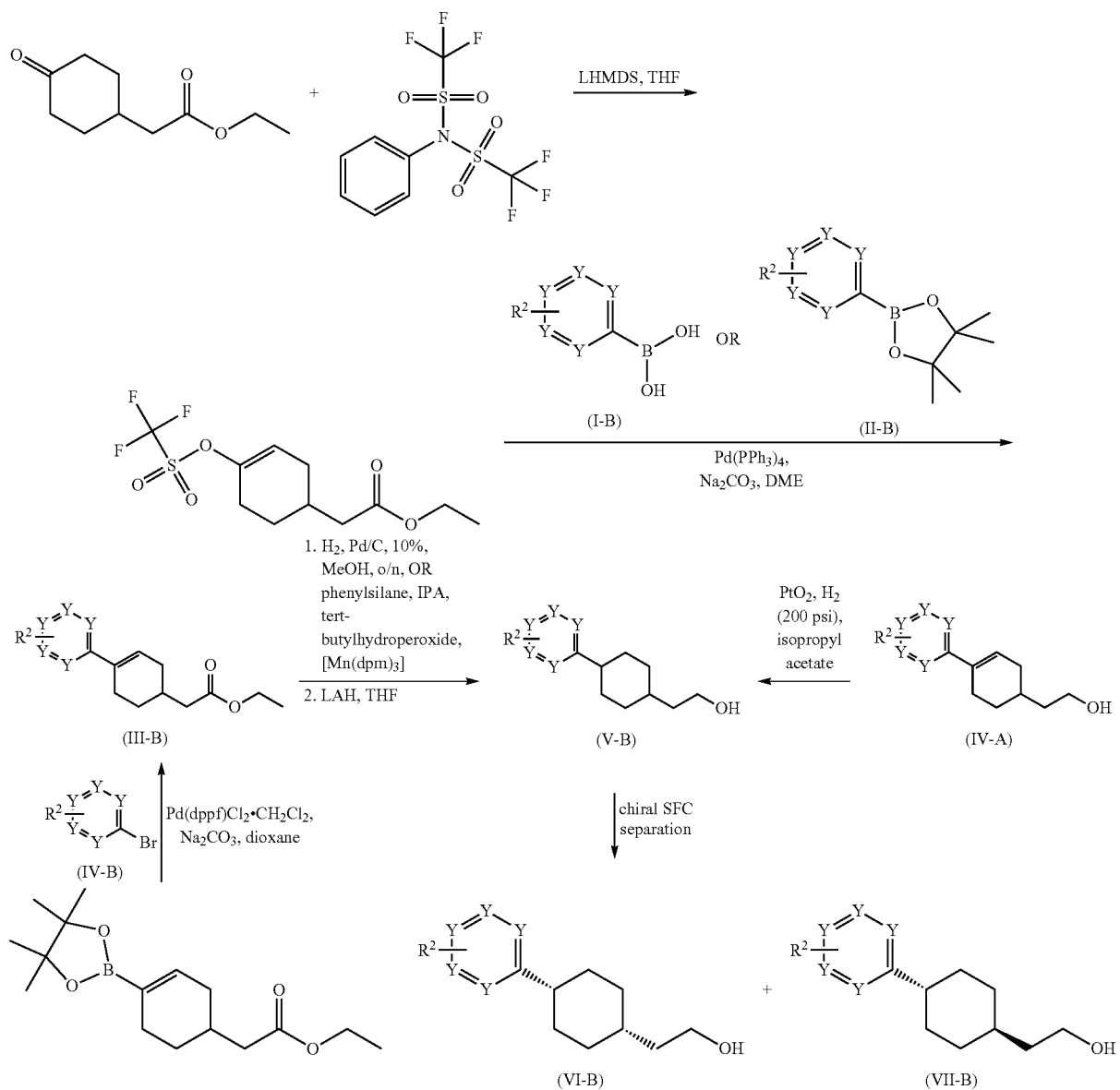

A substituted cyclohexyl compound of formula (V-B) can be synthesized in several ways, as shown above in Scheme B.

In one instance, treatment of ethyl 2-(4-oxocyclohexyl) acetate with 1,1,1-trifluoro-N-phenyl-N-((trifluoromethyl) sulfonyl)methanesulfonamide and a base, such as lithium bis(trimethylsilyl)amide, in a solvent such as THF, at a temperature ranging from −78° C. to 0° C., sometimes a temperature of −40° C., provides ethyl 2-(4-(((trifluoromethyl)sulfonyl)oxy)cyclohex-3-en-1-yl)acetate. A Suzuki coupling of the triflate product and a substituted boronic acid or boronate ester, of formula (I-B) or (II-B), respectively, where each Y is independently C or N and $R^2$ is independently one or more halo, —OH, —$NH_2$, —$NHC_{1-4}$alkyl, —$N(C_{1-4}alkyl)_2$, —CN, —$C_{1-4}$alkyl, —$C_{1-4}$haloalkyl, —$C_{1-6}$alkoxy, or —$C_{1-6}$haloalkoxy, under conditions known to one of skill in the art, such as in the presence of a base, like sodium carbonate, and a catalyst, such a tetrakis(triphenylphosphine)palladium(0), in a solvent such as dimethoxyethane or the like, at a temperature ranging from rt to 100° C., sometimes 70° C., provides a compound of formula (III-B). Alternatively, a Suzuki coupling of ethyl 2-(4-(4,4,5,5-tetramethyl-1,3,2-dioxaborolan-2-yl)cyclohex-3-en-1-yl)acetate and an aryl bromide of formula (IV-B), under conditions similar to those described above, in the presence of a catalyst such as [1,1′-bis(diphenylphosphino)ferrocene] dichloropalladium(II), complex with dichloromethane in the presence of a base such as sodium carbonate or the like, in a solvent such as dioxane or the like, at a temperature ranging from rt to 100° C., sometimes 70° C., provides a compound of formula (III-B).

Subsequent reduction of the double bond of (III-B) under various hydrogenation conditions, known to one of skill in the art, followed by reduction of the ethyl ester to a primary alcohol, provides a compound of formula (V-B), where each Y is independently C or N and $R^2$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy. For example, treatment of a compound of formula (III-B) with a catalyst such as activated palladium on carbon, under an atmosphere of hydrogen gas, in a solvent such as methanol or ethyl acetate or the like, at a temperature ranging from rt to 80° C., sometimes 50° C. provides the substituted cyclohexyl analog. Alternatively, a HAT (hydrogen atom transfer) reduction of the double bond is achieved by treatment of a compound of formula (III-B) with tris(2,2,6,6-tetramethyl-3,5-heptanedionato)manganese(III) (Shenvi hydrogenation catalyst) in the presence of phenylsilane and tert-butylhydroperoxide, in a solvent such as isopropanol, or the like, at a temperature ranging from rt to 80° C., sometimes 50° C. Subsequent reduction of the ethyl ester is achieved using conditions known to one of skill in the art, such as treatment with lithium aluminum hydride or DIBAL, as described in Scheme A, to provide a compound of formula (V-B), as a mixture of cis and trans isomers. In a similar fashion, a compound of formula (V-B) can be synthesized by double bond reduction of a compound of formula (IV-A). For instance, treatment with a catalyst such as platinum(IV) oxide, under an atmosphere of hydrogen, sometimes 200 psi of hydrogen, in a solvent such as isopropyl acetate or the like, at a temperature ranging from rt to 50° C., sometimes rt, provides a compound of formula (V-B), where each Y is independently C or N and R$^2$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy.

Finally, chiral SFC separation of a compound of formula (V-B) provides the pure cis and trans isomers of formula (VI-B) and (VII-B), respectively.

SCHEME C

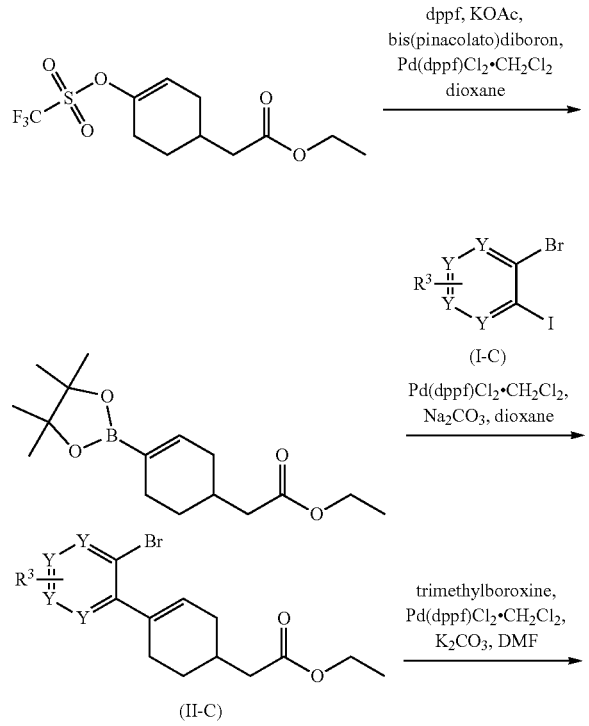

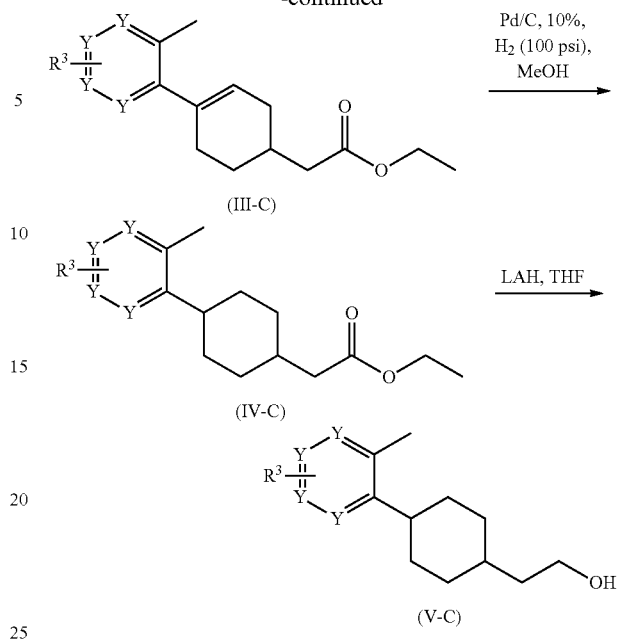

Synthesis of a methyl-substituted aryl cyclohexyl compound of formula (V-C) can be achieved in 5 steps, according to Scheme C.

A palladium-catalyzed coupling of ethyl 2-(4-(((trifluoromethyl)sulfonyl)oxy)cyclohex-3-en-1-yl)acetate and bis(pinacolato)diboron, in the presence of a ligand, such as 1,1'-bis(diphenylphosphino)ferrocene, a base such as potassium acetate, or the like, a catalyst such as [1,1'-bis(diphenylphosphino)ferrocene]dichloropalladium(II)complex with dichloromethane, and a solvent such as dioxane or the like, at a temperature ranging from rt to 100° C., sometimes 80° C., provides ethyl 2-(4-(4,4,5,5-tetramethyl-1,3,2-dioxaborolan-2-yl)cyclohex-3-en-1-yl)acetate. A Suzuki coupling with a bromo-substituted aryl iodide of formula (I-C), in the presence of a base such as sodium carbonate or the like, and a catalyst such as [1,1'-bis(diphenylphosphino)ferrocene]dichloropalladium(II)complex with dichloromethane, and a solvent such as dioxane or the like, at a temperature ranging from rt to 100° C., sometimes 70° C., provides an aryl bromide of formula (II-C), where each Y is independently C or N and R$^3$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy. Another Suzuki coupling with (II-C) and trimethylboroxine, in the presence of a base such as potassium carbonate or the like, and a catalyst such as [1,1'-bis(diphenylphosphino)ferrocene]dichloropalladium(II)complex with dichloromethane, and a solvent such as N,N-dimethylformamide or the like, at a temperature ranging from rt to 100° C., provides a methyl-substituted aryl cyclohexene of formula (III-C).

Subsequent reduction of the double bond of (III-C) under various hydrogenation conditions, known to one of skill in the art, followed by reduction of the ethyl ester to a primary alcohol, provides a compound of formula (V-C). For example, treatment of a compound of formula (III-C) with a catalyst, such as activated palladium on carbon, under an atmosphere of hydrogen gas, at a pressure of 100 psi, in a solvent such as methanol or ethyl acetate or the like, at a temperature ranging from rt to 80° C., sometimes 50° C., provides the substituted cyclohexyl (IV-C). Subsequent reduction of the ethyl ester is achieved using conditions known to one of skill in the art, such as treatment with lithium aluminum hydride or DIBAL, as described in Scheme A, to provide a primary alcohol of formula (V-C), as a mixture of cis and trans isomers, where each Y is independently C or N and $R^3$ is independently one or more halo, —OH, —$NH_2$, —$NHC_{1-4}$alkyl, —$N(C_{1-4}$alkyl$)_2$, —CN, —$C_{1-4}$alkyl, —$C_{1-4}$haloalkyl, —$C_{1-6}$alkoxy, or —$C_{1-6}$haloalkoxy.

SCHEME D

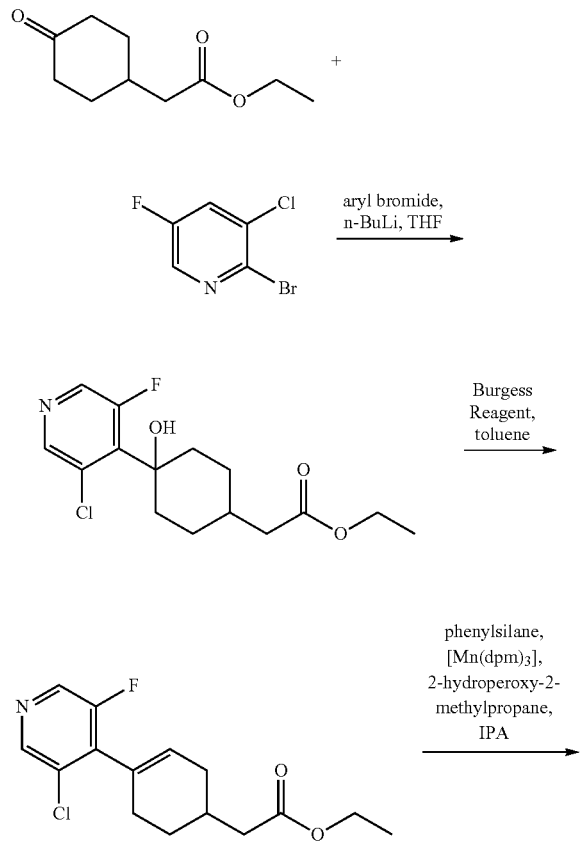

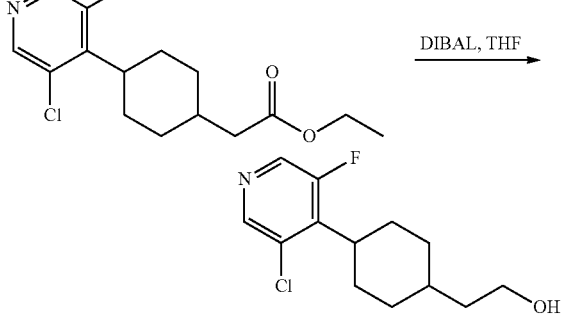

According to Scheme D, 2-(4-(3-chloro-5-fluoropyridin-4-yl)cyclohexyl)ethan-1-ol can be synthesized in 4 steps from commercially available starting materials. Treatment of ethyl 2-(4-oxocyclohexyl)acetate with 2-bromo-3-chloro-5-fluoropyridine, using a base such as n-butyllithium, in a solvent, such as THF or the like, in a manner similar to that described in Scheme A, provides the unexpected compound ethyl 2-(4-(3-chloro-5-fluoropyridin-4-yl)-4-hydroxycyclohexyl)acetate. Next, treatment of ethyl 2-(4-(3-chloro-5-fluoropyridin-4-yl)-4-hydroxycyclohexyl)acetate with (methoxycarbonylsulfamoyl)triethylammonium hydroxide (Burgess reagent), as described in Scheme A, such as in toluene at 80° C., provides ethyl 2-(4-(3-chloro-5-fluoropyridin-4-yl)cyclohex-3-en-1-yl)acetate. As an alternative to Burgess reagent, treatment with trifluoroacetic acid or p-toluenesulfonic acid, as described in Scheme A, also provides ethyl 2-(4-(3-chloro-5-fluoropyridin-4-yl)cyclohex-3-en-1-yl)acetate.

Reduction of the double bond is achieved by various methods known to one of skill in the art, as described in Scheme B for the synthesis of V-B. In one instance, a HAT (hydrogen atom transfer) reduction of the double bond with tris(2,2,6,6-tetramethyl-3,5-heptanedionato)manganese(III) (Shenvi hydrogenation catalyst) in the presence of phenylsilane and tert-butylhydroperoxide, in a solvent such as isopropanol, or the like, at a temperature ranging from rt to 80° C., sometimes rt, provides ethyl 2-(4-(3-chloro-5-fluoropyridin-4-yl)cyclohexyl)acetate. Subsequent reduction of the ethyl ester is achieved using conditions known to one of skill in the art, such as treatment with lithium aluminum hydride or DIBAL, as described in Scheme A, to provide 2-(4-(3-chloro-5-fluoropyridin-4-yl)cyclohexyl)ethan-1-ol, as a mixture of cis and trans isomers.

SCHEME E

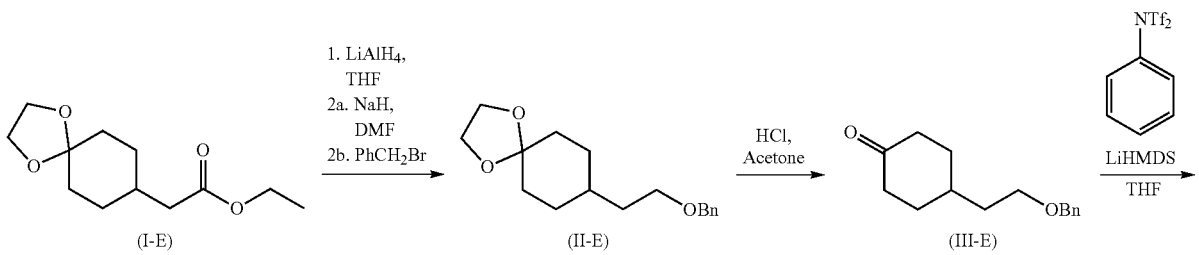

-continued

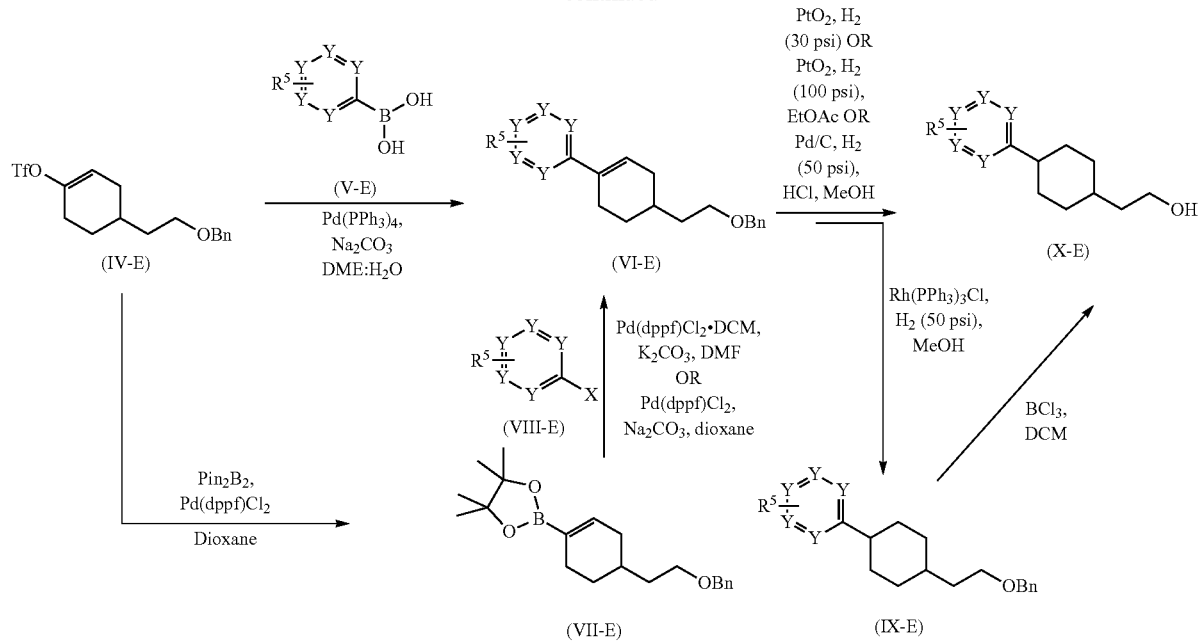

An optionally substituted 4-(2-(benzyloxy)ethyl)-2,3,4,5-tetrahydro-1,1'-biphenyl of formula (VI-E) can be synthesized in several ways from 4-(2-(benzyloxy)ethyl)cyclohex-1-en-1-yl trifluoromethanesulfonate (IV-E), as depicted in Scheme E.

The synthesis of 4-(2-(benzyloxy)ethyl)cyclohex-1-en-1-yl trifluoromethanesulfonate (IV-E) is achieved in four steps, beginning with commercially available ethyl 2-(1,4-dioxaspiro[4.5]decan-8-yl)acetate (I-E). Treatment of ethyl 2-(1,4-dioxaspiro[4.5]decan-8-yl)acetate (I-E) with a reducing agent, such as lithium aluminum hydride or DIBAL, as previously described, provides the primary alcohol. Then, treatment with sodium hydride, in a solvent such as N,N-dimethylformamide, followed by addition of benzyl bromide, provides 8-(2-(benzyloxy)ethyl)-1,4-dioxaspiro[4.5]decane (II-E). Next, conversion of the dioxolane to a ketone is achieved by treatment with an acid, such as hydrochloric acid, in a solvent such as acetone or the like, to provide 4-(2-(benzyloxy)ethyl)cyclohexan-1-one (III-E). Then, addition of 1,1,1-trifluoro-N-phenyl-N-((trifluoromethyl)sulfonyl)methanesulfonamide, in the presence of a base such as LHMDS or the like, in a solvent such as THF, at a temperature ranging from 0° C. to rt, provides 4-(2-(benzyloxy)ethyl)cyclohex-1-en-1-yl trifluoromethanesulfonate (IV-E).

4-(2-(Benzyloxy)ethyl)cyclohex-1-en-1-yl trifluoromethanesulfonate (IV-E) can be converted to a compound of formula (VI-E) either by direct Suzuki coupling of (IV-E) and a boronic acid or boronate ester or by conversion of the triflate into a boronate ester followed by treatment with an aryl halide or heteroaryl halide. For instance, treatment of (IV-E) with a boronic acid of formula (V-E), where each Y is independently C or N and $R^5$ is independently one or more halo, —OH, —$NH_2$, —$NHC_{1-4}$alkyl, —$N(C_{1-4}alkyl)_2$, —CN, —$C_{1-4}$alkyl, —$C_{1-4}$haloalkyl, —$C_{1-6}$alkoxy, or —$C_{1-6}$haloalkoxy, using conditions known to one of skill in the art, such as in the presence of a catalyst such as tetrakis(triphenylphosphine)palladium(0), in the presence of a base, such as sodium carbonate or the like, in a mixture of dimethoxyethane and water, at a temperature ranging from rt to 100° C., sometimes 85° C., provides a compound of formula (VI-E). Alternatively, treatment of (IV-E) with bis(pinacolato)diboron, in the presence of a catalyst such as [1,1'-bis(diphenylphosphino)ferrocene]dichloropalladium (II), in dioxane or the like, at a temperature ranging from 30° C. to 100° C., sometimes 70° C., provides 2-(4-(2-(benzyloxy)ethyl)cyclohex-1-en-1-yl)-4,4,5,5-tetramethyl-1,3,2-dioxaborolane (VII-E). Subsequent treatment with an aryl halide of formula (VIII-E), where X is I, Cl or Br, using Suzuki coupling conditions previously described, provides a compound of formula (VI-E), where each Y is independently C or N and $R^5$ is independently one or more halo, —OH, —$NH_2$, —$NHC_{1-4}$alkyl, —$N(C_{1-4}alkyl)_2$, —CN, —$C_{1-4}$alkyl, —$C_{1-4}$haloalkyl, —$C_{1-6}$alkoxy, or —$C_{1-6}$haloalkoxy.

Reduction of the double bond and removal of the benzyl protecting group can be achieved in one step, or in two, sequential steps to provide a compound of formula (X-E). Simultaneous reduction of the alkene and benzyl group is achieved by hydrogenation using a catalyst such as activated palladium on carbon or platinum(IV) oxide, under an atmosphere of hydrogen, at a pressure ranging from 1 atm to 200 psi, sometimes 30 psi, sometimes 50 psi or sometimes 100 psi, in a solvent such as methanol or ethyl acetate or the like, at a temperature ranging from rt to 50° C.

Alternatively, sequential reduction and removal of the protecting group is achieved by initial treatment of (VI-E) with tris(triphenylphosphine)ruthenium(II) dichloride, in an atmosphere of hydrogen, in methanol or the like, to provide a compound of formula (IX-E). Then, removal of the benzyl protecting group is achieved by addition of boron trichloride in dichloromethane to provide a compound of formula (X-E), as a mixture of cis and trans isomers, where each Y is independently C or N and $R^5$ is independently one or more halo, —OH, —$NH_2$, —$NHC_{1-4}$alkyl, —$N(C_{1-4}alkyl)_2$, —CN, —$C_{1-4}$alkyl, —$C_{1-4}$haloalkyl, —$C_{1-6}$alkoxy, or —$C_{1-6}$haloalkoxy.

SCHEME F

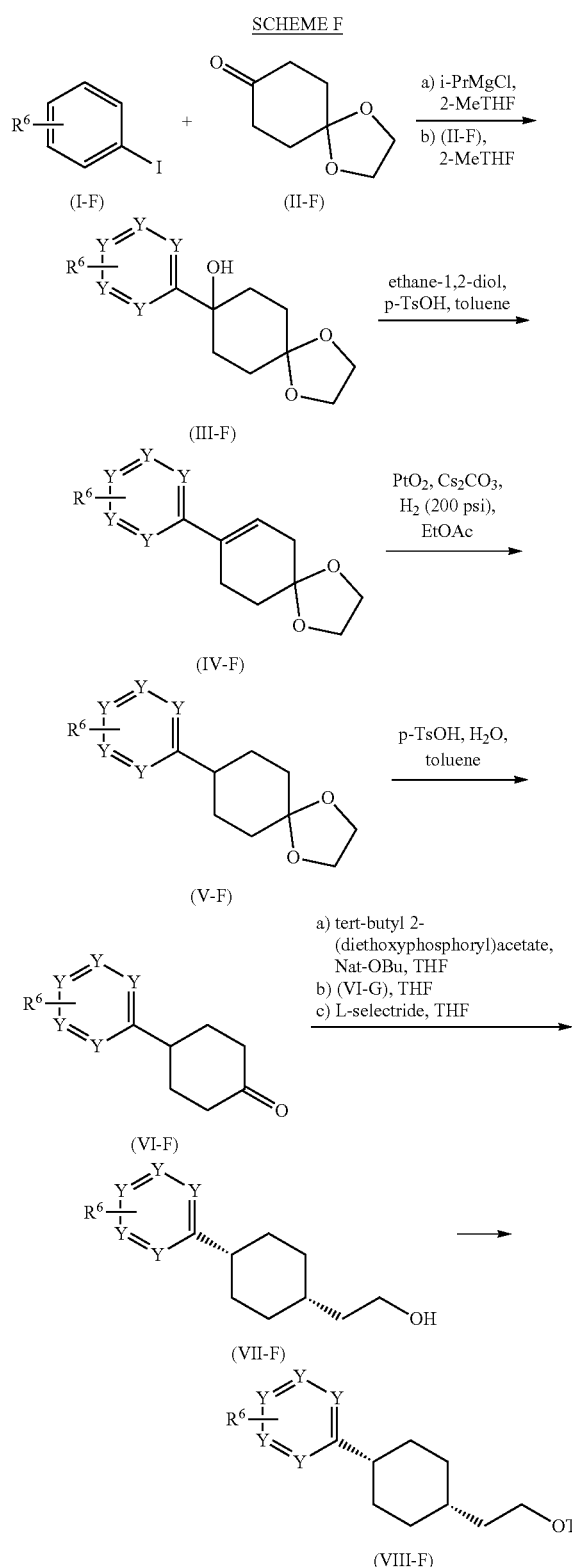

to rt, provides a hydroxyl-substituted compound for formula (III-F), where Y is independently C or N and R⁶ is independently one or more halo, —OH, —NH₂, —NHC₁₋₄alkyl, —N(C₁₋₄alkyl)₂, —CN, —C₁₋₄alkyl, —C₁₋₄haloalkyl, —C₁₋₆alkoxy, or —C₁₋₆haloalkoxy. Dehydration is achieved by treatment with p-toluenesulfonic acid in the presence of ethane-1,2-diol, in toluene or the like, at a temperature ranging from 50° C. to 120° C., sometimes 120° C., to provide a compound of formula (IV-F).

Reduction of the double bond is achieved by hydrogenation in the presence of a base to provide a compound of formula (V-F). For instance, treatment of (IV-F) with platinum(IV) oxide, under and atmosphere of hydrogen at a pressure ranging from 1 atm to 200 psi, sometimes 200 psi, in the presence of a base such as cesium carbonate or the like, in ethyl acetate or the like, provides a compound a formula (V-F), where Y is independently C or N and R⁶ is independently one or more halo, —OH, —NH₂, —NHC₁₋₄ alkyl, —N(C₁₋₄alkyl)₂, —CN, —C₁₋₄alkyl, —C₁₋₄haloalkyl, —C₁₋₆alkoxy, or —C₁₋₆haloalkoxy. Subsequent removal of the dioxolane group under acidic conditions, such as treatment with p-toluenesulfonic acid, in a solvent mixture of water and toluene, at a temperature ranging from rt to 100° C., sometimes 90° C., provides a cyclohexanone of formula (VI-F). A Homer-Wadsworth Emmons Olefination, followed by sequential reduction of the double bond and ethyl ester, provides a cis-compound of formula (VII-F) with a cis to trans ratio of >98:2. For instance, treatment of tert-butyl 2-(diethoxyphosphoryl)acetate with a base, such as sodium tert-butoxide, in a solvent such as tetrahydrofuran, at 50° C., followed by addition of (VI-F) at 0° C., provides the intermediate enone. Subsequent addition of L-selectride, at a temperature ranging from −30° C. to 0° C., affords reduction of the double bond to provide the cis-isomer. Further reduction, at a temperature ranging from rt to 50° C., affords reduction of the ethyl ester to the primary alcohol to provide a compound of formula (VII-F), where Y is independently C or N and R⁶ is independently one or more halo, —OH, —NH₂, —NHC₁₋₄alkyl, —N(C₁₋₄alkyl)₂, —CN, —C₁₋₄alkyl, —C₁₋₄haloalkyl, —C₁₋₆alkoxy, or —C₁₋₆haloalkoxy.

SCHEME G

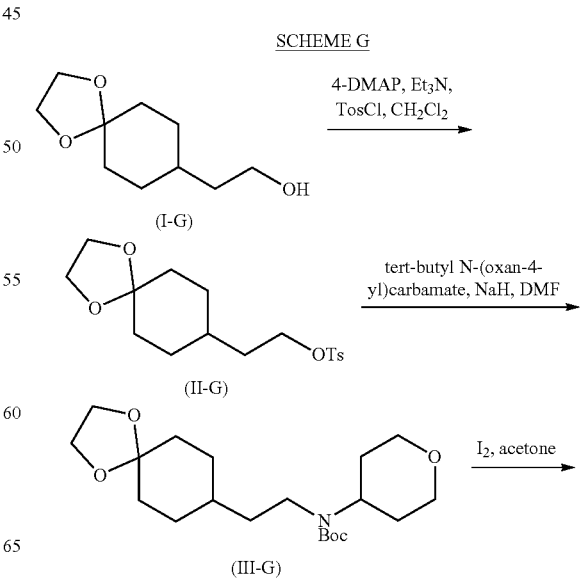

A facial selective synthesis to provide a cis compound of formula (VII-F) is achieved in five steps from commercially available starting materials, as depicted in Scheme F. Initially, Grignard addition of a compound of formula (I-F) to 1,4-dioxaspiro[4.5]decan-8-one (II-F), in a solvent such as 2-methyl tetrahydrofuran, a temperature ranging from 0° C.

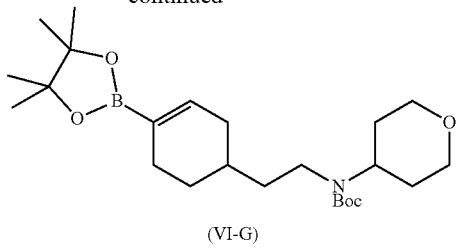

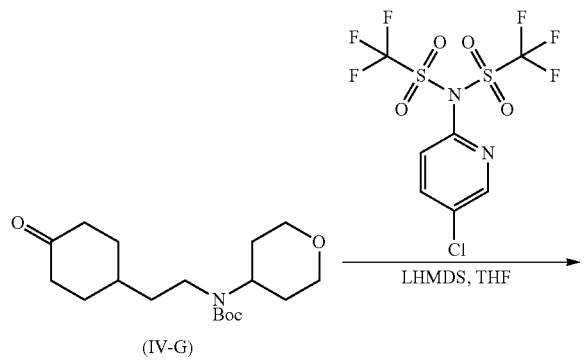

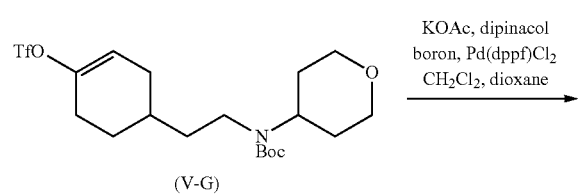

According to Scheme G, tert-butyl (tetrahydro-2H-pyran-4-yl)(2-(4-(4,4,5,5-tetramethyl-1,3,2-dioxaborolan-2-yl)cyclohex-3-en-1-yl)ethyl)carbamate (VI-G) can be synthesized in 5 steps from commercially available 2-(1,4-dioxaspiro[4.5]decan-8-yl)ethan-1-ol (I-G). Initially, formation of the tosylate is achieved by treatment of (I-G) with tosyl chloride, in the presence of a base such as triethylamine, and 4-(dimethylamino)pyridine, in a dichloromethane or the like, to provide 2-(1,4-dioxaspiro[4.5]decan-8-yl)ethyl 4-methylbenzenesulfonate (II-G). Then, addition of tert-butyl N-(oxan-4-yl)carbamate, in the presence of a base such as sodium hydride, in a N,N-dimethylformamide or the like, at a temperature ranging from rt to 100° C., sometimes 50° C., affords tert-butyl (2-(1,4-dioxaspiro[4.5]decan-8-yl)ethyl)(tetrahydro-2H-pyran-4-yl)carbamate (III-G). Removal of the dioxolane group to provide tert-butyl (2-(4-oxocyclohexyl)ethyl)(tetrahydro-2H-pyran-4-yl)carbamate (IV-G) is achieved by treatment with iodine, in acetone or the like, at a temperature ranging from rt to 80° C., sometimes 60° C. Formation of the triflate, followed by a Suzuki coupling with bis(pinacolato)diboron, using conditions known to one of skill in the art, similar to those described in Scheme E, provides tert-butyl (tetrahydro-2H-pyran-4-yl)(2-(4-(4,4,5,5-tetramethyl-1,3,2-dioxaborolan-2-yl)cyclohex-3-en-1-yl)ethyl)carbamate (VI-G).

SCHEME H

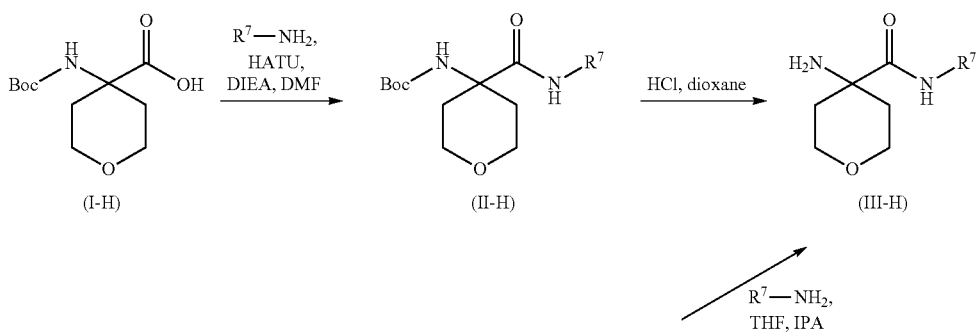

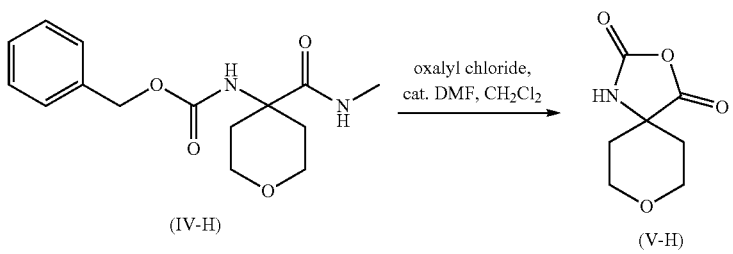

A 4-substituted-4-aminotetrahydropyran of formula (III-H) can be synthesized in two steps using two independent synthetic routes, as shown in Scheme H. In one instance, an amide coupling of an acid of formula (I-H) and a substituted amine, using standard amide coupling conditions known to one of skill in the art, for instance treatment with HATU, in the presence of a base such as DIEA or the like, in a solvent such as DMF, at a temperature ranging from rt to 100° C., provides an amide of formula (II-H), where $R^7$ is $C_{1-4}$alkyl. Subsequent removal of the t-butoxycarbonyl protecting group, under acidic conditions, such as treatment with hydrochloric acid or trifluoroacetic acid, in a solvent such as dioxane or dichloromethane or the like, at a temperature ranging from rt to 50° C. for several hours, provides a substituted tetrahydropyran amine of formula (III-H).

Using an alternative method, treatment of benzyl (4-(methylcarbamoyl)tetrahydro-2H-pyran-4-yl)carbamate (IV-H) with oxalyl chloride, in the presence of a catalytic amount of DMF, in a solvent such as dichloromethane or the like, provides 3,8-dioxa-1-azaspiro[4.5]decane-2,4-dione (V-H). Subsequent addition of a substituted amine, in a solvent mixture such as THF and IPA or the like, at a temperature ranging from rt to 100° C., sometimes 70° C. provides a compound of formula (III-H), where $R^7$ is $C_{1-4}$alkyl.

SCHEME I

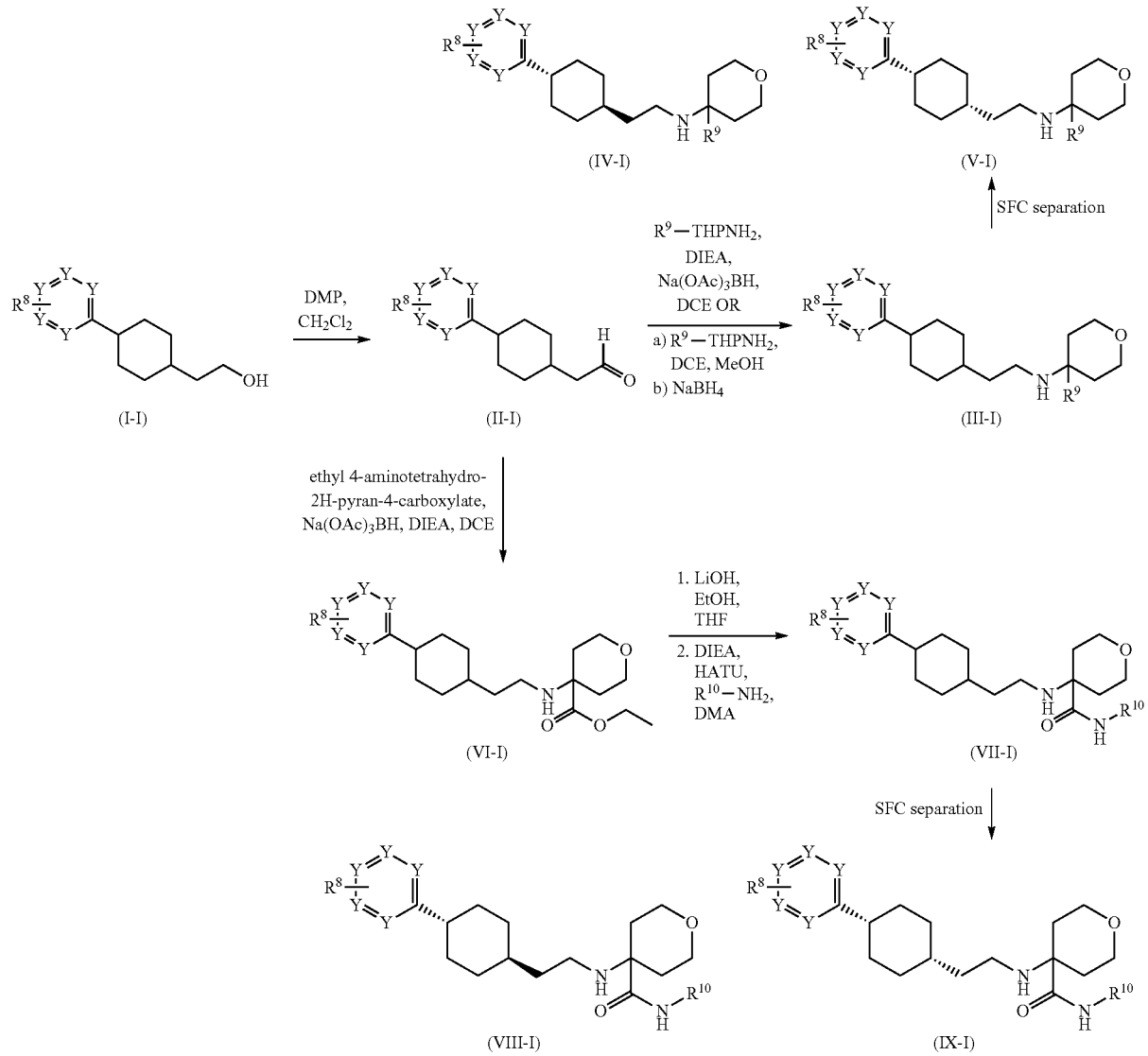

Compounds of formula (IV-I) and (V-I), as well as compounds of formula (VIII-I) and (IX-I) can be synthesized in three steps from a primary alcohol of formula (I-I), according to Scheme I. An aldehyde of formula (II-I) can be obtained by Dess-Martin oxidation, in a solvent such as dichloromethane or the like, at a temperature ranging from 0° C. to 80° C. Then, a reductive amination with a 4-substituted tetrahydropyrane-4-amine, under conditions known to one of skill in the art, provides a compound of formula (III-I), where Y is independently C or N and $R^8$ is independently one or more halo, —OH, —$NH_2$, —$NHC_{1-4}$alkyl, —$N(C_{1-4}alkyl)_2$, —CN, —$C_{1-4}$alkyl, —$C_{1-4}$haloalkyl, —$C_{1-6}$alkoxy, and —$C_{1-6}$haloalkoxy. Specifically, reductive amination conditions may include addition of a reducing agent such as sodium triacetoxyborohydride in the presence of a base such as N,N-diisopropylethylamine, in a solvent such as dichloroethane or the like. Alternatively, treatment of an aldehyde of formula (II-I) with a 4-substituted tetrahydropyrane-4-amine in dichloroethane and methanol, at room temperature provides formation of the imine, which can be subsequently reduced using a reducing agent such as sodium borohydride or sodium triacetoxyborohydride to provide a compound of formula (III-I) as a mixture of cis and trans isomers, where Y is independently C or N; $R^8$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy; and $R^9$ is —H, —C$_{1-6}$alkyl, —C$_{1-6}$haloalkyl, —C$_{1-4}$alkyl-OH, —C$_{1-4}$alkyl-O—C$_{1-3}$alkyl, —C$_{3-6}$cycloalkyl, —C(O)C$_{1-4}$alkyl, —COOC$_{1-4}$alkyl, —C(O)NH$_2$, —C(O)NH—C$_{1-4}$alkyl, —C(O)NH—(C$_{1-3}$alkyl-C$_{3-6}$cycloalkyl), or —C(O)N(C$_{1-4}$alkyl)$_2$. Separation by chiral SFC provides the pure trans-isomer of formula (IV-I) and the pure cis-isomer of formula (V-I).

In a similar manner, reductive amination with ethyl 4-aminotetrahydro-2H-pyran-4-carboxylate, under conditions described above, provides an ester compound of formula (VI-I).

Sequential hydrolysis of the ethyl ester under basic conditions, such as with lithium hydroxide or sodium hydroxide in a mixture of ethanol and tetrahydrofuran or the like, at a temperature ranging from rt to 60° C., followed by an amide coupling, under conditions known to one of skill in the art, provides an amide of formula (VII-I), as a mixture of cis and trans isomers, where Y is independently C or N; $R^8$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy; and $R^{10}$ is —C$_{1-6}$alkyl, —C$_{1-6}$haloalkyl, or —C$_{3-6}$cycloalkyl. Separation by chiral SFC provides the pure trans-isomer of formula (VIII-I) and the pure cis-isomer of formula (IX-I).

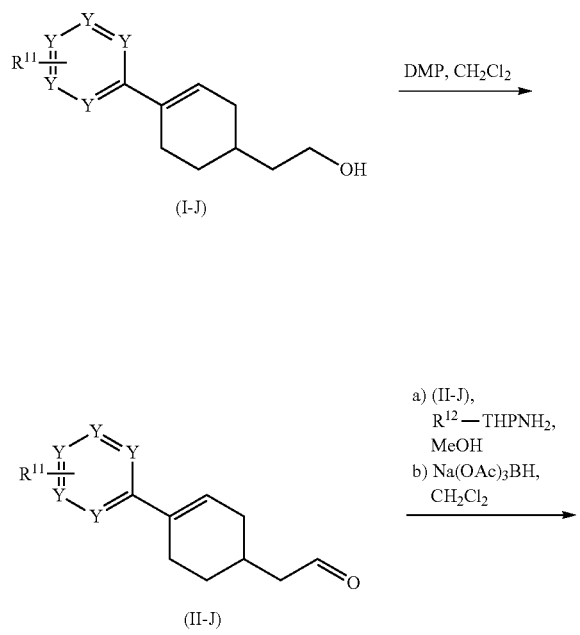

SCHEME J

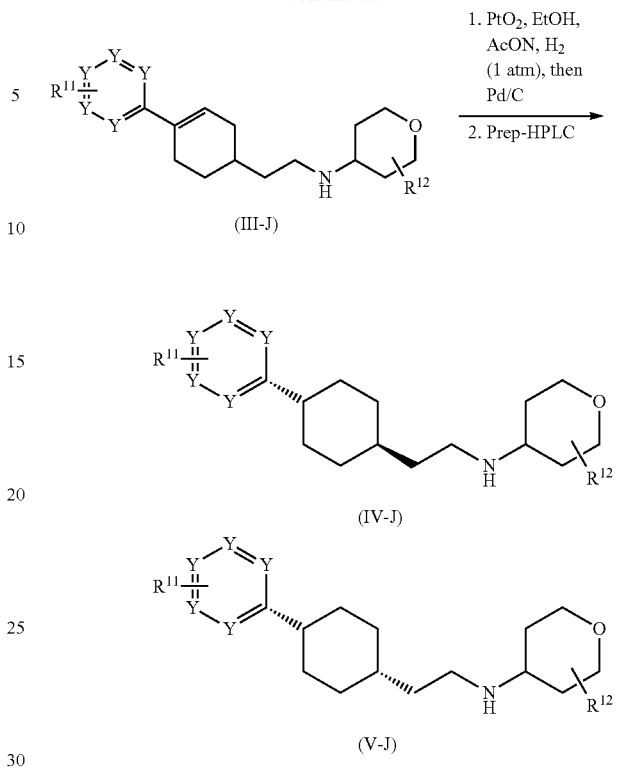

Compounds of formula (IV-J) and (V-J) can be synthesized in three steps from a primary alcohol of formula (I-J), according to Scheme J. An aldehyde of formula (II-J) can be obtained by Dess-Martin oxidation, as described in Scheme I. Then, a reductive amination with a 4-substituted tetrahydropyrane-4-amine, under conditions known to one of skill in the art, provides a compound of formula (III-J), where Y is independently C or N; $R^{11}$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy; and $R^{12}$ is independently selected from the group consisting of: halo, —OH, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —COOC$_{1-4}$alkyl, —C(O)NH$_2$, —C(O)NH—C$_{1-4}$alkyl, and —C(O)N(C$_{1-4}$alkyl)$_2$. Subsequent reduction amination, under conditions known to one of skill in the art, as described in Scheme I, provides a compound of formula (III-J) as a mixture of cis and trans isomers. Reduction of the double bond is achieved using hydrogenation conditions known to one of skill in the art, such as addition of palladium on carbon or platinum(IV) oxide, in a solvent such as ethanol or methanol or the like, under an atmosphere of hydrogen. Separation by chiral SFC provides the pure trans-isomer of formula (IV-J) and the pure cis-isomer of formula (V-J), where Y is independently C or N; $R^{11}$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$ alkoxy, or —C$_{1-6}$haloalkoxy; and $R^{12}$ is independently selected from the group consisting of: halo, —OH, —C$_{1-6}$alkyl, —C$_{1-6}$haloalkyl, —C$_{1-4}$alkyl-OH, —C$_{1-6}$alkoxy, —C$_{1-6}$haloalkoxy, —C$_{1-4}$alkyl-O—C$_{1-3}$alkyl, —C$_{3-6}$cycloalkyl, —COOC$_{1-4}$alkyl, —C(O)NH$_2$, —C(O)NH—C$_{1-4}$alkyl, and —C(O)N(C$_{1-4}$alkyl)$_2$.

SCHEME K

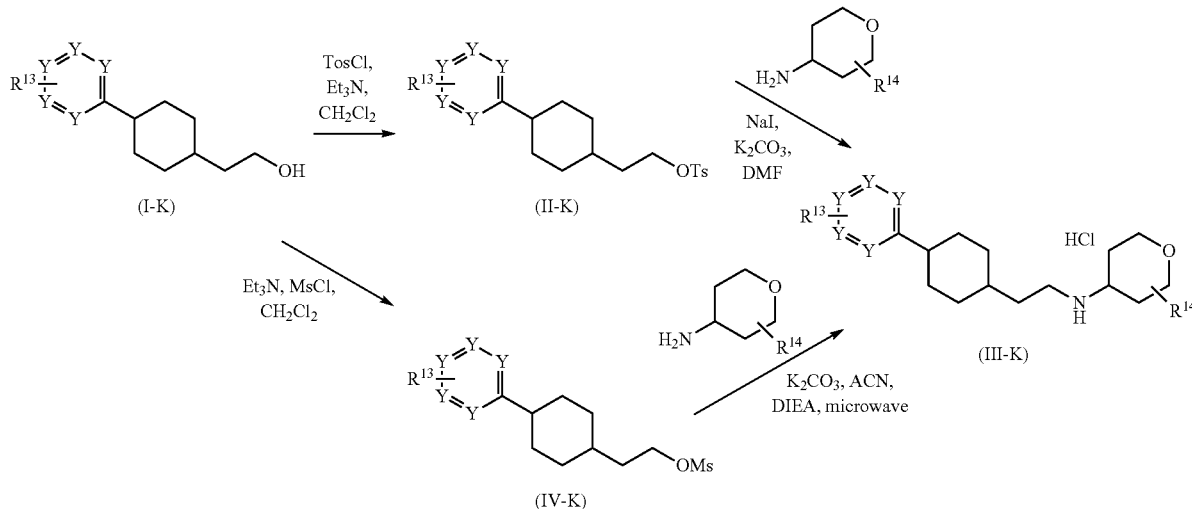

As shown in Scheme K, a compound of formula (III-K) can be synthesized from a primary alcohol of formula (I-K) through a tosylate or mesylate intermediate. In one instance, treatment of a compound of formula (I-K) with p-toluenesulfonyl chloride, in the presence of a base such as triethylamine, in dichloromethane or the like, provides a tosylate of formula (II-K). Displacement using a substituted tetrahydro-2H-pyran-4-amine, in the presence of a base such as potassium carbonate and sodium iodide, in N,N-dimethylformamide or the like, at a temperature ranging from 50° C. to 120° C., sometimes 90° C., provides a compound of formula (III-K), where Y is independently C or N; $R^{14}$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy; and $R^{14}$ is independently selected from the group consisting of: halo, —OH, —C$_{1-6}$alkyl, —C$_{1-6}$haloalkyl, —C$_{1-4}$alkyl-OH, —C$_{1-6}$ alkoxy, —C$_{1-6}$haloalkoxy, —C$_{1-4}$alkyl-O—C$_{1-3}$alkyl, —C$_{3-6}$ cycloalkyl, —COOC$_{1-4}$alkyl, —C(O)NH$_2$, —C(O)NH—C$_{1-4}$alkyl, and —C(O)N(C$_{1-4}$alkyl)$_2$. Similarly, formation of a mesylate intermediate of formula (IV-K) is achieved by treatment of a primary alcohol with mesyl chloride, in the presence of a base such as triethylamine, in dichloromethane or the like. Subsequent displacement, under conditions known to one of skill in the art, similar to that described above, provides a compound of formula (III-K). Specifically, displacement of the mesylate can be achieved in the presence of a base such as potassium bicarbonate and N,N-diisopropylethylamine, in acetonitrile or the like, at a temperature ranging from 50° C. to 120° C.

SCHEME L

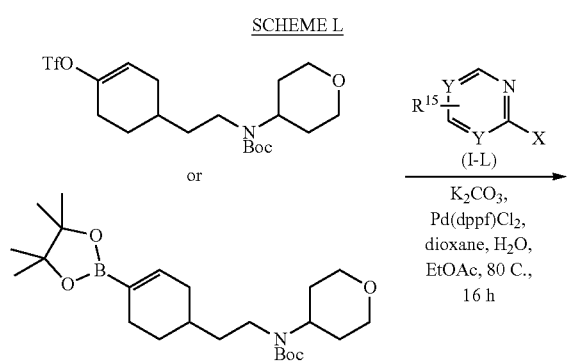

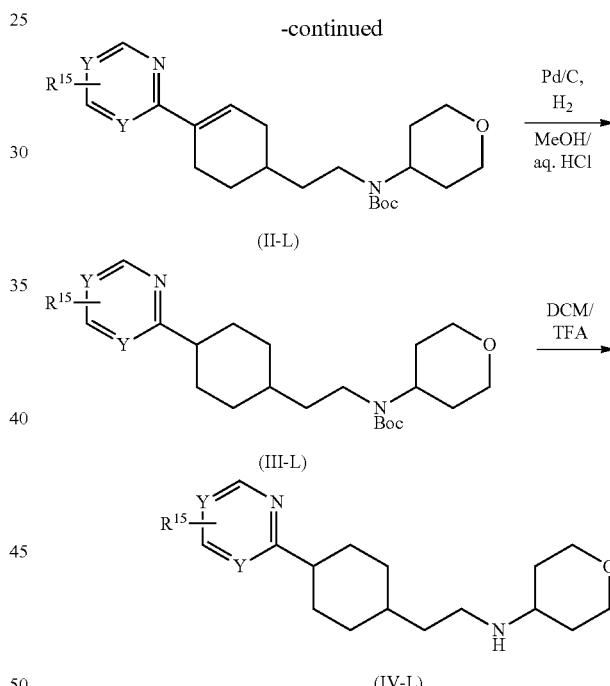

According to Scheme L, a Suzuki coupling with a heteroaryl halide of formula (I-L), where X is Cl, Br or I, and 4-(2-((tert-butoxycarbonyl)(tetrahydro-2H-pyran-4-yl)amino)ethyl)cyclohex-1-en-1-yl trifluoromethanesulfonate or tert-butyl (tetrahydro-2H-pyran-4-yl)(2-(4-(4,4,5,5-tetramethyl-1,3,2-dioxaborolan-2-yl)cyclohex-3-en-1-yl)ethyl)carbamate, under standard conditions known to one of skill in the art, provides a compound of formula (II-L). Specifically, a Suzuki coupling in the presence of a base such as potassium carbonate or the like, a catalyst such as [1,1'-bis(diphenylphosphino)ferrocene]dichloropalladium (II) complex with dichloromethane, in a solvent mixture such as dioxane, water and ethyl acetate, at a temperature ranging from rt to 120° C., sometimes 80° C., provides a compound of formula (II-L), where $R^{15}$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-6}$alkoxy, or —C$_{1-6}$haloalkoxy. Reduction of the double bond is achieved using standard hydrogenation conditions, similar to those previously described. For example, treatment of an alkene of formula (II-L) with activated palladium on carbon, in a solvent such as methanol or ethanol or the like, in the presence of HCl, under an atmosphere of hydrogen provides a compound of formula (III-L). Subsequent removal of the t-butoxycarbonyl protecting group, using HCl or trifluoroacetic acid, provides a compound of formula (IV-L), where R$^{15}$ is independently one or more halo, —OH, —NH$_2$, —NHC$_{1-4}$alkyl, —N(C$_{1-4}$alkyl)$_2$, —CN, —C$_{1-4}$alkyl, —C$_{1-4}$ haloalkyl, —C$_{1-6}$alkoxy, or —C$_{1-6}$haloalkoxy.

EXAMPLES

Chemistry:

In obtaining the compounds described in the examples below, and the corresponding analytical data, the following experimental and analytical protocols were followed unless otherwise indicated.

Unless otherwise stated, reaction mixtures were magnetically stirred at room temperature (rt) under an atmosphere of nitrogen. Where solutions were "dried," they were generally dried over a drying agent such as Na$_2$SO$_4$ or MgSO$_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on Silica (SiO$_2$) using packed or prepackaged cartridges, eluting with the indicated solvents.

Analytical LC/MS were obtained on a Waters 2695 Separations Unit, 2487 Dual Absorbance Detector, Micromass ZQ fitted with ESI Probe, or a Waters Acquity™ Ultra performance LC (UPLC) with PDA ek and SQ detectors. Alternatively, LC-MS was performed on a Waters Acquity UPLC-MS instrument equipped with a Acquity UPLC BEH C18 column (1.7 µm, 2.1×50 mm) and the solvent system A: 0.1% HCOOH in H$_2$O and B: 0.1% HCOOH in ACN. Column temperature was 45° C. All compounds were run using the same elution gradient, i.e., 5% to 95% solvent B in 0.75 min with a flow rate of 1 mL/min.

Analytical SFC-MS was performed on a Waters UPC$^2$-MS instrument equipped with a Acquity UPC$^2$ BEH 2-ethylpyridine column (1.7 µm, 2.1×50 mm) and the solvent system A: CO$_2$ and B: 0.1% NH$_4$OH in MeOH. Column temperature was 55° C. All compounds were run using the same elution gradient, i.e., 3% to 35% solvent B in 0.75 min with a flow rate of 2.5 mL/min.

Preparative HPLC was performed on a Shimadzu SIL-10AP system using a Waters SunFire™ OBD (5 µm, 30×100 mm) C18 column with a 15-minute gradient of 10-100% acetonitrile in water and 0.05% trifluoroacetic acid added as a modifier to both phases. Elution profiles were monitored by UV at 254 and 220 nm.

Some compounds were purified using a Waters Fractionlynx system equipped with a XBridge Prep C18 OBD column (5 µm, 19×50 mm) and the solvent system: H$_2$O: AcCN and 2% TFA in H$_2$O. Specific elution gradients were based on retention times obtained with an analytical UPLC-MS, however, in general all elution gradients of H$_2$O and ACN were run over a 5.9 min run time with a flow rate of 40 mL/min. An autoblend method was used to ensure a concentration of 0.1% TFA throughout each run.

Some compounds were purified using a Waters Fractionlynx system equipped with a XBridge Prep C18 OBD column (5 µm, 30×100 mm) and the solvent system: H$_2$O: AcCN and 2% TFA in H$_2$O. Specific elution gradients were based on retention times obtained with an analytical UPLC-MS, however, in general all elution gradients of H$_2$O and ACN were run over a 9 min run time with a flow rate of 60 mL/min. An autoblend method was used to ensure a concentration of 0.1% TFA throughout each run.

Preparative SFC-MS was run on a Waters Prep100 SFC-MS system equipped with a Viridis 2-ethylpyridine OBD column (5 µm, 30×100 mm) and the solvent system: CO$_2$: MeOH and 0.2% NH$_4$OH in MeOH as a co-solvent. Specific elution gradients were based on retention times obtained with an analytical UPC$^2$-MS, however, in general all elution gradients of CO$_2$ and MeOH were run over a 3.6 min run time with a flow rate of 100 mL/min and a column temperature of 55° C. An autoblend method was used to ensure a concentration of 0.2% NH$_4$OH throughout each run.

Nuclear magnetic resonance (NMR) spectra were obtained in an Agilent 300 MHz VNMR (Varian 300 MHz NMR) or a Varian 400 MHz or Bruker 400 MHz NMR. Samples were analyzed in either deuterated acetone ((CD$_3$)$_2$CO), chloroform (CDCl$_3$), MeOH-d$_4$ (CD$_3$OD), N,N-dimethylformamide-d$_7$ (DMF-d$_7$) or dimethyl sulfoxide-d$_6$ (DMSO-d$_6$). For (CD$_3$)$_2$CO samples, the residual central resonance peak at 2.05 for $^1$H was used for chemical shift assignment for $^1$H NMR spectra. For CDCl$_3$ samples, the residual central resonance peak at 7.26 for $^1$H was used for chemical shift assignment for $^1$H NMR spectra. For CD$_3$OD the residual central resonance peak at 3.31 for $^1$H was used for chemical shift assignment and for DMF-d$_7$ the residual central resonance peaks at 2.92 or 2.75 for $^1$H were used for chemical shift assignment. For DMSO-d$_6$ the residual central resonance peak at 2.50 ppm for $^1$H was used for chemical shift assignment. The format of the $^1$H NMR data below is: chemical shift in ppm downfield the tetramethylsilane reference (multiplicity, coupling constant J in Hz, integration), using conventional abbreviations for designation of major peaks: e.g. s, singlet; d, doublet; t, triplet; q, quartet; p, pentet; m, multiplet; br, broad.

Chemical names were generated using ChemDraw Ultra 12.0 (CambridgeSoft Corp., Cambridge, Mass.), ChemDraw Professional 15.1 (CambridgeSoft Corp., Cambridge, Mass.) or ChemAxon.

Some intermediate and/or example compounds were isolated as free bases, while others were isolated as a salt. In some instances the compound may be isolated as a trifluoroacetic acid salt and in other instances the salt may be isolated as a hydrochloride salt. In some cases, the $^1$H NMR spectrum of those compounds that were isolated as a salt may contain additional proton signals that correspond to hydrogen atoms of the salt, as expected by one of skill in the art.

Intermediate 1. 2-[4-(2-Chloro-4-fluorophenyl)cyclohex-3-en-1-yl]ethan-1-ol

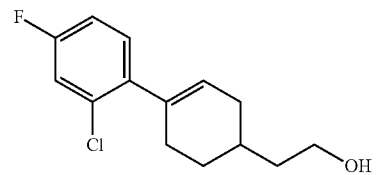 [SMILES: OCCC1CC=C(c2ccc(F)cc2Cl)CC1]

Step 1. Ethyl 2-(4-(2-chloro-4-fluorophenyl)-4-hydroxycyclohexyl)acetate. A solution of n-butyllithium in hexanes (1.6 M, 81.4 mL, 130 mmol) was added dropwise to a solution of 2-chloro-4-fluoro-1-iodobenzene (16.6 mL, 130 mmol) in tetrahydrofuran (197 mL) at −78° C. The reaction mixture was allowed to stir at −78° C. for 1 h before the addition of ethyl 2-(4-oxocyclohexyl)acetate (19.2 mL, 109 mmol) in one portion. The reaction was allowed to warm to room temperature and stirred at room temperature for 1 h. The reaction was quenched with a saturated solution of ammonium chloride (500 mL) and extracted with EtOAc (3×150 mL), combined organics dried (Na$_2$SO$_4$) and concentrated under reduced pressure. The residue was purified by flash chromatography on silica, eluting with 0-40% EtOAc in hexanes to yield the product as a colorless oil (26.7 g, 78%). $^1$H NMR (400 MHz, CDCl$_3$) δ 7.65 (dd, J=8.86, 6.30 Hz, 1H), 7.21-7.09 (m, 1H), 7.03-6.94 (m, 1H), 4.27-4.07 (m, 5H), 2.62-2.47 (m, 2H), 2.46-2.18 (m, 10H), 2.15-1.82 (m, 6H), 1.78-1.34 (m, 7H), 1.34-1.22 (m, 7H). [M−H$_2$O+H]=283.1.

Step 2. Ethyl 2-(2'-chloro-4'-fluoro-2,3,4,5-tetrahydro-[1,1'-biphenyl]-4-yl)acetate. 2,2,2-trifluoroacetic acid (127 mL, 1.65 mol) was added to a solution of ethyl 2-(4-(2-chloro-4-fluorophenyl)-4-hydroxycyclohexyl)acetate (25 g, 80.4 mmol) in dichloromethane (127 mL) and the reaction stirred at room temperature for 1 h. The reaction was concentrated under reduced pressure to yield the product as a colorless oil (21.6 g, 91%). $^1$H NMR (400 MHz, CDCl$_3$) δ 7.18-7.05 (m, 2H), 6.93 (td, J=8.28, 2.63 Hz, 1H), 5.68-5.59 (m, 1H), 4.18 (q, J=7.09 Hz, 2H), 2.48-2.13 (m, 6H), 2.03-1.84 (m, 2H), 1.59 (s, 1H), 1.30 (t, J=7.09 Hz, 3H). [M+H]=297.1.

Step 3. 2-(2'-Chloro-4'-fluoro-2,3,4,5-tetrahydro-[1,1'-biphenyl]-4-yl)ethan-1-ol. To a cooled solution of ethyl 2-(2'-chloro-4'-fluoro-2,3,4,5-tetrahydro-[1,1'-biphenyl]-4-yl)acetate (7.59 g, 25.6 mmol) in tetrahydrofuran (152 mL) at 0° C., was added dropwise a solution of lithium aluminum hydride in tetrahydrofuran (1 M, 51.2 mL, 51.2 mmol). The reaction was stirred at 0° C. for 10 minutes and quenched with water (10 mL), 10% NaOH (20 mL) and water (10 mL). The reaction was diluted with EtOAc, filtered through celite, dried (Na$_2$SO$_4$) and concentrated under reduced pressure. The residue was purified by flash chromatography on silica, eluting with 0-40% EtOAc in hexanes to yield the product as a colorless oil (6.6 g, 101%). $^1$H NMR (400 MHz, CDCl$_3$) δ 7.15-7.04 (m, 2H), 6.96-6.86 (m, 1H), 5.68-5.57 (m, 1H), 3.77 (t, J=6.72 Hz, 2H), 2.32 (ddd, J=9.57, 3.94, 2.38 Hz, 4H), 1.97-1.74 (m, 3H), 1.72-1.54 (m, 2H), 1.52-1.32 (m, 1H).

Intermediate 2. 2-[4-(2-Chloro-4-fluorophenyl)cyclohexyl]ethan-1-ol

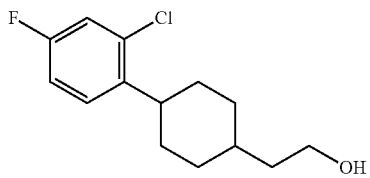 [SMILES: OCCC1CCC(c2ccc(F)cc2Cl)CC1]

In a 500 mL stainless steel reaction vessel 2-(2'-chloro-4'-fluoro-2,3,4,5-tetrahydro-[1,1'-biphenyl]-4-yl)ethanol (10.0 g, 39.3 mmol) was dissolved in isopropyl acetate (100 mL), platinum(IV) oxide (446 mg, 1.96 mmol) added and the reaction was stirred at room temperature under hydrogen at 200 PSI for 24 h. The reaction was filtered through celite and concentrated under reduced pressure. The residue was purified by flash chromatography on silica, eluting with 0-50% EtOAc in hexanes to yield the desired products as a mixture of cis- and trans-isomers (6.7 g, 66%). $^1$H NMR (400 MHz, CDCl$_3$) δ 7.24 (ddd, J=6.2, 8.7, 12.6 Hz, 1H), 7.11 (dd, J=2.7, 8.7 Hz, 1H), 7.01-6.91 (m, 1H), 3.82-3.67 (m, 2H), 3.07-2.87 (m, 1H), 2.02-1.10 (m, 12H).

Intermediate 3 and 4. 2-[(1S,4S)-4-(2-Chloro-4-fluorophenyl)cyclohexyl]ethan-1-ol and 2-[(1R,4R)-4-(2-chloro-4-fluorophenyl)cyclohexyl]ethan-1-ol

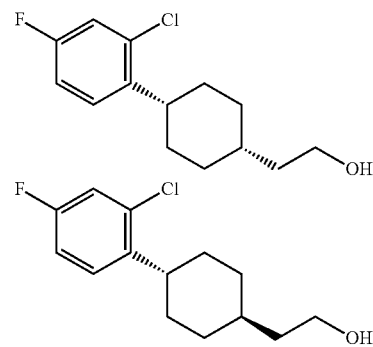

Intermediate 2 was further purified by chiral SFC to yield the pure cis-isomer: $^1$H NMR (400 MHz, CDCl$_3$) δ 7.25 (dd, J=6.2, 8.7 Hz, 1H), 7.11 (dd, J=2.7, 8.7 Hz, 1H), 6.96 (dt, J=2.7, 8.3 Hz, 1H), 3.74 (t, J=6.8 Hz, 2H), 3.00 (tt, J=3.4, 11.4 Hz, 1H), 2.03-1.89 (m, 1H), 1.81-1.55 (m, 11H); and the pure trans-isomer: $^1$H NMR (400 MHz, CDCl$_3$) δ 7.22 (dd, J=6.1, 8.7 Hz, 1H), 7.11 (dd, J=2.7, 8.7 Hz, 1H), 6.96 (dt, J=2.7, 8.4 Hz, 1H), 3.75 (t, J=6.5 Hz, 2H), 2.96 (tt, J=2.8, 12.1 Hz, 1H), 1.92 (d, J=11.0 Hz, 4H), 1.61-1.32 (m, 6H), 1.26-1.12 (m, 2H).

Intermediate 5. 2-[4-(2,4-Difluoro-6-methylphenyl)cyclohexyl]ethan-1-ol

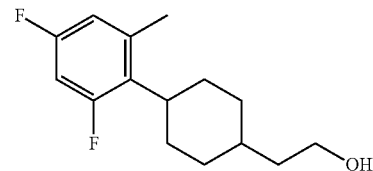 [SMILES: Cc1cc(F)cc(F)c1C1CCC(CCO)CC1]

Step 1. Ethyl 2-(4-(((trifluoromethyl)sulfonyl)oxy)cyclohex-3-en-1-yl)acetate. To a solution of ethyl 2-(4-oxocyclohexyl)acetate (0.50 g, 2.71 mmol) in tetrahydrofuran (2.71 mL) was slowly added a solution of lithium bis(trimethylsilyl)amide in THF (4.07 mL, 1.00 M, 4.07 mmol). The reaction was cooled to −40° C. then stirred for 1 h then a solution of N-phenyl-bis(trifluoromethanesulfonimide) (1.16 g, 3.26 mmol) in tetrahydrofuran (0.90 mL) was added dropwise at −40° C. The reaction was allowed to warm up to room temperature and stirred for an additional 3 h. The reaction mixture was quenched with sat. NH$_4$Cl solution and extracted with EtOAc. The combined organic layers were washed with brine, dried over Na$_2$SO$_4$, filtered and concentrated to give the crude product. The crude oil was purified via flash chromatography 0-30% EtOAc/Heptanes to obtain the title compound as a colorless oil (300 mg, 35%). $^1$H NMR (400 MHz, CDCl$_3$) δ 5.77-5.56 (m, 1H), 4.13 (q, J=7.1 Hz, 2H), 2.50-2.39 (m, 1H), 2.33 (td, J=2.6, 5.0 Hz, 2H), 2.29 (d, J=7.1 Hz, 2H), 2.18-2.04 (m, 1H), 2.01-1.85 (m, 2H), 1.60-1.45 (m, 1H), 1.25 (t, J=7.2 Hz, 3H). [M+H]=317.1.

Step 2. Ethyl 2-(4-(4,4,5,5-tetramethyl-1,3,2-dioxaborolan-2-yl)cyclohex-3-en-1-yl)acetate. A vial was charged with ethyl 2-[4-(trifluoromethanesulfonyloxy)cyclohex-3-en-1-yl]acetate (1.71 g, 0.01 mol), 1,1'-bis(diphenylphosphino)ferrocene (150 mg, 0.27 mmol), potassium acetate (1.59 g, 16.2 mmol) and bis(pinacolato)diboron (1.51 g, 5.94 mmol). The vial was purged with N$_2$ (×3), then dioxane (5.4 mL) was added and the mixture degassed for 5 min. [1,1'-Bis(diphenylphosphino)ferrocene]dichloropalladium(II) complex with dichloromethane (221 mg, 0.27 mol) was then added and the resulting mixture degassed again for 5 min. The resulting orange reaction mixture was stirred at 80° C. overnight. After 18 h, the reaction was cooled to room temperature. A saturated aqueous solution of NaHCO$_3$ (2 mL) was added and the aqueous layer was extracted with EtOAc (3×2 mL). The organic layers were combined and removed solvent in vacuo. Purified by flash chromatography (silica, 0-10% MeOH/DCM) to afford the title compound (1.17 g, 73.5%). $^1$H NMR (400 MHz, CDCl$_3$) δ 6.52 (d, J=1.96 Hz, 1H), 4.14 (d, J=7.09 Hz, 2H), 1.99-2.36 (m, 6H), 1.69-1.91 (m, 2H), 1.55 (s, 1H), 1.21-1.34 (m, 15H).

Step 3. Ethyl 2-(2'-bromo-4',6'-difluoro-2,3,4,5-tetrahydro-[1,1'-biphenyl]-4-yl)acetate. In a sealed microwave tube, a mixture of ethyl 2-[4-(tetramethyl-1,3,2-dioxaborolan-2-yl)cyclohex-3-en-1-yl]acetate (200 mg, 0.68 mmol), [1,1'-bis(diphenylphosphino)ferrocene]dichloropalladium (II) (24.9 mg, 0.03 mmol), 1-bromo-3,5-difluoro-2-iodobenzene (260 mg, 0.82 mmol) and sodium carbonate (0.85 mL, 2.0 M, 1.7 mmol) in dioxane (3.40 mL) was heated at 70° C. for 20 h. Upon completion of the reaction, the reaction mixture was filtered through celite, washed thoroughly with EtOAc, and purified via flash chromatography (0-20% EtOAc/heptanes) to obtain the title compound as a colorless oil (210 mg, 86%). $^1$H NMR (400 MHz, CDCl$_3$) δ 7.13 (td, J=2.0, 8.1 Hz, 1H), 6.78 (dt, J=2.5, 8.8 Hz, 1H), 5.60 (d, J=1.7 Hz, 1H), 4.17 (q, J=7.2 Hz, 2H), 2.45-2.31 (m, 3H), 2.22-2.12 (m, 1H), 2.00-1.84 (m, 2H), 1.63-1.50 (m, 1H), 1.48 (s, 2H), 1.28 (t, J=7.1 Hz, 3H). [M+H]=361.0.

Step 4. Ethyl 2-(2',4'-difluoro-6'-methyl-2,3,4,5-tetrahydro-[1,1'-biphenyl]-4-yl)acetate. To a solution of ethyl 2-(2'-bromo-4',6'-difluoro-2,3,4,5-tetrahydro-[1,1'-biphenyl]-4-yl)acetate (235 mg, 0.65 mmol) in N,N-dimethylformamide (6.54 mL) under a nitrogen environment was added trimethylboroxine (182.9 μL, 1.31 mmol) and potassium carbonate (180.8 mg, 1.31 mmol), followed by [1,1'-bis(diphenylphosphino)ferrocene]dichloropalladium(II) complex with dichloromethane (53.4 mg, 0.07 mmol). The reaction was heated at 100° C. for 3 h, cooled to rt then filtered over a celite pad. The filtrate was extracted with EtOAc and water. The organic layers were combined, washed with brine, dried over Na$_2$SO$_4$ and concentrated. The crude product was purified via flash chromatography (0-30% EtOAc/hexanes) to obtain the title compound as a colorless oil (141 mg, 73.2%). $^1$H NMR (400 MHz, CDCl$_3$) δ 6.71 (d, J=9.2 Hz, 1H), 6.62 (dt, J=2.2, 9.2 Hz, 1H), 5.54 (d, J=1.5 Hz, 1H), 4.18 (q, J=7.1 Hz, 2H), 2.45-2.20 (m, 8H), 2.18-2.06 (m, 1H), 2.00-1.85 (m, 1H), 1.59-1.50 (m, 1H), 1.30 (t, J=7.2 Hz, 3H). [M+H]=295.2.

Step 5. Ethyl 2-(4-(2,4-difluoro-6-methylphenyl)cyclohexyl)acetate. To a solution of ethyl 2-[4-(2,4-difluoro-6-methylphenyl)cyclohex-3-en-1-yl]acetate (130 mg, 0.44 mmol) in methanol (2.21 mL) in a small PARR bomb reactor, was added 10% palladium on carbon (47.0 mg, 0.04 mmol) and the vessel was pressurized to 100 psi under hydrogen and was stirred at 50° C. overnight. Upon completion of the reaction, the mixture was filtered through celite, rinsed well with MeOH and concentrated under reduced pressure to obtain the title compound as a colorless oil. The crude product was taken forward in the next reaction without further purification. [M+H]=297.2

Step 6. 2-(4-(2,4-Difluoro-6-methylphenyl)cyclohexyl)ethan-1-ol. To a solution of ethyl 2-[4-(2,4-difluoro-6-methylphenyl)cyclohexyl]acetate (130 mg, 0.44 mmol) in tetrahydrofuran (4.39 mL) was added lithium aluminum hydride (0.48 mL, 1.00 M, 0.48 mmol) and the reaction was stirred for 1 h at room temperature. Water (2 mL), a solution of NaOH (2 M, 2 mL) and water (2 mL) were sequentially added. The reaction was extracted with EtOAc, combined organics were washed with a saturated brine solution, organics were dried (Na$_2$SO$_4$), then concentrated under reduced pressure to obtain the title compound as a colorless oil, which was carried on without further purification. [M+H–H$_2$O]=237.2.

Intermediate 6. 2-[4-(2,4,6-Trifluorophenyl)cyclohexyl]ethan-1-ol

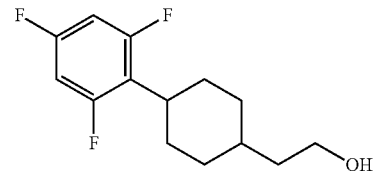 [SMILES: OCCC1CCC(c2c(F)cc(F)cc2F)CC1]

Step 1. Ethyl 2-[4-(trifluoromethanesulfonyloxy)cyclohex-3-en-1-yl]acetate. To a solution of ethyl 2-(4-oxocyclohexyl)acetate (7.70 g, 41.8 mmol) in tetrahydrofuran (41.8 mL) was slowly added a solution of lithium bis(trimethylsilyl)amide (1M, 46.0 mL, 46.0 mmol) in THF. The reaction was stirred at −40° C. (MeCN/dry ice bath) for 1 h then a solution of N-phenyl-bis(trifluoromethanesulfonimide) (17.9 g, 50.2 mmol) in tetrahydrofuran (13.9 mL) was added dropwise at −40° C. The reaction was allowed to warm up to rt and stirred for an additional 3 h. The reaction mixture was quenched with a saturated aqueous solution of NH$_4$Cl and extracted with EtOAc. The combined organic layers were washed with brine, dried over Na$_2$SO$_4$, filtered and concentrated to provide the crude product. The crude oil was purified by flash column chromatography (ISCO amine column, 0-30% EtOAc/heptanes over 15 min) to obtain the title compound as a semi solid (7.00 g, 53.0%). $^1$H NMR (400 MHz, CDCl$_3$) δ 5.73 (br. s., 1H), 4.16 (d, J=7.21 Hz, 2H), 2.24-2.54 (m, 5H), 2.14 (d, J=3.79 Hz, 1H), 1.84-1.99 (m, 2H), 1.47-1.60 (m, 1H), 1.28 (t, J=7.15 Hz, 3H). [M+H]=317.20.

Step 2. Ethyl 2-[4-(2,4,6-trifluorophenyl)cyclohex-3-en-1-yl]acetate. In a sealed microwave tube, a mixture of tetrakis(triphenylphosphine)palladium(0) (96.9 mg, 0.08 mmol), (2,4,6-trifluorophenyl)boronic acid (227 mg, 1.29 mmol), ethyl 2-[4-(trifluoromethanesulfonyloxy)cyclohex-3-en-1-yl]acetate (340 mg, 1.07 mmol) and sodium carbonate (2.52 mL, 2.0 M, 5.03 mmol) in 1,2-dimethoxyethane (8.38 mL) was heated at 70° C. for 20 hours. The reaction mixture was filter through celite and washed thoroughly with EtOAc. The crude product was purified by flash chromatography (silica, 0-20% EtOAc/heptanes) to obtain the title compound as a colorless oil. (130 mg, 40.5%).

Step 3. Ethyl 2-[4-(2,4,6-trifluorophenyl)cyclohexyl]acetate. To a mixture of ethyl 2-[4-(2,4,6-trifluorophenyl)cyclohex-3-en-1-yl]acetate (130 mg, 0.44 mmol) in methanol (2.18 mL) in a small PARR bomb, was added 10% palladium on carbon (46.4 mg, 0.04 mmol) (50% water) and the vessel was pressurized to 100 psi w/H$_2$ and was stirred at 50° C. overnight. The reaction was recharged with EtOH and 0.20 mol % Pd(OH)$_2$ and stirred overnight at 50° C. at 100 psi of H$_2$. Upon completion of the reaction, the reaction mixture was filtered through celite, the celite pad was rinsed with MeOH and the solvent was removed in vacuo. The crude product was used in the next reaction without further purification. [M+H]=301.2.

Step 4. 2-(4-(2,4,6-Trifluorophenyl)cyclohexyl)ethan-1-ol. To a solution of ethyl 2-[4-(2,4,6-trifluorophenyl)cyclohexyl]acetate (130 mg, 0.43 mmol) in tetrahydrofuran (4.33 mL) was added lithium aluminum hydride (0.48 mL, 1.0 M, 0.48 mmol) and the reaction was stirred for 1 h. Upon completion of the reaction, water (2 mL), a solution of NaOH (2 M, 2 mL) and water (2 mL) were sequentially added. The reaction mixture was extracted with EtOAc, and the combined organics were washed with a saturated brine solution, dried (Na$_2$SO$_4$), and concentrated under reduced pressure to provide a crude white solid, which was taken forward in the next reaction without further purification. $^1$H NMR (400 MHz, CDCl$_3$) δ 6.60 (dt, J=2.3, 8.7 Hz, 2H), 3.95-3.60 (m, 2H), 3.16-2.62 (m, 1H), 2.06-1.53 (m, 10H), 1.27-0.97 (m, 2H). [M+H−H$_2$O]=241.1.

Intermediate 7. 2-[4-(2-Chlorophenyl)cyclohexyl]ethan-1-ol

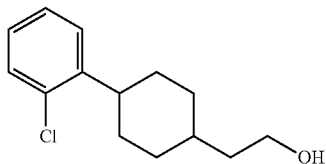 [SMILES: OCCC1CCC(c2ccccc2Cl)CC1]

Step 1. 2-(1,4-Dioxaspiro[4.5]decan-8-yl)ethan-1-ol. To a volume of THF (1000 mL) at 0° C. was slowly added LiAlH$_4$ (36.6 g, 964 mmol), followed by a dropwise addition of a solution of ethyl 2-(1,4-dioxaspiro[4.5]decan-8-yl)acetate (220 g, 964 mmol) in THF (1000 mL). The suspension was stirred at 0° C. for 1 h. Upon completion of the reaction, as monitored by TLC, the reaction was maintained at 0° C. and water (36 mL) was added dropwise, then a solution of NaOH (10%, 36 mL) was added dropwise, followed by water (110 mL). The resulting suspension was stirred at 25° C. for 30 min, and MgSO$_4$ (50 g) was added. The suspension was stirred at 20° C. for 1 h. The reaction was conducted under identical conditions a total of 3 times and the combined suspension filtered and the filter cake washed with EtOAc (1 L×5). The filtrate was concentrated to provide the title compound (456 g, 85%) as a colorless gum, which was used directly in the next step without further purification. $^1$H NMR (400 MHz, CDCl$_3$) δ 3.94 (s, 4H), 3.68 (t, J=5.6 Hz, 2H), 1.75-1.71 (m, 4H), 1.54-1.44 (m, 5H), 1.28-1.25 (m, 2H).

Step 2. 8-(2-(Benzyloxy)ethyl)-1,4-dioxaspiro[4.5]decane. To a solution of 2-(1,4-dioxaspiro[4.5]decan-8-yl)ethan-1-ol (228 g, 1.2 mol) in DMF (1.2 L) at 0-10° C. was added NaH (58.8 g, 1.5 mol, 60% purity), then the solution was stirred at 20° C. for 1 h. Then the reaction mixture was cooled to at 0° C. and benzyl bromide (159 mL, 1.3 mol) was added dropwise then the solution was stirred at 20° C. for 2 h. Upon completion of the reaction, as determined by TLC the suspension was poured into cold water (4 L). The reaction was repeated under identical conditions and the combined reaction mixtures extracted with MTBE (2 L×3). The combined organic layers were washed with water (1 L) and brine (1 L), dried over Na$_2$SO$_4$, filtered and concentrated. The crude product was purified by column chromatography (silica gel, 10:1 petroleum ether/EtOAc) to provide the title compound (600 g, 89%) as a colorless oil. $^1$H NMR (400 MHz, CDCl$_3$) δ 7.37-7.27 (m, 5H), 4.51 (s, 2H), 3.94 (s, 4H), 3.51 (t, J=5.6 Hz, 2H), 1.75-1.71 (m, 4H), 1.58-1.53 (m, 5H), 1.27-1.24 (m, 2H).

Step 3. 4-(2-(Benzyloxy)ethyl)cyclohexan-1-one. To a solution of 8-(2-(benzyloxy)ethyl)-1,4-dioxaspiro[4.5]decane (300 g, 1.1 mol) in acetone (500 mL) at 25° C. was added HCl (2 M, 1.1 L). The solution was stirred at 50° C. for 3 h. Upon completion of the reaction, as determined by TLC (7:1 Petroleum ether/EtOAc, R$_f$=0.45), the solution was concentrated. The reaction was repeated under identical conditions and the combined reaction residues extracted with EtOAc (1 L×3). The combined organic layers were washed with an aqueous solution of NaHCO$_3$ (1 L), water (500 mL) and brine (500 mL), dried over Na$_2$SO$_4$, filtered and concentrated to provide the title compound (480 g, 95%) as a light yellow solid. $^1$H NMR (400 MHz, CDCl$_3$) δ 7.36-7.30 (m, 5H), 4.53 (s, 2H), 3.55 (t, J=8.4 Hz, 2H), 2.37-2.32 (m, 4H), 2.07-2.03 (m, 2H), 1.96-1.91 (m, 1H), 1.66-1.63 (m, 2H), 1.44-1.41 (m, 2H).

Step 4. 4-(2-(Benzyloxy)ethyl)cyclohex-1-en-1-yl trifluoromethanesulfonate. To a solution of 4-(2-(benzyloxy)ethyl)cyclohexan-1-one (400 g, 172 mmol) in THF (600 mL) was added a solution of LiHMDS in THF (1 M, 194 mL, 194 mmol). The reaction mixture was stirred at −20° C. for 1 h. Then a solution of 1,1,1-trifluoro-N-phenyl-N-(trifluoromethylsulfonyl) methanesulfonamide (73.9 g, 207 mmol) in THF (200 mL) was added dropwise. After addition, the solution was warmed to 20° C. and stirred for another 3 h. Upon completion of the reaction, as determined by TLC (6:1 petroleum ether/EtOAc, R$_f$=0.6), the reaction was quenched with a cold NH$_4$Cl solution (1000 mL) and then extracted with EtOAc (500 mL×3). The combined organic layers were washed with brine (500 mL), dried over Na$_2$SO$_4$, filtered and concentrated to give the crude product. The crude product was purified by column chromatography (silica gel, 20:1 petroleum ether/EtOAc) to provide the title compound (520 g, 83%) as a yellow oil. $^1$H NMR (400 MHz, CDCl$_3$) δ 7.43-7.27 (m, 5H), 5.73-5.71 (m, 1H), 4.51 (s, 2H), 3.53 (t, J=8.4 Hz, 2H), 2.71-2.40 (m, 3H), 1.89-1.83 (m, 3H), 1.64-1.61 (m, 2H), 1.49-1.46 (m, 1H).

Step 5. 4-(2-(Benzyloxy)ethyl)-2'-chloro-2,3,4,5-tetrahydro-1,1'-biphenyl. A solution of 4-(2-(benzyloxy)ethyl)cyclohex-1-en-1-yl trifluoromethanesulfonate (18.0 g, 49.4 mmol), (2-chlorophenyl) boronic acid (9.3 g, 59.3 mmol), Na$_2$CO$_3$ (15.7 g, 148 mmol) and Pd(PPh$_3$)$_4$ (2.8 g, 2.5 mmol) in DME (200 mL) and H$_2$O (40 mL) was stirred at 85° C. for 16 h. Upon completion of the reaction, as determined by TLC (20:1 petroleum ether/EtOAc, R$_f$=0.5), the reaction was concentrated and the crude product was purified by column chromatography (silica gel, 30:1 petroleum ether/EtOAc) to provide the title compound (10.5 g, 65%) as a yellow oil. ¹H NMR (400 MHz, CDCl₃) δ 7.38-7.33 (m, 6H), 7.19-7.16 (m, 3H), 5.64 (s, 1H), 4.55 (s, 2H), 3.59 (t, J=6.8 Hz, 2H), 2.38-2.29 (m, 3H), 1.89-1.86 (m, 3H), 1.72-1.66 (m, 2H), 1.45-1.43 (m, 1H).

Step 6. 2-(4-(2-Chlorophenyl)cyclohexyl)ethan-1-ol. A suspension of 4-(2-(benzyloxy)ethyl)-2'-chloro-2,3,4,5-tetrahydro-1,1'-biphenyl (24.0 g, 73.4 mmol) and PtO₂ (1.2 g, 5.1 mmol) in EtOAc (200 mL) was stirred at 25° C. under a H₂ atmosphere (30 psi) for 50 min. Upon completion of the reaction, as determined by TLC (3:1 petroleum ether/EtOAc, R_f=0.3), the suspension was filtered and the filtrate was concentrated. The crude product was purified by column chromatography (silica gel, 10:1 to 5:1 petroleum ether/EtOAc) to provide the title compound (10.0 g, 57%) as a light yellow oil. ¹H NMR (400 MHz, CDCl₃) δ 7.35-7.24 (m, 3H), 7.22-7.12 (m, 1H), 3.76-3.72 (m, 2H), 3.07-2.97 (m, 1H), 1.93-1.91 (m, 3H), 1.77-1.73 (m, 8H), 1.20-1.14 (m, 1H).

Intermediate 8. 2-[4-(2-Chloro-3-fluorophenyl)cyclohexyl]ethan-1-ol

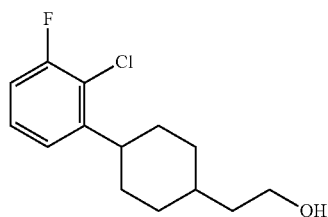 [SMILES: OCCC1CCC(c2cccc(F)c2Cl)CC1]

Step 1. 2-(4-(2-(Benzyloxy)ethyl)cyclohex-1-en-1-yl)-4,4,5,5-tetramethyl-1,3,2-dioxaborolane. A suspension of 4-(2-(benzyloxy)ethyl)cyclohex-1-en-1-yl trifluoromethanesulfonate (Intermediate 7, Step 4, 100 g, 220 mmol), Pin₂B₂ (66.9 g, 263 mmol), KOAc (53.9 g, 549 mmol) and Pd(dppf)Cl₂·CH₂Cl₂ (9.0 g, 11.0 mmol) in dioxane (800 mL) was degassed with N₂ for three times and then stirred at 70° C. for 20 h. Upon completion of the reaction, as determined by TLC (8:1 petroleum ether/EtOAc, R_f=0.45), the reaction suspension was concentrated, and the residue was purified by column chromatography (silica gel, 100:1 to 10:1 petroleum ether/EtOAc) to provide the title compound (110 g, 73%) as light yellow oil. ¹H NMR (400 MHz, DMSO) δ 7.46-7.17 (m, 5H), 6.41 (d, J=2.2 Hz, 1H), 4.45 (s, 2H), 3.48 (t, J=6.5 Hz, 2H), 2.24-2.03 (m, 2H), 2.02-1.87 (m, 1H), 1.78-1.57 (m, 3H), 1.50 (td, J=6.8, 14.2 Hz, 2H), 1.32-1.15 (m, 13H).

Step 2. 4-(2-(Benzyloxy)ethyl)-2'-chloro-3'-fluoro-2,3,4,5-tetrahydro-1,1'-biphenyl. A suspension of 2-(4-(2-(benzyloxy)ethyl)cyclohex-1-en-1-yl)-4,4,5,5-tetramethyl-1,3,2-dioxaborolane (30.0 g, 87.6 mmol), 1-bromo-2-chloro-3-fluoro-benzene (22.0 g, 105 mmol), K₂CO₃ (18.2 g, 131 mmol) and Pd(dppf)Cl₂·CH₂Cl₂ (3.6 g, 4.4 mmol) in DMF (200 mL) was degassed with N₂ (×5), and stirred at 100° C. for 16 h. Upon completion of the reaction, as determined by TLC (6:1 petroleum ether/EtOAc, R_f=0.6) the reaction suspension was quenched with water (500 mL), and extracted with EtOAc (100 mL×3). The combined organic layers were washed with water (100 mL) and brine (100 mL), dried over Na₂SO₄, filtered and concentrated. The crude product was purified by column chromatography (silica gel, 100:1 to 20:1 petroleum ether/EtOAc) to provide the title compound (21.0 g, 69%) as a yellow oil. ¹H NMR (400 MHz, CDCl₃) δ 7.37-7.30 (m, 5H), 7.16-7.14 (m, 1H), 7.04-7.02 (m, 1H), 6.96-6.94 (m, 1H), 5.67-5.66 (m, 1H), 4.55 (s, 2H), 3.59 (t, J=8.4 Hz, 2H), 2.35-2.30 (m, 3H), 1.89-1.86 (m, 3H), 1.70-1.68 (m, 2H), 1.45-1.42 (m, 1H).

Step 3. 2-(4-(2-Chloro-3-fluorophenyl)cyclohexyl)ethan-1-ol. The title compound was synthesized according to Intermediate 7, Step 6, using 4-(2-(benzyloxy)ethyl)-2'-chloro-3'-fluoro-2,3,4,5-tetrahydro-1,1'-biphenyl. The title compound as a mixture of cis and trans isomers was obtained as a light yellow oil (11.3 g, 76%). ¹H NMR (400 MHz, CDCl₃) δ 7.23-7.18 (m, 1H), 7.09-6.96 (m, 2H), 3.76-3.71 (m, 2H), 3.09-2.98 (m, 1H), 1.96-1.90 (m, 3H), 1.76-1.71 (m, 6H), 1.57-1.42 (m, 2H), 1.20-1.17 (m, 1H).

Intermediate 9. 2-[4-(2-Chloro-4,6-difluorophenyl)cyclohexyl]ethan-1-ol

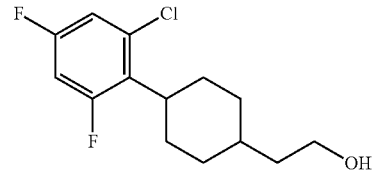 [SMILES: OCCC1CCC(c2c(F)cc(F)cc2Cl)CC1]

Step 1. 4-(2-(Benzyloxy)ethyl)-2'-chloro-4',6'-difluoro-2,3,4,5-tetrahydro-1,1'-biphenyl. In a sealed microwave tube, a mixture of 2-{4-[2-(benzyloxy)ethyl]cyclohex-1-en-1-yl}-4,4,5,5-tetramethyl-1,3,2-dioxaborolane (Intermediate 8, Step 1, 350 mg, 1.02 mmol), [1,1'-bis(diphenylphosphino)ferrocene]dichloropalladium(II) (37.4 mg, 0.05 mmol), 2-bromo-1-chloro-3,5-difluorobenzene (279 mg, 1.23 mmol) and sodium carbonate (1.28 mL, 2 M, 2.56 mmol) in dioxane (5.11 mL) was heated at 70° C. for 20 hours. Upon completion of the reaction, as determined by LCMS, the reaction mixture was filtered through celite, washed thoroughly with EtOAc, and purified via flash chromatography (silica gel, 0-20% EtOAc/Heptanes) to provide the title compound as a yellow oil (216 mg, 58.2%). ¹H NMR (400 MHz, CDCl₃) δ 7.49-7.31 (m, 5H), 6.99 (d, J=8.3 Hz, 1H), 6.77 (dt, J=2.3, 8.9 Hz, 1H), 5.68 (br s, 1H), 4.59 (s, 2H), 3.63 (t, J=6.6 Hz, 2H), 2.48-2.13 (m, 3H), 2.02-1.84 (m, 3H), 1.82-1.68 (m, 2H), 1.59-1.40 (m, 1H).

Step 2. 2-(4-(2-Chloro-4,6-difluorophenyl)cyclohexyl)ethan-1-ol. To a solution of 2-{4-[2-(benzyloxy)ethyl]cyclohex-1-en-1-yl}-1-chloro-3,5-difluorobenzene (220 mg, 0.61 mmol) in ethyl acetate (4.40 mL) was added platinum(IV) oxide (20.7 mg, 0.09 mmol). The reaction was placed under hydrogen (100 psi) for 4 hours. Upon completion of the reaction, as determined by LCMS, the mixture was purified using flash chromatography (0-50% EtOAc/heptanes) to obtain the title compound as a clear semi-solid, (65 mg, 39%), as a mixture of cis and trans isomers. ¹H NMR (400 MHz, CDCl₃) δ 6.94 (td, J=2.1, 8.2 Hz, 1H), 6.80-6.47 (m, 1H), 3.74 (t, J=6.8 Hz, 2H), 3.38-2.97 (m, 1H), 2.11-2.01 (m, 1H), 2.00-1.93 (m, 1H), 1.89 (d, J=11.2 Hz, 1H), 1.83-1.68 (m, 5H), 1.60-1.50 (m, 2H), 1.19-1.06 (m, 1H). [M+H−H₂O]= 257.1.

Intermediate 10. 2-[4-(3-Methylpyridin-2-yl)cyclohexyl]ethan-1-ol

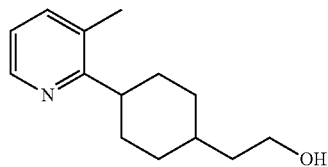 [SMILES: Cc1cccnc1C1CCC(CCO)CC1]

Step 1. 2-(4-(2-(Benzyloxy)ethyl)cyclohex-1-en-1-yl)-3-methylpyridine. The title compound was synthesized according to Intermediate 8, Step 2 using the appropriate starting material substitutions. $^1$H NMR (400 MHz, CDCl$_3$) δ 8.40 (d, J=4.4 Hz, 1H), 7.47 (d, J=8.0 Hz, 1H), 7.37-7.27 (m, 5H), 7.04-7.07 (m, 1H), 5.73-5.72 (m, 1H), 4.54 (s, 2H), 3.59 (t, J=8.4 Hz, 2H), 2.40-2.31 (m, 6H), 1.92-1.87 (m, 3H), 1.71-1.66 (m, 2H), 1.49-1.46 (m, 1H).

Step 2. 2-[4-(3-Methylpyridin-2-yl)cyclohexyl]ethan-1-ol. A suspension of 2-(4-(2-(benzyloxy)ethyl)cyclohex-1-en-1-yl)-3-methylpyridine (20.0 g, 65.1 mmol), Pd/C (5 g) and HCl (19.8 g, 195 mmol, 36% purity) in MeOH (200 mL) was stirred at 30° C. under an H$_2$ atmosphere (50 psi) for 4 h. Upon completion of the reaction, as determined by LCMS, the reaction suspension was filtered and the filter cake was washed with MeOH (50 mL×3). The combined filtrate was concentrated to give a residue, then a saturated aqueous solution of NaHCO$_3$ was added to pH=8, and extracted with EtOAc (50 mL×3). The combined organic layers were washed with brine (50 mL), dried over Na$_2$SO$_4$, filtered and concentrated. The crude product was purified by column chromatography (silica gel, 10:1 to 1:1 petroleum ether/EtOAc) to provide the title compound as a mixture of cis and trans isomers (9.0 g, 63%) as a light yellow oil. $^1$H NMR (400 MHz, CDCl$_3$) δ 8.40 (s, 1H), 7.40-7.38 (m, 1H), 7.01-6.98 (m, 1H), 3.75-3.70 (m, 2H), 2.88-2.83 (m, 1H), 2.33 (s, 3H), 1.94-1.56 (m, 11H), 1.17-1.12 (m, 1H).

Intermediate 11. 2-[4-(3-Chloropyridin-2-yl)cyclohexyl]ethan-1-ol

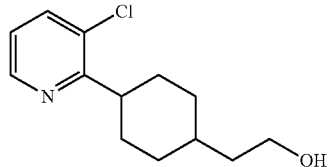 [SMILES: OCCC1CCC(c2ncccc2Cl)CC1]

Step 1. 2-(4-(2-(Benzyloxy)ethyl)cyclohex-1-en-1-yl)-3-chloropyridine. The title compound was synthesized according to Intermediate 8, Step 2 using the appropriate starting material substitutions. $^1$H NMR (400 MHz, CDCl$_3$) δ 8.50-8.45 (m, 1H), 7.68 (d, J=4.4 Hz, 1H), 7.37-7.29 (m, 5H), 7.12-7.09 (m, 1H), 6.01 (s, 1H), 4.54 (s, 2H), 3.59 (t, J=6.8 Hz, 2H), 2.49-2.34 (m, 3H), 1.93-1.90 (m, 3H), 1.73-1.65 (m, 2H), 1.49-1.47 (m, 1H).

Step 2. 2-(4-(2-(Benzyloxy)ethyl)cyclohexyl)-3-chloropyridine. A suspension of 2-(4-(2-(benzyloxy)ethyl)cyclohex-1-en-1-yl)-3-chloropyridine (16.0 g, 48.8 mmol), Rh(PPh$_3$)$_3$Cl (1.8 g, 2.0 mmol) in MeOH (200 mL) was stirred at 50° C. under an H$_2$ atmosphere (50 psi) for 3 h. Upon completion of the reaction, as determined by TLC (3:1 petroleum ether/EtOAc, R$_f$=0.4), the solution was concentrated and the crude product was purified by column chromatography (silica gel, 10:1 to 2:1 petroleum ether/ethyl acetate) to provide the title compound (15.0 g, 93%) as a yellow oil. $^1$H NMR (400 MHz, CDCl$_3$) δ 8.47-8.42 (m, 1H), 7.63-7.61 (m, 1H), 7.36-7.27 (m, 5H), 7.08-7.05 (m, 1H), 4.53 (s, 2H), 3.57-3.53 (m, 2H), 3.20-3.16 (m, 1H), 1.98-1.87 (m, 4H), 1.68-1.58 (m, 6H), 1.16-1.13 (m, 1H).

Step 3. 2-[4-(3-Chloropyridin-2-yl)cyclohexyl]ethan-1-ol. To a solution of 2-(4-(2-(benzyloxy)ethyl)cyclohexyl)-3-chloropyridine (13.0 g, 39.4 mmol) in DCM (150 mL) at 0° C. was added a solution of BCl$_3$ in DCM (1 M, 158 mL, 158 mmol) dropwise. Then the solution was stirred at 0° C. for 1 h. Upon completion of the reaction, as determined by TLC (2:1 petroleum ether/EtOAc, R$_f$=0.2), the solution was poured into a saturated aqueous solution of NaHCO$_3$ (100 mL) and extracted with DCM (50 mL×3). The combined organic layers were washed with brine (50 mL), dried over Na$_2$SO$_4$, filtered and concentrated. The crude product was purified by column chromatography (silica gel, 10:1 to 2:1 petroleum ether/EtOAc) to provide the title compound as a mixture of cis and trans isomers (11.3 g, 86%) as a yellow oil. $^1$H NMR (400 MHz, CDCl$_3$) δ 8.44 (d, J=4.4 Hz, 1H), 7.62-7.60 (m, 1H), 7.07-7.04 (m, 1H), 3.74-3.69 (m, 2H), 3.21-3.14 (m, 1H), 1.92-1.66 (m, 9H), 1.54-1.53 (m, 2H), 1.17-1.10 (m, 1H).

Intermediate 12. 2-[(cis)-4-(4-Fluoro-2-methylphenyl)cyclohexyl]ethan-1-ol

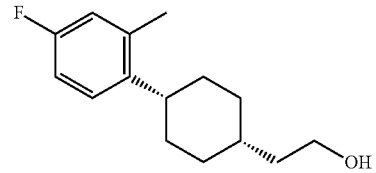 [SMILES: Cc1cc(F)ccc1[C@H]1CC[C@@H](CCO)CC1]

Step 1. 8-(4-Fluoro-2-methylphenyl)-1,4-dioxaspiro[4.5]decan-8-ol. To a solution of 4-fluoro-1-iodo-2-methylbenzene (43.6 mL, 330 mmol) in 2-methyltetrahydrofuran (650 mL) at 0° C. was slowly added a solution of isopropylmagnesium chloride in tetrahydrofuran (2 M, 165 mL, 330 mmol) over 30 minutes. The reaction was allowed to warm to room temperature and stirred for an additional 30 minutes at room temperature. A suspension of 1,4-dioxaspiro[4.5]decan-8-one (43.0 g, 275 mmol) in 2-methyltetrahydrofuran (65 mL) was added over 10 minutes. A mild reaction exotherm was observed and an ice bath was introduced for 10 minutes to prevent excess heating, then the ice bath was removed. The reaction mixture was stirred at room temperature for 1 h, poured into a saturated solution of ammonium chloride (1000 mL), extracted with EtOAc (3×200 mL), then the combined organics were dried (Na$_2$SO$_4$) and concentrated under reduced pressure. The crude material taken up in a minimum amount of dichloromethane (200 mL) and the product precipitated upon standing. Hexanes (~100 mL) was added, the suspension was filtered and the solid was washed with additional hexanes (100 mL) to provide the title compound as a white powder (52 g, 71%). $^1$H NMR (400 MHz, CDCl$_3$) δ 7.42 (dd, J=6.1, 8.7 Hz, 1H), 6.92-6.75 (m, 2H), 4.07-3.91 (m, 4H), 2.61 (s, 3H), 2.35-2.05 (m, 4H), 2.03-1.88 (m, 2H), 1.69 (d, J=11.5 Hz, 2H). [M+H−H$_2$O]=249.2.

Step 2. 8-(4-Fluoro-2-methylphenyl)-1,4-dioxaspiro[4.5]dec-7-ene. To a solution of 8-(4-fluoro-2-methylphenyl)-1,4-dioxaspiro[4.5]decan-8-ol (50.6 g, 190 mmol) in toluene (253 mL), was added ethane-1,2-diol (253 mL) followed by p-toluenesulfonic acid (8.18 g, 47.5 mmol) and the reaction was heated to 120° C. under Dean-Stark conditions for 15 h. The reaction was poured into water (1000 mL), the layers were separated and the aqueous layer was extracted with toluene (3×100 mL). The combined organics were washed with a saturated solution of sodium hydrogencarbonate (500 mL), dried (Na$_2$SO$_4$), and concentrated under reduced pressure then purified by flash chromatography (silica, 0-100% EtOAc in hexanes) to yield the title compound as a colorless oil (42 g, 89%). [M+H]=249.2

Step 3. 8-(4-Fluoro-2-methylphenyl)-1,4-dioxaspiro[4.5]decane. To a solution of 8-(4-fluoro-2-methylphenyl)-1,4-dioxaspiro[4.5]dec-7-ene (42.0 g, 169 mmol) in ethyl acetate (420 mL) was added cesium carbonate (5.51 g, 16.9 mmol) followed by platinum(IV) oxide (1.92 g, 8.46 mmol) and the reaction was stirred vigorously at room temperature under an atmosphere of hydrogen (200 PSI) in a high pressure reactor for 15 h. The resulting suspension filtered through celite, the cake was washed with additional EtOAc (200 mL), and the solvent was concentrated under reduced pressure to provide the title compound as a colorless oil (41.8 g, 99%). $^1$H NMR (400 MHz, CDCl$_3$) δ 7.21 (dd, J=5.9, 9.4 Hz, 1H), 6.86 (td, J=2.8, 7.2 Hz, 2H), 4.01 (s, 4H), 2.74 (tt, J=4.8, 9.7 Hz, 1H), 2.35 (s, 3H), 1.90 (d, J=9.3 Hz, 2H), 1.83-1.68 (m, 6H).

Step 4. 4-(4-Fluoro-2-methylphenyl)cyclohexanone. To a solution of 8-(4-fluoro-2-methylphenyl)-1,4-dioxaspiro[4.5]decane (41.8 g, 167 mmol) in toluene (209 mL), was added water (418 mL) followed by p-toluenesulfonic acid (28.8 g, 170 mmol) in one portion and the biphasic reaction was heated at 90° C. with vigorous stirring for 15 h. The layers were separated, organics were washed with a saturated solution of sodium hydrogen carbonate (500 mL) and water (500 mL) and the organics concentrated under reduced pressure to give the title compound as a waxy, white powder (34.1 g, 99%). $^1$H NMR (400 MHz, CDCl$_3$) δ 7.15 (dd, J=5.8, 8.3 Hz, 1H), 6.97-6.83 (m, 2H), 3.20 (tt, J=3.2, 12.1 Hz, 1H), 2.54 (dd, J=4.3, 9.0 Hz, 4H), 2.42 (s, 3H), 2.21-2.10 (m, 2H), 1.99-1.84 (m, 2H). [M+H]=207.2.

Step 5. 2-((cis)-4-(4-fluoro-2-methylphenyl)cyclohexyl)ethan-1-ol. To a solution of sodium tert-butoxide (7.93 g, 80.0 mmol) in tetrahydrofuran (150 mL) was added tert-butyl 2-(diethoxyphosphoryl)acetate (19.2 mL, 80 mmol) and the reaction heated at 50° C. for 0.5 h. The reaction was cooled to 0° C. and a solution of 4-(4-fluoro-2-methylphenyl)cyclohexanone (15.0 g, 72 mmol) in tetrahydrofuran (30 mL) was added dropwise over ~2 minutes. The reaction was allowed to warm to room temperature and stirred at room temperature for 1 h. The reaction was cooled to −15° C., a solution of L-Selectride in tetrahydrofuran (1 M, 160 mL, 160 mmol) was added dropwise and the reaction was stirred at −15° C. for 4 h. Additional L-Selectride in tetrahydrofuran (1 M, 124 mL, 124 mmol) was added dropwise, the reaction was slowly warmed to room temperature and stirred for 15 h, then heated for an additional 15 h at 50° C. The reaction was cooled to 0° C. and quenched by careful dropwise addition of H$_2$O (20 mL). MTBE (50 mL) added followed by dropwise addition of a sodium hydroxide solution (1 M, 182 mL, 182 mmol) and the reaction was stirred at room temperature for 10 min. The reaction was cooled to 0° C., then a 30% hydrogen peroxide solution (24 mL, 1091 mmol) was added slowly over 30 min at 0° C. (caution: exotherm). The mixture was stirred at 50° C. for 3 h. The organic layer was diluted with heptanes (100 mL) and washed with a 1 M sodium hydroxide solution (50 mL) and a saturated ammonium chloride solution (50 mL). The organic layer was separated, dried (Na$_2$SO$_4$) and concentrated under reduced pressure to give the title compound as an oil with a cis to trans ratio of >98:2 (17.1 g, 99%). [M+H−H$_2$O]=219.2.

Intermediate 13. 3-[4-(2-Hydroxyethyl)cyclohexyl]-2-methylbenzonitrile

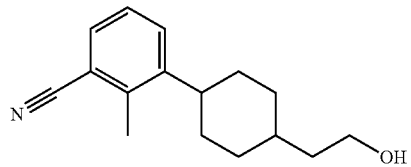 [SMILES: Cc1c(C#N)cccc1C1CCC(CCO)CC1]

Step 1. Ethyl 2-(3'-cyano-2'-methyl-2,3,4,5-tetrahydro-[1,1'-biphenyl]-4-yl)acetate. The title compound was prepared in a manner analogous to Intermediate 5, Step 3 using 3-bromo-2-methylbenzonitrile and any appropriate starting material substitutions. [M+H]=284.2.

Step 2. Ethyl 2-(4-(3-cyano-2-methylphenyl)cyclohexyl)acetate. To a solution of ethyl 2-(3'-cyano-2'-methyl-2,3,4,5-tetrahydro-[1,1'-biphenyl]-4-yl)acetate (190 mg, 0.671 mmol) in 2-propanol (1.34 mL) was added phenylsilane (82.7 µL, 0.671 mmol) followed by a solution of tert-butyl hydroperoxide in decane (5-6 M, 201 µL, 1.0 mmol). The mixture was degassed by bubbling N$_2$ for 5 min. then [Mn(dpm)$_3$] (28.3 mg, 0.0671 mmol) was added quickly in one portion. The reaction mixture was degassed for an additional 30 seconds and subsequently stirred at room temperature. After 1 h, the reaction was complete, as determined by LCMS analysis. The reaction mixture was diluted with DCM (2 mL) and filtered through a small pad of Celite®. The filtrate was concentrated in vacuo and the resulting crude material was purified by flash chromatography (SiO$_2$, 0-60% EtOAc/Hexanes) to provide the title compound (118 mg, 61%) as a colorless oil, as a mixture of cis and trans isomers. $^1$H NMR (400 MHz, CDCl$_3$) δ 7.57-7.40 (m, 2H), 7.28-7.18 (m, 1H), 4.27-4.07 (m, 2H), 2.93-2.68 (m, 1H), 2.56-2.23 (m, 5H), 2.01-1.41 (m, 9H), 1.35-1.12 (m, 3H).

Step 3. 3-(4-(2-Hydroxyethyl)cyclohexyl)-2-methylbenzonitrile. To a stirring solution of ethyl 2-[4-(3-cyano-2-methylphenyl)cyclohexyl]acetate (110 mg, 0.39 mmol) in tetrahydrofuran (963.6 µL) at −78° C. was added lithium aluminum hydride (1.0 M, 848 µL, 0.86 mmol) dropwise. The colorless solution was stirred at −78° C. for 10 min., until the reaction had reached completion, as monitored by LCMS. The reaction mixture was quenched by the addition of EtOAc (10 mL) then a solution of Rochelle's salt was added and the reaction mixture was agitated. The organic layer was separated and was extracted with EtOAc (10 mL). The combined organic extracts were concentrated in vacuo to give the title compound as a crude product as a mixture of cis and trans isomers (94 mg, 100%), which was used in the next step without further purification. [M+H]=244.2.

Intermediate 14. 4-(2-((tert-Butoxycarbonyl)(tetrahydro-2H-pyran-4-yl)amino)ethyl)cyclohex-1-en-1-yl trifluoromethanesulfonate

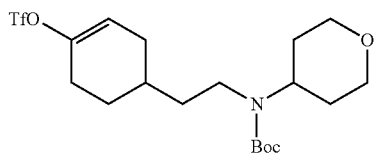 [SMILES: CC(C)(C)OC(=O)N(CCC1CC=C(OS(=O)(=O)C(F)(F)F)CC1)C1CCOCC1]

Step 1. 2-(1,4-Dioxaspiro[4.5]decan-8-yl)ethyl 4-methylbenzenesulfonate. To a solution of 2-{1,4-dioxaspiro[4.5]decan-8-yl}ethan-1-ol (11.0 g, 59.1 mmol), 4-dimethylaminopyridine (360.8 mg, 2.95 mmol), and triethylamine (9.85 mL, 71.1 mmol) in dichloromethane (59.1 mL) was added 4-toluenesulfonyl chloride (13.5 g, 70.9 mmol), portionwise. The mixture was stirred at room temperature for 3 h, then the resulting suspension was poured into a saturated aqueous solution of NaHCO$_3$ (100 mL). The aqueous layer was extracted with EtOAc (3×100 mL) then the solvent was removed in vacuo. The remaining residue was purified by flash chromatography (silica, 0-100% EtOAc/hep) to provide the title compound as a colorless oil (18.2 g, 91%). $^1$H NMR (400 MHz, CDCl$_3$) δ 7.73-7.86 (m, 2H), 7.35 (d, J=7.95 Hz, 2H), 4.03-4.13 (m, 2H), 3.86-3.98 (m, 4H), 2.46 (s, 3H), 1.08-1.75 (m, 11H).

Step 2. tert-Butyl (2-(1,4-dioxaspiro[4.5]decan-8-yl)ethyl)(tetrahydro-2H-pyran-4-yl)carbamate. To a solution of tert-butyl N-(oxan-4-yl)carbamate (1.77 g, 8.81 mmol) in N,N-dimethylformamide (29.4 mL) was added sodium hydride (60 wt %, 353 mg, 8.81 mmol) in one portion. The mixture was stirred at room temperature for 10 min and then a solution of 2-(1,4-dioxaspiro[4.5]decan-8-yl)ethyl 4-methylbenzenesulfonate (3.00 g, 8.81 mmol) in DMF (10 mL) was added over 1 min., then the reaction mixture was stirred at 50° C. After 3 h, a second portion of sodium hydride (60 wt %, 353 mg, 8.81 mmol) was added and the reaction mixture was stirred at 50° C. overnight. After 16 h, the reaction mixture was cooled to room temperature, quenched by the addition of a saturated aq. solution of NH$_4$Cl (10 mL) and extracted with EtOAc (3×100 mL). The combined organics were concentrated in vacuo and the resulting crude mixture was purified by flash chromatography (0-100% EtOAc/hep) to provide the title compound (2.01 g, 62%). $^1$H NMR (400 MHz, CDCl$_3$) δ 3.85-4.17 (m, 7H), 3.35-3.52 (m, 2H), 3.05-3.17 (m, 2H), 1.22-1.84 (m, 24H).

Step 3. tert-Butyl (2-(4-oxocyclohexyl)ethyl)(tetrahydro-2H-pyran-4-yl)carbamate. To a solution of tert-butyl (2-(1,4-dioxaspiro[4.5]decan-8-yl)ethyl)(tetrahydro-2H-pyran-4-yl)carbamate (2.0 g, 5.41 mmol) in acetone (54.1 mL) was added iodine (137 mg, 0.54 mmol) was added in one portion. The orange solution was stirred at 60° C. overnight. After 16 h, the reaction mixture was complete, as determined by LCMS analysis. The solvent was removed in vacuo and the crude product was purified via flash chromatography (SiO$_2$, 0-100% EtOAc/hep) to yield the title compound (1.60 g, 91%). $^1$H NMR (400 MHz, CDCl$_3$) δ 4.41-3.93 (m, 3H), 3.53-3.35 (m, 2H), 3.16 (m, 2H), 2.50-2.24 (m, 4H), 2.17-1.98 (m, 2H), 1.88-1.36 (m, 18H).

Step 4. rac-4-(2-((tert-Butoxycarbonyl)(tetrahydro-2H-pyran-4-yl)amino)ethyl)cyclohex-1-en-1-yl trifluoromethanesulfonate. To a solution of tert-butyl (2-(4-oxocyclohexyl)ethyl)(tetrahydro-2H-pyran-4-yl)carbamate (2.0 g, 6.15 mmol) in tetrahydrofuran (20 mL) at −78° C. was slowly added a solution of lithium bis(trimethylsilyl)amide in THF (1.0 M, 7.37 mL; 7.38 mmol), keeping the internal temperature near −78° C. After stirring for 1 h at the same temperature, N,N-bis(trifluoromethylsulfonyl)-5-chloro-2-pyridylamine (2.90 g, 7.38 mmol) was added and the resulting yellow-orange mixture was stirred at room temperature for 20 h and subsequently quenched by the addition of water (100 mL). The resulting aqueous mixture was extracted with EtOAc (3×60 mL) and the combined organic extracts were concentrated in vacuo and dried over Na$_2$SO$_4$. The resulting crude product was purified by flash chromatography (0-100% EtOAc/Hep), to yield the title compound, which was used without further purification. $^1$H NMR (400 MHz, CDCl$_3$) δ 5.87-5.66 (m, 1H), 4.24-4.03 (m, 3H), 3.44 (m, 2H), 3.15 (m, 2H), 2.50-2.23 (m, 3H), 2.00-1.43 (m, 19H).

Intermediate 15. tert-Butyl (tetrahydro-2H-pyran-4-yl)(2-(4-(4,4,5,5-tetramethyl-1,3,2-dioxaborolan-2-yl)cyclohex-3-en-1-yl)ethyl)carbamate

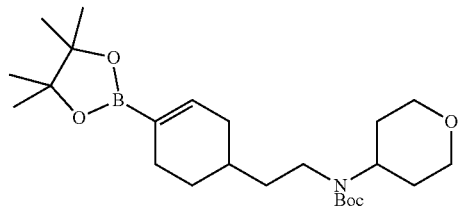 [SMILES: CC(C)(C)OC(=O)N(CCC1CC=C(B2OC(C)(C)C(C)(C)O2)CC1)C1CCOCC1]

rac-tert-Butyl (tetrahydro-2H-pyran-4-yl)(2-(4-(4,4,5,5-tetramethyl-1,3,2-dioxaborolan-2-yl)cyclohex-3-en-1-yl)ethyl)carbamate. A reaction vessel was charged with 4-(2-((tert-butoxycarbonyl)(tetrahydro-2H-pyran-4-yl)amino)ethyl)cyclohex-1-en-1-yl trifluoromethanesulfonate (2.50 g, 5.46 mmol), potassium acetate (1.07 g, 10.9 mmol), [1,1'-bis(diphenylphosphino)ferrocene]dichloropalladium(II) complex with dichloromethane (446 mg, 0.546 mmol), and bis(pinacolato)diboron (1.67 g, 6.55 mmol) in dioxane (18.2 mL). The mixture was purged with N$_2$, sealed and then stirred at 80° C. After 16 h, the reaction mixture was cooled to room temperature, diluted with EtOAc (100 mL) and washed with a saturated aqueous solution of NaHCO$_3$ (100 mL). The organic layer was separated, dried over Na$_2$SO$_4$ and concentrated in vacuo. The crude product was purified by flash chromatography (SiO$_2$, 0-30% EtOAc/Hexanes) to yield the target vinyl boronate (1.02 g, 43%) as an orange solid. $^1$H NMR (400 MHz, CDCl$_3$) δ 6.55 (m, 1H), 4.27-4.02 (m, 3H), 3.44 (m, 2H), 3.14 (m, 2H), 2.39-2.02, (m, 3H), 1.87-1.28 (m, 31H).

Intermediate 16. 2-(4-(3-Chloro-5-fluoropyridin-4-yl)cyclohexyl)ethan-1-ol

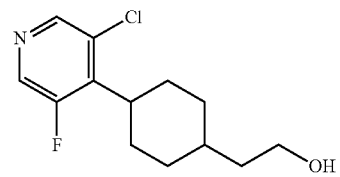 [SMILES: OCCC1CCC(c2c(F)cncc2Cl)CC1]

Step 1. Ethyl 2-(4-(3-chloro-5-fluoropyridin-4-yl)-4-hydroxycyclohexyl)acetate. To a solution of 2-bromo-3- chloro-5-fluoropyridine (5.03 g, 23.9 mmol) in tetrahydrofuran (60 mL) at −78° C. was added a solution of n-butyllithium in hexanes (2.5 M, 10.4 mL, 26.1 mmol) dropwise. The reaction mixture was allowed to stir at −78° C. for 1 h before the addition of ethyl 2-(4-oxocyclohexyl)acetate (3.85 mL, 21.7 mmol) in one portion. The reaction allowed to warm to room temperature and stirred for 1 h, then was quenched with a saturated solution of ammonium chloride (100 mL) and extracted with EtOAc (3×50 mL), combined organics dried ($Na_2SO_4$) and concentrated under reduced pressure. The residue was purified by flash chromatography on silica, eluting with 0-40% EtOAc in hexanes to yield the unexpected product as a colorless oil (2.65 g, 39%). [M+H]=316.1.

Step 2. Ethyl 2-(4-(3-chloro-5-fluoropyridin-4-yl)cyclohex-3-en-1-yl)acetate. To a solution of ethyl 2-(4-(3-chloro-5-fluoropyridin-4-yl)-4-hydroxycyclohexyl)acetate (2.6 g, 8.23 mmol) in toluene (26 mL) was added Burgess Reagent (2.35 g, 9.9 mmol) in one portion. The resulting mixture was stirred at 80° C. for 15 h, cooled to room temperature and concentrated under reduced pressure. The residue was purified by flash chromatography (silica, 0-40% EtOAc in hexanes) yield the desired product (1.8 g, 73%). $^1$H NMR (400 MHz, $CDCl_3$) δ 8.42 (s, 1H), 8.35 (s, 1H), 5.94-5.61 (m, 1H), 4.18 (q, J=7.2 Hz, 2H), 2.47-2.18 (m, 6H), 2.05-1.87 (m, 2H), 1.55 (dtd, J=5.4, 10.2, 12.9 Hz, 1H), 1.30 (t, J=7.2 Hz, 3H). [M+H]=298.1.

Step 3. Ethyl 2-(4-(3-chloro-5-fluoropyridin-4-yl)cyclohexyl)acetate. To a solution of ethyl 2-(4-(3-chloro-5-fluoropyridin-4-yl)cyclohex-3-en-1-yl)acetate (1.22 g, 4.10 mmol) in dry 2-propanol (16.4 mL) was added phenylsilane (0.51 mL, 4.10 mmol) followed by 2,4,8,10-tetra-tert-butyl-1λ$^3$,5,7λ$^3$,11-tetraoxa-6-manganaspiro[5.5]undeca-1,3,7,9-tetraene (0.17 g, 0.41 mmol) in one portion. Nitrogen bubbled through the suspension for 2 minutes before the dropwise addition of a 2-hydroperoxy-2-methylpropane solution in decane (5.0 M, 1.23 mL, 6.15 mmol) (caution: exothermic). The reaction was stirred for 6 h, diluted with EtOAc (100 mL), filtered through a pad of celite, partitioned between water and EtOAc (100 mL each), and layers were separated. The aqueous layer extracted with EtOAc (3×50 mL), organics washed with a saturated ammonium chloride solution (100 mL), dried ($Na_2SO_4$) and concentrated under reduced pressure. The residue was purified by flash chromatography on silica, eluting with 0-100% EtOAc in hexanes to yield the product (1.23 g, 66%). $^1$H NMR (400 MHz, $CDCl_3$) δ 8.39-8.35 (m, 1H), 8.30-8.24 (m, 1H), 4.17 (dq, J=3.1, 7.1 Hz, 2H), 3.27-3.09 (m, 1H), 2.55-2.51 (m, 1H), 2.46-2.24 (m, 1H), 2.11-1.54 (m, 9H), 1.29 (t, J=7.2 Hz, 3H). [M+H]=300.14.

Step 4. 2-(4-(3-Chloro-5-fluoropyridin-4-yl)cyclohexyl)ethan-1-ol. To a solution of ethyl 2-(4-(3-chloro-5-fluoropyridin-4-yl)cyclohexyl)acetate (800 mg, 2.67 mmol) in tetrahydrofuran (20 mL) at −78° C. was added a solution of DIBAL-H in THF (1.0 M, 8.01 mL, 8.01 mmol) and the reaction stirred at −78° C. for 0.5 h. The reaction was quenched with a 30% aqueous solution of Rochelle's salt (10 mL), diluted with DCM (20 mL), filtered and the filtrate was concentrated under reduced pressure. The residue was purified by flash chromatography on silica, eluting with 0-100% EtOAc in hexanes to yield the product (0.61 g, 89%) as a mixture of cis and trans isomers. [M+H]=258.12.

Intermediate 17. 2-(2',6'-Dichloro-2,3,4,5-tetrahydro-[1,1'-biphenyl]-4-yl)ethan-1-ol

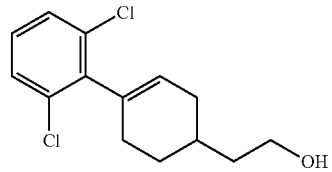 [SMILES: OCCC1CC=C(c2c(Cl)cccc2Cl)CC1]

Step 1. Ethyl 2-(4-(2,6-dichlorophenyl)-4-hydroxycyclohexyl)acetate. To a solution of 2-bromo-1,3-dichlorobenzene (22.6 g, 0.1 mol) in THF (200 mL) −78° C. was added n-BuLi (2.5 M in hexane, 40 mL, 0.1 mol) dropwise under $N_2$. After stirring for 1 h, a solution of ethyl 2-(4-oxocyclohexyl)acetate (18.4 g, 0.1 mol) in THF (100 mL) was added and the resulting mixture was stirred at −78° C. for 2 h. The reaction was quenched with brine (100 mL) and extracted with EtOAc (300 mL×2). The combined organic layer was dried over $Na_2SO_4$, filtered and concentrated to give the title compound (31 g) as a crude yellow oil, which was used for the next step without further purification.

Step 2. Ethyl 2-(2',6'-dichloro-2,3,4,5-tetrahydro-[1,1'-biphenyl]-4-yl)acetate. To a solution of crude ethyl 2-(4-(2,6-dichlorophenyl)-4-hydroxycyclohexyl)acetate (31 g) in toluene (150 mL) was added p-TSA (3.0 g, 17.4 mmol). The mixture was heated to reflux for 6 h. After cooling to rt the mixture was quenched with saturated aqueous $NaHCO_3$ (40 mL) and extracted with EtOAc (200 mL×2). The combined organic layer was dried over $Na_2SO_4$, filtered and concentrated to give a crude residue which was purified by column chromatography (silica gel. 100:1 PE/EtOAc) to afford the title compound (2.8 g, 9% yield for 2 steps) as a yellow oil. $^1$H NMR ($CDCl_3$, 400 MHz) δ 9.28 (d, J=8.0 Hz, 2H), 7.09 (t, J=8.0 Hz, 1H), 5.56 (s, 1H), 4.16 (q, J=7.2 Hz, 2H), 2.39-2.19 (m, 6H), 1.98-1.87 (m, 2H), 1.59-1.51 (m, 1H), 1.28 (t, J=7.2 Hz, 3H).

Step 3. 2-(2',6'-Dichloro-2,3,4,5-tetrahydro-[1,1'-biphenyl]-4-yl)ethan-1-ol. To the suspension of LiAlH$_4$ (0.78 g, 21.0 mmol) in THF (60 mL) was added a solution of ethyl 2-(2',6'-dichloro-2,3,4,5-tetrahydro-[1,1'-biphenyl]-4-yl)acetate (4.3 g, 13.8 mmol) at 0° C. The mixture was stirred at 0° C. for 2 h, then quenched with $H_2O$ (2 mL), NaOH (10%, 2 mL) and filtered. The filtrate was dried over $MgSO_4$, then concentrated to afford the crude product, which was purified by column chromatography (silica gel, 10:1 PE/EtOAc) to afford the title compound (3.6 g, 96.7% yield) as colorless oil. $^1$H NMR ($CDCl_3$, 400 MHz) δ 9.28 (d, J=8.0 Hz, 2H), 7.09 (t, J=8.0 Hz, 1H), 5.57 (s, 1H), 3.78 (t, J=6.4 Hz, 2H), 2.40-2.32 (m, 2H), 2.18-2.12 (m, 1H), 1.93-1.82 (m, 3H), 1.69-1.61 (m, 2H), 1.57-1.51 (m, 1H), 1.35 (br s, 1H).

Intermediate 18. 2-{4-[4-Fluoro-2-(trifluoromethyl)phenyl]cyclohexyl}ethan-1-ol

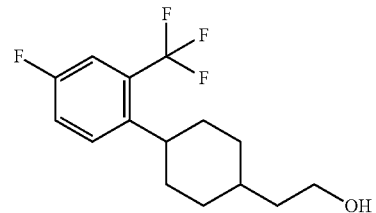 [SMILES: OCCC1CCC(c2ccc(F)cc2C(F)(F)F)CC1]

The title compound was synthesized in a manner analogous to Intermediate 6, using the appropriate starting material substitutions. $^1$H NMR (400 MHz, CDCl$_3$) δ 7.49-7.36 (m, 1H), 7.31 (dd, J=2.3, 9.3 Hz, 1H), 7.19 (t, J=8.2 Hz, 1H), 3.74 (t, J=6.5 Hz, 2H), 3.06-2.71 (m, 1H), 2.01-1.42 (m, 11H), 1.28-1.04 (m, 1H).

Intermediate 19. 2-[4-(3,4-Difluoro-2-methylphenyl)cyclohexyl]ethan-1-ol

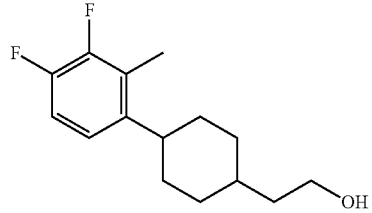 [SMILES: Cc1c(C2CCC(CCO)CC2)ccc(F)c1F]

The title compound was synthesized in a manner analogous to Intermediate 6, using the appropriate starting material substitutions. [M+CH$_3$CN+H]=296.2 Intermediate 20. 2-[4-(2-Chloro-6-fluorophenyl)cyclohexyl]ethan-1-ol

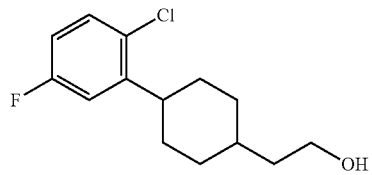 [SMILES: OCCC1CCC(c2cc(F)ccc2Cl)CC1]

The title compound was synthesized in a manner analogous to Intermediate 8, using the appropriate starting material substitutions. $^1$H NMR (400 MHz, CDCl$_3$) δ 7.15 (d, J=8.0 Hz, 1H), 7.10-7.05 (m, 1H), 6.95-6.85 (m, 1H), 3.74 (t, J=6.4 Hz, 2H), 3.19 (q, J=12.8 Hz, 1H), 2.15-1.05 (m, 12H). [M−H$_2$O+H]=239.1

Intermediate 21. 2-[4-(2-Chloro-5-fluorophenyl)cyclohexyl]ethan-1-ol

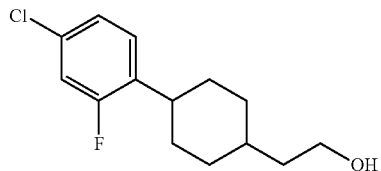 [SMILES: OCCC1CCC(c2ccc(Cl)cc2F)CC1]

The title compound was synthesized in a manner analogous to Intermediate 8, using the appropriate starting material substitutions. $^1$H NMR (400 MHz, CDCl$_3$) δ 7.31-7.28 (m, 1H), 6.98 (t, J=10.0 Hz, 2H), 6.86-6.80 (m, 1H), 3.75-3.70 (m, 2H), 3.05-2.90 (m, 1H), 1.92 (d, J=11.6 Hz, 2H), 1.76-1.65 (m, 4H), 1.57-1.50 (m, 2H), 1.30-1.15 (m, 3H). [M−H$_2$O+H]=239.1

Intermediate 22. 2-[4-(4-Chloro-2-fluorophenyl)cyclohexyl]ethan-1-ol

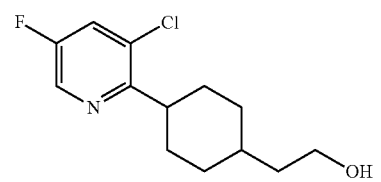 [SMILES: OCCC1CCC(c2ncc(F)cc2Cl)CC1]

The title compound was synthesized in a manner analogous to Intermediate 8, using the appropriate starting material substitutions. $^1$H NMR (400 MHz, CDCl$_3$) δ 7.17-7.01 (m, 3H), 3.75-3.70 (m, 2H), 2.84-2.76 (m, 1H), 1.94-1.88 (m, 3H), 1.74-1.64 (m, 5H), 1.55-1.41 (m, 3H), 1.16-1.13 (m, 1H). [M−H$_2$O+H]=239.1

Intermediate 23. 2-[4-(3-Chloro-5-fluoropyridin-2-yl)cyclohexyl]ethan-1-ol

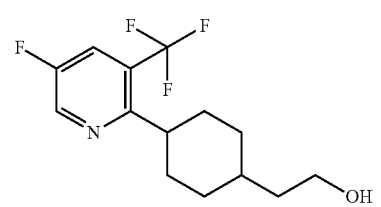 [SMILES: OCCC1CCC(c2ncc(F)cc2C(F)(F)F)CC1]

The title compound was synthesized in a manner analogous to Intermediate 9, Steps 1-3, 5 and 6, using the appropriate starting material substitutions. $^1$H NMR (400 MHz, CDCl$_3$) δ 8.38-8.32 (m, 1H), 7.42-7.40 (m, 1H), 3.73-3.69 (m, 2H), 3.21-3.08 (m, 1H), 1.91-1.52 (m, 11H), 1.16-1.12 (m, 1H). [M+H]=258.

Intermediate 24. 2-{4-[5-Fluoro-3-(trifluoromethyl)pyridin-2-yl]cyclohexyl}ethan-1-ol The title compound was synthesized in a manner analogous to Intermediate 9 Step 1-3, 5 and 6, using the appropriate starting material substitutions. [M+H]=292.2.

Intermediate 25. 2-[4-(4,5-Difluoro-2-methylphenyl)cyclohexyl]ethan-1-ol

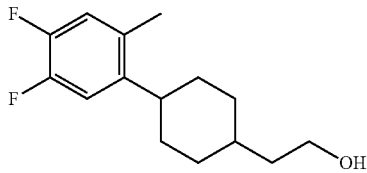 [SMILES: Cc1cc(F)c(F)cc1C1CCC(CCO)CC1]

The title compound was synthesized in a manner analogous to Intermediate 10, using the appropriate starting material substitutions. $^1$H NMR (400 MHz, CDCl$_3$) δ 7.19-6.57 (m, 2H), 3.74 (br s, 2H), 2.63 (d, J=10.8 Hz, 1H), 2.27 (br s, 3H), 2.13-1.92 (m, 2H), 1.89-1.67 (m, 4H), 1.57 (br s, 3H), 1.46-1.03 (m, 2H). [M–H$_2$O+H]=237.2.

Intermediate 26. 2-[4-(3-Methylpyridin-4-yl)cyclohexyl]ethan-1-ol

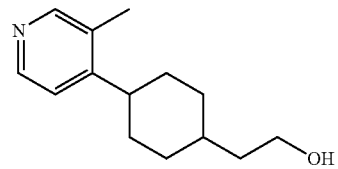 [SMILES: Cc1cnccc1C1CCC(CCO)CC1]

The title compound was synthesized in a manner analogous to Intermediate 10, using the appropriate starting material substitutions. $^1$H NMR (400 MHz, CDCl$_3$) δ 8.35 (d, J=4.8 Hz, 1H), 8.31 (s, 1H), 7.12-7.07 (m, 1H), 3.74-3.70 (m, 2H), 2.74-2.65 (m, 1H), 2.29 (s, 3H), 2.29-1.43 (m, 11H), 1.15-1.12 (m, 1H). [M+H]=220.1.

Intermediate 27. 2-[4-(4-Methylpyridin-3-yl)cyclohexyl]ethan-1-ol

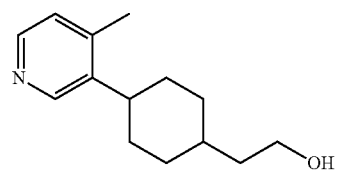 [SMILES: Cc1ccncc1C1CCC(CCO)CC1]

The title compound was synthesized in a manner analogous to Intermediate 10, using the appropriate starting material substitutions. $^1$H NMR (400 MHz, CDCl$_3$) δ 8.41-8.39 (m, 1H), 8.27 (d, J=4.8 Hz, 1H), 7.03 (d, J=4.8 Hz, 1H), 3.72 (t, J=8.4 Hz, 2H), 2.70-2.64 (m, 1H), 2.39-2.32 (m, 4H), 1.97-1.55 (m, 10H), 1.14-1.11 (m, 1H). [M+H]=220.

Intermediate 28. 2-[4-(2,4-Difluorophenyl)cyclohexyl]ethan-1-ol

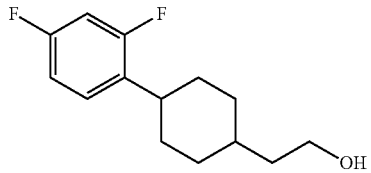 [SMILES: OCCC1CCC(c2ccc(F)cc2F)CC1]

The title compound was synthesized in a manner analogous to Intermediate 10, using the appropriate starting material substitutions. $^1$H NMR (400 MHz, CDCl$_3$) δ 7.23-7.13 (m, 1H), 6.85-6.70 (m, 2H), 3.75-3.70 (m, 2H), 2.90-2.75 (m, 1H), 1.95-1.85 (m, 2H), 1.75-1.60 (m, 5H), 1.55-1.40 (m, 4H), 1.20-1.10 (m, 1H). [M–H$_2$O+H]=223.1.

Intermediate 29. 2-[4-(4-Fluoro-2-methylphenyl)cyclohexyl]ethan-1-ol

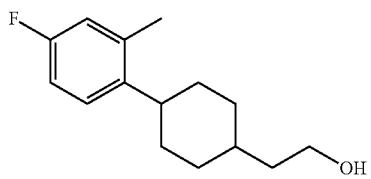 [SMILES: Cc1cc(F)ccc1C1CCC(CCO)CC1]

The title compound was synthesized in a manner analogous to Intermediate 10, using the appropriate starting material substitutions. $^1$H NMR (400 MHz, CDCl$_3$) δ 7.16-7.10 (m, 1H), 6.85-6.81 (m, 2H), 3.74-3.69 (m, 2H), 2.70-2.62 (m, 1H), 2.30 (s, 3H), 1.94-1.68 (m, 6H), 1.57-1.40 (m, 5H), 1.14-1.13 (m, 1H). [M–H$_2$O+H]=219.1.

Intermediate 30. 2-[4-(5-Chlorothiophen-2-yl)cyclohexyl]ethan-1-ol

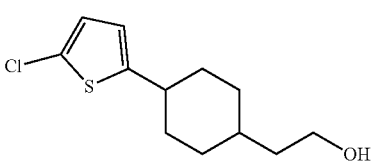 [SMILES: OCCC1CCC(c2ccc(Cl)s2)CC1]

The title compound was synthesized in a manner analogous to Intermediate 11, using the appropriate starting material substitutions. $^1$H NMR (400 MHz, CDCl$_3$) δ 6.74-6.71 (m, 1H), 6.59-6.56 (m, 1H), 3.73-3.67 (m, 2H), 2.94-2.67 (m, 1H), 2.03-1.89 (m, 1H), 1.80-1.34 (m, 10H), 1.11-1.07 (m, 1H). [M+H]=245.1.

Intermediate 31.
4-Amino-N-ethyltetrahydro-2H-pyran-4-carboxamide Hydrochloride

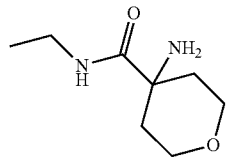

Step 1. tert-Butyl N-[4-(ethylcarbamoyl)oxan-4-yl]carbamate. To a solution of ethanamine (5.3 mL, 0.01 mol) in N,N-dimethylformamide (32.6 mL) was added HATU (4.65 g, 0.01 mol), 4-{[(tert-butoxy)carbonyl]amino}oxane-4-carboxylic acid (2.00 g, 0.01 mol) and DIEA (4.79 mL, 0.03 mol) and the reaction was stirred at room temperature for 30 min. The reaction was extracted with EtOAc (3×15 mL), the layers were separated, the organics washed with a saturated brine solution (15 mL), dried over Na$_2$SO$_4$ and concentrated under reduced pressure. The crude product was purified by flash chromatography (silica, 0-10% MeOH in DCM) to yield the desired product as an off-white solid (2.10 g, 94.6%). $^1$H NMR (400 MHz, DMSO-d$_6$) δ 7.40 (br s, 1H), 7.02-6.62 (m, 1H), 3.71-3.58 (m, 2H), 3.54 (d, J=9.7 Hz, 2H), 3.16-2.97 (m, 2H), 2.03-1.70 (m, 4H), 1.38 (br s, 9H), 0.97 (t, J=6.6 Hz, 3H). [M+H]=273.3.

Step 2. 4-Amino-N-methyltetrahydro-2H-pyran-4-carboxamide hydrochloride. To a solution of tert-Butyl N-[4-(ethylcarbamoyl)oxan-4-yl]carbamate (2.5 g, 9.18 mmol) in dioxane (2.29 mL) was added HCl (4.0 M, 18.4 mL, 73.4 mmol) and the reaction mixture was stirred vigorously at room temperature for 2 h until the formation of a white precipitate. The white precipitate was filtered and washed with cold heptane and dried under vacuum to obtain the title compound as a white solid.

Intermediate 32.
4-Amino-N-methyltetrahydro-2H-pyran-4-carboxamide

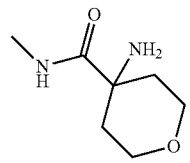

Step 1. 3,8-Dioxa-1-azaspiro[4.5]decane-2,4-dione. To a suspension of 4-{[(benzyloxy)carbonyl]amino}oxane-4-carboxylic acid (10.0 g, 35.8 mmol) in dichloromethane (150 mL) at rt was added oxalyl chloride (4.61 mL, 53.7 mmol), followed by a catalytic amount of N,N-dimethylformamide (27.72 µL) and stirring was continued at rt for 24 h. Upon completion of the reaction, as determined by $^1$H NMR, the solution was concentrated in vacuo to give an off-white waxy residue, which was triturated with MTBE (20 mL) and sonicated. The off-white solids were collected by filtration and dried under vacuum for a couple of hours, to provide the title compound as a crude solid (5.28 g, 86.2%). $^1$H NMR (400 MHz, DMSO-d$_6$) δ 9.59-9.74 (m, 1H), 3.75-3.85 (m, 2H), 3.55-3.68 (m, 2H), 1.89-2.03 (m, 2H), 1.71-1.82 (m, 2H).

Step 2. To a 500 mL pressure vessel with a stir bar was added 3,8-dioxa-1-azaspiro[4.5]decane-2,4-dione (10.7 g, 62.3 mmol) and a solution of methanamine in THF (2.0 M, 186.9 mL, 373.7 mmol) with stirring at rt. Vigorous bubbling, smoking and warming was observed upon addition. Then 2-propanol (26.7 mL) was added to solubilize the reaction mixture, and the vessel was sealed with a teflon pressure cap, then heated at 70° C. for 60 minutes. Some white precipitate had formed (by-product), which was collected by hot filtration and rinsed with MTBE (3×5 mL). The cloudy filtrate solution was concentrated in vacuo to provide the title compound as an off-white solid (9.78 g, 100%). $^1$H NMR (400 MHz, DMSO-d$_6$) δ 7.84-8.07 (m, 1H), 3.55-3.71 (m, 4H), 2.59 (d, J=4.77 Hz, 3H), 1.98-2.26 (m, 1H), 1.89-1.97 (m, 2H), 1.12-1.27 (m, 2H). [M+H]=159.1.

Example 1 and 2. 4-((2-((cis)-4-(3-chloro-5-fluoropyridin-2-yl)cyclohexyl)ethyl)amino)tetrahydro-2H-pyran-4-carboxamide and 4-((2-((trans)-4-(3-chloro-5-fluoropyridin-2-yl)cyclohexyl)ethyl)amino)tetrahydro-2H-pyran-4-carboxamide

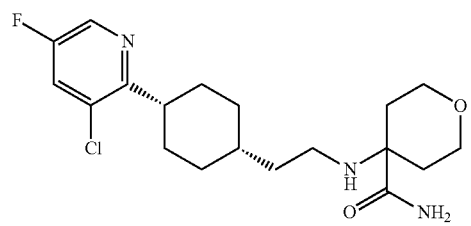

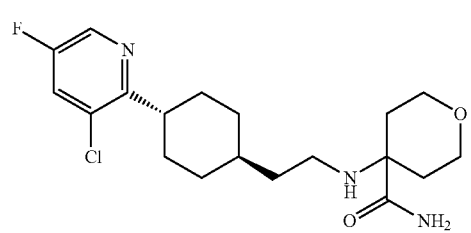

Step 1. 2-(4-(3-Chloro-5-fluoropyridin-2-yl)cyclohexyl)acetaldehyde. 2-[4-(3-Chloro-5-fluoropyridin-2-yl)cyclohexyl]ethan-1-ol (15.2 g, 0.06 mol) was dissolved in dichloromethane (300 mL) (DCM was shaken with water, separated, and used "wet") along with Dess-Martin Periodinane (50.1 g, 0.12 mol). The reaction mixture was stirred at room temperature for 2 h. The reaction was quenched with saturated sodium thiosulfate solution and extracted with DCM. The organic layer was washed with a saturated solution of NaHCO$_3$ and a saturated sodium chloride solution. The organic layer was separated, dried (MgSO$_4$) and concentrated under reduced pressure. The crude material was purified by flash chromatography (silica, 30-100% ethyl acetate in heptanes) to yield the title compound (9.98 g, 66%). $^1$H NMR (400 MHz, CDCl$_3$) δ 9.80 (t, J=2.26 Hz, 1H), 8.38-8.34 (m, 1H), 7.44 (d, J=7.56 Hz, 1H), 3.25-1.14 (m, 12H).

Step 2. 4-((2-((cis)-4-(3-chloro-5-fluoropyridin-2-yl)cyclohexyl)ethyl)amino)tetrahydro-2H-pyran-4-carboxamide and 4-((2-((trans)-4-(3-chloro-5-fluoropyridin-2-yl)cyclohexyl)ethyl)amino)tetrahydro-2H-pyran-4-carboxamide. Sodium triacetoxyborohydride (124 mg, 0.59 mmol) was added to a solution of 2-(4-(3-chloro-5-fluoropyridin-2-yl)cyclohexyl)acetaldehyde (50 mg, 0.20 mmol) and 4-aminotetrahydro-2H-pyran-4-carboxamide (37 mg, 0.25 mmol) in 1,2-dichloroethane (0.50 mL) and DIEA (0.17 ml, 0.98 mmol) and the reaction was stirred at room temperature for 15 h. A saturated solution of NaHCO₃ (10 mL) added, extracted with EtOAc (3×5 mL), the layers separated, the organics washed with a saturated NaHCO₃ solution (10 mL) and concentrated under reduced pressure. Purified by LCMS eluting with CH₃CN:H₂O to yield the desired product as a mixture of cis and trans isomers. Further purified by SFC to yield the pure cis and trans isomers, single isomer product 1 as a colorless oil (9.3 mg, 12%). ¹H NMR (400 MHz, Acetone) δ 8.46 (d, J=2.7 Hz, 1H), 7.76 (dd, J=2.6, 8.4 Hz, 1H), 7.10 (br s, 1H), 6.23 (br s, 1H), 3.79-3.63 (m, 4H), 3.23 (tt, J=3.8, 10.3 Hz, 1H), 2.53 (t, J=7.3 Hz, 2H), 2.05-1.98 (m, 2H), 1.93-1.81 (m, 3H), 1.79-1.53 (m, 11H). [M+H]=384.3; and single isomer product 2 as a colorless oil (10.1 mg, 13%). ¹H NMR (400 MHz, Acetone) S 8.45 (d, J=2.6 Hz, 1H), 7.75 (dd, J=2.6, 8.4 Hz, 1H), 7.08 (br s, 1H), 6.24 (br s, 1H), 3.78-3.63 (m, 4H), 3.15 (tt, J=3.4, 11.8 Hz, 1H), 2.55 (t, J=7.1 Hz, 2H), 2.02 (dt, J=4.5, 9.1 Hz, 2H), 1.95-1.81 (m, 4H), 1.76-1.37 (m, 8H), 1.21-1.06 (m, 2H). [M+H]=384.4.

Example 3. N-{2-[4-(2-Chloro-4-fluorophenyl)cyclohexyl]ethyl}oxan-4-amine

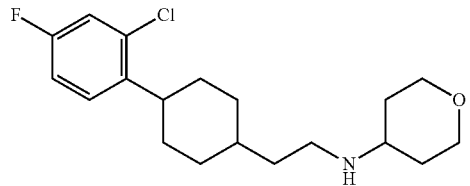 [SMILES: Fc1ccc(C2CCC(CCNC3CCOCC3)CC2)c(Cl)c1]

Step 1. 2-(4-(2-Chloro-4-fluorophenyl)cyclohexyl)acetaldehyde. The title compound was prepared in a manner similar to Example 1, Step 1, using the appropriate starting material substitutions. ¹H NMR (300 MHz, DMSO-d₆) δ 9.69 (s, 1H), 7.52-7.34 (m, 2H), 7.21-7.15 (m, 1H), 2.89-2.81 (m, 1H), 2.64-2.61 (m, 1H), 2.40-2.34 (m, 1H), 1.90-1.41 (m, 8H), 1.27-1.15 (m, 1H).

Step 2. N-(2-(4-(2-Chloro-4-fluorophenyl)cyclohexyl)ethyl)tetrahydro-2H-pyran-4-amine. A solution of 2-(4-(2-chloro-4-fluorophenyl)cyclohexyl)acetaldehyde (25.5 mg, 0.1 mmol) and tetrahydro-2H-pyran-4-amine (10.4 μL, 0.1 mmol) in 1,2-dichloroethane (400 μL) and MeOH (200 μL) was stirred at room temperature overnight. After 16 h, a solution of sodium borohydride (0.5 M in diglyme, 400 μL, 0.2 mmol) was added slowly. After the end of the addition, the reaction mixture was allowed to stir at room temperature for 1 h and then filtered through a pad of Celite® and washed with MeOH. The filtrate was collected and purified by preparative HPLC to yield the title product (13.6 mg, 40%) as a mixture of cis and trans isomers. [M+H]=340.2.

Example 4. 4-({2-[(cis)-4-(2-Chloro-4-fluorophenyl)cyclohexyl]ethyl}amino)oxane-4-carboxamide hydrochloride

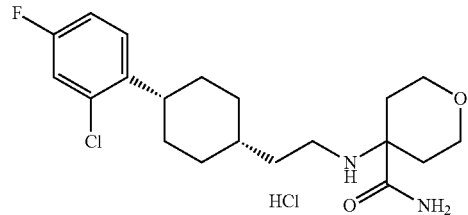 [SMILES: NC(=O)C1(NCC[C@H]2CC[C@@H](c3ccc(F)cc3Cl)CC2)CCOCC1 ; Cl]

Step 1. 2-((cis)-4-(2-Chloro-4-fluorophenyl)cyclohexyl)ethyl 4-methylbenzenesulfonate. To a solution of 2-[(cis)-4-(2-chloro-4-fluorophenyl)cyclohexyl]ethan-1-ol (640 mg, 2.49 mmol) in dichloromethane (6.40 mL) was added triethylamine (1.74 mL, 12.5 mmol) and 4-methylbenzene-1-sulfonyl chloride (570 mg, 2.99 mmol) and the reaction stirred at room temperature for 15 h. The reaction was diluted with DCM (100 mL), washed with a saturated solution of sodium bicarbonate (100 mL), dried (Na₂SO₄) and concentrated under reduced pressure. Purified by ISCO, eluting with 0-100% EtOAc in hexanes, yielded the product as a colorless oil (956 mg, 93%). ¹H NMR (400 MHz, CDCl₃) δ 7.87-7.77 (m, 2H), 7.36 (d, J=8.07 Hz, 2H), 7.23-7.15 (m, 1H), 7.12-7.06 (m, 1H), 6.98-6.89 (m, 1H), 4.11 (t, J=6.60 Hz, 2H), 3.03-2.88 (m, 1H), 2.46 (s, 3H), 1.97-1.77 (m, 3H), 1.72-1.54 (m, 6H), 1.51-1.37 (m, 2H).

Step 2. 4-((2-((cis)-4-(2-Chloro-4-fluorophenyl)cyclohexyl)ethyl)amino)tetrahydro-2H-pyran-4-carboxamide. 4-Aminotetrahydro-2H-pyran-4-carboxamide (442 mg, 3.07 mmol) and 2-((cis)-4-(2-chloro-4-fluorophenyl)cyclohexyl)ethyl 4-methylbenzenesulfonate (630 mg, 1.53 mmol) were taken up in N,N-dimethylformamide (6.30 mL), sodium iodide (1.15 g, 7.67 mmol) and potassium carbonate (636 mg, 4.60 mmol) were added and the suspension was heated at 90° C. for 2 h. A saturated solution of NaHCO₃ (20 mL) added, extracted with EtOAc (3×10 mL), the layers separated, the organics washed with a saturated NaHCO₃ solution (20 mL) and concentrated under reduced pressure. Purified by reverse phase eluting with 30-50% CH₃CN in H₂O to yield the desired product as a semi-solid. The product was taken up in dioxane (3.15 mL), a solution of HCl in dioxane (4 N, 1.92 mL, 7.67 mmol) was added and the reaction was stirred at room temperature for 1 h then concentrated under reduced pressure. The residue was triturated with MTBE (~10 mL), then the suspension was filtered, washed with additional MTBE (5 mL), and dried under reduced pressure to yield the product as a white powder (106 mg, 17%). ¹H NMR (400 MHz, DMSO-d₆) δ 9.35 (br s, 2H), 8.05 (d, J=19.8 Hz, 2H), 7.49-7.35 (m, 2H), 7.22 (dt, J=2.8, 8.5 Hz, 1H), 3.94-3.83 (m, 2H), 3.44 (t, J=10.0 Hz, 2H), 2.99-2.86 (m, 1H), 2.81 (br s, 2H), 2.30 (d, J=13.6 Hz, 2H), 1.97-1.82 (m, 5H), 1.70-1.52 (m, 8H). [M+H]=383.4.

Example 5. N-(2-((trans)-4-(2-chloro-4-fluorophenyl)cyclohexyl)ethyl)tetrahydro-2H-pyran-4-amine

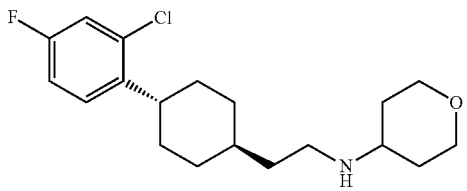 [SMILES: Fc1ccc([C@H]2CC[C@H](CCNC3CCOCC3)CC2)c(Cl)c1]

Step 1. 2-((trans)-4-(2-Chloro-4-fluorophenyl)cyclohexyl)ethyl methanesulfonate. To a solution of 2-[4-(2-chloro-4-fluorophenyl)cyclohexyl]ethan-1-ol (80 mg, 0.312 mmol) and triethylamine (69.5 µL, 0.499 mmol) in dichloromethane (1.56 mL) was added methanesulfonyl chloride (42.8 mg, 0.373 mmol), dropwise. The resulting solution was stirred at room temperature for 2 h and then quenched by the addition of saturated aq. solution of $NaHCO_3$ (2 mL). The mixture was then diluted with EtOAc (2 mL) and the layers were separated. The aqueous layer was further extracted with EtOAc (2×2 mL). The combined organic extracts were concentrated in vacuo to give the crude mesylate which was used in the next step directly.

Step 2. N-(2-((trans)-4-(2-chloro-4-fluorophenyl)cyclohexyl)ethyl)tetrahydro-2H-pyran-4-amine. To a solution of 2-[4-(2-chloro-4-fluorophenyl)cyclohexyl]ethyl methanesulfonate (100 mg, 0.299 mmol), tetrabutylammonium bromide (19.3 mg, 0.0597 mmol) and tetrahydro-2H-pyran-4-amine (61.8 µL, 0.596 mmol) in acetonitrile (1.49 mL) was added potassium carbonate (82.6 mg, 0.597 mmol). The resulting mixture was stirred at 70° C. for 1 h, then N,N-diisopropylethylamine (53.2 µL, 0.299 mmol) was added and the mixture was stirred in the microwave at 120° C. for 1 h. The reaction mixture was then filtered to remove salts and the filtrate was concentrated in vacuo. The resulting oily residue was purified by preparative HPLC (10-60% ACN/$H_2O$, 0.05% TFA) over 15 min to give the title product as a TFA salt (58.3 mg, 46%) as a white solid. $^1$H NMR (400 MHz, $CD_3OD$) δ 7.36 (dd, J=6.17, 8.74 Hz, 1H), 7.18 (dd, J=2.57, 8.68 Hz, 1H), 7.04 (m, 1H), 4.04 (dd, J=4.58, 11.80 Hz, 2H), 3.36-3.52 (m, 3H), 3.16-2.97 (m, 3H), 2.14-1.51 (m, 15H). [M+H]=340.3.

Example 6 and 7. 4-((2-((cis)-4-(2,4-difluorophenyl)cyclohexyl)ethyl)amino)-N-methyltetrahydro-2H-pyran-4-carboxamide and 4-((2-((trans)-4-(2,4-difluorophenyl)cyclohexyl)ethyl)amino)-N-methyltetrahydro-2H-pyran-4-carboxamide

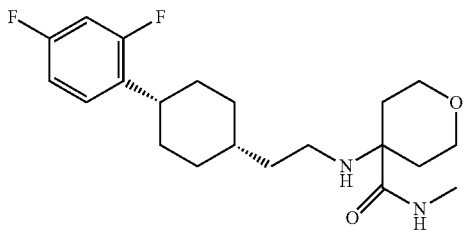

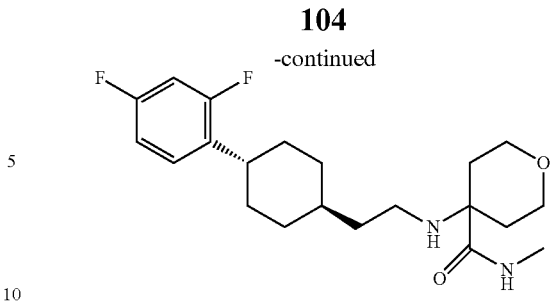

Step 1. 2-(4-(2,4-Difluorophenyl)cyclohexyl)acetaldehyde. The title compound was prepared in a manner similar to Example 1, Step 1, using the appropriate starting material substitutions. $^1$H NMR (400 MHz, $CDCl_3$) δ 9.80 (m, 1H), 7.28-6.73 (m, 3H), 6.85-1.14 (m, 12H).

Step 2. Ethyl 4-((2-(4-(2,4-difluorophenyl)cyclohexyl)ethyl)amino)tetrahydro-2H-pyran-4-carboxylate. To a solution of 2-(4-(2,4-difluorophenyl)cyclohexyl)acetaldehyde (2.0 g, 0.84 mmol) and ethyl 4-aminotetrahydro-2H-pyran-4-carboxylate (189 mg, 1.09 mmol) in 1,2-dichloroethane (1.0 mL) was added sodium triacetoxyborohydride (534 mg, 2.52 mmol) and DIEA (0.44 mL, 2.52 mmol) and the reaction was stirred at 60° C. for 15 h. A saturated solution of $NaHCO_3$ (10 mL) was added, the layers were separated and the aqueous layer was extracted with DCM (3×10 mL), the combined organics were dried ($Na_2SO_4$) and then concentrated under reduced pressure. The crude product was purified by flash chromatography using an amine column, eluting with 0-100% EtOAc in hexanes, to yield the desired compound as a mixture of cis and trans isomers (320 mg, 96%). [M+H]=396.2.

Step 3. 4-((2-(4-(2,4-Difluorophenyl)cyclohexyl)ethyl)amino)tetrahydro-2H-pyran-4-carboxylic acid. To a solution of ethyl 4-((2-(4-(2,4-difluorophenyl)cyclohexyl)ethyl)amino)tetrahydro-2H-pyran-4-carboxylate (300 mg, 0.76 mmol) in ethanol (2.0 mL) and tetrahydrofuran (2.0 mL), was added a solution of lithium hydroxide (2 M, 0.76 mL, 1.52 mmol) and the reaction was heated at 60° C. for 5 h. The reaction was concentrated under reduced pressure to yield a white powder (297 mg), which was used directly in the next step without further purification. [M+H]=368.2.

Step 4. 4-((2-((cis)-4-(2,4-difluorophenyl)cyclohexyl)ethyl)amino)-N-methyltetrahydro-2H-pyran-4-carboxamide and 4-((2-((trans)-4-(2,4-difluorophenyl)cyclohexyl)ethyl)amino)-N-methyltetrahydro-2H-pyran-4-carboxamide. To a solution of 4-((2-(4-(2,4-difluorophenyl)cyclohexyl)ethyl)amino)tetrahydro-2H-pyran-4-carboxylic acid (100 mg, 0.27 mmol) in dimethyl acetamide (1.0 mL) was added DIEA (0.19 mL, 1.09 mmol), HATU (155 mg, 0.41 mmol) and a solution of methanamine in THF (2M, 0.68 mL, 1.36 mmol) and the reaction was stirred at room temperature for 15 h. A saturated solution of $NaHCO_3$ (10 mL) was added, the reaction was extracted with EtOAc (3×5 mL), the layers were separated, the organics washed with a saturated $NaHCO_3$ solution (10 mL) and concentrated under reduced pressure. The crude product was purified by HPLC eluting with $CH_3CN:H_2O$ to yield the desired products as a mixture of cis and trans isomers. The product was further purified by SFC to yield one of the single isomers as a semi-solid (15 mg, 14%): $^1$H NMR (400 MHz, DMSO-$d_6$) δ 7.68 (q, J=4.4 Hz, 1H), 7.35 (dt, J=6.8, 8.7 Hz, 1H), 7.13 (ddd, J=2.6, 9.3, 10.9 Hz, 1H), 7.02 (dt, J=2.9, 8.3 Hz, 1H), 3.75-3.61 (m, 2H), 3.58-3.48 (m, 2H), 2.72 (t, J=12.0 Hz, 1H), 2.62 (d, J=4.6 Hz, 3H), 2.30 (t, J=7.0 Hz, 2H), 1.89-1.41 (m, 12H), 1.33 (q, J=6.8 Hz, 2H), 1.13-0.96 (m, 2H). [M+H]=381.2;

and the other single isomer as a semi-solid (19 mg, 18%): $^1$H NMR (400 MHz, DMSO-d$_6$) δ 7.76-7.64 (m, 1H), 7.40 (dt, J=6.7, 8.7 Hz, 1H), 7.13 (ddd, J=2.6, 9.4, 11.0 Hz, 1H), 7.03 (dt, J=2.4, 8.5 Hz, 1H), 3.72-3.61 (m, 2H), 3.57-3.49 (m, 2H), 2.84-2.72 (m, 1H), 2.62 (d, J=4.5 Hz, 3H), 2.28 (q, J=7.1 Hz, 2H), 1.94 (t, J=7.1 Hz, 1H), 1.90-1.79 (m, 3H), 1.70-1.41 (m, 12H). [M+H]=381.2.

Example 8 and 9. N-(2-((cis)-4-(2,6-dichlorophenyl)cyclohexyl)ethyl)tetrahydro-2H-pyran-4-amine and N-(2-((trans)-4-(2,6-dichlorophenyl)cyclohexyl)ethyl)tetrahydro-2H-pyran-4-amine

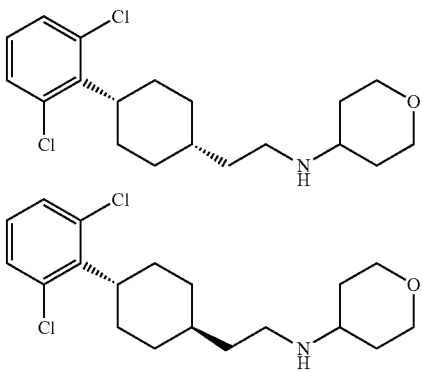

Step 1. Ethyl 2-(4-(2,6-dichlorophenyl)-4-hydroxycyclohexyl)acetate. To a solution of 2-bromo-1,3-dichlorobenzene (22.6 g, 0.1 mol) in THF (200 mL) −78° C. under N$_2$, was added n-BuLi (2.5 M in hexane, 40 mL, 0.1 mol) dropwise. After stirring for 1 h, a solution of ethyl 2-(4-oxocyclohexyl)acetate (18.4 g, 0.1 mol) in THF (100 mL) was added and the resulting mixture was stirred at −78° C. for 2 h. The reaction was quenched with brine (100 mL) and extracted with EtOAc (300 mL×2). The combined organic layer was dried over Na$_2$SO$_4$, filtered and concentrated to give the title compound as a crude yellow oil (31 g), which was used for next step without further purification.

Step 2. Ethyl 2-(2',6'-dichloro-2,3,4,5-tetrahydro-[1,1'-biphenyl]-4-yl)acetate. To a solution of crude ethyl 2-(4-(2,6-dichlorophenyl)-4-hydroxycyclohexyl)acetate (31 g, 93.9 mmol) in toluene (150 mL) was added p-TSA (3.0 g, 17.4 mmol). The mixture was heated to reflux for 6 h. After cooling to rt, the mixture was quenched with a saturated aqueous solution of NaHCO$_3$ (40 mL) and extracted with EtOAc (200 mL×2). The combined organic layer was dried over Na$_2$SO$_4$, filtered and concentrated to provide a residue, which was purified by column chromatography (silica, 100:1 PE/EtOAc) to afford the title compound (2.8 g, 9% yield for 2 steps) as a yellow oil. $^1$H NMR (CDCl$_3$, 400 MHz) δ 9.28 (d, J=8.0 Hz, 2H), 7.09 (t, J=8.0 Hz, 1H), 5.56 (s, 1H), 4.16 (q, J=7.2 Hz, 2H), 2.39-2.19 (m, 6H), 1.98-1.87 (m, 2H), 1.59-1.51 (m, 1H), 1.28 (t, J=7.2 Hz, 3H).

Step 3. 2-(2',6'-Dichloro-2,3,4,5-tetrahydro-[1,1'-biphenyl]-4-yl)ethan-1-ol. To a suspension of LiAlH$_4$ (0.78 g, 21.0 mmol) in THF (60 mL) was added a solution of ethyl 2-(2',6'-dichloro-2,3,4,5-tetrahydro-[1,1'-biphenyl]-4-yl)acetate (4.3 g, 13.8 mmol) at 0° C. The mixture was stirred at 0° C. for 2 h then was quenched with H$_2$O (2 mL) and NaOH (10%, 2 mL) and filtered. The filtrate was dried over MgSO$_4$, then concentrated to afford the crude product, which was purified by column chromatography (silica gel 10:1 PE/EtOAc) to afford the title compound (3.6 g, 96.7%) as a colorless oil. $^1$H NMR (CDCl$_3$, 400 MHz) δ 9.28 (d, J=8.0 Hz, 2H), 7.09 (t, J=8.0 Hz, 1H), 5.57 (s, 1H), 3.78 (t, J=6.4 Hz, 2H), 2.40-2.32 (m, 2H), 2.18-2.12 (m, 1H), 1.93-1.82 (m, 3H), 1.69-1.61 (m, 2H), 1.57-1.51 (m, 1H), 1.35 (br, 1H).

Step 4. 2-(2',6'-Dichloro-2,3,4,5-tetrahydro-[1,1'-biphenyl]-4-yl)acetaldehyde. To a solution of 2-(2',6'-dichloro-2,3,4,5-tetrahydro-[1,1'-biphenyl]-4-yl)ethan-1-ol (3.6 g, 13.3 mmol) in DCM (100 mL) was added Dess-Martin periodinane (8.6 g, 20 mmol) and the mixture was stirred at rt for 4 h. The mixture was quenched with NaOH (10%, 30 mL) and brine (100 mL), then extracted with DCM (200 mL×3), the organic layer was dried over NaSO$_4$, filtered and concentrated to afford the crude product, which was purified by column chromatography (silica, 100:1 PE/EtOAc) to afford the title compound (2.5 g, 70%) as yellow oil. $^1$H NMR (CDCl$_3$, 400 MHz) δ 9.86 (t, J=1.8 Hz, 1H), 7.28 (d, J=8.0 Hz, 2H), 7.10 (t, J=8.0 Hz, 1H), 5.57 (s, 1H), 2.53-2.50 (m, 2H), 2.41-2.30 (m, 3H), 2.20-2.14 (m, 1H), 1.99-1.85 (m, 2H), 1.61-1.54 (m, 1H). [M+H]=268.8.

Step 5. N-(2-(2',6'-Dichloro-2,3,4,5-tetrahydro-[1,1'-biphenyl]-4-yl)ethyl)tetrahydro-2H-pyran-4-amine. A solution of 2-[4-(2,6-dichlorophenyl)cyclohex-3-en-1-yl]acetaldehyde (500 mg, 1.86 mmol) and tetrahydro-2H-pyran-4-amine (212 uL, 2.05 mmol) in methanol (3.72 mL) was stirred at room temperature. After 24 h, dichloromethane (3.72 mL) was added, followed by sodium triacetoxyborohydride (591 mg, 2.76 mmol) and the resulting mixture stirred at room temperature for 5 h, until complete consumption of starting material. The reaction mixture was quenched by the addition of a saturated aq. solution of NaHCO$_3$ (10 mL) and extracted with EtOAc (3×10 mL). The combined organic extracts were concentrated in vacuo to give the target amine as a mixture of mono and bis-alkylated products and the mixture was used without further purification. A small sample was purified by preparative HPLC (ACN/H$_2$O, 0.05% TFA) for analysis. $^1$H NMR (400 MHz, CD$_3$OD) δ 7.43-7.32 (m, 2H), 7.27-7.13 (m, 1H), 5.57 (m, 1H), 4.04 (dd, J=4.65, 11.74 Hz, 2H), 3.51-3.33 (m, 3H), 3.16 (dd, J=6.42, 8.99 Hz, 2H), 2.50-1.47 (m, 13H). [M+H]=354.5.

Step 6. The title compound, as a mixture of cis and trans isomers, was prepared in a manner analogous to Intermediate 5, step 5, using PtO$_2$ then Pd/C, with the appropriate starting material substitutions. The crude product was purified by prep-HPLC to give the pure cis- and trans-isomers, the assignment of which were not confirmed.

One of the two single isomers: $^1$H NMR (400 MHz, CD$_3$OD) δ 7.45-7.24 (m, 2H), 7.21-7.05 (m, 1H), 4.04 (dd, J=4.58, 11.68 Hz, 2H), 3.62 (tt, J=3.91, 12.72 Hz, 1H), 3.49-3.32 (m, 3H), 3.16-2.99 (m, 2H), 2.51 (dq, J=4.34, 13.02 Hz, 2H), 2.08-1.55 (m, 11H), 1.49-1.34 (m, 2H). [M+H]=356.1.

The other single isomer: $^1$H NMR (400 MHz, CD$_3$OD) δ 7.37 (d, J=7.95 Hz, 1H), 7.29 (d, J=7.83 Hz, 1H), 7.17-7.07 (m, 1H), 4.04 (dd, J=4.52, 11.62 Hz, 2H), 3.58 (tt, J=3.55, 12.53 Hz, 1H), 3.50-3.33 (m, 3H), 3.18-3.05 (m, 2H), 2.45 (dq, J=3.42, 12.88 Hz, 2H), 2.11-1.89 (m, 4H), 1.74-1.43 (m, 7H), 1.19 (dq, J=3.55, 12.51 Hz, 2H). [M+H]=356.1.

Example 10. N-{2-[4-(2,4-Difluorophenyl)cyclohexyl]ethyl}cyclopentanamine

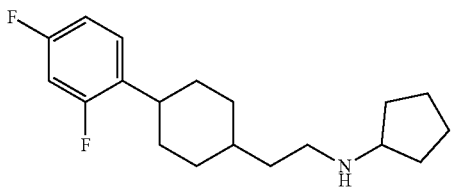

To a solution of the aldehyde (0.33 M, 0.3 mL, 0.10 mmol) in a mixture of anhydrous DMA:methanol (3:1) was added a solution of amine (0.67 M, 0.3 mL, 0.20 mmol) and DIEA (0.225 mmol) in anhydrous DMA. The reaction mixture was shaken at room temperature for 16 h. Then, a solution of zinc chloride (0.5 eq) in anhydrous methanol was added to a solution of sodium cyanoborohydride in anhydrous methanol (1.2 M). The resulting zinc cyanoborohydride solution (0.6 M, 0.2 mL, 0.12 mmol, 1.2 eq) was transferred to the solution of aldehyde and amine and the reaction mixture was shaken at room temperature for 18 h. If the starting aldehyde or the imine was present in the UPLC-MS analysis, then NaBH$_4$ in diglyme (0.5 M, 0.10 mL, 0.05 mmol) was added and the reaction was shaken for 1 h. Vigorous gas evolution was observed in the wells! Upon completion of the reaction, the crude reaction mixture was filtered and purified to provide the title compound. [M+H]=308.4

Example 11 and 12. N-(2-((cis)-4-(5-fluoropyrimidin-2-yl)cyclohexyl)ethyl)tetrahydro-2H-pyran-4-amine and N-(2-((trans)-4-(5-fluoropyrimidin-2-yl)cyclohexyl)ethyl)tetrahydro-2H-pyran-4-amine

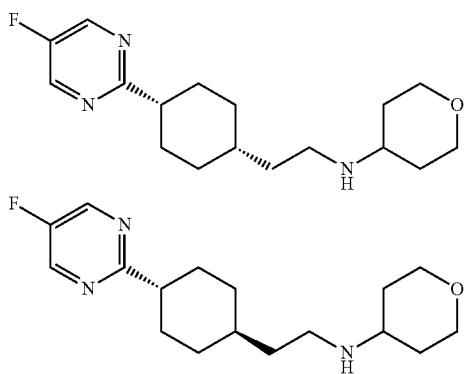

Step 1. tert-Butyl (2-(4-(5-fluoropyrimidin-2-yl)cyclohex-3-en-1-yl)ethyl)(tetrahydro-2H-pyran-4-yl)carbamate. A vial was charged with tert-butyl (tetrahydro-2H-pyran-4-yl)(2-(4-(4,4,5,5-tetramethyl-1,3,2-dioxaborolan-2-yl)cyclohex-3-en-1-yl)ethyl)carbamate (Intermediate 16, 150 mg, 0.344 mmol), 2-bromo-5-fluoropyrimidine (73.2 mg, 0.413 mmol), potassium carbonate (142.8 mg, 1.03 mmol) and Pd(dppf)Cl$_2$ (14.1 mg, 0.019 mmol) and flushed with N$_2$ (3×). Dioxane (0.57 mL), ethyl acetate (0.43 mL) and water (0.17 mL) were then introduced and the mixture degassed briefly (3×1 min). The resulting mixture was stirred at 80° C. for 16 h, until complete conversion of boronic acid. The solvent was removed in vacuo and the crude product was purified by flash chromatography (silica, 0-70% EtOAc/Hep) to provide the title compound as an, off-white sticky solid (110 mg, 78.7%). $^1$H NMR (400 MHz, CDCl$_3$) δ 8.55 (s, 2H), 7.22-7.14 (m, 1H), 4.02 (br dd, J=11.31, 4.34 Hz, 2H), 3.44 (br t, J=11.19 Hz, 2H), 3.19 (br s, 2H), 2.78 (br dd, J=17.91, 2.26 Hz, 1H), 2.57-2.36 (m, 2H), 2.08-1.37 (m, 20H). [M+H]=406.3.

Step 2. tert-Butyl (2-(4-(5-fluoropyrimidin-2-yl)cyclohexyl)ethyl)(tetrahydro-2H-pyran-4-yl)carbamate. A reaction vessel was charged with tert-butyl (2-(4-(5-fluoropyrimidin-2-yl)cyclohex-3-en-1-yl)ethyl)(tetrahydro-2H-pyran-4-yl)carbamate (105 mg, 0.259 mmol), 10 wt % palladium on carbon (11.0 mg, 0.010 mmol) and methanol (2.6 mL). The reaction vessel was evacuated and backfilled with N$_2$ (3×), evacuated and backfilled with H$_2$ (100 psi), then the reaction mixture was stirred at rt for 16 h, until reaction was complete. The reaction mixture was filtered through a pad of silica/Celite. The filtrate was concentrated in vacuo to give a near colorless oil, which was used in the next step without further purification. [M+H-t-Bu]=352.2.

Step 3. N-(2-(4-(5-fluoropyrimidin-2-yl)cyclohexyl)ethyl)tetrahydro-2H-pyran-4-amine. To a solution of crude tert-butyl (2-(4-(5-fluoropyrimidin-2-yl)cyclohexyl)ethyl)(tetrahydro-2H-pyran-4-yl)carbamate (105 mg) in DCM (2 mL) was added TFA (1 mL) and the reaction was stirred at room temperature for 1.5 h, until the reaction had reaction completion. Solvents were removed in vacuo to provide the crude product as a residue as a mixture of cis and trans isomers. The cis and trans isomers were separated by chiral HPLC to give the first single isomers: 11.0 mg, 14%. $^1$H NMR (400 MHz, CD$_3$OD) δ 8.65 (s, 2H), 3.95 (br dd, J=11.07, 3.73 Hz, 2H), 3.41 (td, J=11.92, 1.83 Hz, 2H), 3.03 (tt, J=8.41, 4.13 Hz, 1H), 2.87-2.60 (m, 3H), 2.22-2.01 (m, 2H), 1.94-1.29 (m, 13H). [M+H]=308.3; and the second single isomer: 11.4 mg, 14%. $^1$H NMR (400 MHz, CDCl$_3$) δ 8.77-8.52 (m, 2H), 3.96 (br dd, J 11.07, 3.85 Hz, 2H), 3.42 (td, J 11.92, 1.83 Hz, 2H), 2.96-2.61 (m, 4H), 1.81-2.10 (m, 6H), 1.66 (qd, J=12.84, 3.18 Hz, 2H), 1.55-1.32 (m, 5H), 1.22-1.05 (m, 2H). [M+H]=308.3.

Example 13-Example 52 were prepared in a manner analogous to Example 1, with the appropriate starting material substitutions.

Example 13. 4-((2-((trans)-4-(4-fluoro-2-methylphenyl)cyclohexyl)ethyl)amino)tetrahydro-2H-pyran-4-carboxamide

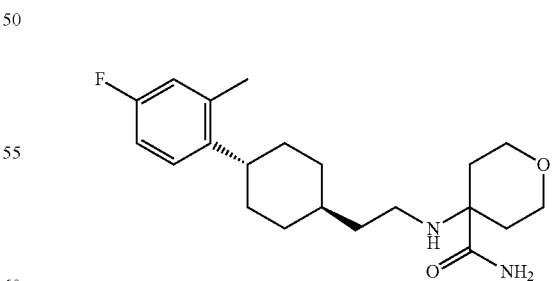

$^1$H NMR (400 MHz, Acetone) δ 7.23 (dd, J=6.2, 8.1 Hz, 1H), 7.07 (br s, 1H), 6.98-6.80 (m, 2H), 6.23 (br s, 1H), 3.83-3.58 (m, 4H), 2.91-2.64 (m, 3H), 2.55 (t, J=7.1 Hz, 2H), 2.34 (s, 3H), 2.01 (td, J=4.4, 9.1 Hz, 2H), 1.90 (d, J=12.1 Hz, 2H), 1.79 (d, J=12.6 Hz, 2H), 1.62-1.43 (m, 6H), 1.23-1.08 (m, 2H). [M+H]=363.3.

Example 14 and 15. N-(2-((cis)-4-(3-chloropyridin-2-yl)cyclohexyl)ethyl)tetrahydro-2H-pyran-4-amine and N-(2-((trans)-4-(3-chloropyridin-2-yl)cyclohexyl)ethyl)tetrahydro-2H-pyran-4-amine

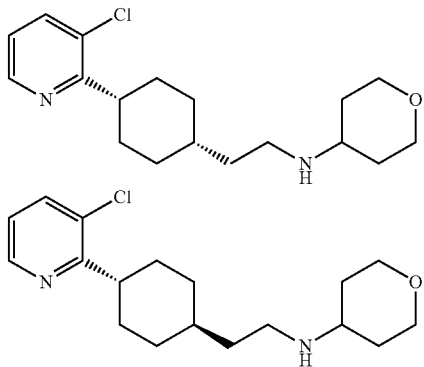

One of the two single isomers: ¹H NMR (400 MHz, CD₃OD) δ 8.44 (dd, J=4.77, 1.47 Hz, 1H), 7.81 (dd, J=8.07, 1.59 Hz, 1H) 7.23 (dd, J=8.07, 4.65 Hz, 1H), 4.01 (dd, J=11.49, 4.52 Hz, 2H), 3.51-3.40 (m, 2H), 3.11-2.97 (m, 1H), 2.93-2.82 (m, 2H), 2.02-1.61 (m, 16H). [M+H]= 323.54.

The other single isomer: ¹H NMR (400 MHz, CD₃OD) δ 8.40 (dd, J=4.65, 1.47 Hz, 1H), 7.78 (dd, J=8.07, 1.59 Hz, 1H), 7.20 (dd, J=8.07, 4.77 Hz, 1H), 3.95 (dd, J=10.70, 3.97 Hz, 2H), 3.42 (td, J=11.92, 2.08 Hz, 2H), 3.22 (tt, J=11.88, 3.47 Hz, 1H), 2.76-2.63 (m, 3H), 1.98-1.80 (m, 6H), 1.61-1.77 (m, 2H), 1.54-1.33 (m, 5H), 1.25-1.09 (m, 2H). [M+H]= 323.54.

Example 16 and 17. N-(2-((cis)-4-(2,4-difluorophenyl)cyclohexyl)ethyl)tetrahydro-2H-pyran-4-amine and N-(2-((trans)-4-(2,4-difluorophenyl)cyclohexyl)ethyl)tetrahydro-2H-pyran-4-amine

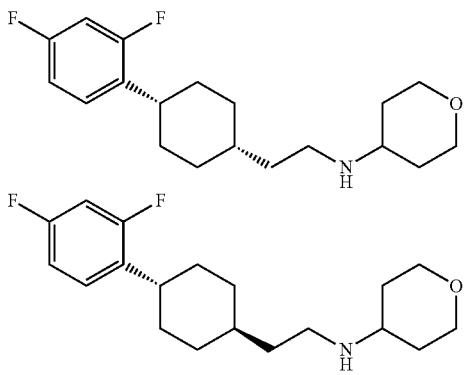

One of the two single isomers: ¹H NMR (400 MHz, CD₃OD) δ 7.32 (td, J=8.56, 6.48 Hz, 1H), 7.03-6.71 (m, 2H), 4.03-3.89 (m, 2H), 3.42 (td, J=11.92, 1.96 Hz, 2H), 2.94-2.78 (m, 1H), 2.76-2.58 (m, 3H), 1.96-1.58-1.31 (m, 15H). [M+H]=324.56.

The other single isomer: ¹H NMR (400 MHz, CD₃OD) δ 7.38-7.18 (m, 1H), 6.98-6.71 (m, 2H), 3.95 (dd, J=10.88, 3.91 Hz, 2H), 3.42 (td, J=11.92, 1.96 Hz, 2H), 2.88-2.60 (m, 4H), 2.00-1.75 (m, 6H), 1.65-1.31 (m, 7H), 1.26-1.06 (m, 2H). [M+H]=324.56.

Example 18 and 19. N-(2-((cis)-4-(4-fluoro-2-methylphenyl)cyclohexyl)ethyl)tetrahydro-2H-pyran-4-amine and N-(2-((trans)-4-(4-fluoro-2-methylphenyl)cyclohexyl)ethyl)tetrahydro-2H-pyran-4-amine

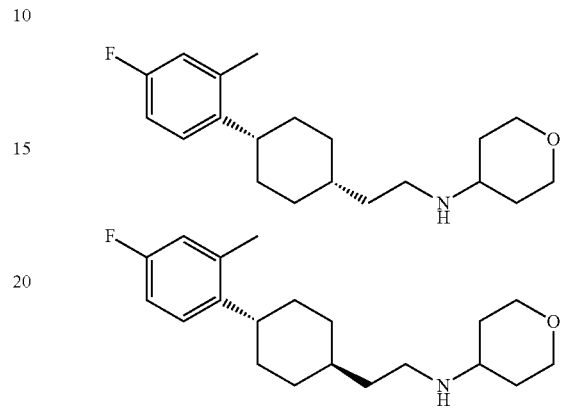

One of the two single isomers: ¹H NMR (400 MHz, CD₃OD) δ 7.21 (s, 1H), 6.91-6.76 (m, 2H), 3.42 (td, J=11.92, 1.96 Hz, 2H), 3.95 (dd, J=10.88, 4.03 Hz, 2H), 2.82-2.51 (m, 4H), 2.31 (s, 3H), 1.95-1.78 (m, 3H), 1.72 (br s, 10H), 1.48-1.35 (m, 2H). [M+H]=320.60.

The other single isomer: ¹H NMR (400 MHz, CD₃OD) δ 7.27-7.11 (m, 1H), 6.92-6.79 (m, 1H), 4.04-3.91 (m, 2H), 3.54-3.35 (m, 2H), 2.84-2.62 (m, 4H), 2.33 (s, 3H), 2.07-1.72 (m, 6H), 1.66-1.33 (m, 7H), 1.27-1.11 (m, 2H). [M+H]= 320.60.

Example 20 and 21. N-(2-((cis)-4-(2-chloro-6-fluorophenyl)cyclohexyl)ethyl)tetrahydro-2H-pyran-4-amine and N-(2-((trans)-4-(2-chloro-6-fluorophenyl)cyclohexyl)ethyl)tetrahydro-2H-pyran-4-amine

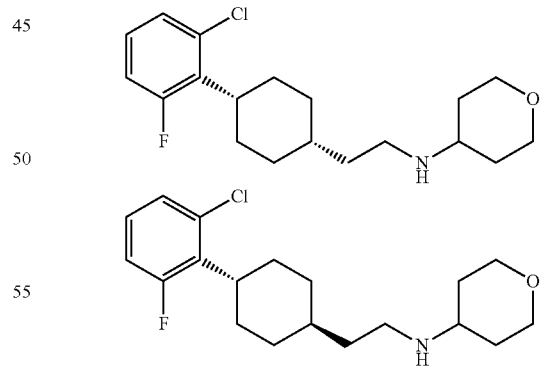

One of the two single isomers: ¹H NMR (400 MHz, CD₃OD) δ 7.26-7.09 (m, 2H), 7.00 (ddd, J=11.52, 7.86, 1.65 Hz, 1H), 3.95 (dd, J=10.82, 3.97 Hz, 2H), 3.42 (d, J=1.96 Hz, 2H), 3.29-3.20 (m, 1H), 2.79-2.61 (m, 3H), 2.13 (d, J=13.20 Hz, 2H), 1.97-1.80 (m, 3H), 1.79-1.59 (m, 6H), 1.55-1.33 (m, 4H). [M+H]=340.52.

The other single isomer: ¹H NMR (400 MHz, CD₃OD) δ 7.28-7.09 (m, 2H), 7.05-6.91 (m, 1H), 3.97 (dd, J=11.19, 4.22 Hz, 2H), 3.52-3.35 (m, 2H), 3.28-3.13 (m, 1H), 2.97-2.72 (m, 3H), 2.10-1.82 (m, 6H), 1.80-1.67 (m, 2H), 1.59-1.36 (m, 5H), 1.25-1.03 (m, 2H). [M+H]=340.52.

Example 22. N-{2-[4-(3-Chloro-5-fluoropyridin-2-yl)cyclohexyl]ethyl}-4-cyclopropyloxan-4-amine

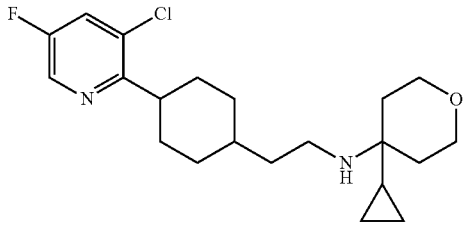 [SMILES: Fc1cnc(C2CCC(CCNC3(C4CC4)CCOCC3)CC2)c(Cl)c1]

¹H NMR (400 MHz, CD₃OD) δ 8.44-8.24 (m, 1H), 7.72 (dd, J=8.31, 2.57 Hz, 1H), 4.02-3.62 (m, 4H), 3.36-3.21 (m, 1H), 3.31-3.08 (m, 3H), 2.05-1.19 (m, 14H), 1.09-1.05 (m, 1H), 0.93-0.79 (m, 2H), 0.69 (q, J=5.67 Hz, 2H). [M+H]=381.2.

Example 23 and 24. N-(2-((cis)-4-(3-chloro-5-fluoropyridin-2-yl)cyclohexyl)ethyl)-4-(methoxymethyl)tetrahydro-2H-pyran-4-amine and N-(2-((trans)-4-(3-chloro-5-fluoropyridin-2-yl)cyclohexyl)ethyl)-4-(methoxymethyl)tetrahydro-2H-pyran-4-amine

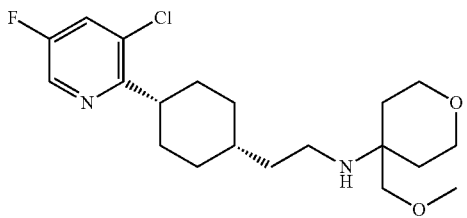

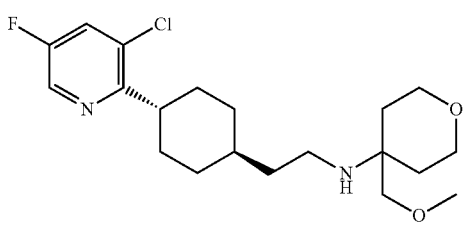

One of the two single isomers: ¹H NMR (400 MHz, Acetone) δ 8.46 (d, J=2.4 Hz, 1H), 7.75 (dd, J=2.6, 8.4 Hz, 1H), 3.89-3.79 (m, 2H), 3.71-3.50 (m, 4H), 3.41 (s, 3H), 3.31-3.18 (m, 1H), 2.89-2.85 (m, 2H), 1.99-1.50 (m, 17H). [M+H]=385.2.

The other single isomer: ¹H NMR (400 MHz, Acetone) δ 8.45 (d, J=2.7 Hz, 1H), 7.75 (dd, J=2.6, 8.4 Hz, 1H), 3.78 (dt, J=3.5, 10.4 Hz, 2H), 3.55 (td, J=3.9, 11.0 Hz, 2H), 3.35 (s, 3H), 3.25 (s, 2H), 3.21-3.10 (m, 1H), 2.57 (t, J=7.0 Hz, 2H), 2.07 (td, J=2.2, 4.4 Hz, 2H), 1.97-1.81 (m, 4H), 1.75-1.61 (m, 2H), 1.57-1.38 (m, 7H), 1.21-1.08 (m, 2H). [M+H]=385.2.

Example 25. 4-({2-[(cis)-4-(2-Chloro-4-fluorophenyl)cyclohexyl]ethyl}amino)oxan-3-ol

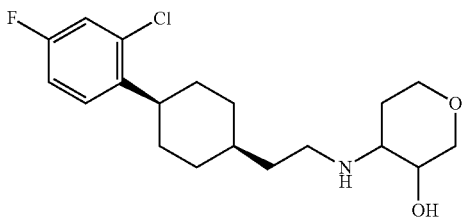 [SMILES: OC1COCCC1NCC[C@H]1CC[C@@H](c2ccc(F)cc2Cl)CC1]

¹H NMR (400 MHz, CD₃OD) δ 7.50-7.32 (m, 1H), 7.15 (dd, J=8.80, 2.69 Hz, 1H), 7.03 (td, J=8.44, 2.69 Hz, 1H), 3.96-3.79 (m, 2H), 3.47-3.35 (m, 2H), 3.16-2.94 (m, 2H), 2.77 (ddd, J=11.28, 9.20, 6.17 Hz, 1H), 2.64-2.45 (m, 2H), 1.97 (ddt, J=13.25, 4.33, 1.97, 1.97 Hz, 1H), 1.85 (tq, J=7.07, 3.40 Hz, 1H), 1.79-1.57 (m, 10H), 1.49-1.35 (m, 1H). [M+H]=356.2.

Example 26. (3S,4S)—N-(2-((cis)-4-(2-chloro-4-fluorophenyl)cyclohexyl)ethyl)-3-methoxytetrahydro-2H-pyran-4-amine

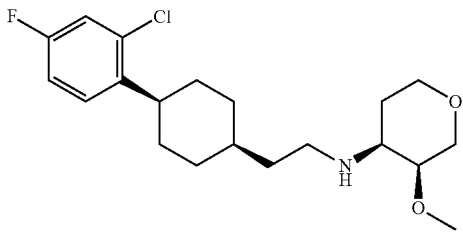 [SMILES: CO[C@@H]1COCC[C@@H]1NCC[C@H]1CC[C@@H](c2ccc(F)cc2Cl)CC1]

¹H NMR (400 MHz, CD₃OD) δ 7.38 (dd, J=8.74, 6.17 Hz, 1H), 7.15 (dd, J=8.80, 2.69 Hz, 1H), 7.03 (td, J=8.47, 2.75 Hz, 1H), 4.15 (dt, J=12.75, 1.27 Hz, 1H), 3.96-3.88 (m, 1H), 3.49-3.39 (m, 5H), 3.35-3.32 (m, 1H), 3.09-2.92 (m, 1H), 2.79 (ddd, J=10.67, 5.29, 3.12 Hz, 1H), 2.74-2.51 (m, 2H), 1.93-1.55 (m, 13H). [M+H]=370.3.

Example 27. 2-((2-((cis)-4-(2-chloro-4-fluorophenyl)cyclohexyl)ethyl)amino)cyclopentan-1-ol

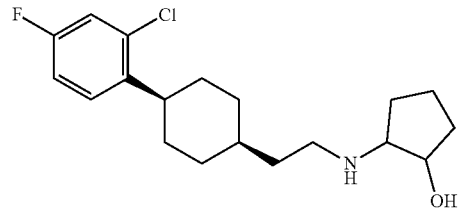 [SMILES: OC1CCCC1NCC[C@H]1CC[C@@H](c2ccc(F)cc2Cl)CC1]

¹H NMR (400 MHz, CD₃OD) δ 7.44-7.34 (m, 1H), 7.15 (dd, J=8.80, 2.69 Hz, 1H), 7.03 (td, J=8.44, 2.69 Hz, 1H), 3.98-3.83 (m, 1H), 3.09-2.96 (m, 1H), 2.89 (td, J=7.58, 5.26 Hz, 1H), 2.75-2.56 (m, 2H), 2.12-1.89 (m, 2H), 1.87-1.51 (m, 14H), 1.37 (dq, J=12.85, 8.06 Hz, 1H). [M+H]=340.3.

Example 28 and 29. 4-((2-((cis)-4-(3-chloropyridin-2-yl)cyclohexyl)ethyl)amino)tetrahydro-2H-pyran-4-carboxamide and 4-((2-((trans)-4-(3-chloropyridin-2-yl)cyclohexyl)ethyl)amino)tetrahydro-2H-pyran-4-carboxamide

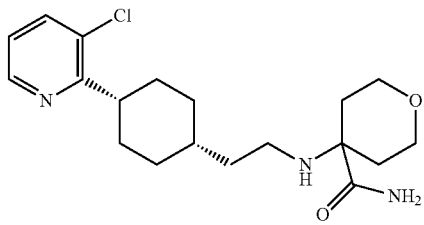

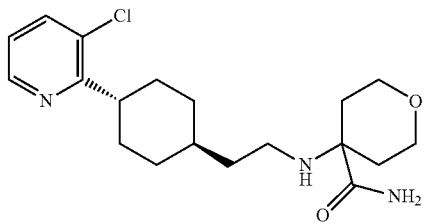

One of the two single isomers: ¹H NMR (400 MHz, CD₃OD) δ 8.48 (dd, J=1.3, 4.9 Hz, 1H), 7.95 (dd, J=1.5, 8.2 Hz, 1H), 7.35 (dd, J=4.9, 8.2 Hz, 1H), 3.95 (td, J=4.4, 12.5 Hz, 2H), 3.65 (ddd, J=2.7, 9.5, 12.3 Hz, 2H), 3.32-3.24 (m, 1H), 3.09-2.94 (m, 2H), 2.42 (d, J=13.9 Hz, 2H), 2.10-1.83 (m, 6H), 1.81-1.62 (m, 4H), 1.54 (dt, J=3.3, 7.3 Hz, 1H), 1.35-1.12 (m, 2H). [M+H]=366.1.

The other single isomer: ¹H NMR (400 MHz, CD₃OD) δ 8.48 (dd, J=1.4, 4.8 Hz, 1H), 7.90 (dd, J=1.5, 8.1 Hz, 1H), 7.31 (dd, J=4.8, 8.1 Hz, 1H), 3.95 (td, J=4.5, 12.6 Hz, 2H), 3.66 (ddd, J=2.8, 9.4, 12.4 Hz, 2H), 3.42-3.34 (m, 1H), 3.11-2.92 (m, 2H), 2.42 (d, J=13.9 Hz, 2H), 2.01-1.83 (m, 7H), 1.81-1.74 (m, 4H), 1.73-1.66 (m, 2H). [M+H]=366.1.

Example 30 and 31. 4-((2-((cis)-4-(2-chloro-5-fluorophenyl)cyclohexyl)ethyl)amino)tetrahydro-2H-pyran-4-carboxamide and 4-((2-((trans)-4-(2-chloro-5-fluorophenyl)cyclohexyl)ethyl)amino)tetrahydro-2H-pyran-4-carboxamide

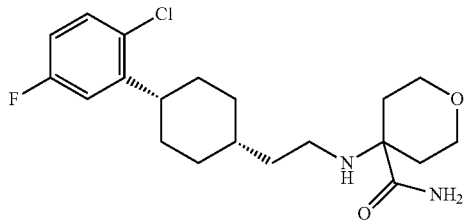

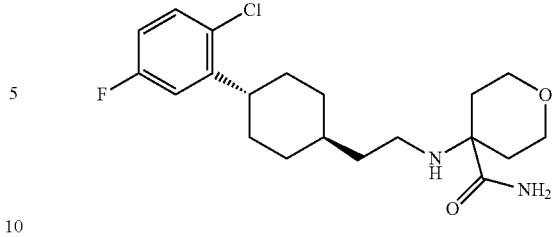

One of the two single isomers: ¹H NMR (400 MHz, CD₃OD) δ 7.37 (dd, J=5.4, 8.8 Hz, 1H), 7.13 (dd, J=3.1, 10.1 Hz, 1H), 6.93 (ddd, J=3.1, 7.9, 8.7 Hz, 1H), 3.84 (ddd, J=3.2, 8.1, 11.4 Hz, 2H), 3.75-3.60 (m, 2H), 3.02 (d, J=7.2 Hz, 1H), 2.51 (t, J=7.5 Hz, 2H), 2.16-2.00 (m, 2H), 1.91 (dt, J=3.5, 7.1 Hz, 1H), 1.83-1.58 (m, 12H). [M+H]=383.1.

The other single isomer: ¹H NMR (400 MHz, CD₃OD) δ 7.36 (dd, J=5.3, 8.8 Hz, 1H), 7.09 (dd, J=3.1, 10.1 Hz, 1H), 6.92 (dt, J=3.0, 8.3 Hz, 1H), 3.84 (ddd, J=3.2, 8.1, 11.4 Hz, 2H), 3.75-3.58 (m, 2H), 2.99 (t, J=12.2 Hz, 1H), 2.52 (t, J=7.2 Hz, 2H), 2.13-1.99 (m, 2H), 1.97-1.85 (m, 4H), 1.70-1.57 (m, 2H), 1.56-1.40 (m, 5H), 1.25-1.10 (m, 2H). [M+H]=383.1.

Example 32 and 33. 4-((2-((cis)-4-(2-chloro-3-fluorophenyl)cyclohexyl)ethyl)amino)tetrahydro-2H-pyran-4-carboxamide and 4-((2-((trans)-4-(2-chloro-3-fluorophenyl)cyclohexyl)ethyl)amino)tetrahydro-2H-pyran-4-carboxamide

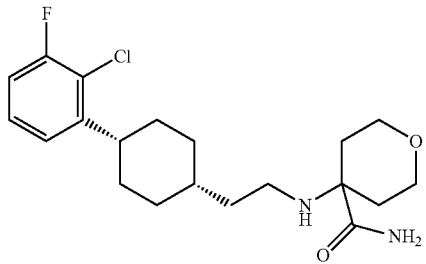

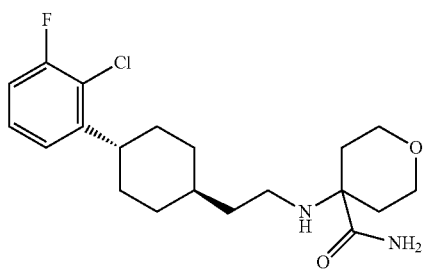

One of the two single isomers: ¹H NMR (400 MHz, CD₃OD) δ 7.34-7.24 (m, 1H), 7.23-7.17 (m, 1H), 7.06 (dt, J=1.5, 8.6 Hz, 1H), 3.84 (ddd, J=3.3, 8.1, 11.5 Hz, 2H), 3.74-3.62 (m, 2H), 3.18-2.99 (m, 1H), 2.51 (t, J=7.5 Hz, 2H), 2.16-2.00 (m, 2H), 1.96-1.90 (m, 1H), 1.81-1.57 (m, 12H). [M+H]=383.1.

The other single isomer: ¹H NMR (400 MHz, CD₃OD) δ 7.27 (dd, J=5.5, 8.1 Hz, 1H), 7.16 (d, J=7.9 Hz, 1H), 7.11-7.02 (m, 1H), 3.83 (dt, J=4.1, 7.7 Hz, 2H), 3.75-3.60 (m, 2H), 3.11-2.97 (m, 1H), 2.52 (t, J=7.2 Hz, 2H), 2.10-1.98 (m, 2H), 1.98-1.84 (m, 4H), 1.72-1.60 (m, 2H), 1.59-1.41 (m, 5H), 1.27-1.09 (m, 2H). [M+H]=383.1.

Example 34 and 35. 4-((2-((cis)-4-(2,4-difluorophenyl)cyclohexyl)ethyl)amino)tetrahydro-2H-pyran-4-carboxamide and 4-((2-((trans)-4-(2,4-difluorophenyl)cyclohexyl)ethyl)amino)tetrahydro-2H-pyran-4-carboxamide

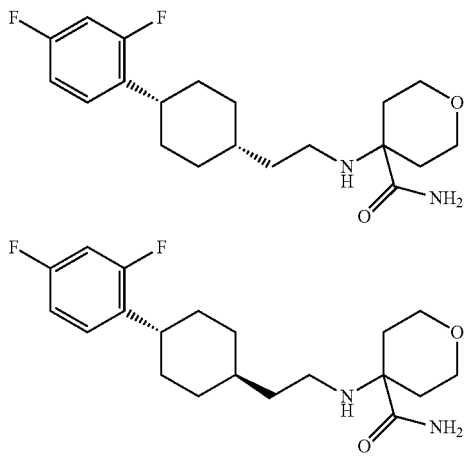

One of the two single isomers: ¹H NMR (400 MHz, CD₃OD) δ 7.46-7.21 (m, 1H), 7.03-6.73 (m, 2H), 3.84 (ddd, J=3.2, 8.1, 11.4 Hz, 2H), 3.75-3.59 (m, 2H), 2.93-2.78 (m, 1H), 2.50 (t, J=7.5 Hz, 2H), 2.16-1.99 (m, 2H), 1.88 (dd, J=3.7, 6.8 Hz, 1H), 1.80-1.54 (m, 12H). [M+H]=367.2.

The other single isomer: ¹H NMR (400 MHz, CD₃OD) δ 7.41-7.18 (m, 1H), 7.05-6.63 (m, 2H), 3.83 (ddd, J=3.3, 8.1, 11.5 Hz, 2H), 3.73-3.62 (m, 2H), 2.80 (tt, J=3.2, 12.2 Hz, 1H), 2.52 (t, J=7.2 Hz, 2H), 2.11-1.97 (m, 2H), 1.96-1.79 (m, 4H), 1.74-1.41 (m, 7H), 1.25-1.04 (m, 2H). [M+H]=367.2.

Example 36 and 37. 4-((2-((cis)-4-(2-chloro-4,6-difluorophenyl)cyclohexyl)ethyl)amino)tetrahydro-2H-pyran-4-carboxamide and 4-((2-((trans)-4-(2-chloro-4,6-difluorophenyl)cyclohexyl)ethyl)amino)tetrahydro-2H-pyran-4-carboxamide

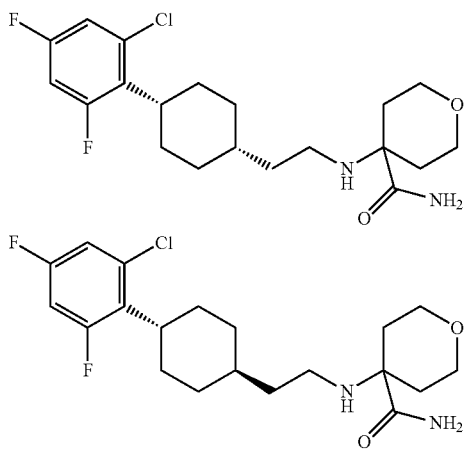

One of the two single isomers: ¹H NMR (400 MHz, CDCl₃) δ 7.09 (br s, 1H), 6.95 (td, J=2.1, 8.1 Hz, 1H), 6.72 (ddd, J=2.6, 8.7, 11.5 Hz, 1H), 5.38 (br s, 1H), 4.01-3.82 (m, 2H), 3.70 (ddd, J=3.1, 8.8, 11.7 Hz, 2H), 3.27-3.03 (m, 1H), 2.54 (t, J=7.3 Hz, 2H), 2.19 (ddd, J=3.9, 9.1, 13.4 Hz, 2H), 2.11-1.95 (m, 2H), 1.89 (br s, 1H), 1.69-1.57 (m, 9H), 1.56-1.46 (m, 2H). [M+H]=401.2.

The other single isomer: ¹H NMR (400 MHz, CDCl₃) δ 7.09 (br s, 1H), 6.95 (td, J=2.3, 7.9 Hz, 1H), 6.72 (ddd, J=2.6, 8.7, 11.5 Hz, 1H), 5.31 (br s, 1H), 3.96-3.80 (m, 2H), 3.77-3.64 (m, 2H), 3.12 (t, J=12.3 Hz, 1H), 2.57 (br s, 2H), 2.20 (t, J=9.2 Hz, 2H), 1.98-1.72 (m, 6H), 1.47 (br s, 4H), 1.11 (d, J=10.9 Hz, 2H). [M+H]=401.2.

Example 38 and 39. 4-((2-((cis)-4-(4-fluoro-2-(trifluoromethyl)phenyl)cyclohexyl)ethyl)amino)tetrahydro-2H-pyran-4-carboxamide and 4-((2-((trans)-4-(4-fluoro-2-(trifluoromethyl)phenyl)cyclohexyl)ethyl)amino)tetrahydro-2H-pyran-4-carboxamide

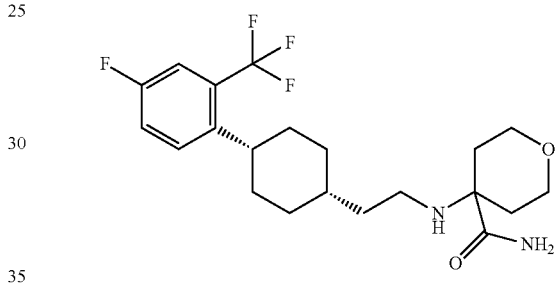

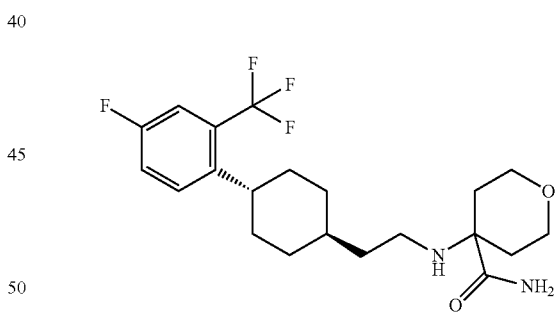

One of the two single isomers: ¹H NMR (400 MHz, CDCl₃) δ 7.44 (dd, J=5.6, 8.6 Hz, 1H), 7.33 (dd, J=2.7, 9.4 Hz, 1H), 7.21 (dt, J=2.6, 8.3 Hz, 1H), 7.02 (br s, 1H), 5.40 (br s, 1H), 3.96-3.80 (m, 2H), 3.72 (t, J=9.1 Hz, 2H), 2.91 (d, J=5.3 Hz, 1H), 2.56 (br s, 2H), 2.20 (br s, 2H), 1.92 (td, J=3.4, 6.9 Hz, 1H), 1.78-1.53 (m, 12H). [M+H]=417.2.

The other single isomer: ¹H NMR (400 MHz, CDCl₃) δ 7.41 (dd, J=5.6, 8.7 Hz, 1H), 7.32 (dd, J=2.7, 9.3 Hz, 1H), 7.20 (dt, J=2.6, 8.2 Hz, 1H), 7.03 (br s, 1H), 5.57 (br s, 1H), 3.94-3.79 (m, 2H), 3.71-3.62 (m, 2H), 2.88 (t, J=11.6 Hz, 1H), 2.55 (t, J=7.0 Hz, 2H), 2.18 (ddd, J=4.0, 9.1, 13.5 Hz, 2H), 1.92-1.78 (m, 4H), 1.66-1.57 (m, 2H), 1.53-1.38 (m, 5H), 1.30-1.06 (m, 2H). [M+H]=417.2.

Example 40 and 41. 4-((2-((cis)-4-(4,5-difluoro-2-methylphenyl)cyclohexyl)ethyl)amino)tetrahydro-2H-pyran-4-carboxamide and 4-((2-((trans)-4-(4,5-difluoro-2-methylphenyl)cyclohexyl)ethyl)amino)tetrahydro-2H-pyran-4-carboxamide

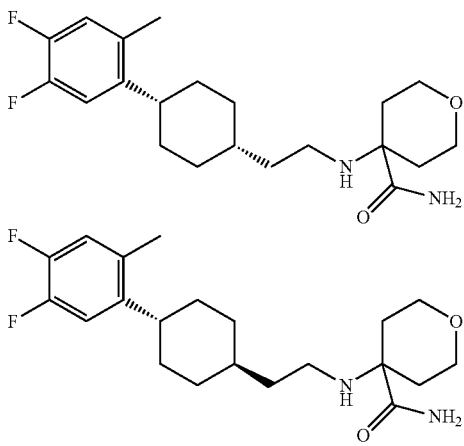

One of the two single isomers: $^1$H NMR (400 MHz, CDCl$_3$) δ 7.06-6.87 (m, 2H), 3.99-3.63 (m, 4H), 3.52 (s, 3H), 2.78-2.47 (m, 3H), 2.28 (s, 5H), 1.90 (dd, J=3.7, 7.2 Hz, 1H), 1.69 (dd, J=3.6, 5.9 Hz, 5H), 1.64-1.46 (m, 7H). [M+H]=381.2.

The other single isomer: $^1$H NMR (400 MHz, CDCl$_3$) δ 6.95 (ddd, J=8.3, 11.8, 15.7 Hz, 2H), 4.21-3.54 (m, 4H), 2.74-2.49 (m, 2H), 2.27 (s, 4H), 1.99-1.78 (m, 4H), 1.74-1.02 (m, 11H). [M+H]=381.2.

Example 42 and 43. 4-((2-((cis)-4-(2,4-difluoro-6-methylphenyl)cyclohexyl)ethyl)amino)tetrahydro-2H-pyran-4-carboxamide and 4-((2-((trans)-4-(2,4-difluoro-6-methylphenyl)cyclohexyl)ethyl)amino)tetrahydro-2H-pyran-4-carboxamide

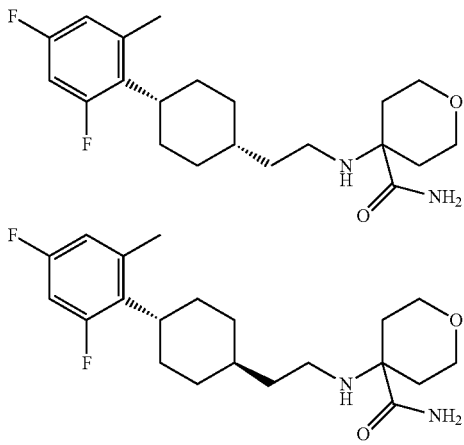

One of the two single isomers: $^1$H NMR (400 MHz, CDCl$_3$) δ 6.73-6.56 (m, 2H), 5.39 (br s, 1H), 3.94-3.66 (m, 4H), 2.84-2.69 (m, 1H), 2.59 (br s, 2H), 2.34 (s, 3H), 2.24 (br s, 2H), 2.09-1.95 (m, 2H), 1.88 (br s, 1H), 1.82-1.56 (m, 9H), 1.51-1.43 (m, 2H). [M+H]=381.2.

The other single isomer: $^1$H NMR (400 MHz, CDCl$_3$) δ 7.11 (br s, 1H), 6.75-6.43 (m, 2H), 5.40 (br s, 1H), 3.98-3.79 (m, 2H), 3.77-3.63 (m, 2H), 2.71 (br s, 1H), 2.57 (t, J=6.7 Hz, 2H), 2.34 (s, 3H), 2.24-2.13 (m, 2H), 1.95-1.82 (m, 4H), 1.76-1.55 (m, 5H), 1.47 (d, J=6.0 Hz, 3H), 1.18-0.96 (m, 2H). [M+H]=381.2.

Example 44 and 45. 4-((2-((cis)-4-(2,4,6-trifluorophenyl)cyclohexyl)ethyl)amino)tetrahydro-2H-pyran-4-carboxamide and 4-((2-((trans)-4-(2,4,6-trifluorophenyl)cyclohexyl)ethyl)amino)tetrahydro-2H-pyran-4-carboxamide

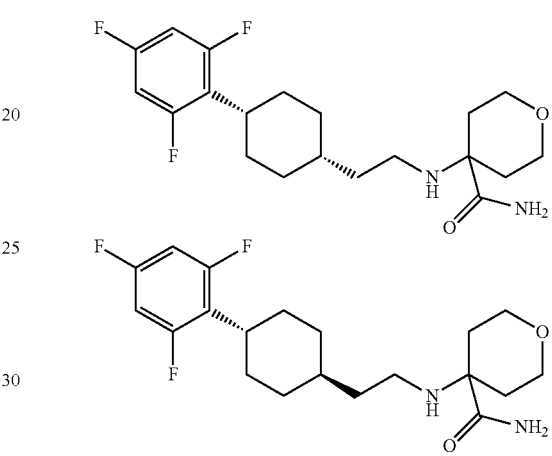

One of the two single isomers: $^1$H NMR (400 MHz, CD$_3$OD) δ 6.78 (t, J=9.0 Hz, 2H), 3.84 (ddd, J=3.2, 8.1, 11.4 Hz, 2H), 3.76-3.58 (m, 2H), 3.02-2.85 (m, 1H), 2.51 (t, J=7.2 Hz, 2H), 2.22-2.14 (m, 2H), 2.10-2.00 (m, 2H), 1.93-1.72 (m, 8H), 1.70-1.59 (m, 2H), 1.18-1.02 (m, 2H). [M+H]=385.2.

The other single isomer: $^1$H NMR (400 MHz, CDCl$_3$) δ 6.62 (t, J=8.7 Hz, 2H), 5.45 (br s, 1H), 3.94-3.64 (m, 4H), 3.08-2.82 (m, 1H), 2.63 (d, J=14.5 Hz, 1H), 2.27 (d, J=17.9 Hz, 2H), 2.04-1.88 (m, 3H), 1.82-1.58 (m, 10H), 1.51 (br s, 2H). [M+H]=385.2.

Example 46 and 47. N-Methyl-4-({2-[(cis)-4-[4-fluoro-2-(trifluoromethyl)phenyl]cyclohexyl]ethyl}amino)oxane-4-carboxamide and N-Methyl-4-({2-[(trans)-4-[4-fluoro-2-(trifluoromethyl)phenyl]cyclohexyl]ethyl}amino)oxane-4-carboxamide

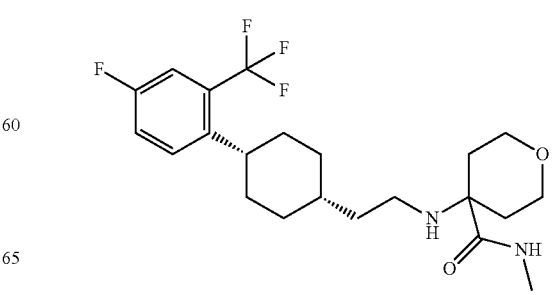

-continued

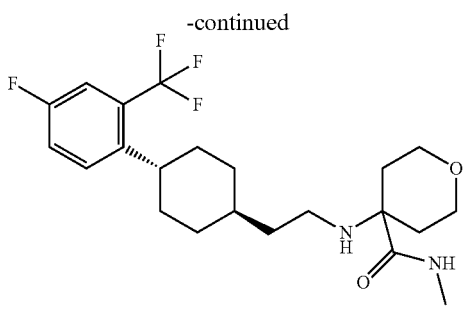

One of the two single isomers: ¹H NMR (400 MHz, CD₃OD) δ 7.63 (dd, J=5.5, 8.6 Hz, 1H), 7.50-7.20 (m, 2H), 3.83 (ddd, J=3.1, 8.4, 11.5 Hz, 2H), 3.75-3.63 (m, 2H), 2.93 (d, J=10.0 Hz, 1H), 2.79 (s, 3H), 2.45 (t, J=7.3 Hz, 2H), 2.05 (dt, J=4.3, 9.0 Hz, 2H), 1.92 (br s, 1H), 1.82-1.50 (m, 12H). [M+H]=431.3.

The other single isomer: ¹H NMR (400 MHz, CDCl₃) δ 7.41 (dd, J=5.5, 8.7 Hz, 1H), 7.32 (dd, J=2.8, 9.4 Hz, 1H), 7.28-7.13 (m, 2H), 3.95-3.80 (m, 2H), 3.65 (ddd, J=3.0, 9.1, 11.8 Hz, 2H), 2.88 (br s, 1H), 2.84 (d, J=5.0 Hz, 3H), 2.48 (t, J=7.0 Hz, 2H), 2.18 (ddd, J=4.0, 9.4, 13.7 Hz, 2H), 1.86 (d, J=11.0 Hz, 4H), 1.62-1.40 (m, 9H). [M+H]=431.48.

Example 48 and 49. 4-((2-((cis)-4-(3,4-difluoro-2-methylphenyl)cyclohexyl)ethyl)amino)tetrahydro-2H-pyran-4-carboxamide and 4-((2-((trans)-4-(3,4-difluoro-2-methylphenyl)cyclohexyl)ethyl)amino)tetrahydro-2H-pyran-4-carboxamide

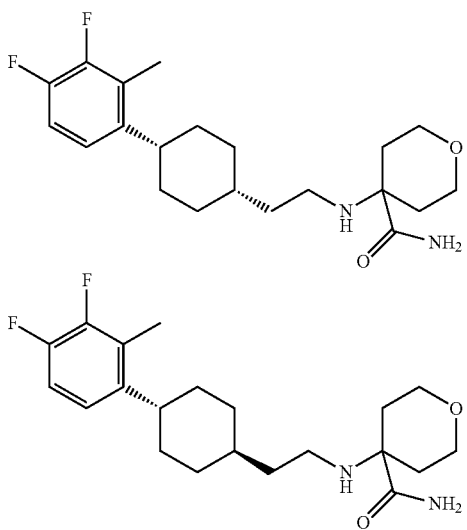

One of the two single isomers: ¹H NMR (400 MHz, CD₃OD) δ 7.10-6.89 (m, 2H), 3.84 (ddd, J=3.3, 8.1, 11.5 Hz, 2H), 3.76-3.60 (m, 2H), 2.75 (br s, 1H), 2.50 (t, J=7.5 Hz, 2H), 2.27 (d, J=2.7 Hz, 3H), 2.17-1.99 (m, 2H), 1.90 (dd, J=3.5, 7.2 Hz, 1H), 1.80-1.49 (m, 12H). [M+H]=381.2.

The other single isomer: ¹H NMR (400 MHz, CD₃OD) δ 7.00 (d, J=4.5 Hz, 2H), 3.84 (ddd, J=3.1, 8.1, 11.4 Hz, 2H), 3.73-3.59 (m, 2H), 2.77-2.64 (m, 1H), 2.52 (t, J=7.1 Hz, 2H), 2.27 (d, J=2.6 Hz, 3H), 2.15-2.00 (m, 2H), 1.91 (d, J=13.7 Hz, 2H), 1.81 (d, J=11.9 Hz, 2H), 1.70-1.59 (m, 2H), 1.56-1.42 (m, 5H), 1.25-1.10 (m, 2H). [M+H]=381.3.

Example 50 and 51. 4-((2-((cis)-4-(5-fluoro-3-(trifluoromethyl)pyridin-2-yl)cyclohexyl)ethyl)amino)-N-methyltetrahydro-2H-pyran-4-carboxamide and 4-((2-((trans)-4-(5-fluoro-3-(trifluoromethyl)pyridin-2-yl)cyclohexyl)ethyl)amino)-N-methyltetrahydro-2H-pyran-4-carboxamide

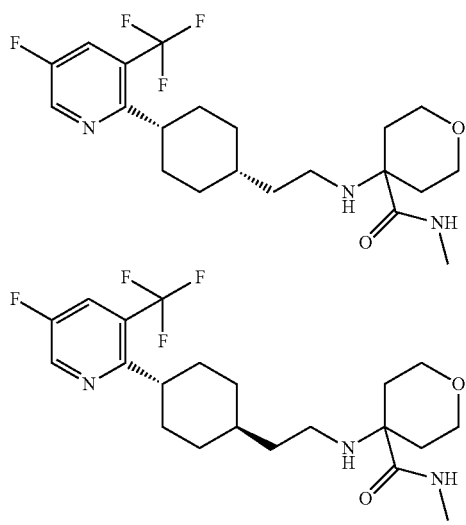

One of the two single isomers: ¹H NMR (400 MHz, CDCl₃) δ 8.65 (s, 1H), 7.57 (d, J=8.1 Hz, 1H), 4.07-3.63 (m, 4H), 3.17-3.05 (m, 1H), 2.86 (d, J=4.3 Hz, 3H), 2.61-2.03 (m, 4H), 1.91 (d, J=11.0 Hz, 4H), 1.83-1.49 (m, 10H). [M+H]=432.3.

The other single isomer: ¹H NMR (400 MHz, CD₃OD) δ 8.67 (s, 1H), 7.88 (d, J=9.8 Hz, 1H), 3.81 (ddd, J=3.0, 8.6, 11.5 Hz, 2H), 3.74-3.61 (m, 2H), 3.23 (t, J=9.7 Hz, 1H), 2.79 (s, 3H), 2.44 (t, J=7.4 Hz, 2H), 2.15-1.92 (m, 4H), 1.86 (d, J=3.4 Hz, 1H), 1.77-1.59 (m, 10H). [M+H]=432.3.

Example 52. N-Ethyl-4-({2-[(cis)-4-[4-fluoro-2-(trifluoromethyl)phenyl]cyclohexyl]ethyl}amino)oxane-4-carboxamide

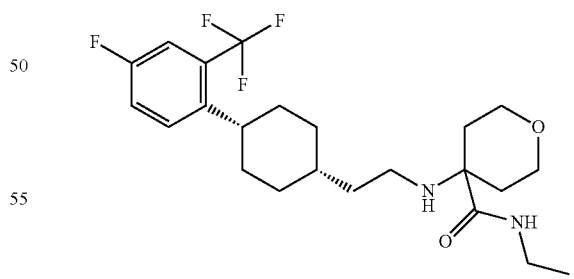

¹H NMR (400 MHz, CD₃OD) δ 7.62 (dd, J=5.6, 8.5 Hz, 1H), 7.44-7.30 (m, 2H), 3.81 (dd, J=3.1, 8.4 Hz, 2H), 3.75-3.62 (m, 2H), 3.30-3.22 (m, 2H), 2.92 (br s, 1H), 2.47 (t, J=7.3 Hz, 2H), 2.11-2.05 (m, 1H), 1.92 (br s, 1H), 1.83-1.53 (m, 11H), 1.38-1.32 (m, 6H). [M+H]=445.3.

Example 53-Example 60 were prepared in a manner analogous to Example 3, with the appropriate starting material substitutions.

Example 53. (1S,3R)—N-{2-[4-(2-Chloro-4-fluorophenyl)cyclohexyl]ethyl}-3-fluorocyclopentan-1-amine

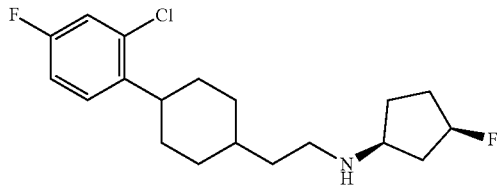 [SMILES: Fc1ccc(C2CCC(CCN[C@H]3CC[C@@H](F)C3)CC2)c(Cl)c1]

[M+H]=342.2.

Example 54. 3,3-Difluoro-N-{2-[(cis)-4-(2-chloro-4-fluorophenyl)cyclohexyl]ethyl}cyclopentan-1-amine

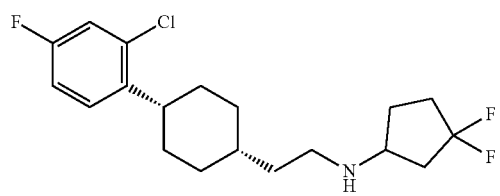 [SMILES: Fc1ccc([C@H]2CC[C@@H](CCNC3CCC(F)(F)C3)CC2)c(Cl)c1]

¹H NMR (400 MHz, CD₃OD) δ 7.36 (dd, J=6.30, 8.50 Hz, 1H), 7.17 (dd, J=2.69, 8.68 Hz, 1H), 7.08-6.94 (m, 1H), 3.93-3.44 (m, 2H), 3.15-2.96 (m, 3H), 2.81-2.57 (m, 1H), 2.49-2.07 (m, 4H), 1.98-1.52 (m, 12H). [M+H]=360.5.

Example 55. N-(2-((cis)-4-(2-chloro-4-fluorophenyl)cyclohexyl)ethyl)-3-fluorotetrahydro-2H-pyran-4-amine

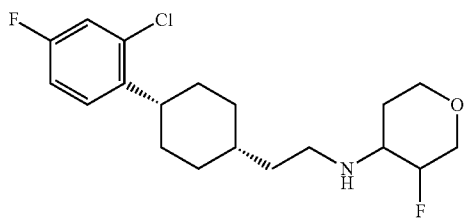 [SMILES: Fc1ccc([C@H]2CC[C@@H](CCNC3CCOCC3F)CC2)c(Cl)c1]

The title compound was isolated as a mixture of stereoisomers. [M+H]=358.5.

Example 56 and 57. Two Enantiomers of N-(2-((cis)-4-(2-chloro-4-fluorophenyl)cyclohexyl)ethyl)-3-fluorotetrahydro-2H-pyran-4-amine

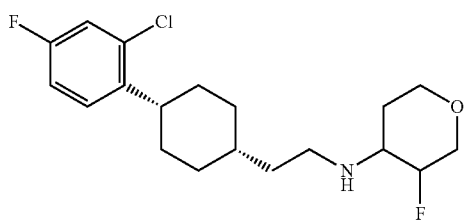

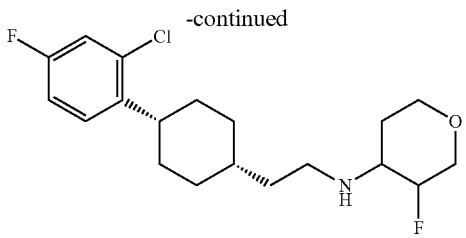

Further separation of Example 55 provided two single enantiomers, the absolute structure of which were not determined.

One of the two single enantiomers: ¹H NMR (400 MHz, CD₃OD) δ 7.49-7.34 (m, 1H), 7.15 (dd, J=2.69, 8.80 Hz, 1H), 7.03 (dt, J=2.69, 8.44 Hz, 1H), 4.80-4.60 (m, 1H), 4.09 (t, J=12.84 Hz, 1H), 4.01-3.89 (m, 1H), 3.58 (d, J=13.20 Hz, 1H), 3.64-3.40 (m, 1H), 3.10-2.96 (m, 1H), 2.92-2.60 (m, 3H), 1.89-1.55 (m, 13H). [M+H]=358.2.

The other single enantiomer: ¹H NMR (400 MHz, CD₃OD) δ 7.50-7.35 (m, 1H), 7.17 (dd, J=2.69, 8.80 Hz, 1H), 7.05 (dt, J=2.69, 8.44 Hz, 1H), 4.82-4.63 (m, 1H), 4.16-4.05 (m, 1H), 4.02-3.93 (m, 1H), 3.60 (d, J=13.20 Hz, 1H), 3.65-3.43 (m, 1H), 3.15-2.96 (m, 1H), 2.94-2.63 (m, 3H), 1.92-1.56 (m, 13H). [M+H]=358.2.

Example 58 and 59. N-(2-((cis)-4-(4-methylpyridin-3-yl)cyclohexyl)ethyl)tetrahydro-2H-pyran-4-amine and N-(2-((trans)-4-(4-methylpyridin-3-yl)cyclohexyl)ethyl)tetrahydro-2H-pyran-4-amine

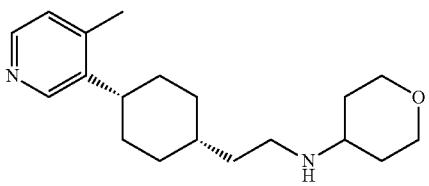

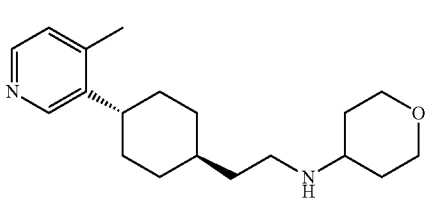

One of the two single isomers: ¹H NMR (400 MHz, CD₃OD) δ 8.36 (s, 1H) 8.23-8.15 (m, 1H), 7.19 (d, J=5.14 Hz, 1H), 3.91-4.01 (m, 2H), 3.43 (td, J=11.92, 1.96 Hz, 2H), 2.91-2.64 (m, 4H), 2.38 (s, 3H), 1.96-1.81 (m, 3H), 1.80-1.57 (m, 10H), 1.51-1.35 (m, 2H). [M+H]=303.3.

The other single isomer: ¹H NMR (400 MHz, CD₃OD) δ 8.42-8.29 (m, 1H), 8.18 (d, J=5.01 Hz, 1H), 7.19 (d, J=5.14 Hz, 1H), 3.96 (dd, J=4.03, 11.13 Hz, 2H), 3.42 (dt, J=1.71, 11.92 Hz, 2H), 2.88-2.62 (m, 4H), 2.45-2.31 (m, 3H), 2.03-1.74 (m, 6H), 1.67-1.34 (m, 7H), 1.30-1.08 (m, 2H). [M+H]=303.3.

Example 60. 4-((2-((cis)-4-(4-fluoro-2-methylphenyl)cyclohexyl)ethyl)amino)tetrahydro-2H-pyran-4-carboxamide

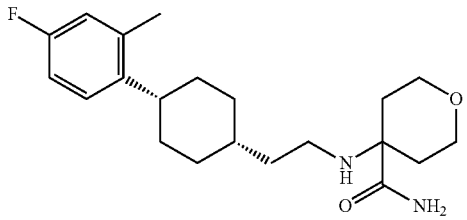 [SMILES: Cc1cc(F)ccc1[C@H]1CC[C@@H](CCNC2(C(N)=O)CCOCC2)CC1]

¹H NMR (400 MHz, Acetone) δ 7.28 (dd, J=6.1, 14.2 Hz, 1H), 7.10 (br s, 1H), 6.98-6.75 (m, 2H), 6.25 (br s, 1H), 3.82-3.57 (m, 4H), 2.88-2.69 (m, 3H), 2.54 (t, J=7.3 Hz, 2H), 2.34 (s, 3H), 2.06-1.89 (m, 6H), 1.71-1.53 (m, 8H). [M+H]=363.3.

Example 61-Example 84 were prepared in a manner analogous to Example 4, with the appropriate starting material substitutions.

Example 61. N-{2-[(cis)-4-(2-Chloro-4-fluorophenyl)cyclohexyl]ethyl}oxan-4-amine

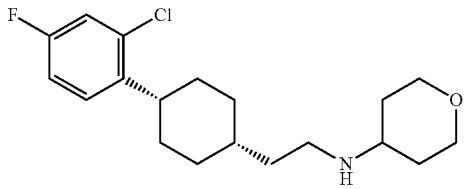 [SMILES: Fc1ccc([C@H]2CC[C@@H](CCNC3CCOCC3)CC2)c(Cl)c1]

¹H NMR (400 MHz, CD₃OD) δ 7.36 (dd, J=6.17, 8.74 Hz, 1H), 7.18 (dd, J=2.57, 8.68 Hz, 1H), 7.04 (dt, J=2.69, 8.44 Hz, 1H), 4.04 (dd, J=4.58, 11.80 Hz, 2H), 3.52-3.36 (m, 3H), 3.16-2.97 (m, 3H), 2.14-1.51 (m, 15H). [M+H]=340.3.

Example 62 and 63. 4-((2-((cis)-4-(3-chloro-5-fluoropyridin-2-yl)cyclohexyl)ethyl)amino)-N-methyltetrahydro-2H-pyran-4-carboxamide and 4-((2-((trans)-4-(3-chloro-5-fluoropyridin-2-yl)cyclohexyl)ethyl)amino)-N-methyltetrahydro-2H-pyran-4-carboxamide

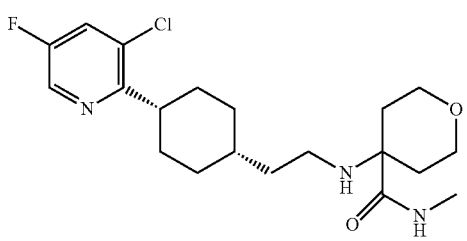

-continued

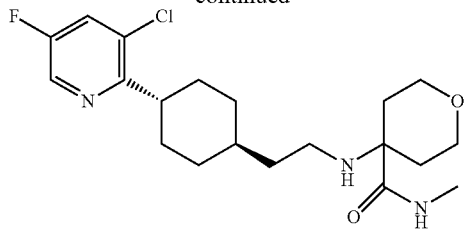

One of the two single isomers: ¹H NMR (400 MHz, Acetone) δ 8.51-8.38 (m, 1H), 7.82-7.69 (m, 1H), 7.46 (br s, 1H), 3.80-3.64 (m, 4H), 3.28-3.11 (m, 1H), 2.75 (d, J=4.8 Hz, 3H), 2.50 (t, J=7.2 Hz, 2H), 2.06-2.00 (m, 2H), 1.96-1.78 (m, 4H), 1.77-1.51 (m, 10H). [M+H]=398.4.

The other single isomer: ¹H NMR (400 MHz, Acetone) δ 8.45 (d, J=2.6 Hz, 1H), 7.75 (dd, J=2.6, 8.4 Hz, 1H), 7.42 (br s, 1H), 3.76-3.64 (m, 4H), 3.15 (tt, J=3.3, 11.8 Hz, 1H), 2.74 (d, J=4.9 Hz, 3H), 2.49 (t, J=7.1 Hz, 2H), 2.05-1.97 (m, 2H), 1.96-1.78 (m, 5H), 1.75-1.60 (m, 2H), 1.60-1.40 (m, 5H), 1.23-1.04 (m, 2H). [M+H]=398.4.

Example 64. N-{2-[(cis)-4-(2-Chloro-4-fluorophenyl)cyclohexyl]ethyl}cyclopentanamine

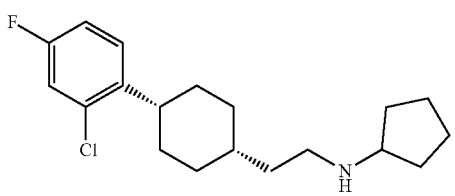 [SMILES: Fc1ccc([C@H]2CC[C@@H](CCNC3CCCC3)CC2)c(Cl)c1]

¹H NMR (400 MHz, CD₃OD) δ 7.42-7.29 (m, 1H), 7.17 (dd, J=2.69, 8.68 Hz, 1H), 7.04 (dt, J=2.69, 8.44 Hz, 1H), 3.57 (t, J=7.21 Hz, 1H), 3.14-2.91 (m, 3H), 2.24-2.06 (m, 2H), 1.95-1.54 (m, 17H). [M+H]=324.2.

Example 65. 2,2-Difluoro-N-{2-[(cis)-4-(2-chloro-4-fluorophenyl)cyclohexyl]ethyl}cyclopentan-1-amine

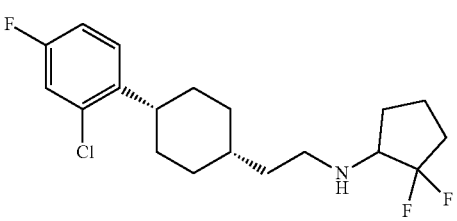 [SMILES: Fc1ccc([C@H]2CC[C@@H](CCNC3CCCC3(F)F)CC2)c(Cl)c1]

¹H NMR (400 MHz, CDCl₃) δ 7.36 (dd, J=6.11, 8.68 Hz, 1H), 7.17 (dd, J=2.69, 8.80 Hz, 1H), 7.04 (dt, J=2.69, 8.44 Hz, 1H), 4.03-3.83 (m, 1H), 3.21-2.97 (m, 3H), 2.48-2.17 (m, 3H), 2.06-1.56 (m, 14H). [M+H]=360.2.

Example 66. [4-({2-[(cis)-4-(2-Chloro-4-fluorophenyl)cyclohexyl]ethyl}amino)oxan-4-yl]methanol

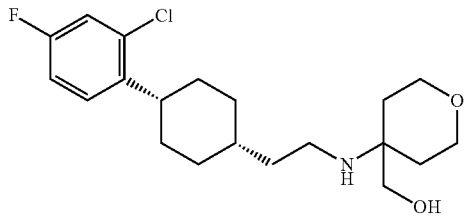 [SMILES: OCC1(NCC[C@H]2CC[C@@H](c3ccc(F)cc3Cl)CC2)CCOCC1]

$^1$H NMR (400 MHz, CDCl$_3$) δ 8.62 (br s, 2H), 7.22 (dd, J=6.1, 8.7 Hz, 1H), 7.09 (dd, J=2.7, 8.6 Hz, 1H), 6.94 (dt, J=2.7, 8.4 Hz, 1H), 4.06-3.90 (m, 4H), 3.54 (t, J=11.0 Hz, 2H), 3.11-2.92 (m, 3H), 2.12-1.98 (m, 2H), 1.97-1.59 (m, 12H), 1.57-1.41 (m, 2H). [M+H]=370.3.

Example 67. N,N-Dimethyl-1-({2-[(cis)-4-(2-chloro-4-fluorophenyl)cyclohexyl]ethyl}amino)cyclopentane-1-carboxamide

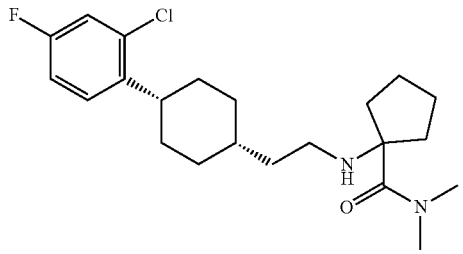 [SMILES: CN(C)C(=O)C1(NCC[C@H]2CC[C@@H](c3ccc(F)cc3Cl)CC2)CCCC1]

$^1$H NMR (400 MHz, DMSO-d$_6$) δ 8.53 (br s, 2H), 7.50-7.34 (m, 2H), 7.23 (dt, J=2.7, 8.6 Hz, 1H), 3.05-2.81 (m, 9H), 2.32-2.19 (m, 2H), 2.17-2.04 (m, 2H), 1.98-1.77 (m, 7H), 1.72-1.50 (m, 8H). [M+H]=395.3.

Example 68. 1-({2-[(cis)-4-(2-Chloro-4-fluorophenyl)cyclohexyl]ethyl}amino)cyclopentane-1-carboxamide

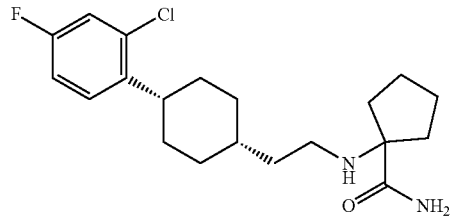 [SMILES: NC(=O)C1(NCC[C@H]2CC[C@@H](c3ccc(F)cc3Cl)CC2)CCCC1]

$^1$H NMR (400 MHz, DMSO-d$_6$) δ 8.70 (br s, 2H), 7.88-7.58 (m, 2H), 7.52-7.34 (m, 2H), 7.22 (dt, J=2.7, 8.5 Hz, 1H), 3.13-3.01 (m, 1H), 2.99-2.86 (m, 1H), 2.81 (d, J=4.9 Hz, 3H), 2.20-2.06 (m, 2H), 2.06-1.95 (m, 2H), 1.83-1.54 (m, 13H). [M+H]=367.3.

Example 69. 4-({2-[(trans)-4-(2-Chloro-4-fluorophenyl)cyclohexyl]ethyl}amino)oxane-4-carboxamide

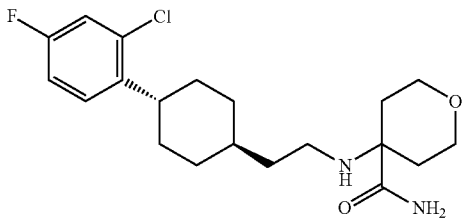 [SMILES: NC(=O)C1(NCC[C@H]2CC[C@H](c3ccc(F)cc3Cl)CC2)CCOCC1]

$^1$H NMR (400 MHz, DMSO-d$_6$) δ 8.85 (br s, 2H), 7.84-8.15 (m, 2H), 7.32-7.47 (m, 2H), 7.19 (dt, J=2.69, 8.50 Hz, 1H), 3.77-3.94 (m, 2H), 3.46-3.51 (m, 2H), 2.77-2.96 (m, 3H), 2.28 (d, J=13.94 Hz, 2H), 1.74-1.92 (m, 6H), 1.54-1.63 (m, 2H), 1.37-1.50 (m, 3H), 1.06-1.19 (m, 2H). [M+H]=383.4.

Example 70. N-Methyl-1-({2-[(cis)-4-(2-chloro-4-fluorophenyl)cyclohexyl]ethyl}amino)cyclopentane-1-carboxamide

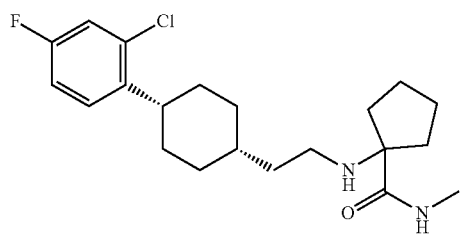 [SMILES: CNC(=O)C1(NCC[C@H]2CC[C@@H](c3ccc(F)cc3Cl)CC2)CCCC1]

$^1$H NMR (400 MHz, DMSO-d$_6$) δ 8.73 (br s, 2H), 8.07 (d, J=4.5 Hz, 1H), 7.48-7.33 (m, 2H), 7.22 (dt, J=2.5, 8.5 Hz, 1H), 2.90 (d, J=10.5 Hz, 1H), 2.80 (d, J=4.6 Hz, 2H), 2.69 (d, J=4.4 Hz, 3H), 2.16-1.93 (m, 4H), 1.90-1.71 (m, 7H), 1.69-1.49 (m, 8H). [M+H]=381.3.

Example 71. 3-({2-[(cis)-4-(2-Chloro-4-fluorophenyl)cyclohexyl]ethyl}amino)oxane-3-carboxamide

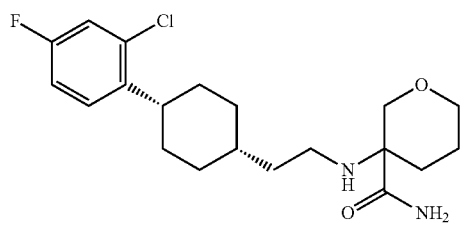 [SMILES: NC(=O)C1(NCC[C@H]2CC[C@@H](c3ccc(F)cc3Cl)CC2)CCCOC1]

$^1$H NMR (400 MHz, DMSO-d$_6$) δ 8.73 (br s, 2H), 7.96 (s, 1H), 7.83 (s, 1H), 7.48-7.33 (m, 2H), 7.24 (dt, J=2.8, 8.4 Hz, 1H), 3.88 (s, 3H), 3.57 (d, J=8.4 Hz, 2H), 2.93 (br s, 1H), 2.83 (br s, 2H), 2.30-2.05 (m, 2H), 1.98-1.80 (m, 4H), 1.68-1.57 (m, 8H). [M+H]=383.2.

Example 72. 3-({2-[(cis)-4-(2-Chloro-4-fluorophenyl)cyclohexyl]ethyl}amino)oxolane-3-carboxamide

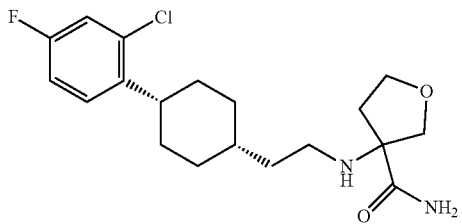 [SMILES: NC(=O)C1(NCC[C@H]2CC[C@@H](c3ccc(F)cc3Cl)CC2)CCOC1]

$^1$H NMR (400 MHz, Acetone) δ 7.64-7.46 (m, 1H), 7.22 (dd, J=2.7, 8.8 Hz, 1H), 7.09 (dt, J=2.7, 8.5 Hz, 1H), 4.18 (s, 1H), 4.06-3.78 (m, 2H), 3.17-2.91 (m, 7H), 2.58 (t, J=8.3 Hz, 3H), 2.02-1.92 (m, 2H), 1.85-1.50 (m, 9H). [M+H]=369.1.

Example 73 and 74. N-(2-((cis)-4-(3-methylpyridin-4-yl)cyclohexyl)ethyl)tetrahydro-2H-pyran-4-amine and N-(2-((trans)-4-(3-methylpyridin-4-yl)cyclohexyl)ethyl)tetrahydro-2H-pyran-4-amine

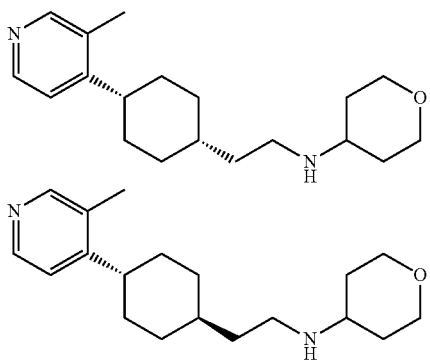

One of the two single isomers: $^1$H NMR (400 MHz, CD$_3$OD) δ 8.28 (br s, 2H), 7.31 (d, J=4.52 Hz, 1H), 3.96 (dd, J=3.97, 10.94 Hz, 2H), 3.43 (dt, J=1.96, 11.98 Hz, 2H), 2.87-2.61 (m, 4H), 2.34 (s, 3H), 1.99-1.54 (m, 13H), 1.43 (dq, J=4.58, 12.12 Hz, 2H). [M+H]=303.3.

The other single isomer: $^1$H NMR (400 MHz, CD$_3$OD) δ 9.24 (br s, 2H), 8.40-8.12 (m, 1H), 4.94 (dd, J=3.79, 11.25 Hz, 2H), 4.40 (dt, J=1.83, 11.92 Hz, 2H), 3.94-3.56 (m, 4H), 3.31 (s, 3H), 3.02-2.65 (m, 7H), 2.31-2.61 (m, 7H), 2.24-2.07 (m, 2H). [M+H]=303.3.

Example 75. N-(Cyclopropylmethyl)-1-({2-[(cis)-4-(2-chloro-4-fluorophenyl)cyclohexyl]ethyl}amino)cyclopentane-1-carboxamide

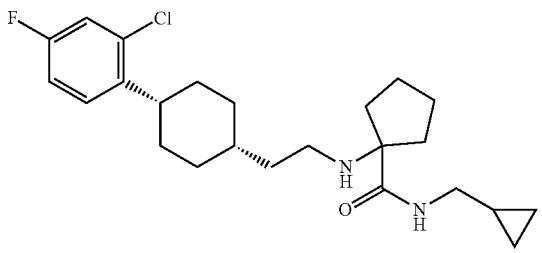 [SMILES: O=C(NCC1CC1)C1(NCC[C@H]2CC[C@@H](c3ccc(F)cc3Cl)CC2)CCCC1]

$^1$H NMR (400 MHz, DMSO-d$_6$) δ 8.80 (br s, 2H), 8.26 (t, J=5.7 Hz, 1H), 7.47-7.33 (m, 2H), 7.22 (dt, J=2.8, 8.5 Hz, 1H), 3.05 (t, J=6.2 Hz, 2H), 2.98-2.87 (m, 1H), 2.80 (br s, 2H), 2.21-2.09 (m, 2H), 2.06-1.94 (m, 2H), 1.91-1.73 (m, 7H), 1.69-1.47 (m, 8H), 1.03-0.90 (m, 1H), 0.45-0.37 (m, 2H), 0.23-0.16 (m, 2H). [M+H]=421.5.

Example 76. N-Methyl-4-({2-[(cis)-4-(2-chloro-4-fluorophenyl)cyclohexyl]ethyl}amino)oxane-4-carboxamide

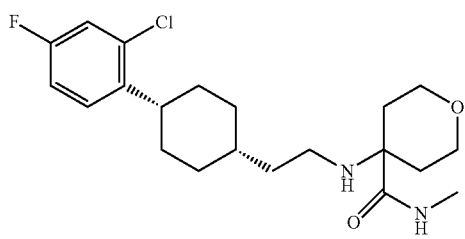

$^1$H NMR (400 MHz, DMSO-d$_6$) δ 8.92 (br s, 2H), 8.35 (d, J=4.6 Hz, 1H), 7.47-7.34 (m, 2H), 7.22 (dt, J=2.7, 8.5 Hz, 1H), 3.89-3.83 (m, 2H), 3.41 (t, J=9.8 Hz, 2H), 2.98-2.85 (m, 1H), 2.85-2.69 (m, 4H), 2.30 (d, J=13.7 Hz, 2H), 1.91-1.72 (m, 5H), 1.71-1.44 (m, 9H). [M+H]=397.3.

Example 77. N-Ethyl-4-({2-[(cis)-4-(2-chloro-4-fluorophenyl)cyclohexyl]ethyl}amino)oxane-4-carboxamide

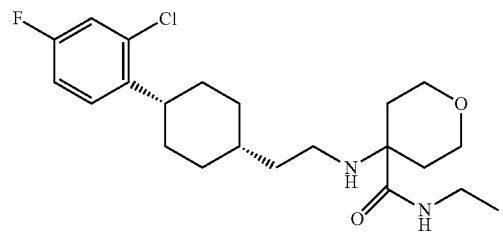 [SMILES: CCNC(=O)C1(NCC[C@H]2CC[C@@H](c3ccc(F)cc3Cl)CC2)CCOCC1]

$^1$H NMR (400 MHz, DMSO-d$_6$) δ 8.91 (br s, 2H), 8.50-8.29 (m, 1H), 7.48-7.33 (m, 2H), 7.22 (dt, J=2.7, 8.6 Hz, 1H), 3.90-3.82 (m, 2H), 3.41 (t, J=9.8 Hz, 2H), 3.29-3.16 (m, 2H), 3.13-2.70 (m, 4H), 2.32 (d, J=13.9 Hz, 2H), 1.92-1.72 (m, 5H), 1.69-1.52 (m, 7H), 1.18-0.88 (m, 3H). [M+H]=411.4.

Example 78 and 79. N-(2-((cis)-4-(3-chloro-5-fluoropyridin-2-yl)cyclohexyl)ethyl)tetrahydro-2H-pyran-4-amine and N-(2-((trans)-4-(3-chloro-5-fluoropyridin-2-yl)cyclohexyl)ethyl)tetrahydro-2H-pyran-4-amine

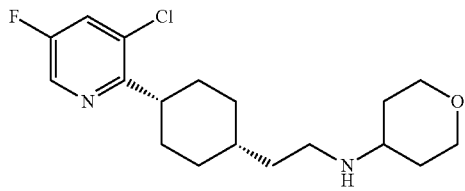

-continued

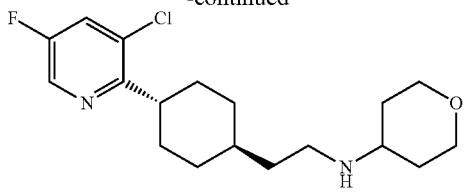

One of the two single isomers: ¹H NMR (400 MHz, CD₃OD) δ 8.36 (d, J=2.69 Hz, 1H), 7.69 (dd, J=2.57, 8.31 Hz, 1H), 3.95 (dd, J=4.10, 10.82 Hz, 2H), 3.42 (dt, J=1.96, 11.98 Hz, 2H), 3.28-3.17 (m, 1H), 2.84-2.62 (m, 3H), 1.99-1.56 (m, 13H), 1.42 (dq, J=4.58, 12.12 Hz, 2H). [M+H]=341.6.

The other single isomer: ¹H NMR (400 MHz, CD₃OD) δ 8.44-8.34 (m, 1H), 7.72 (dd, J=2.63, 8.38 Hz, 1H), 3.97 (dd, J=4.03, 10.88 Hz, 2H), 3.44 (dt, J=1.96, 11.92 Hz, 2H), 3.19 (tt, J=3.44, 11.84 Hz, 1H), 2.80-2.61 (m, 3H), 2.02-1.78 (m, 6H), 1.74-1.60 (m, 2H), 1.54-1.36 (m, 5H), 1.30-1.06 (m, 2H). [M+H]=341.6.

Example 80 and 81. N-(2-((cis)-4-(3-methylpyridin-2-yl)cyclohexyl)ethyl)tetrahydro-2H-pyran-4-amine and N-(2-((trans)-4-(3-methylpyridin-2-yl)cyclohexyl)ethyl)tetrahydro-2H-pyran-4-amine

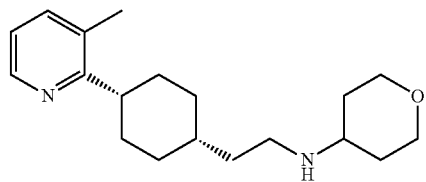

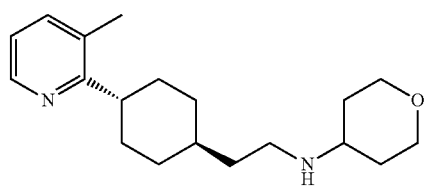

One of the two single isomers: ¹H NMR (400 MHz, CD₃OD) δ 8.29 (dd, J=4.83, 1.28 Hz, 1H), 7.55 (dd, J=7.58, 0.86 Hz, 1H), 7.11 (dd, J=7.70, 4.89 Hz, 1H), 3.96 (dd, J=10.76, 4.03 Hz, 2H), 3.43 (td, J=11.92, 2.08 Hz, 2H), 3.04-2.89 (m, 1H), 2.81-2.70 (m, 1H), 2.69-2.62 (m, 2H), 2.36 (s, 3H), 1.95-1.81 (m, 5H), 1.80-1.64 (m, 6H), 1.60-1.49 (m, 2H), 1.49-1.36 (m, 2H). [M+H]=303.6.

The other single isomer: ¹H NMR (400 MHz, CD₃OD) δ 8.27 (dd, J=4.77, 1.34 Hz, 1H), 7.60-7.50 (m, 1H), 7.10 (dd, J=7.58, 4.89 Hz, 1H), 3.95 (dd, J=10.76, 4.03 Hz, 2H), 3.42 (td, J=11.92, 1.96 Hz, 2H), 2.92 (tt, J=11.42, 3.87 Hz, 1H), 2.77-2.64 (m, 3H), 2.35 (s, 3H), 1.98-1.82 (m, 4H), 1.81-1.63 (m, 4H), 1.55-1.33 (m, 5H), 1.26-1.08 (m, 2H). [M+H]= 303.6.

Example 82. 4-(Methoxymethyl)-N-{2-[(cis)-4-(2-chloro-4-fluorophenyl)cyclohexyl]ethyl}oxan-4-amine

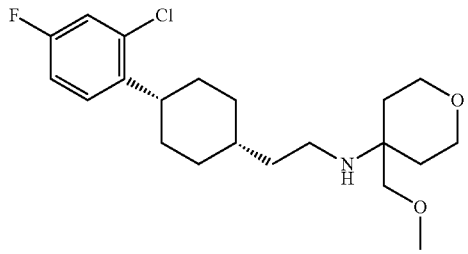 [SMILES: COCC1(NCC[C@H]2CC[C@@H](c3ccc(F)cc3Cl)CC2)CCOCC1]

¹H NMR (400 MHz, DMSO-d₆) δ 8.41 (br s, 2H), 7.46-7.34 (m, 2H), 7.22 (dt, J=2.7, 8.5 Hz, 1H), 3.82 (dd, J=2.8, 12.1 Hz, 2H), 3.74 (s, 2H), 3.47 (d, J=1.7 Hz, 4H), 3.39 (s, 3H), 2.98-2.78 (m, 3H), 1.89-1.53 (m, 13H). [M+H]= 384.5.

Example 83 and 84. 4-((2-((cis)-4-(3-chloro-5-fluoropyridin-4-yl)cyclohexyl)ethyl)amino)-N-methyltetrahydro-2H-pyran-4-carboxamide and 4-((2-((trans)-4-(3-chloro-5-fluoropyridin-4-yl)cyclohexyl)ethyl)amino)-N-methyltetrahydro-2H-pyran-4-carboxamide

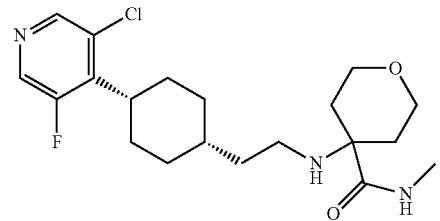

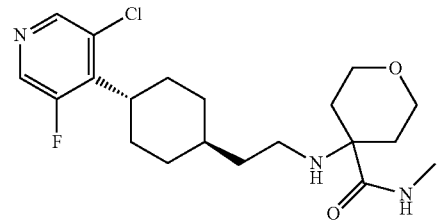

One of the two single isomers: ¹H NMR (400 MHz, Acetone) δ 8.42 (s, 1H), 8.39 (d, J=2.2 Hz, 1H), 3.75-3.65 (m, 4H), 3.32 (s, 3H), 3.28-3.18 (m, 1H), 3.18-3.17 (m, 1H), 2.74 (d, J=4.6 Hz, 2H), 2.52-2.45 (m, 2H), 2.06-1.98 (m, 4H), 1.80-1.63 (m, 6H), 1.55 (dd, J=3.3, 13.4 Hz, 4H). [M+H]=398.1.

The other single isomer: ¹H NMR (400 MHz, DMSO-d₆) δ 9.52 (br s, 2H), 8.69 (d, J=4.5 Hz, 1H), 8.49 (s, 1H), 3.88 (d, J=12.0 Hz, 2H), 3.16-3.04 (m, 2H), 2.75 (br s, 2H), 2.72 (d, J=4.4 Hz, 3H), 2.32 (d, J=12.5 Hz, 2H), 2.04-1.93 (m, 3H), 1.88-1.70 (m, 6H), 1.67-1.58 (m, 2H), 1.48 (br s, 1H), 1.15-0.96 (m, 2H). [M+H]=398.1.

Example 85-Example 86 were prepared in a manner analogous to Example 6, with the appropriate starting material substitutions.

Example 85 and 86. 4-((2-((cis)-4-(3-chloro-5-fluoropyridin-2-yl)cyclohexyl)ethyl)amino)-N-ethyltetrahydro-2H-pyran-4-carboxamide and 4-((2-((trans)-4-(3-chloro-5-fluoropyridin-2-yl)cyclohexyl)ethyl)amino)-N-ethyltetrahydro-2H-pyran-4-carboxamide

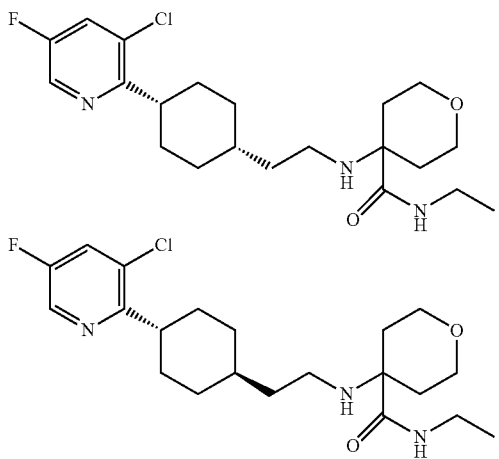

One of the two single isomers: ¹H NMR (400 MHz, Acetone) δ 8.47 (d, J=2.6 Hz, 1H), 7.77 (dd, J=2.6, 8.4 Hz, 1H), 7.68 (br s, 1H), 3.86-3.67 (m, 4H), 3.35-3.18 (m, 3H), 2.77 (br s, 2H), 2.21 (d, J=9.3 Hz, 2H), 1.94-1.52 (m, 14H), 1.13 (t, J=7.2 Hz, 3H). [M+H]=412.4.

The other single isomer: ¹H NMR (400 MHz, Acetone) δ 8.45 (d, J=2.6 Hz, 1H), 7.75 (dd, J=2.6, 8.4 Hz, 1H), 7.48 (br s, 1H), 3.76-3.63 (m, 4H), 3.29-3.21 (m, 2H), 3.15 (tt, J=3.4, 11.8 Hz, 1H), 2.51 (t, J=7.1 Hz, 2H), 2.05-1.98 (m, 2H), 1.96-1.79 (m, 5H), 1.76-1.61 (m, 2H), 1.60-1.42 (m, 5H), 1.22-1.06 (m, 5H). [M+H]=412.4.

Example 87-Example 92 were prepared in a manner analogous to Example 11, with the appropriate starting material substitutions.

Example 87 and 88. N-(2-((cis)-4-(3-methylpyrazin-2-yl)cyclohexyl)ethyl)tetrahydro-2H-pyran-4-amine and N-(2-((trans)-4-(3-methylpyrazin-2-yl)cyclohexyl)ethyl)tetrahydro-2H-pyran-4-amine

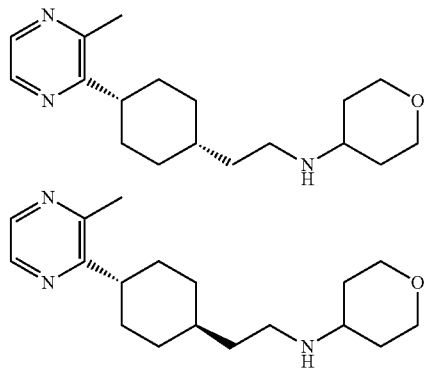

One of the two single isomers: ¹H NMR (400 MHz, CD₃OD) δ 8.47-8.34 (m, 1H), 8.26 (d, J=2.69 Hz, 1H), 3.99 (dd, J=11.19, 4.22 Hz, 2H), 3.45 (td, J=11.98, 1.83 Hz, 2H), 3.04 (tt, J=10.58, 3.79 Hz, 1H), 2.92 (tt, J=11.19, 4.03 Hz, 1H), 2.84-2.72 (m, 2H), 2.61 (s, 3H), 2.04-1.41 (m, 15H). [M+H]=304.2.

The other single isomer: ¹H NMR (400 MHz, CD₃OD) δ 8.49-8.33 (m, 1H), 8.25 (d, J=2.45 Hz, 1H), 3.98 (br dd, J=11.43, 4.10 Hz, 2H), 3.43 (br t, J=11.86 Hz, 2H), 3.03-2.74 (m, 4H), 2.59 (s, 3H), 2.02-1.11 (m, 16H). [M+H]=304.2.

Example 89 and 90. 3-((cis)-4-(2-((tetrahydro-2H-pyran-4-yl)amino)ethyl)cyclohexyl)phenol and 3-((trans)-4-(2-((tetrahydro-2H-pyran-4-yl)amino)ethyl)cyclohexyl)phenol

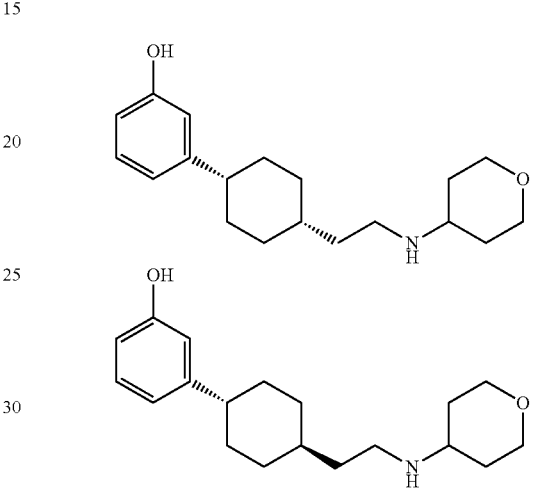

One of the two single isomers: ¹H NMR (400 MHz, CD₃OD) δ 7.09-6.99 (m, 1H), 6.70-6.50 (m, 3H), 4.04-3.86 (m, 2H), 3.41 (d, J=1.83 Hz, 2H), 2.86-2.61 (m, 3H), 2.47-2.30 (m, 1H), 1.93-1.75 (m, 6H), 1.61-1.31 (m, 7H), 1.20-1.01 (m, 2H). [M+H]=304.3.

The other single isomer: ¹H NMR (400 MHz, CD₃OD) δ 7.18-6.99 (m, 1H), 6.76-6.47 (m, 3H), 3.95 (br dd, J=10.88, 4.03 Hz, 2H), 3.41 (td, J=11.92, 1.83 Hz, 2H), 2.89-2.61 (m, 3H), 2.56-2.39 (m, 1H), 1.92-1.53 (m, 12H), 1.52-1.31 (m, 3H). [M+H]=304.3.

Example 91 and 92. 2-methyl-3-((cis)-4-(2-((tetrahydro-2H-pyran-4-yl)amino)ethyl)cyclohexyl)benzonitrile and 2-methyl-3-((trans)-4-(2-((tetrahydro-2H-pyran-4-yl)amino)ethyl)cyclohexyl)benzonitrile

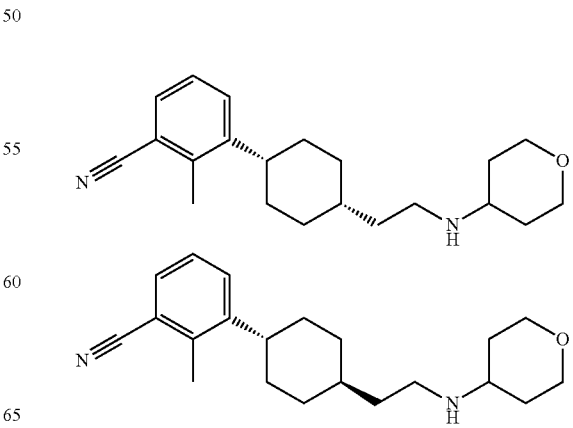

One of the two single isomers: $^1$H NMR (400 MHz, CD$_3$OD) δ 7.66-7.55 (m, 1H), 7.48 (dd, J=7.70, 1.10 Hz, 1H), 7.38-7.15 (m, 1H), 3.96 (br dd, J=10.82, 3.97 Hz, 2H), 3.42 (td, J=11.95, 2.02 Hz, 2H), 2.93-2.82 (m, 1H), 2.78-2.61 (m, 3H), 2.53 (s, 3H), 1.96-1.51 (m, 13H), 1.42 (qd, J=12.10, 4.52 Hz, 2H). [M+H]=327.3.

The other single isomer: $^1$H NMR (400 MHz, CD$_3$OD) δ 7.61-7.50 (m, 1H), 7.47 (dd, J=7.64, 1.16 Hz, 1H), 7.35-7.19 (m, 1H), 3.95 (br dd, J=10.88, 4.03 Hz, 2H), 3.41 (td, J=11.92, 1.96 Hz, 2H), 2.89-2.62 (m, 4H), 2.53 (s, 3H), 2.00-1.76 (m, 6H), 1.61-1.33 (m, 7H), 1.28-1.07 (m, 2H). [M+H]=327.3.

Example 93 was prepared in a manner analogous to Example 3, with the appropriate starting material substitutions.

Example 93. (cis)-4-({2-[(cis)-4-[4-Fluoro-2-(trifluoromethyl)phenyl]cyclohexyl]ethyl}amino)cyclohexane-1-carbonitrile

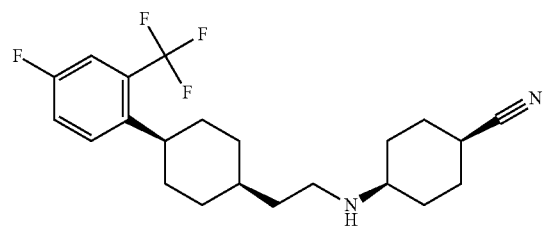 [SMILES: N#C[C@H]1CC[C@@H](NCC[C@H]2CC[C@@H](c3ccc(F)cc3C(F)(F)F)CC2)CC1]

$^1$H NMR (400 MHz, CDCl$_3$) δ 9.28 (br s, 1H), 7.48-7.37 (m, 1H), 7.31 (d, J=2.6 Hz, 1H), 7.17 (t, J=7.0 Hz, 1H), 3.02 (d, J=19.4 Hz, 4H), 2.87-2.81 (m, 2H), 2.29-1.86 (m, 8H), 1.83-1.47 (m, 10H). [M+H]=397.3.

Example 94-Example 150 were prepared in a manner analogous to Example 10, with the appropriate starting material substitutions.

Example 94. N-{2-[4-(3-Methylpyridin-2-yl)cyclohexyl]ethyl}cyclopentanamine

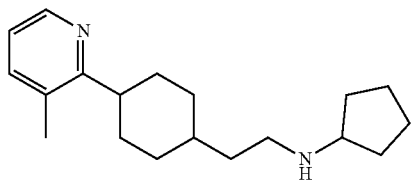 [SMILES: Cc1cccnc1C1CCC(CCNC2CCCC2)CC1]

[M+H]=287.13.

Example 95. N-{2-[4-(2-Chloro-6-fluorophenyl)cyclohexyl]ethyl}cyclopentanamine

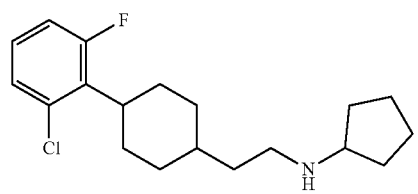 [SMILES: Fc1cccc(Cl)c1C1CCC(CCNC2CCCC2)CC1]

[M+H]=324.15.

Example 96. N-{2-[4-(4-Chloro-2-fluorophenyl)cyclohexyl]ethyl}cyclopentanamine

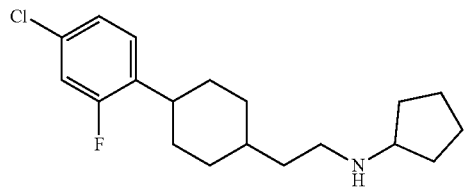 [SMILES: Fc1cc(Cl)ccc1C1CCC(CCNC2CCCC2)CC1]

[M+H]=324.16.

Example 97. N-{2-[4-(4-Fluoro-2-methylphenyl)cyclohexyl]ethyl}cyclopentanamine

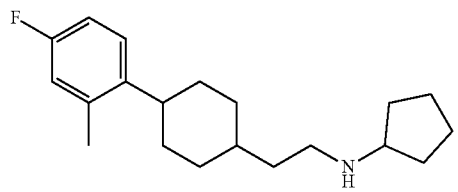 [SMILES: Cc1cc(F)ccc1C1CCC(CCNC2CCCC2)CC1]

[M+H]=304.43.

Example 98. N-{2-[4-(2-Chloro-5-fluorophenyl)cyclohexyl]ethyl}cyclopentanamine

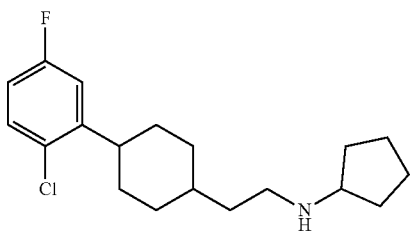 [SMILES: Fc1ccc(Cl)c(C2CCC(CCNC3CCCC3)CC2)c1]

[M+H]=324.17.

Example 99. N-{2-[4-(2-Chlorophenyl)cyclohexyl]ethyl}oxan-4-amine

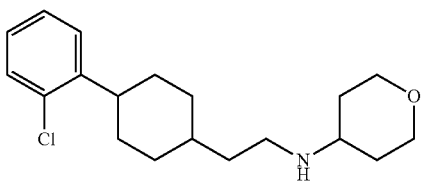 [SMILES: Clc1ccccc1C1CCC(CCNC2CCOCC2)CC1]

[M+H]=322.14.

Example 100. N-{2-[4-(3-Methylpyridin-2-yl)cyclohexyl]ethyl}oxan-4-amine

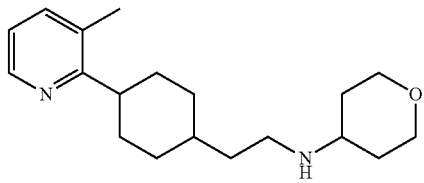 [SMILES: Cc1cccnc1C1CCC(CCNC2CCOCC2)CC1]

[M+H]=303.2.

Example 101. N-{2-[4-(4-Chloro-2-fluorophenyl)cyclohexyl]ethyl}oxan-4-amine

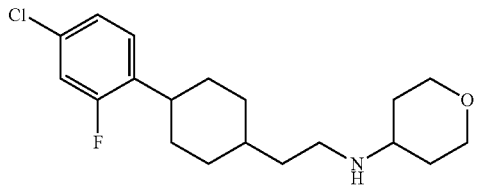 [SMILES: Fc1cc(Cl)ccc1C1CCC(CCNC2CCOCC2)CC1]

[M+H]=340.18.

Example 102. N-{2-[4-(4-Fluoro-2-methylphenyl)cyclohexyl]ethyl}oxan-4-amine

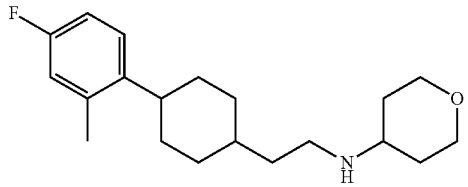 [SMILES: Cc1cc(F)ccc1C1CCC(CCNC2CCOCC2)CC1]

[M+H]=320.22.

Example 103. N-{2-[4-(2-Chloro-5-fluorophenyl)cyclohexyl]ethyl}oxan-4-amine

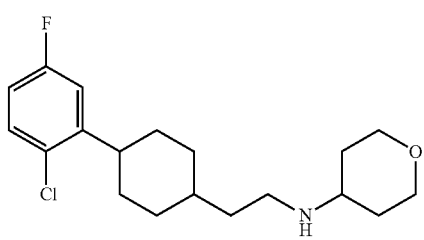 [SMILES: Fc1ccc(Cl)c(C2CCC(CCNC3CCOCC3)CC2)c1]

[M+H]=340.15.

Example 104. N-{2-[4-(3-Methylpyridin-4-yl)cyclohexyl]ethyl}oxan-4-amine

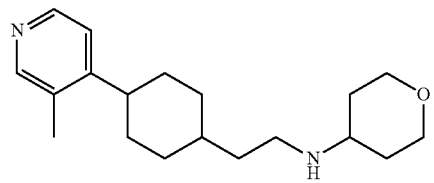 [SMILES: Cc1cnccc1C1CCC(CCNC2CCOCC2)CC1]

[M+H]=303.22.

Example 105. N-{2-[4-(2-Chlorophenyl)cyclohexyl]ethyl}-1-methylcyclopentan-1-amine

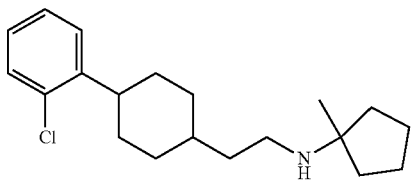 [SMILES: CC1(NCCC2CCC(c3ccccc3Cl)CC2)CCCC1]

[M+H]=320.4.

Example 106. N-{2-[4-(2-Chloro-3-fluorophenyl)cyclohexyl]ethyl}-1-methylcyclopentan-1-amine

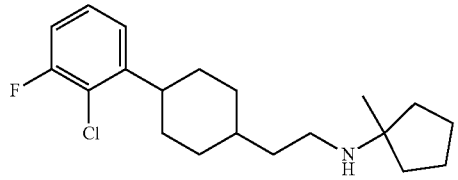 [SMILES: CC1(NCCC2CCC(c3cccc(F)c3Cl)CC2)CCCC1]

[M+H]=338.19.

Example 107. N-{2-[4-(2,4-Difluorophenyl)cyclohexyl]ethyl}-1-methylcyclopentan-1-amine

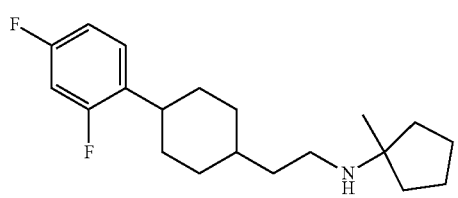 [SMILES: CC1(NCCC2CCC(c3ccc(F)cc3F)CC2)CCCC1]

[M+H]=322.23.

Example 108. N-{2-[4-(3-Chloro-5-fluoropyridin-2-yl)cyclohexyl]ethyl}-1-methylcyclopentan-1-amine

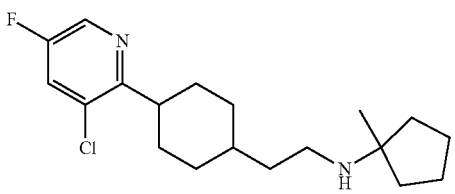 [SMILES: CC1(NCCC2CCC(c3ncc(F)cc3Cl)CC2)CCCC1]

[M+H]=339.17.

Example 109. N-{2-[4-(3-Chloropyridin-2-yl)cyclohexyl]ethyl}-1-methylcyclopentan-1-amine

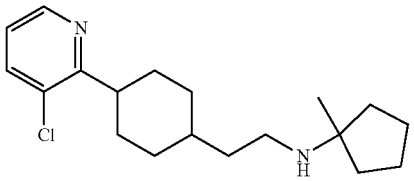 [SMILES: CC1(NCCC2CCC(c3ncccc3Cl)CC2)CCCC1]

[M+H]=321.17.

Example 110. 1-Methyl-N-{2-[4-(3-methylpyridin-2-yl)cyclohexyl]ethyl}cyclopentan-1-amine

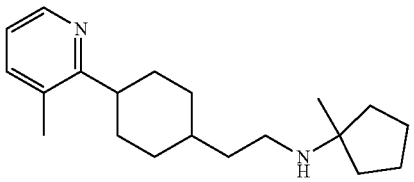 [SMILES: Cc1cccnc1C1CCC(CCNC2(C)CCCC2)CC1]

[M+H]=301.25.

Example 111. 1-Methyl-N-{2-[4-(4-methylpyridin-3-yl)cyclohexyl]ethyl}cyclopentan-1-amine

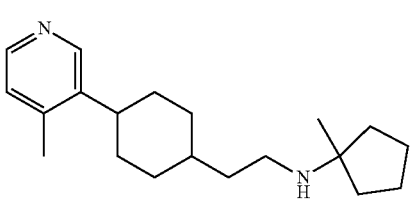 [SMILES: Cc1ccncc1C1CCC(CCNC2(C)CCCC2)CC1]

[M+H]=301.23.

Example 112. N-{2-[4-(2-Chloro-6-fluorophenyl)cyclohexyl]ethyl}-1-methylcyclopentan-1-amine

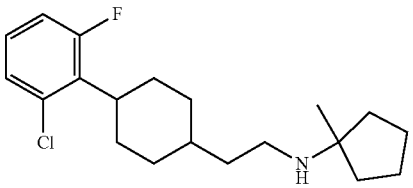 [SMILES: CC1(NCCC2CCC(c3c(F)cccc3Cl)CC2)CCCC1]

[M+H]=338.2.

Example 113. 1-({2-[4-(2-Chlorophenyl)cyclohexyl]ethyl}amino)cyclopentane-1-carboxamide

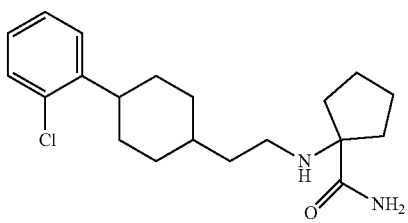 [SMILES: NC(=O)C1(NCCC2CCC(c3ccccc3Cl)CC2)CCCC1]

[M+H]=349.2.

Example 114. 1-({2-[4-(2-Chloro-3-fluorophenyl)cyclohexyl]ethyl}amino)cyclopentane-1-carboxamide

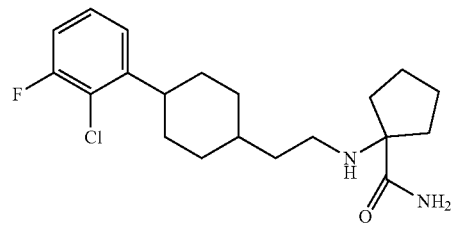 [SMILES: NC(=O)C1(NCCC2CCC(c3cccc(F)c3Cl)CC2)CCCC1]

[M+H]=367.16.

Example 115. 1-({2-[4-(2,4-Difluorophenyl)cyclohexyl]ethyl}amino)cyclopentane-1-carboxamide

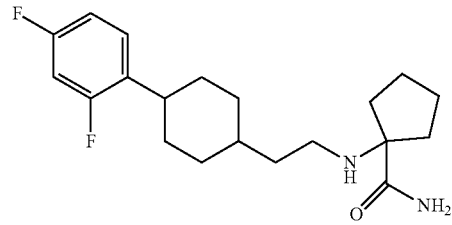 [SMILES: NC(=O)C1(NCCC2CCC(c3ccc(F)cc3F)CC2)CCCC1]

[M+H]=351.21.

Example 116. 1-({2-[4-(3-Chloropyridin-2-yl)cyclohexyl]ethyl}amino)cyclopentane-1-carboxamide

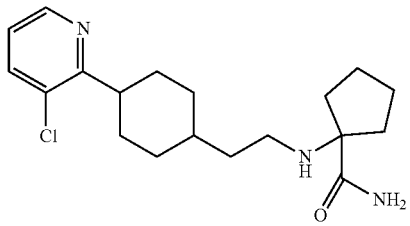 [SMILES: NC(=O)C1(NCCC2CCC(c3ncccc3Cl)CC2)CCCC1]

[M+H]=350.35.

Example 117. 1-({2-[4-(3-Methylpyridin-2-yl)cyclohexyl]ethyl}amino)cyclopentane-1-carboxamide

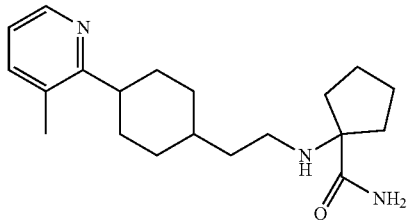 [SMILES: Cc1cccnc1C1CCC(CCNC2(C(N)=O)CCCC2)CC1]

[M+H]=330.25.

Example 118. 1-({2-[4-(4-Methylpyridin-3-yl)cyclohexyl]ethyl}amino)cyclopentane-1-carboxamide

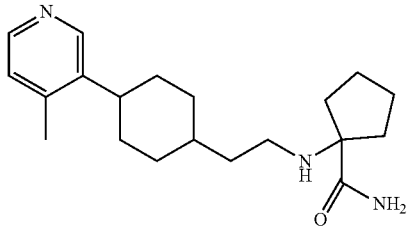 [SMILES: Cc1ccncc1C1CCC(CCNC2(C(N)=O)CCCC2)CC1]

[M+H]=330.29.

Example 119. N-{2-[4-(4-Fluoro-2-methylphenyl)cyclohexyl]ethyl}-1-methylcyclopentan-1-amine

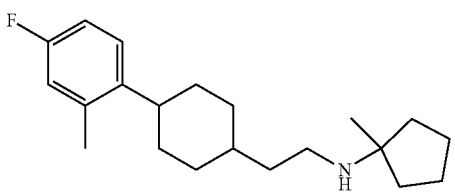 [SMILES: Cc1cc(F)ccc1C1CCC(CCNC2(C)CCCC2)CC1]

[M+H]=318.44.

Example 120. N-{2-[4-(2-Chloro-5-fluorophenyl)cyclohexyl]ethyl}-1-methylcyclopentan-1-amine

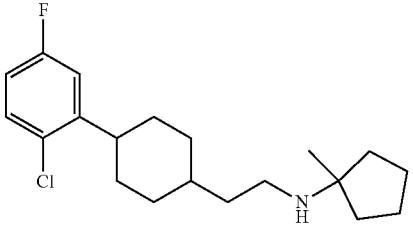 [SMILES: CC1(NCCC2CCC(c3cc(F)ccc3Cl)CC2)CCCC1]

[M+H]=338.38.

Example 121. 1-Methyl-N-{2-[4-(3-methylpyridin-4-yl)cyclohexyl]ethyl}cyclopentan-1-amine

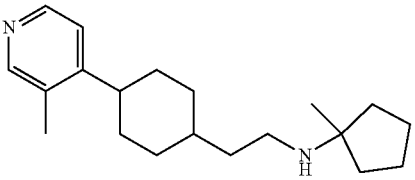 [SMILES: Cc1cnccc1C1CCC(CCNC2(C)CCCC2)CC1]

[M+H]=301.2.

Example 122. 1-({2-[4-(2-Chloro-5-fluorophenyl)cyclohexyl]ethyl}amino)cyclopentane-1-carboxamide

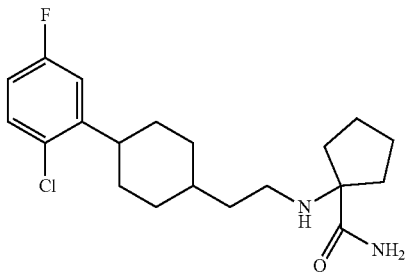 [SMILES: NC(=O)C1(NCCC2CCC(c3cc(F)ccc3Cl)CC2)CCCC1]

[M+H]=367.18.

Example 123. 1-({2-[4-(3-Methylpyridin-4-yl)cyclohexyl]ethyl}amino)cyclopentane-1-carboxamide

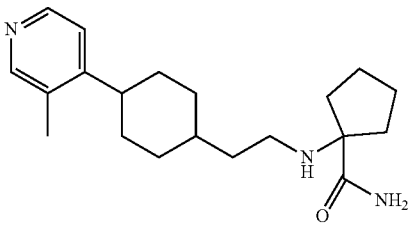 [SMILES: Cc1cnccc1C1CCC(CCNC2(C(N)=O)CCCC2)CC1]

[M+H]=330.25.

Example 124. N-{2-[4-(2-Chloro-3-fluorophenyl)cyclohexyl]ethyl}cyclohexanamine

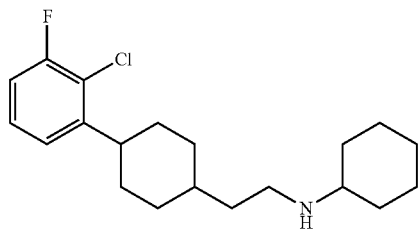 [SMILES: Fc1cccc(C2CCC(CCNC3CCCCC3)CC2)c1Cl]

[M+H]=338.4.

Example 125. N-{2-[4-(2,4-Difluorophenyl)cyclohexyl]ethyl}cyclohexanamine

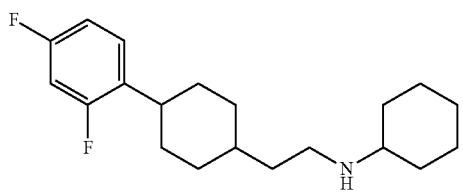

[M+H]=322.23.

Example 126. N-{2-[4-(3-Chloro-5-fluoropyridin-2-yl)cyclohexyl]ethyl}cyclohexanamine

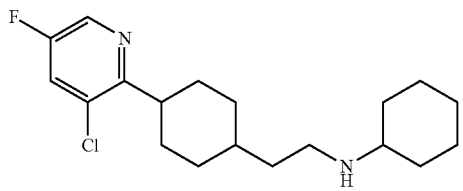 [SMILES: Fc1cnc(C2CCC(CCNC3CCCCC3)CC2)c(Cl)c1]

[M+H]=339.19.

Example 127. N-{2-[4-(3-Chloropyridin-2-yl)cyclohexyl]ethyl}cyclohexanamine

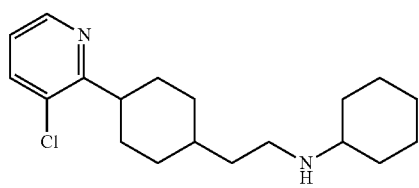 [SMILES: Clc1cccnc1C1CCC(CCNC2CCCCC2)CC1]

[M+H]=321.39.

Example 128. N-{2-[4-(3-Methylpyridin-2-yl)cyclohexyl]ethyl}cyclohexanamine

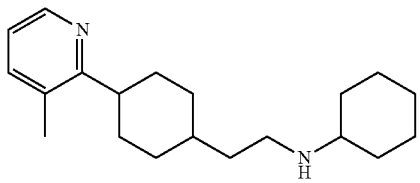 [SMILES: Cc1cccnc1C1CCC(CCNC2CCCCC2)CC1]

[M+H]=301.25.

Example 129. N-{2-[4-(2-Chloro-6-fluorophenyl)cyclohexyl]ethyl}cyclohexanamine

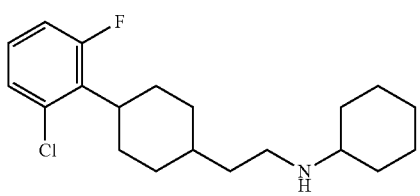 [SMILES: Fc1cccc(Cl)c1C1CCC(CCNC2CCCCC2)CC1]

[M+H]=338.17.

Example 130. N-{2-[4-(2-Chlorophenyl)cyclohexyl]ethyl}-4-methyloxan-4-amine

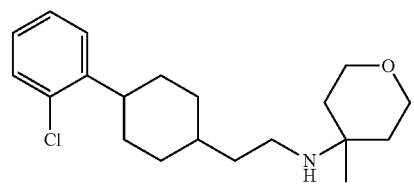

[M+H]=336.18.

Example 131. N-{2-[4-(3-Chloro-5-fluoropyridin-2-yl)cyclohexyl]ethyl}-4-methyloxan-4-amine

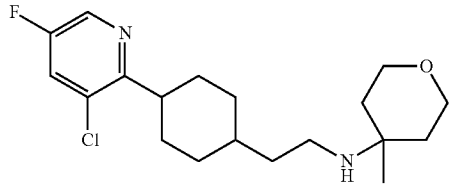

[M+H]=355.2.

Example 132. N-{2-[4-(3-Chloropyridin-2-yl)cyclo-
hexyl]ethyl}-4-methyloxan-4-amine

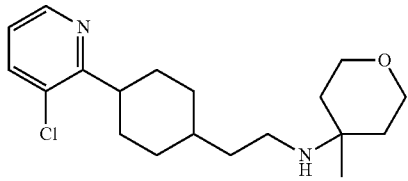 [SMILES: CC1(NCCC2CCC(c3ccccc3Cl)CC2)CCOCC1]

[M+H]=337.17.

Example 133. 4-Methyl-N-{2-[4-(3-methylpyridin-
2-yl)cyclohexyl]ethyl}oxan-4-amine

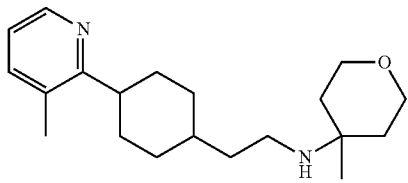 [SMILES: Cc1cccnc1C1CCC(CCNC2(C)CCOCC2)CC1]

[M+H]=317.22.

Example 134. N-{2-[4-(4-Chloro-2-fluorophenyl)
cyclohexyl]ethyl}cyclohexanamine

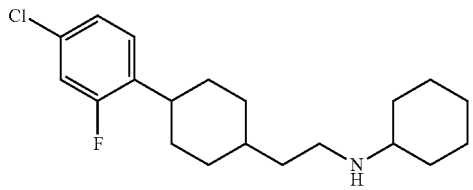 [SMILES: Fc1cc(Cl)ccc1C1CCC(CCNC2CCCCC2)CC1]

[M+H]=338.19.

Example 135. N-{2-[4-(4-Fluoro-2-methylphenyl)
cyclohexyl]ethyl}cyclohexanamine

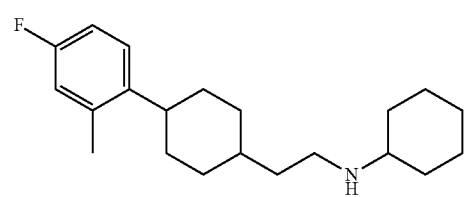

[M+H]=318.22.

Example 136. N-{2-[4-(2-Chloro-5-fluorophenyl)
cyclohexyl]ethyl}cyclohexanamine

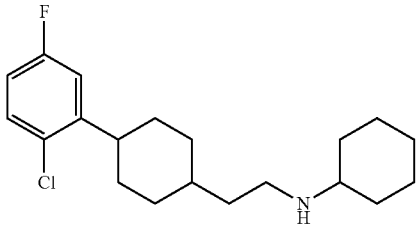 [SMILES: Fc1ccc(Cl)c(C2CCC(CCNC3CCCCC3)CC2)c1]

[M+H]=338.17.

Example 137. N-{2-[4-(3-Methylpyridin-4-yl)cyclo-
hexyl]ethyl}cyclohexanamine

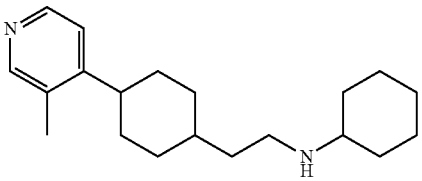 [SMILES: Cc1cnccc1C1CCC(CCNC2CCCCC2)CC1]

[M+H]=301.2.

Example 138. N-{2-[4-(4-Fluoro-2-methylphenyl)
cyclohexyl]ethyl}-4-methyloxan-4-amine

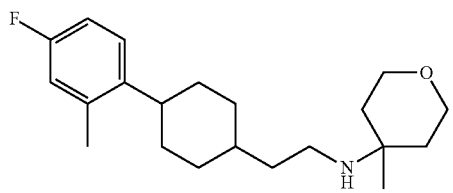 [SMILES: Cc1cc(F)ccc1C1CCC(CCNC2(C)CCOCC2)CC1]

[M+H]=334.24.

Example 139. 4-Methyl-N-{2-[4-(3-methylpyridin-
4-yl)cyclohexyl]ethyl}oxan-4-amine

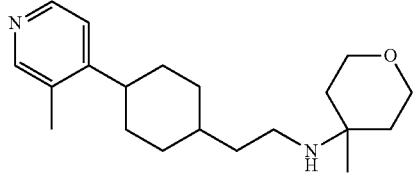 [SMILES: Cc1cnccc1C1CCC(CCNC2(C)CCOCC2)CC1]

[M+H]=317.22.

Example 140. 1-({2-[4-(3-Chloro-5-fluoropyridin-2-yl)cyclohexyl]ethyl}amino)-N-methylcyclopentane-1-carboxamide

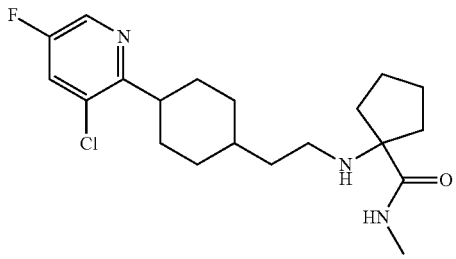 [SMILES: CNC(=O)C1(NCCC2CCC(c3ncc(F)cc3Cl)CC2)CCCC1]

[M+H]=382.4.

Example 141. 1-({2-[4-(3-Chloropyridin-2-yl)cyclohexyl]ethyl}amino)-N-methylcyclopentane-1-carboxamide

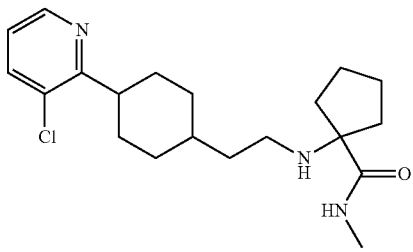 [SMILES: CNC(=O)C1(NCCC2CCC(c3ncccc3Cl)CC2)CCCC1]

[M+H]=364.2.

Example 142. N-{2-[4-(2-Chlorophenyl)cyclohexyl]ethyl}-4-(methoxymethyl)oxan-4-amine

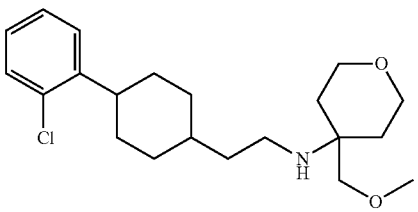

[M+H]=366.35.

Example 143. N-{2-[4-(2-Chloro-3-fluorophenyl)cyclohexyl]ethyl}-4-(methoxymethyl)oxan-4-amine

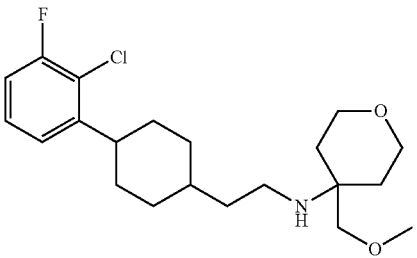 [SMILES: COCC1(NCCC2CCC(c3cccc(F)c3Cl)CC2)CCOCC1]

[M+H]=384.33.

Example 144. N-{2-[4-(2,4-Difluorophenyl)cyclohexyl]ethyl}-4-(methoxymethyl)oxan-4-amine

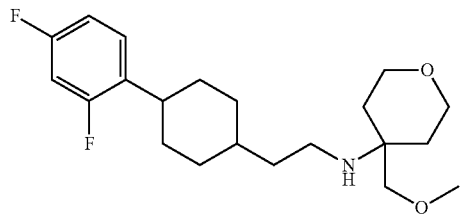 [SMILES: COCC1(NCCC2CCC(c3ccc(F)cc3F)CC2)CCOCC1]

[M+H]=368.36.

Example 145. N-{2-[4-(3-Chloro-5-fluoropyridin-2-yl)cyclohexyl]ethyl}-4-(methoxymethyl)oxan-4-amine

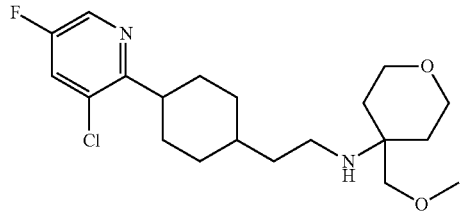 [SMILES: COCC1(NCCC2CCC(c3ncc(F)cc3Cl)CC2)CCOCC1]

[M+H]=385.31.

Example 146. N-{2-[4-(3-Chloropyridin-2-yl)cyclohexyl]ethyl}-4-(methoxymethyl)oxan-4-amine

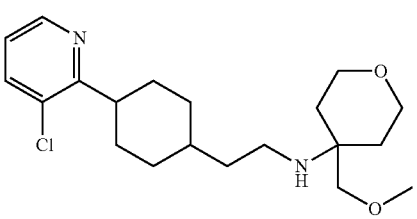 [SMILES: COCC1(NCCC2CCC(c3ncccc3Cl)CC2)CCOCC1]

[M+H]=367.32.

Example 147. 4-(Methoxymethyl)-N-{2-[4-(4-methylpyridin-3-yl)cyclohexyl]ethyl}oxan-4-amine

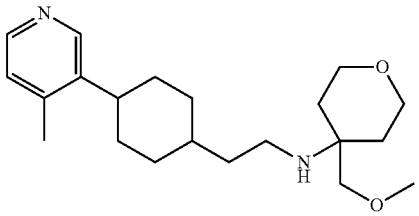 [SMILES: COCC1(NCCC2CCC(c3cnccc3C)CC2)CCOCC1]

[M+H]=347.41.

Example 148. N-{2-[4-(2-Chloro-6-fluorophenyl)cyclohexyl]ethyl}-4-(methoxymethyl)oxan-4-amine

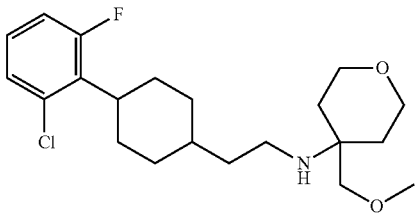 [SMILES: COCC1(NCCC2CCC(c3c(F)cccc3Cl)CC2)CCOCC1]

[M+H]=384.33.

Example 149. 1-({2-[4-(4-Chloro-2-fluorophenyl)cyclohexyl]ethyl}amino)-N-methylcyclopentane-1-carboxamide

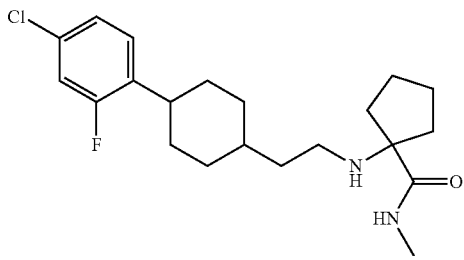 [SMILES: CNC(=O)C1(NCCC2CCC(c3ccc(Cl)cc3F)CC2)CCCC1]

[M+H]=381.32.

Example 150. N-{2-[4-(2-Chloro-5-fluorophenyl)cyclohexyl]ethyl}-4-(methoxymethyl)oxan-4-amine

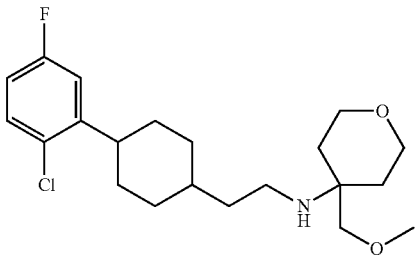 [SMILES: COCC1(NCCC2CCC(c3cc(F)ccc3Cl)CC2)CCOCC1]

[M+H]=384.39.

Example 151-Example 154 were prepared in a manner analogous to Example 1, with the appropriate starting material substitutions.

Example 151 and 152. (R)-4-((2-((cis)-4-(3-chloro-5-fluoropyridin-2-yl)cyclohexyl)ethyl)amino)piperidin-2-one and (R)-4-((2-((trans)-4-(3-chloro-5-fluoropyridin-2-yl)cyclohexyl)ethyl)amino)piperidin-2-one

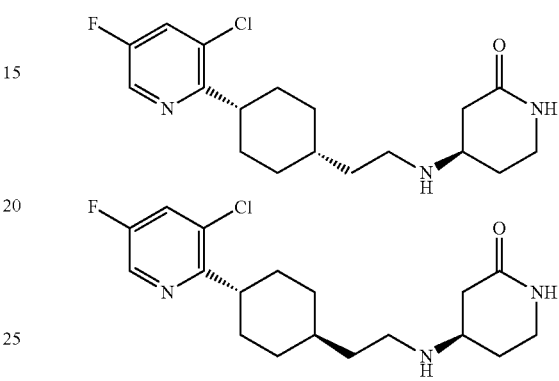

One of the two single isomers: $^1$H NMR (400 MHz, CD$_3$OD) δ 8.37 (d, J=2.57 Hz, 1H), 7.77-7.61 (m, 1H), 3.42-3.33 (m, 1H), 3.29-3.19 (m, 2H), 3.11-2.94 (m, 1H), 2.76-2.53 (m, 3H), 2.23-2.02 (m, 2H), 1.95-1.51 (m, 12H). [M+H]=354.1.

The other single isomer: $^1$H NMR (400 MHz, CD$_3$OD) δ 8.36 (d, J=2.69 Hz, 1H), 7.70 (dd, J=2.57, 8.31 Hz, 1H), 3.42-3.33 (m, 1H), 3.29-3.11 (m, 2H), 3.08-2.92 (m, 1H), 2.75-2.54 (m, 3H), 2.19-2.03 (m, 2H), 1.98-1.78 (m, 4H), 1.74-1.37 (m, 6H), 1.24-1.09 (m, 2H).
[M+H]=354.1.

Example 153 and 154. (S)-4-((2-((cis)-4-(3-chloro-5-fluoropyridin-2-yl)cyclohexyl)ethyl)amino)piperidin-2-one and (S)-4-((2-((trans)-4-(3-chloro-5-fluoropyridin-2-yl)cyclohexyl)ethyl)amino)piperidin-2-one

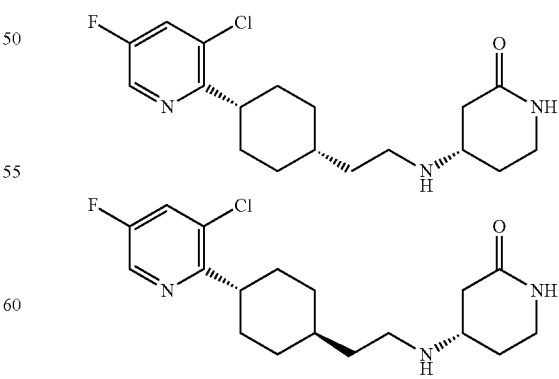

One of the two single isomers: $^1$H NMR (400 MHz, CD$_3$OD) δ 8.37 (d, J=2.57 Hz, 1H), 7.83-7.47 (m, 1H), 3.41-3.33 (m, 1H), 3.29-3.15 (m, 2H), 3.02 (ddt, J=3.24, 5.72, 9.46 Hz, 1H), 2.74-2.55 (m, 3H), 2.21-2.00 (m, 2H), 1.94-1.52 (m, 12H). [M+H]=354.1.

The other single isomer: $^1$H NMR (400 MHz, CD$_3$OD) δ 8.38 (d, J=2.45 Hz, 1H), 7.72 (dd, J=2.57, 8.31 Hz, 1H), 3.43-3.36 (m, 1H), 3.30-3.12 (m, 2H), 3.08-2.94 (m, 1H), 2.79-2.56 (m, 3H), 2.23-2.01 (m, 2H), 2.00-1.78 (m, 4H), 1.76-1.40 (m, 6H), 1.29-1.08 (m, 2H).

[M+H]=354.1.

Example 155-Example 163 were prepared in a manner analogous to Example 20, with the appropriate starting material substitutions Example 155. 1-Methanesulfonyl-N-{2-[(cis)-4-(2-chloro-4-fluorophenyl)cyclohexyl]ethyl}piperidin-4-amine

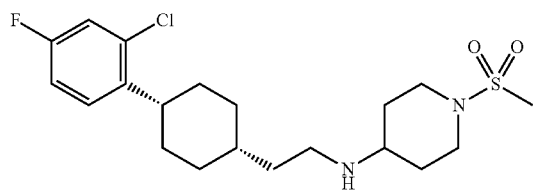 [SMILES: CS(=O)(=O)N1CCC(NCC[C@H]2CC[C@@H](c3ccc(F)cc3Cl)CC2)CC1]

$^1$H NMR (400 MHz, DMSO-d$_6$) δ 8.50 (br. s., 2H), 7.46-7.35 (m, 2H), 7.22 (dt, J=2.7, 8.5 Hz, 1H), 3.65 (d, J=12.2 Hz, 2H), 3.22 (br. s., 2H), 3.04-2.88 (m, 6H), 2.85-2.73 (m, 2H), 2.12 (d, J=10.8 Hz, 2H), 1.89-1.48 (m, 12H). [M+H]=417.4.

Example 156. 1-[4-({2-[(cis)-4-(2-Chloro-4-fluorophenyl)cyclohexyl]ethyl}amino)piperidin-1-yl]ethan-1-one

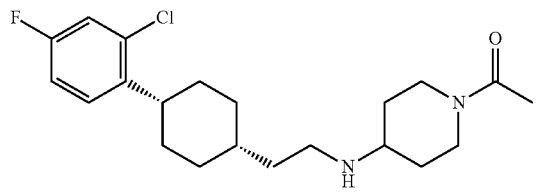 [SMILES: CC(=O)N1CCC(NCC[C@H]2CC[C@@H](c3ccc(F)cc3Cl)CC2)CC1]

$^1$H NMR (400 MHz, CDCl$_3$) δ 9.51-9.18 (m, 2H), 7.20 (dd, J=6.1, 8.7 Hz, 1H), 7.09 (dd, J=2.6, 8.6 Hz, 1H), 6.93 (dt, J=2.6, 8.3 Hz, 1H), 4.73 (d, J=13.7 Hz, 1H), 3.94 (d, J=13.9 Hz, 1H), 3.46-3.24 (m, 5H), 3.13 (t, J=12.4 Hz, 1H), 3.06-2.87 (m, 3H), 2.63 (t, J=12.6 Hz, 1H), 2.24-2.14 (m, 2H), 2.11 (s, 3H), 1.93-1.82 (m, 3H), 1.79-1.67 (m, 4H), 1.56-1.40 (m, 2H).

[M+H]=381.3.

Example 157. 1-[3-({2-[(cis)-4-(2-Chloro-4-fluorophenyl)cyclohexyl]ethyl}amino)pyrrolidin-1-yl]ethan-1-one

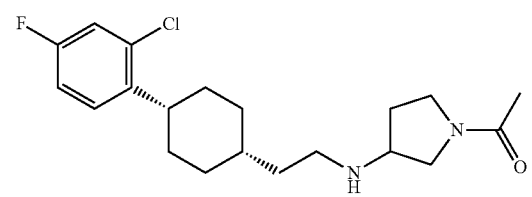 [SMILES: CC(=O)N1CCC(NCC[C@H]2CC[C@@H](c3ccc(F)cc3Cl)CC2)C1]

$^1$H NMR (400 MHz, DMSO-d$_6$) δ 8.75 (br. s., 2H), 7.47-7.35 (m, 2H), 7.21 (dt, J=2.8, 8.5 Hz, 1H), 3.94-3.75 (m, 2H), 3.67-3.51 (m, 3H), 3.09-2.87 (m, 3H), 2.36-2.00 (m, 2H), 1.99-1.94 (m, 3H), 1.89-1.72 (m, 3H), 1.72-1.49 (m, 8H). [M+H]=367.3.

Example 158. 4-({2-[(cis)-4-(2-Chloro-4-fluorophenyl)cyclohexyl]ethyl}amino)piperidin-2-one

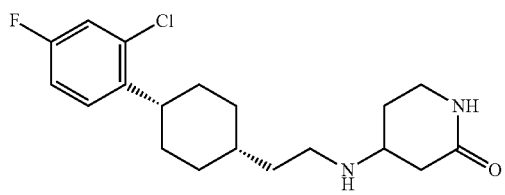

$^1$H NMR (400 MHz, DMSO-d$_6$) δ 8.57 (br. s., 2H), 7.77 (br. s., 1H), 7.48-7.34 (m, 2H), 7.22 (dt, J=2.7, 8.5 Hz, 1H), 3.62-3.51 (m, 2H), 3.28-3.19 (m, 1H), 3.19-3.08 (m, 1H), 3.04-2.87 (m, 3H), 2.69-2.60 (m, 1H), 2.28 (dd, J=10.1, 16.9 Hz, 1H), 2.16 (d, J=12.3 Hz, 1H), 1.88-1.51 (m, 11H). [M+H]=353.3.

Example 159. 1-Methyl-4-({2-[(cis)-4-(2-chloro-4-fluorophenyl)cyclohexyl]ethyl}amino)piperidin-2-one

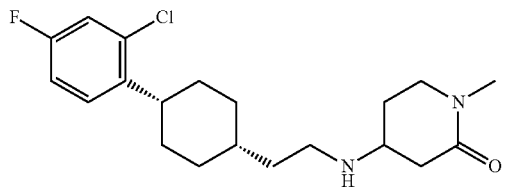 [SMILES: CN1CCC(NCC[C@H]2CC[C@@H](c3ccc(F)cc3Cl)CC2)CC1=O]

$^1$H NMR (400 MHz, DMSO-d$_6$) δ 8.60 (br. s., 2H), 7.46-7.33 (m, 2H), 7.22 (dt, J=2.8, 8.5 Hz, 1H), 3.63-3.52 (m, 2H), 3.38-3.24 (m, 2H), 3.05-2.87 (m, 3H), 2.82 (s, 3H), 2.72 (dd, J=4.0, 16.8 Hz, 1H), 2.35 (dd, J=10.0, 16.8 Hz, 1H), 2.23 (d, J=12.6 Hz, 1H), 1.90-1.50 (m, 11H). [M+H]=367.3.

Example 160. 3-({2-[(cis)-4-(2-Chloro-4-fluorophenyl)cyclohexyl]ethyl}amino)pyrrolidin-2-one

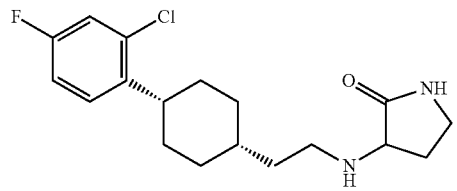 [SMILES: O=C1NCCC1NCC[C@H]1CC[C@@H](c2ccc(F)cc2Cl)CC1]

$^1$H NMR (400 MHz, DMSO-d$_6$) δ 9.21-8.88 (m, 2H), 8.42 (s, 1H), 7.52-7.33 (m, 2H), 7.22 (dt, J=2.8, 8.5 Hz, 1H), 4.04 (br. s., 2H), 3.38-3.21 (m, 2H), 3.11 (br. s., 1H), 3.04-2.85 (m, 2H), 2.49-2.40 (m, 1H), 2.11-1.97 (m, 1H), 1.93-1.79 (m, 2H), 1.73 (td, J=5.4, 10.9 Hz, 1H), 1.67-1.53 (m, 7H). [M+H]=339.1.

Example 161. (4R)-4-({2-[(cis)-4-(2-Chloro-4-fluorophenyl)cyclohexyl]ethyl}amino)piperidin-2-one

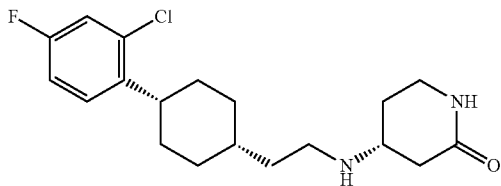 [SMILES: O=C1C[C@H](NCC[C@H]2CC[C@@H](c3ccc(F)cc3Cl)CC2)CCN1]

¹H NMR (400 MHz, DMSO-d₆) δ 8.93 (br. s., 2H), 7.77 (br. s., 1H), 7.49-7.34 (m, 2H), 7.22 (dt, J=2.7, 8.6 Hz, 1H), 3.73-3.55 (m, 1H), 3.22 (d, J=5.1 Hz, 1H), 3.14 (dd, J=4.0, 11.3 Hz, 1H), 3.03-2.87 (m, 3H), 2.66 (dd, J=4.2, 16.8 Hz, 1H), 2.35 (dd, J=10.1, 16.9 Hz, 1H), 2.19 (d, J=11.5 Hz, 1H), 1.90-1.51 (m, 12H). [M+H]=353.2.

Example 162. (4S)-4-({2-[(cis)-4-(2-Chloro-4-fluorophenyl)cyclohexyl]ethyl}amino)piperidin-2-one

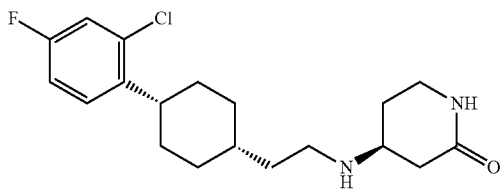 [SMILES: O=C1C[C@@H](NCC[C@H]2CC[C@@H](c3ccc(F)cc3Cl)CC2)CCN1]

¹H NMR (400 MHz, DMSO-d₆) δ 8.87 (br s, 2H), 7.77 (br. s., 1H), 7.50-7.34 (m, 2H), 7.22 (dt, J=2.7, 8.6 Hz, 1H), 3.54 (d, J=4.2 Hz, 1H), 3.29-3.20 (m, 1H), 3.13 (dt, J=4.1, 11.8 Hz, 1H), 3.03-2.86 (m, 3H), 2.66 (dd, J=4.2, 16.9 Hz, 1H), 2.34 (dd, J=10.2, 16.8 Hz, 1H), 2.19 (d, J=10.5 Hz, 1H), 1.89-1.51 (m, 12H). [M+H]=353.3.

Example 163. Racemic-4-({2-[(trans)-4-(2-Chloro-4-fluorophenyl)cyclohexyl]ethyl}amino)piperidin-2-one

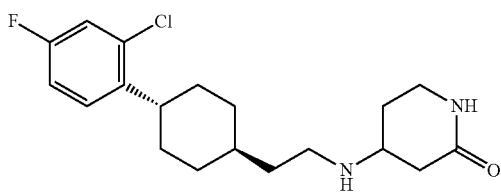 [SMILES: O=C1CC(NCC[C@H]2CC[C@H](c3ccc(F)cc3Cl)CC2)CCN1]

¹H NMR (400 MHz, DMSO-d₆) δ 9.00 (br s, 2H), 7.75 (d, J=2.4 Hz, 1H), 7.45-7.35 (m, 2H), 7.19 (dt, J=2.8, 8.5 Hz, 1H), 3.51 (d, J=3.7 Hz, 1H), 3.29-3.18 (m, 1H), 3.12 (dt, J=3.9, 11.8 Hz, 1H), 3.03-2.82 (m, 3H), 2.65 (dd, J=4.5, 16.9 Hz, 1H), 2.37 (dd, J=10.2, 16.8 Hz, 1H), 2.20 (d, J=11.7 Hz, 1H), 1.91-1.70 (m, 5H), 1.66-1.54 (m, 2H), 1.52-1.37 (m, 3H), 1.22-1.05 (m, 2H). [M+H]=353.3.

Example 164-Example 168 were prepared in a manner analogous to Example 4, with the appropriate starting material substitutions Example 164. 4-({2-[4-(3-Chloro-5-fluoropyridin-2-yl)cyclohexyl]ethyl}amino)piperidine-1-carboxamide

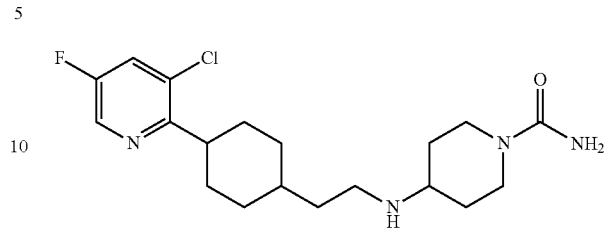

¹H NMR (400 MHz, CD₃OD) δ 8.37 (d, J=2.57 Hz, 1H), 7.79-7.63 (m, 1H), 4.15 (d, J=14.06 Hz, 2H), 3.27-3.06 (m, 3H), 2.97-2.75 (m, 2H), 2.11 (d, J=11.98 Hz, 2H), 2.43-2.02 (m, 12H), 1.11-1.39 (m, 2H). [M+H]=383.2.

Example 165 and 166. 4-((2-((cis)-4-(3-chloro-5-fluoropyridin-2-yl)cyclohexyl)ethyl)amino)-4-methylpiperidin-2-one and 4-((2-((trans)-4-(3-chloro-5-fluoropyridin-2-yl)cyclohexyl)ethyl)amino)-4-methylpiperidin-2-one

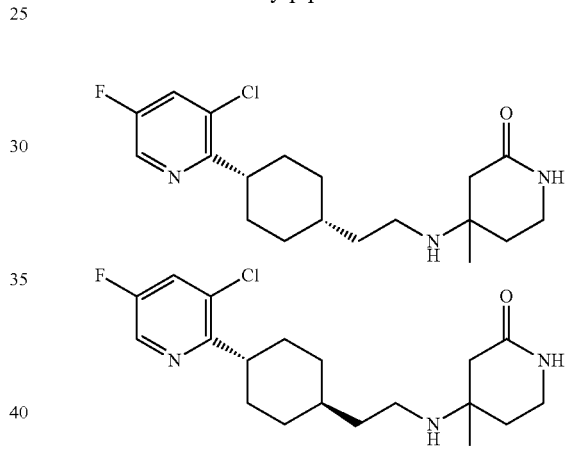

One of the two single isomers: ¹H NMR (400 MHz, CD₃OD) δ 8.42-8.31 (m, 1H), 7.71 (dd, J=8.31, 2.57 Hz, 1H), 3.52-3.33 (m, 2H), 3.25-3.01 (m, 3H), 2.71-2.48 (m, 2H), 2.17-1.82 (m, 6H), 1.77-1.60 (m, 4H), 1.56-1.43 (m, 4H), 1.29-1.12 (m, 2H). [M+H]=368.2.

The other single isomer: ¹H NMR (400 MHz, CD₃OD) δ 8.37 (d, J=2.57 Hz, 1H), 7.84-7.60 (m, 1H), 3.54-3.24 (m, 3H), 3.17-2.97 (m, 2H), 2.70-2.47 (m, 2H), 2.17-1.58 (m, 13H), 1.46 (s, 3H). [M+H]=368.2.

Example 167. 4-Methyl-4-({2-[(cis)-4-(2-chloro-4-fluorophenyl)cyclohexyl]ethyl}amino)piperidin-2-one

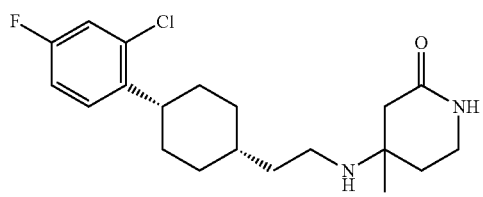 [SMILES: CC1(NCC[C@H]2CC[C@@H](c3ccc(F)cc3Cl)CC2)CCNC(=O)C1]

¹H NMR (400 MHz, CD₃OD) δ 7.41-7.31 (m, 1H), 7.19 (dd, J=8.68, 2.69 Hz, 1H), 7.05 (td, J=8.47, 2.75 Hz, 1H), 3.55-3.35 (m, 2H), 3.15-2.99 (m, 3H), 2.70-2.49 (m, 2H), 2.15-2.03 (m, 2H), 1.97-1.56 (m, 11H), 1.48 (s, 3H). [M+H]= 367.2.

Example 168. 4-(Methoxymethyl)-4-({2-[(cis)-4-(2-chloro-4-fluorophenyl)cyclohexyl]ethyl}amino)piperidin-2-one

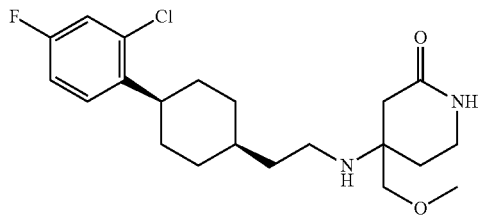 [SMILES: COCC1(NCC[C@H]2CC[C@@H](c3ccc(F)cc3Cl)CC2)CCNC(=O)C1]

¹H NMR (400 MHz, CD₃OD) δ 7.37 (dd, J=8.68, 6.11 Hz, 1H), 7.18 (dd, J=8.68, 2.69 Hz, 1H), 7.10-6.99 (m, 1H), 3.65-3.54 (m, 2H), 3.48 (s, 3H), 3.45-3.34 (m, 2H), 3.14-2.96 (m, 3H), 2.76-2.64 (m, 1H), 2.61-2.51 (m, 1H), 2.33-2.19 (m, 1H), 2.10-1.99 (m, 1H), 1.99-1.58 (m, 11H). [M+H]=397.2.

Example 169-Example 170 were prepared in a manner analogous to Example 3, with the appropriate starting material substitutions.

Example 169 and 170. (R)-4-((2-((cis)-4-(4,5-difluoro-2-methylphenyl)cyclohexyl)ethyl)amino)piperidin-2-one and (R)-4-((2-((trans)-4-(4,5-difluoro-2-methylphenyl)cyclohexyl)ethyl)amino)piperidin-2-one

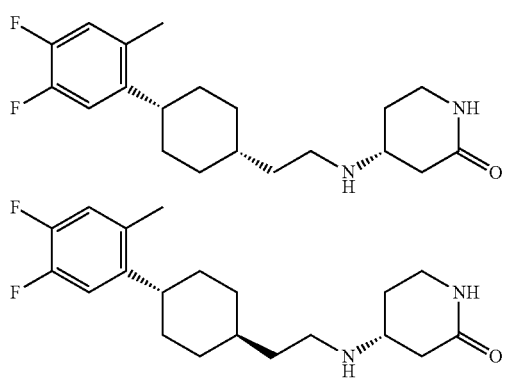

One of the two single isomers: ¹H NMR (400 MHz, CDCl₃) δ 7.08-6.82 (m, 2H), 5.91 (br s, 1H), 3.65-3.40 (m, 3H), 3.37-3.24 (m, 1H), 3.20-3.03 (m, 1H), 2.79-2.59 (m, 4H), 2.39-2.24 (m, 4H), 2.07 (d, J=9.3 Hz, 1H), 1.87 (d, J=6.4 Hz, 1H), 1.74-1.67 (m, 6H), 1.59-1.49 (m, 4H). [M+H]=351.2.

The other single isomer: ¹H NMR (400 MHz, CDCl₃) δ 7.10-6.81 (m, 2H), 3.47 (dd, J=2.7, 12.1 Hz, 1H), 3.37-3.25 (m, 1H), 3.09 (br s, 1H), 2.79-2.69 (m, 2H), 2.69-2.55 (m, 2H), 2.37-2.19 (m, 4H), 2.06 (d, J=13.2 Hz, 1H), 1.96-1.81 (m, 5H), 1.74 (br. s., 2H), 1.56-1.33 (m, 5H), 1.23-1.06 (m, 2H). [M+H]=351.2.

Example 171-Example 187 were prepared in a manner analogous to Example 10, with the appropriate starting material substitutions.

Example 171. 1-[4-({2-[4-(2-Chloro-3-fluorophenyl)cyclohexyl]ethyl}amino)piperidin-1-yl]ethan-1-one

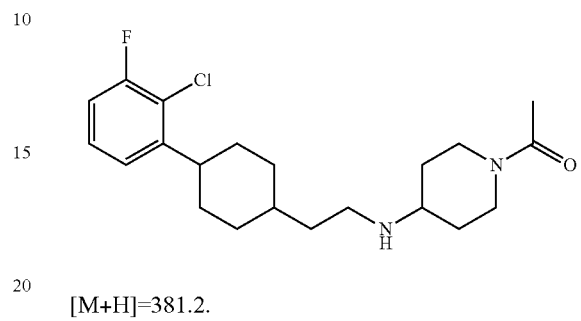

[M+H]=381.2.

Example 172. 1-[4-({2-[4-(3-Chloro-5-fluoropyridin-2-yl)cyclohexyl]ethyl}amino)piperidin-1-yl]ethan-1-one

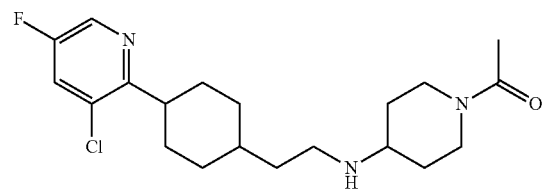

[M+H]=382.2.

Example 173. 1-[4-({2-[4-(3-Chloropyridin-2-yl)cyclohexyl]ethyl}amino)piperidin-1-yl]ethan-1-one

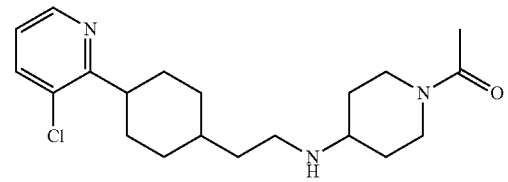 [SMILES: CC(=O)N1CCC(NCCC2CCC(c3ncccc3Cl)CC2)CC1]

[M+H]=364.19.

Example 174. 1-[4-({2-[4-(3-Methylpyridin-2-yl)cyclohexyl]ethyl}amino)piperidin-1-yl]ethan-1-one

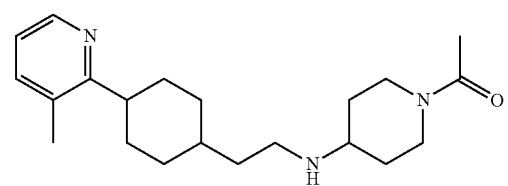 [SMILES: CC(=O)N1CCC(NCCC2CCC(c3ncccc3C)CC2)CC1]

[M+H]=344.26.

Example 175. 1-[4-({2-[4-(4-Methylpyridin-3-yl)cyclohexyl]ethyl}amino)piperidin-1-yl]ethan-1-one

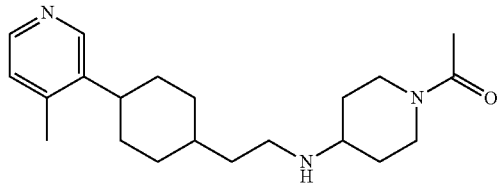 [SMILES: CC(=O)N1CCC(NCCC2CCC(c3cnccc3C)CC2)CC1]

[M+H]=344.29.

Example 176. 1-[4-({2-[4-(4-Chloro-2-fluorophenyl)cyclohexyl]ethyl}amino)piperidin-1-yl]ethan-1-one

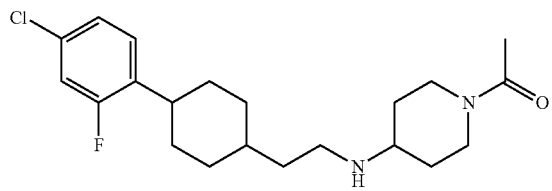 [SMILES: CC(=O)N1CCC(NCCC2CCC(c3ccc(Cl)cc3F)CC2)CC1]

[M+H]=381.22.

Example 177. 1-[4-({2-[4-(4-Fluoro-2-methylphenyl)cyclohexyl]ethyl}amino)piperidin-1-yl]ethan-1-one

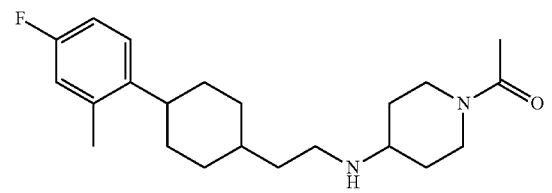

[M+H]=361.21.

Example 178. 1-[4-({2-[4-(2-Chloro-5-fluorophenyl)cyclohexyl]ethyl}amino)piperidin-1-yl]ethan-1-one

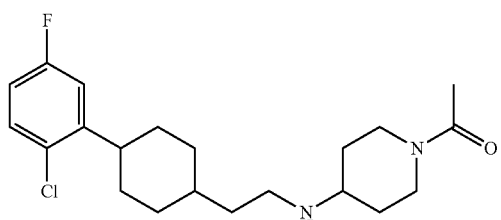

[M+H]=381.22.

Example 179. N-{2-[4-(2-Chloro-3-fluorophenyl)cyclohexyl]ethyl}-1-methylpiperidin-4-amine

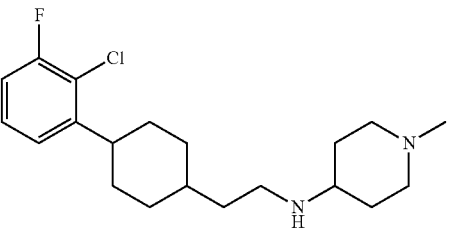 [SMILES: CN1CCC(NCCC2CCC(c3cccc(F)c3Cl)CC2)CC1]

[M+H]=353.13.

Example 180. N-{2-[4-(3-Chloro-5-fluoropyridin-2-yl)cyclohexyl]ethyl}-1-methylpiperidin-4-amine

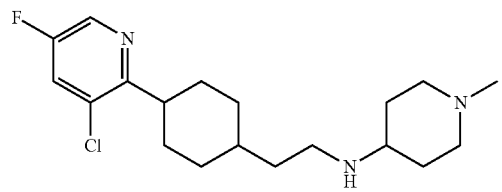 [SMILES: CN1CCC(NCCC2CCC(c3ncc(F)cc3Cl)CC2)CC1]

[M+H]=354.39.

Example 181. N-{2-[4-(3-Chloropyridin-2-yl)cyclohexyl]ethyl}-1-methylpiperidin-4-amine

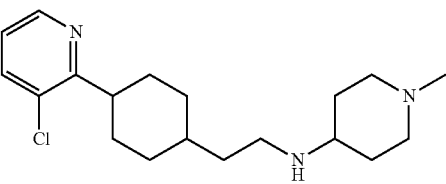 [SMILES: CN1CCC(NCCC2CCC(c3ncccc3Cl)CC2)CC1]

[M+H]=336.19.

Example 182. 1-Methyl-N-{2-[4-(3-methylpyridin-2-yl)cyclohexyl]ethyl}piperidin-4-amine

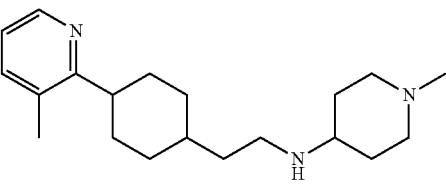 [SMILES: Cc1cccnc1C1CCC(CCNC2CCN(C)CC2)CC1]

[M+H]=316.25.

Example 183. N-{2-[4-(2-Chloro-6-fluorophenyl)cyclohexyl]ethyl}-1-methylpiperidin-4-amine

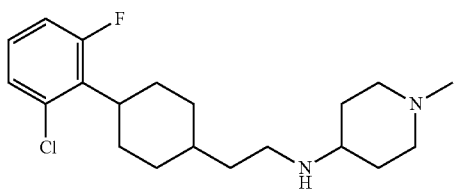 [SMILES: CN1CCC(NCCC2CCC(c3c(F)cccc3Cl)CC2)CC1]

[M+H]=353.2.

Example 184. N-{2-[4-(4-Chloro-2-fluorophenyl)cyclohexyl]ethyl}-1-methylpiperidin-4-amine

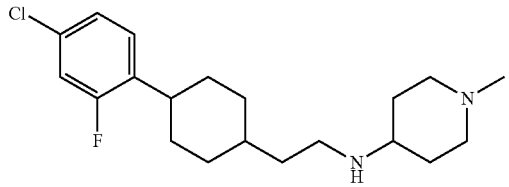 [SMILES: CN1CCC(NCCC2CCC(c3ccc(Cl)cc3F)CC2)CC1]

[M+H]=353.21.

Example 185. N-{2-[4-(4-Fluoro-2-methylphenyl)cyclohexyl]ethyl}-1-methylpiperidin-4-amine

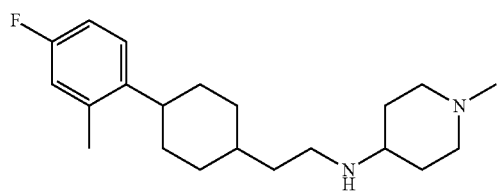 [SMILES: Cc1cc(F)ccc1C1CCC(CCNC2CCN(C)CC2)CC1]

[M+H]=333.23.

Example 186. N-{2-[4-(2-Chloro-5-fluorophenyl)cyclohexyl]ethyl}-1-methylpiperidin-4-amine

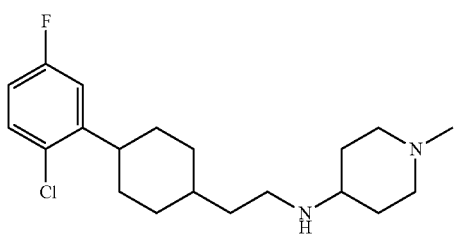 [SMILES: CN1CCC(NCCC2CCC(c3cc(F)ccc3Cl)CC2)CC1]

[M+H]=353.17.

Example 187. 1-Methyl-N-{2-[4-(3-methylpyridin-4-yl)cyclohexyl]ethyl}piperidin-4-amine

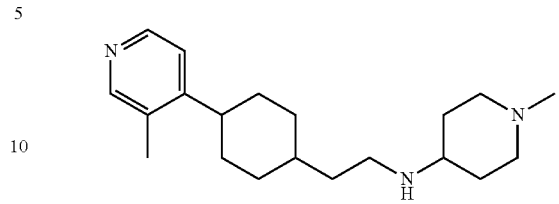

[M+H]=316.25.

Pharmacological Examples

The present disclosure will be further illustrated by the following pharmacological examples. These examples are understood to be exemplary only and are not intended to limit the scope of the invention disclosed herein.

Cell-Based NOP Assay

Assay

Formula (I) compounds were tested for antagonism of the nociceptin receptor (NOP) in a cell-based cAMP assay, using the LANCE cAMP Detection Kit, Perkin Elmer (Waltham, Mass.). This assay (LANCE cAMP) is a homogeneous, time-resolved fluorescence resonance energy transfer (TR-FRET) immunoassay designed to measure cAMP produced upon modulation of adenylyl cyclase activity by G protein-coupled receptors (GPCRs).

Protocol

Cells expressing human opioid NOP (ValiScreen cell line, cat #ES-230-C Perkin Elmer (Waltham, Mass.) were dispensed in simulation buffer (5 mM Hepes, 0.1% BSA, 0.5 mM IBMX in Hanks Buffered Saline Solution) at 2.5 µL cells per well (400 cells/well) into a 1536 white TC-treated assay plate. Compound was then added and plates were incubated for 15 minutes at room temperature. To each well was added 2.5 µL of a solution containing forskolin (3 µM final) and nociceptin peptide (390 pM final) diluted in stimulation buffer, and the plates were incubated for 30 minutes at room temperature. To each well was dispensed 5 µL of LANCE Ultra detection (1:300 dilution of anti-cAMP ULight with a 1:100 dilution of Eu-cAMP tracer diluted in cAMP Detection Buffer) reagent, and the plates were incubated for 1 hr at room temperature. The plate was then read on the ViewLux microplate reader (Perkin Elmer, Waltham, Mass.) using the LANCE 1536 protocol with 60 second exposure times and 50 µs delay. This protocol has an excitation wavelength of 340 nm (DUG11 filter) and emission wavelengths of 615 nm (Eu-Donor) and 665 nm (Alexa 647 cAMP antibody acceptor).

Data Analysis

Data was analyzed, normalized, and visualized using ACAS (John McNeil & Co.). Efficacy was calculated using activity of the vehicle (DMSO) as 0% efficacy and the activity of the corresponding reference positive control (SCH 221510, Tocris Bioscience (Pittsburgh, Pa.), Catalog number 3240) as 100% efficacy. Activity was calculated as the ratio of donor and acceptor emissions. All curve fits and IC50 determinations were performed using a non-linear regression model. The IC50 value was measured as the concentration at which half-maximal response was calculated.

Results

Table 2 presents the negative log of the half-maximal molar inhibitory concentration ($pIC_{50}$), with respect to NOP activity, for Formula I compounds.

TABLE 2

| NOP ($pIC_{50}$) | Example Numbers |
|---|---|
| >9 | 3, 18, 20, 25, 27, 53, 54, 55, 56, 57, 61, 64, 76, 78, 93, 158, 161 |
| 8-9 | 4, 5, 7, 8, 9, 16, 17, 19, 21, 26, 36, 37, 38, 42, 43, 45, 46, 47, 52, 60, 62, 63, 66, 70, 77, 79, 82, 83, 85, 95, 97, 99, 101, 102, 103, 126, 129, 134, 151, 152, 160, 162, 163, 169 |
| 7-8 | 1, 2, 6, 10, 13, 14, 15, 22, 23, 30, 31, 34, 39, 40, 48, 65, 68, 69, 80, 84, 86, 96, 98, 100, 108, 112, 119, 124, 125, 140, 142, 144, 148, 150, 153, 155, 156, 157, 159, 166, 167, 168, 170 |
| 6-7 | 11, 24, 28, 29, 32, 33, 35, 41, 44, 49, 58, 59, 67, 71, 72, 73, 74, 75, 81, 87, 89, 90, 91, 92, 94, 104, 105, 107, 109, 110, 113, 115, 120, 122, 127, 128, 130, 131, 132, 133, 135, 136, 137, 138, 141, 143, 145, 147, 149, 154, 164, 165, 176, 177, 180, 183, 184, 186 |
| <6 | 12, 50, 51, 88, 106, 111, 114, 116, 117, 118, 121, 123, 139, 146, 171, 172, 173, 174, 175, 178, 179, 181, 182, 187 |

NOP and Opioid Receptor Binding

Assay

Exemplary Formula (I) compounds were tested for binding to membrane preparations expressing either NOP, MOP, KOP, or DOP, using scintillation proximity assay (SPA) technology. SPA technology provides a rapid and sensitive assay of a wide range of biological processes, including those based on enzyme and receptor targets, radioimmunoassays, and molecular interactions.

Protocol

Briefly, test compounds were diluted in Assay Buffer (50 mM Tris HCl, pH 7.4, 10 mM $MgCl_2$, 1 mM EDTA, 0.2% BSA) and added to multi-well assay plates. To each well was then added radioligand, comprising $^{125}$I-Tyr14-Nociceptin for NOP binding assays, and 3H-DAMGO for MOP, KOP, and DOP binding assays. To each well was then added membrane aliquots expressing human NOP, MOP, KOP, or DOP at the desired assay concentration (typically 50 µg/ml for the NOP binding assay, 75 µg/ml for the MOP binding assay; 62.5 µg/ml for the KOP binding assay, and 18.75 µg/ml for the DOP binding assay). After incubation of the assay plates at RT for 1 h, SPA scintillation beads coated with Wheat Germ Agglutinin (which binds cell membranes) were added to each well, and plates incubated on a shaker at RT for 1 h. After centrifugation at 5000 RPM for 5 minutes, the plates were read using a MicroBeta Microplate Counter.

Data Analysis

Data was analyzed, normalized, and visualized using ACAS (John McNeil & Co.). Efficacy was calculated using activity of the vehicle (DMSO) as 0% efficacy and the activity of the appropriate reference positive control as 100% efficacy or binding. All curve fits and Ki determinations were performed using a non-linear regression model. The Ki value was determined by utilizing the $K_d$ of the radioligand and the curve fit from the non-linear regression model.

Results

Exemplary Formula (I) compounds show highly selective binding to NOP, compared to MOP, KOP, and DOP. For the most compounds tested, the Ki ratio for MOP/NOP, KOP/NOP, and DOP/NOP was at least 1000, with individual Ki ratios ranging from 1000 to greater than 150,000.

Biological Examples

The present disclosure will be further illustrated by the following biological examples. These examples are understood to be exemplary only, and not to limit the scope of the invention disclosed herein.

Effect of Exemplary Compounds on Memory

These studies evaluated the effect of exemplary compounds of the present disclosure on memory in rats.

Fear Conditioning

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. See, e.g., Fanselow, 1984, *Behav. Neurosci.* 98, 269-277; Fanselow, 1984, *Behav. Neurosci.* 98, 79-95; Phillips and LeDoux, 1992, *Behav. Neurosci.* 106, 274-285.

Contextual conditioning has been used to investigate the neural substrates mediating fear-motivated learning. See, e.g., Phillips and LeDoux, 1992, *Behav. Neurosc.* 106, 274-285; Kim et al., 1993, *Behav. Neurosc.* 107, 1093-1098. Studies in mice and rats have provided evidence for functional interaction between hippocampal and non-hippocampal systems during contextual conditioning training. See, e.g., Maren et al., 1997, *Behav. Brain Res.* 88, 261-274; Maren et al., 1997, *Neurobiol. Learn. Mem.* 67, 142-149; Frankland et al., 1998, *Behav. Neurosci.* 112, 863-874. Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning and memory and strain differences in mice. See, e.g., Bourtchouladze et al., 1994, *Cell* 79, 59-68; Bourtchouladze et al., 1998, *Learn Mem.* 5, 365-374; Kogan et al., 1997, *Current Biology* 7, 1-11; Silva et al., 1996,

*Current Biology* 6, 1509-1518; Abel et al., 1997, *Cell* 88, 615-626; Giese et al., 1998, *Science* 279, 870-873; Logue et al., 1997, *Neuroscience* 80, 1075-1086; Chen et al., 1996, *Behav. Neurosc.* 110, 1177-1180; Nguyen et al., 2000, *Learn Mem.* 7, 170-179.

Because robust learning can be triggered with a few minutes training session, contextual conditioning has been especially useful to study the biology of temporally distinct processes of short- and long-term memory. See, e.g., Kim et al., 1993, *Behav. Neurosc.* 107, 1093-1098; Abel et al., 1997, *Cell* 88, 615-626; Bourtchouladze et al., 1994, *Cell* 79, 59-68; Bourtchouladze et al., 1998, *Learn. Mem.* 5, 365-374. As such, contextual conditioning provides an excellent model to evaluate the role of various novel genes in hippocampal-dependent memory formation.

Previous investigations had established that training with 1× or 2×CS-US pairings induces sub-maximal (weak) memory in wild-type mice. See, e.g., U.S. 2009/0053140; Tully et al., 2003, *Nat. Rev. Drug Discov.* 2, 267-77; Bourtchouladze et al., 1998, *Learn. Mem.* 5, 365-374. The studies here evaluated the effect of exemplary compounds of the present disclosure on memory in rats.

Methods

Subjects

Male, Long Evans rats (400 g average weight, Envigo Inc., or Taconic Biosciences, Inc.) were used for rat object recognition and contextual fear conditioning tasks. Rats were housed in standard cages in groups of two and maintained on a 12:12 hour light-dark cycle. Experiments were conducted during the light phase of the cycle. The animals received food and water ad libitum except during training and testing. All procedures were consistent with National Institutes of Health (NIH) guidelines and approved by the Dart Neuroscience LLC Institutional Animal Care and Use Committee.

Drug Administration

NOP inhibitors were dosed in a vehicle containing 10% NMP, 50% PEG400 and 40% $H_2O$ at a volume of 1 ml/kg. Animals were dosed orally 60 minutes prior to training.

Contextual Fear Conditioning

Protocol

Contextual conditioning was carried out using an automated fear conditioning system (Med Associates Inc.). Rats were placed in the conditioning chamber and allowed to explore for 2 min. A total of two foot-shocks was delivered (0.4 mA, 2 s duration; "weak training") with an inter-shock interval of 1 min. A 5 foot-shocks group (0.4 mA, 2 s duration, "strong training") was used as positive control. After the final foot-shock, rats remained in the chamber for 30 sec and then were removed to their home cage. The weak training conditions generate sub-maximal, or weak, memory in control rats, thereby allowing one to evaluate whether a NOP inhibitor of the present disclosure can enhance memory formation.

Memory was assessed 24 h after training by placing the rat back into the training context and in the absence of a foot-shock measuring the percent time freezing during the 3 minute re-exposure to the chamber.

Object Recognition Memory

Rationale

Novel Object Recognition (NOR) is an assay of recognition learning and memory, which takes advantage of the spontaneous preference of rodents to investigate a novel object compared with a familiar one.

The NOR test has been employed extensively to assess the potential cognitive-enhancing properties of novel compounds derived from high-throughput screening. Object recognition is an ethologically relevant memory task that does not result from negative reinforcement (i.e. footshock). This task relies on the natural curiosity of rodents to explore novel objects in their environments more than familiar ones. (Antunes and Bial, 2012, *Cogn. Process.* 13, 93-110). For an object to be "familiar," the animal must have attended to it before and remembered that experience. Hence, animals with better memory will attend to and explore a new object more than an object familiar to them. During testing, the animal is presented with the training object and a second, novel one. Memory of the training object renders it familiar to the animal, and it then spends more time exploring the new novel object rather than the familiar one. See Bourtchouladze et al., 2003, *Proc. Natl. Acad. Sci. USA* 100, 10518-10522.

Studies indicate that the NOR procedure involves several brain regions, including the hippocampus and perirhinal cortex. Recent neuroimaging studies in humans have also demonstrated that object recognition memory depends on the prefrontal cortex (PFC). See Delbert et al., 1999, *Neurology* 52, 1413-1417. Consistent with these findings, rats with PFC lesions show poor working memory when they are required to discriminate between familiar and novel objects. See Mitchell, 1998, *Behav. Brain Res.* 97, 107-113. Other studies with monkeys and rodents suggest that the hippocampus is important for novel object recognition. See, e.g., Teng et al., 2000, *J. Neurosci* 20, 3853-3863; Cohen et al., 2015, *Behav. Brain Res.* 285, 105-117; Clark et al., 2000, *J. Neurosci*, 20, 8853-8860; Broadbent et al., 2010, *Learning Mem.* 17, 5-11. Hence, object recognition provides an excellent behavioral model to evaluate drug-compound effects on memory tasks associated with function of the hippocampus and cortex.

Protocol

The novel object recognition task was performed similarly to that described by Bevins and Besheer, 2006, *Nat. Protoc.* 1, 1306-1311, using a standard novel object recognition system for rats (Stoelting Co.). Objects were placed in a central location in the test arena, testing was carried out in low light, and time exploring objects was assessed using the automated Ethovision animal tracking Software.

For 3 consecutive days, rats were habituated to handling and the empty training arena for 7 min. The next day, rats were treated with vehicle or drug 60 min before training and were then placed into the arena and allowed to explore either two grey blocks or two white balls (~4 cm in width/diameter) for 3 min. Approximately 24 h after training, rats were placed back into the arena that now contained one familiar object and one novel object (white ball is replaced with a grey block and vice versa) and the time spent exploring each object was measured. Memory was scored by calculation of a discrimination index $((T_N-T_F)/(T_N+T_F))*100$; between group comparison).

Statistical Analyses

All behavioral experiments were designed and performed in a balanced fashion: (i) For each experimental condition (e.g., a specific dose-effect) an equal number of experimental and control rats were used; (ii) Each experimental condition was replicated several times, and (iii) The location of the novel object was counterbalanced across animals and treatment groups. In each experiment, the experimenter was unaware (blind) to the treatment of the subjects during training and testing. Animals that did not explore the objects for at least 5 seconds during the training and test phases were excluded from the analysis. Data were analyzed by ANOVA using JMP software, followed by contrast analysis comparing treatment groups to vehicle.

Results

Exemplary compounds of the disclosure were found to significantly enhance 24 hour memory in the object recognition assay. Control experiments showed that compound administration did not significantly affect the cumulative distance traveled or the total exploration time. Significant effects were seen at 0.1, mg/kg, 0.3 mg/kg, 1.0 mg/kg or 3.0 mg/kg depending on the drug.

Exemplary compounds of the disclosure were also found to enhance contextual memory in the fear conditioning assay. Significant effects were seen at one or several concentrations, depending on the compound, in the range of 0.3-3.0 mg/kg.

Effect of Exemplary Compounds on Vas Deferens Contractility Assay

Exemplary compounds of the present disclosure are evaluated for antagonism against NOP using the vas deferens assay. The vas deferens has a dense sympathetic innervation, making it a useful system for studying sympathetic nerve function and for studying drugs that modify neurotransmission, as measured by contractile responses. For example, it has been used as a bioassay for the discovery of enkephalins, the endogenous opiates. See Hughes et al., 1975, Nature 258, 577-580; Burnstock, 2010, Trends Pharmacol. Sci. 31, 131-139; Sjöstrand, 1965, Acta Physiologica. Scandinavica. 257, S1-S82.

Protocol

Segments of mouse vas deferens are suspended in 20-ml organ baths filled with an oxygenated (95% $O_2$ and 5% $CO_2$) and pre-warmed (37° C.) physiological salt solution (118 mM NaCl, 4.7 mM KCl, 2.5 mM $CaCl_2$), 1.2 mM $KH_2PO_4$, 25 mM $NaHCO_3$, and 11 mM glucose, pH 7.4). Yohimbine (1 µM), AM 281 (1 µM), atropine (1 µM) and naloxone (1 µM) are also present throughout the experiments to block the a2-adrenergic, CB1, muscarinic and opioid receptors, respectively. The tissues are connected to force transducers for isometric tension recordings. They are stretched to a resting tension of 0.5 g then allowed to equilibrate for 60 min during which time they are washed repeatedly and the tension readjusted. Thereafter, they are stimulated electrically with rectangular pulses (maximal intensity, 1 ms duration, 0.1 Hz) delivered by a constant current stimulator.

The tissues are exposed to a submaximal concentration of the reference agonist nociceptin (0.1 µM) to obtain a control response. After stabilization of the nociceptin-induced response, the tissues are exposed to increasing concentrations of the test compound or the reference antagonist, UFP-101. The concentrations are added cumulatively, and each is left in contact with the tissues until a stable response is obtained or for a maximum of 15 min. An inhibition of the nociceptin-induced response by the test compound indicates an antagonist activity at the nociceptin receptor.

Results.

Administration of several compounds of the present disclosure inhibited the effect of nociceptin in the vas deferens assay, with estimated EC50 values (µM) ranging from 0.010 to 0.046.

It will be understood by one skilled in the art that the described embodiments herein do not limit the scope of the invention. The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound of Formula (I):

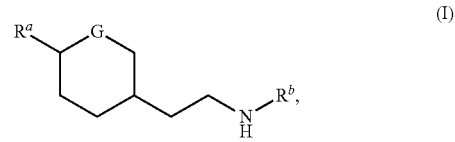

or a pharmaceutically acceptable salt thereof,
wherein,
G is C(=O), C(=N—OH), $CH_2$, $CHR^{1B}$, or $C(R^{1B})_2$;
$R^a$ is a 6 or 10-membered aryl or 6 or 10-membered heteroaryl, optionally substituted with 1 to 4 $R^{1A}$;
each $R^{1A}$ is independently selected from the group consisting of: halo, —OH, —NH2, —$NHC_{1-4}$alkyl, —$N(C_{1-4}$alkyl$)_2$, —CN, —$C_{1-6}$alkyl, —$C_{1-6}$haloalkyl, —$C_{1-6}$ alkoxy, and —$C_{1-6}$ haloalkoxy; and
$R^b$ is a —$C_{3-7}$cycloalkyl or 5-10-membered heterocycloalkyl, optionally substituted with 1 to 7 $R^{1B}$; and
each $R^{1B}$ is independently selected from the group consisting of: halo, —OH,=O, —$NH_2$, —$NHC_{1-4}$alkyl, —$N(C_{1-4}$alkyl$)_2$, —$NO_2$, —$SO_2CH_3$, —CN, —$C_{1-6}$alkyl, —$C_{1-6}$haloalkyl, —$C_{1-4}$alkyl-OH, —$C_{1-6}$alkoxy, —$C_{1-6}$haloalkoxy, —$C_{1-4}$alkyl-O—$C_{1-3}$alkyl, —$C_{3-6}$ cycloalkyl, —$C(O)C_{1-4}$alkyl, —$C(O)C_{3-6}$cycloalkyl, —$COOC_{1-4}$alkyl, —$C(O)NH_2$, —$OC(O)NH_2$, —C(O)NH—$C_{1-4}$alkyl, —NHC(O)—$C_{1-4}$alkyl, —C(O)NH—($C_{1-3}$alkyl-$C_{3-6}$cycloalkyl), 5-6-membered heterocycloalkyl, and —$C(O)N(C_{1-4}$alkyl$)_2$.

2. A compound as in claim 1, having the structure of Formula (Ia):

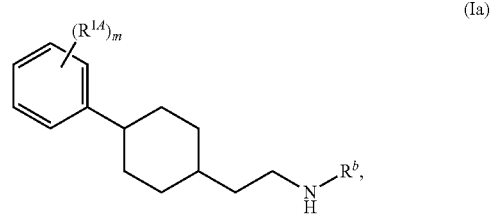

or a pharmaceutically acceptable salt thereof,
wherein,
each $R^{1A}$ is independently selected from the group consisting of: halo, —OH, —$NH_2$, —$NHC_{1-4}$ alkyl, —$N(C_{1-4}$ alkyl$)_2$, —CN, —$C_{1-4}$ alkyl, —$C_{1-4}$ haloalkyl, —$C_{1-6}$ alkoxy, and —$C_{1-6}$ haloalkoxy; and
m is 0, 1, 2, or 3, preferably m is 0, 1, or 2;
$R^b$ is a —$C_{5-6}$ cycloalkyl or 5-6-membered heterocycloalkyl, optionally substituted with 1 to 4 $R^{1B}$; and
each $R^{1B}$ is independently selected from the group consisting of: —H, halo, —OH, =O, —$NH_2$, —$NHC_{1-4}$ alkyl, —$N(C_{1-4}$ alkyl$)_2$, —$NO_2$, —$SO_2CH_3$, —CN, —$C_{1-6}$ alkyl, —$C_{1-6}$ haloalkyl, —$C_{1-4}$ alkyl-OH, —$C_{1-6}$ alkoxy, —$C_{1-6}$ haloalkoxy, —$C_{1-4}$ alkyl-O—

C$_{1-3}$ alkyl, —C$_{3-6}$ cycloalkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$alkyl)$_2$.

3. A compound as in claim 1, having the structure of Formula (Ib):

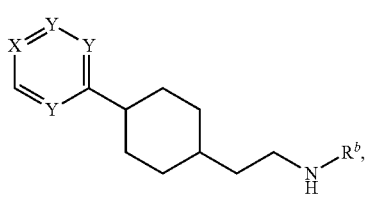

(Ib)

or a pharmaceutically acceptable salt thereof,
wherein,
each Y is independently CH, CR$^{1A}$, or N (nitrogen);
X is CH, CR$^{1A}$, or N (nitrogen);
each R$^{1A}$ is independently selected from the group consisting of: halo, —OH, —NH$_2$, —NHC$_{1-4}$ alkyl, —N(C$_{1-4}$ alkyl)$_2$, —CN, —C$_{1-4}$ alkyl, —C$_{1-4}$ haloalkyl, —C$_{1-6}$ alkoxy, and —C$_{1-6}$ haloalkoxy; and
R$^b$ is a —C$_{5-6}$ cycloalkyl or 5-6-membered heterocycloalkyl, optionally substituted with 1 to 4 R$^{1B}$;
each R$^{1B}$ is independently selected from the group consisting of: halo, —OH, =O, —NH$_2$, —NHC$_{1-4}$ alkyl, —N(C$_{1-4}$ alkyl)$_2$, —NO$_2$, —SO$_2$CH$_3$, —CN, —C$_{1-6}$ alkyl, —C$_{1-6}$ haloalkyl, —C$_{1-4}$ alkyl-OH, —C$_{1-6}$ alkoxy, —C$_{1-6}$ haloalkoxy, —C$_{1-4}$ alkyl-O—C$_{1-3}$ alkyl, —C$_{3-6}$ cycloalkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$alkyl)$_2$.

4. A compound, or pharmaceutically acceptable salt thereof, of claim 3, wherein X is CH, CR$^{1A}$, or N (nitrogen) where when X is N (nitrogen) each Y is independently CH or CR$^{1A}$.

5. A compound as in claim 1, having the structure of Formula (Ic):

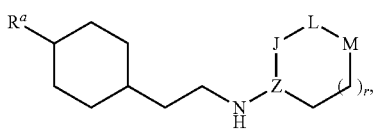

(Ic)

or a pharmaceutically acceptable salt thereof,
wherein,
R$^a$ is a 6-membered aryl or heteroaryl, optionally substituted with 1 to 4 R$^{1A}$, where each R$^{1A}$ is independently selected from the group consisting of: halo, —OH, —NH$_2$, —NHC$_{1-4}$alkyl, —N(C$_{1-4}$ alkyl)$_2$, —CN, —C$_{1-4}$ alkyl, —C$_{1-4}$ haloalkyl, —C$_{1-6}$ alkoxy, and —C$_{1-6}$ haloalkoxy;
J, L and M are each independently S(O)$_2$, NH, NR$^{1B}$, C(=O), CH$_2$, CHR$^{1B}$, C(R$^{1B}$)$_2$, or O (oxygen);
Z is CH or CR$^{1B}$; and
r is 0 or 1.

6. A compound, or pharmaceutically acceptable salt thereof, of claim 5, wherein Z is CH.

7. A compound, or pharmaceutically acceptable salt thereof, of claim 5, wherein Z is CR$^{1B}$; and R$^{1B}$ is selected from the group consisting of: —OH, —NH$_2$, —NHC$_{1-4}$ alkyl, —N(C$_{1-4}$alkyl)$_2$, —CN, —C$_{1-6}$ alkyl, —C$_{1-6}$ halo alkyl, —C$_{1-4}$ alkyl-OH, —C$_{1-6}$ alkoxy, —C$_{1-6}$ haloalkoxy, —C$_{1-4}$ alkyl-O—C$_{1-3}$ alkyl, —C$_{3-6}$ cycloalkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$ alkyl)$_2$.

8. A compound, or pharmaceutically acceptable salt thereof, of claim 5, wherein J, L and M are each independently C(=O), NR$^{1B}$, CHR$^{1B}$, or C(R$^{1B}$)$_2$, where each R$^{1B}$ is independently selected from the group consisting of: halo, —OH, =O, —NH$_2$, —NHC$_{1-4}$ alkyl, —N(C$_{1-4}$ alkyl)$_2$, —NO$_2$, —SO$_2$CH$_3$, —CN, —C$_{1-6}$ alkyl, —C$_{1-6}$ haloalkyl, —C$_{1-4}$ alkyl-OH, —C$_{1-6}$ alkoxy, —C$_{1-6}$ haloalkoxy, —C$_{1-4}$ alkyl-O—C$_{1-3}$ alkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$ alkyl)$_2$.

9. A compound, or pharmaceutically acceptable salt thereof, of claim 5, wherein M is NH, NR$^{1B}$, CH$_2$, CHR$^{1B}$, C(R$^{1B}$)$_2$, or O (oxygen).

10. A compound, or pharmaceutically acceptable salt thereof, of claim 5, wherein L is C(=O), CH$_2$, CHR$^{1B}$, or C(R$^{1B}$)$_2$.

11. A compound, or pharmaceutically acceptable salt thereof, of claim 5, wherein J is CH$_2$, CHR$^{1B}$, or C(R$^{1B}$)$_2$.

12. A compound as in claim 1, having the structure of Formula (Id):

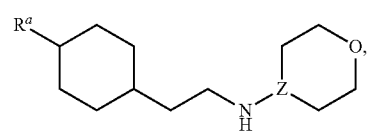

(Id)

or a pharmaceutically acceptable salt thereof,
wherein,
Z is CH or CR$^{1B}$;
R$^a$ is a 6-membered aryl or heteroaryl, optionally substituted with 1 to 4 R$^{1A}$, where each R$^{1A}$ is independently selected from the group consisting of: halo, —OH, —NH$_2$, —NHC$_{1-4}$ alkyl, —N(C$_{1-4}$ alkyl)$_2$, —CN, —C$_{1-4}$ alkyl, —C$_{1-4}$ haloalkyl, —C$_{1-6}$ alkoxy, and —C$_{1-6}$ haloalkoxy;
R$^{1B}$ is selected from the group consisting of: —OH, —NH$_2$, —NHC$_{1-4}$ alkyl, —N(C$_{1-4}$alkyl)$_2$, —CN, —C$_{1-6}$alkyl, —C$_{1-6}$ haloalkyl, —C$_{1-4}$ alkyl-OH, —C$_{1-6}$ alkoxy, —C$_{1-6}$ haloalkoxy, —C$_{1-4}$ alkyl-O—C$_{1-3}$ alkyl, —C$_{3-6}$ cycloalkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$ alkyl)$_2$.

13. A compound as in claim 1, having the structure of Formula (Ie):

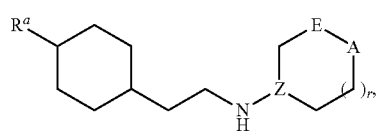

(Ie)

or a pharmaceutically acceptable salt thereof,
wherein,
each $R^{1A}$ is independently selected from the group consisting of: halo, —OH, —NH$_2$, —NHC$_{1-4}$ alkyl, —N(C$_{1-4}$ alkyl)$_2$, —CN, —C$_{1-4}$ alkyl, —C$_{1-4}$ haloalkyl, —C$_{1-6}$ alkoxy, and —C$_{1-6}$ haloalkoxy;
E is C(=O), CH$_2$, CHR$^{1B}$, or C(R$^{1B}$)$_2$;
A is NH or NR$^{1B}$;
Z is CH or CR$^{1B}$; and
each $R^{1B}$ is independently selected from the group consisting of: halo, —OH, —NH$_2$, —NHC$_{1-4}$ alkyl, —N(C$_{1-4}$ alkyl)$_2$, —NO$_2$, —SO$_2$CH$_3$, —CN, —C$_{1-6}$ alkyl, —C$_{1-6}$ haloalkyl, —C$_{1-4}$ alkyl-OH, —C$_{1-6}$ alkoxy, —C$_{1-6}$ haloalkoxy, —C$_{1-4}$ alkyl-O—C$_{1-3}$ alkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$ alkyl)$_2$; and
r is 0 or 1.

14. A compound as in claim 1, having the structure of Formula (If):

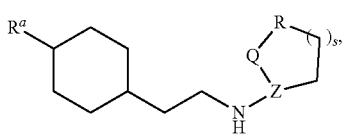

(If)

or a pharmaceutically acceptable salt thereof,
wherein,
Q and R are each independently CH$_2$CH$_2$, CH$_2$, CHR$^{1B}$, or C(R$^{1B}$)$_2$;
each $R^{1A}$ is independently selected from the group consisting of: halo, —OH, —NH$_2$, —NHC$_{1-4}$ alkyl, —N(C$_{1-4}$ alkyl)$_2$, —CN, —C$_{1-4}$ alkyl, —C$_{1-4}$ haloalkyl, —C$_{1-6}$ alkoxy, and —C$_{1-6}$ haloalkoxy;
Z is CH or CR$^{1B}$;
each $R^{1B}$ is independently selected from the group consisting of: halo, —OH, —NH$_2$, —NHC$_{1-4}$ alkyl, —N(C$_{1-4}$ alkyl)$_2$, —NO$_2$, —SO$_2$CH$_3$, —CN, —C$_{1-6}$ alkyl, —C$_{1-6}$ haloalkyl, —C$_{1-4}$ alkyl-OH, —C$_{1-6}$ alkoxy, —C$_{1-6}$ haloalkoxy, —C$_{1-4}$ alkyl-O—C$_{1-3}$ alkyl, —C(O)C$_{1-4}$ alkyl, —C(O)C$_{3-6}$ cycloalkyl, —COOC$_{1-4}$ alkyl, —C(O)NH$_2$, —C(O)NH—C$_{1-4}$ alkyl, —C(O)NH—(C$_{1-3}$ alkyl-C$_{3-6}$ cycloalkyl), and —C(O)N(C$_{1-4}$ alkyl)$_2$; and
s is 1 or 2.

15. A compound, or pharmaceutically acceptable salt thereof, of claim 1, wherein R$^a$ is phenyl, optionally substituted with 1 to 3 R$^{1A}$, where each R$^{1A}$ is independently selected from the group consisting of: halo, —CN, —C$_{1-4}$ alkyl, —C$_{1-4}$ haloalkyl, —C$_{1-6}$ alkoxy, and —C$_{1-6}$ haloalkoxy.

16. A compound, or pharmaceutically acceptable salt thereof, of claim 1, wherein R$^a$ is a 6-membered heteroaryl, containing 1 or 2 nitrogen atoms, optionally substituted with 1 to 3 R$^{1A}$, where each R$^{1A}$ is independently selected from the group consisting of: halo, —CN, —C$_{1-4}$ alkyl, —C$_{1-4}$ haloalkyl, —C$_{1-6}$ alkoxy, and —C$_{1-6}$ haloalkoxy.

17. A compound, or pharmaceutically acceptable salt thereof, of claim 1, wherein R$^b$ is a tetrahydropyran or tetrahydrofuran, each optionally substituted with 1 to 2 R$^{1B}$, where each R$^{1B}$ is independently selected from the group consisting of: halo, —CN, —C$_{1-6}$alkyl, and —C$_{1-6}$ haloalkyl.

18. A compound, or pharmaceutically acceptable salt thereof, of claim 5, wherein M is NH, CH$_2$ or O.

19. A compound, or pharmaceutically acceptable salt thereof, of claim 5, wherein Z is CR$^{1B}$; and R$^{1B}$ is selected from the group consisting of: —C$_{1-4}$ alkyl, —C$_{1-4}$haloalkyl, —C$_{1-3}$ alkyl-OH, —C$_{1-3}$ alkyl-O—C$_{1-2}$ alkyl, —COOC$_{1-3}$ alkyl, —C(O)NH$_2$, —C(O)NH—C$_{1-3}$alkyl, and —C(O)N(C$_{1-3}$alkyl)$_2$.

20. A compound, or pharmaceutically acceptable salt thereof, selected from the group consisting of
4-((2-((cis)-4-(3-chloro-5-fluoropyridin-2-yl)cyclohexyl)ethyl)amino)tetrahydro-2H-pyran-4-carboxamide;
4-((2-((trans)-4-(3-chloro-5-fluoropyridin-2-yl)cyclohexyl)ethyl)amino)tetrahydro-2H-pyran-4-carboxamide;
N-{2-[4-(2-Chloro-4-fluorophenyl)cyclohexyl]ethyl}oxan-4-amine;
4-({2-[(cis)-4-(2-Chloro-4-fluorophenyl)cyclohexyl]ethyl}amino)oxane-4-carboxamide;
N-(2-((trans)-4-(2-chloro-4-fluorophenyl)cyclohexyl)ethyl)tetrahydro-2H-pyran-4-amine;
4-((2-((cis)-4-(2,4-difluorophenyl)cyclohexyl)ethyl)amino)-N-methyltetrahydro-2H-pyran-4-carboxamide;
4-((2-((trans)-4-(2,4-difluorophenyl)cyclohexyl)ethyl)amino)-N-methyltetrahydro-2H-pyran-4-carboxamide;
N-(2-((cis)-4-(2,6-dichlorophenyl)cyclohexyl)ethyl)tetrahydro-2H-pyran-4-amine;
N-(2-((trans)-4-(2,6-dichlorophenyl)cyclohexyl)ethyl)tetrahydro-2H-pyran-4-amine;
N-{2-[4-(2,4-Difluorophenyl)cyclohexyl]ethyl}cyclopentanamine;
N-(2-((cis)-4-(5-fluoropyrimidin-2-yl)cyclohexyl)ethyl)tetrahydro-2H-pyran-4-amine;
N-(2-((trans)-4-(5-fluoropyrimidin-2-yl)cyclohexyl)ethyl)tetrahydro-2H-pyran-4-amine;
4-((2-((trans)-4-(4-fluoro-2-methylphenyl)cyclohexyl)ethyl)amino)tetrahydro-2H-pyran-4-carboxamide;
N-(2-((cis)-4-(3-chloropyridin-2-yl)cyclohexyl)ethyl)tetrahydro-2H-pyran-4-amine;
N-(2-((trans)-4-(3-chloropyridin-2-yl)cyclohexyl)ethyl)tetrahydro-2H-pyran-4-amine;
N-(2-((cis)-4-(2,4-difluorophenyl)cyclohexyl)ethyl)tetrahydro-2H-pyran-4-amine;
N-(2-((trans)-4-(2,4-difluorophenyl)cyclohexyl)ethyl)tetrahydro-2H-pyran-4-amine;
N-(2-((cis)-4-(4-fluoro-2-methylphenyl)cyclohexyl)ethyl)tetrahydro-2H-pyran-4-amine;
N-(2-((trans)-4-(4-fluoro-2-methylphenyl)cyclohexyl)ethyl)tetrahydro-2H-pyran-4-amine;
N-(2-((cis)-4-(2-chloro-6-fluorophenyl)cyclohexyl)ethyl)tetrahydro-2H-pyran-4-amine;
N-(2-((trans)-4-(2-chloro-6-fluorophenyl)cyclohexyl)ethyl)tetrahydro-2H-pyran-4-amine;
N-{2-[4-(3-Chloro-5-fluoropyridin-2-yl)cyclohexyl]ethyl}-4-cyclopropyloxan-4-amine;
N-(2-((cis)-4-(3-chloro-5-fluoropyridin-2-yl)cyclohexyl)ethyl)-4-(methoxymethyl)tetrahydro-2H-pyran-4-amine;
N-(2-((trans)-4-(3-chloro-5-fluoropyridin-2-yl)cyclohexyl)ethyl)-4-(methoxymethyl)tetrahydro-2H-pyran-4-amine;
4-({2-[(cis)-4-(2-Chloro-4-fluorophenyl)cyclohexyl]ethyl}amino)oxan-3-ol;
(3S,4S)—N-(2-((cis)-4-(2-chloro-4-fluorophenyl)cyclohexyl)ethyl)-3-methoxytetrahydro-2H-pyran-4-amine;
2-((2-((cis)-4-(2-chloro-4-fluorophenyl)cyclohexyl)ethyl)amino)cyclopentan-1-ol;

4-((2-((cis)-4-(3-chloropyridin-2-yl)cyclohexyl)ethyl)amino)tetrahydro-2H-pyran-4-carboxamide;
4-((2-((trans)-4-(3-chloropyridin-2-yl)cyclohexyl)amino)tetrahydro-2H-pyran-4-carboxamide;
4-((2-((cis)-4-(2-chloro-5-fluorophenyl)cyclohexyl)ethyl)amino)tetrahydro-2H-pyran-4-carboxamide;
4-((2-((trans)-4-(2-chloro-5-fluorophenyl)cyclohexyl)ethyl)amino)tetrahydro-2H-pyran-4-carboxamide;
4-((2-((cis)-4-(2-chloro-3-fluorophenyl)cyclohexyl)ethyl)amino)tetrahydro-2H-pyran-4-carboxamide;
4-((2-((trans)-4-(2-chloro-3-fluorophenyl)cyclohexyl)ethyl)amino)tetrahydro-2H-pyran-4-carboxamide;
4-((2-((cis)-4-(2,4-difluorophenyl)cyclohexyl)ethyl)amino)tetrahydro-2H-pyran-4-carboxamide;
4-((2-((trans)-4-(2,4-difluorophenyl)cyclohexyl)ethyl)amino)tetrahydro-2H-pyran-4-carboxamide;
4-((2-((cis)-4-(2-chloro-4,6-difluorophenyl)cyclohexyl)ethyl)amino)tetrahydro-2H-pyran-4-carboxamide;
4-((2-((trans)-4-(2-chloro-4,6-difluorophenyl)cyclohexyl)ethyl)amino)tetrahydro-2H-pyran-4-carboxamide;
4-((2-((cis)-4-(4-fluoro-2-(trifluoromethyl)phenyl)cyclohexyl)ethyl)amino)tetrahydro-2H-pyran-4-carboxamide;
4-((2-((trans)-4-(4-fluoro-2-(trifluoromethyl)phenyl)cyclohexyl)ethyl)amino)tetrahydro-2H-pyran-4-carboxamide;
4-((2-((cis)-4-(4,5-difluoro-2-methylphenyl)cyclohexyl)ethyl)amino)tetrahydro-2H-pyran-4-carboxamide;
4-((2-((trans)-4-(4,5-difluoro-2-methylphenyl)cyclohexyl)ethyl)amino)tetrahydro-2H-pyran-4-carboxamide;
4-((2-((cis)-4-(2,4-difluoro-6-methylphenyl)cyclohexyl)ethyl)amino)tetrahydro-2H-pyran-4-carboxamide;
4-((2-((trans)-4-(2,4-difluoro-6-methylphenyl)cyclohexyl)ethyl)amino)tetrahydro-2H-pyran-4-carboxamide;
4-((2-((cis)-4-(2,4,6-trifluorophenyl)cyclohexyl)ethyl)amino)tetrahydro-2H-pyran-4-carboxamide;
4-((2-((trans)-4-(2,4,6-trifluorophenyl)cyclohexyl)ethyl)amino)tetrahydro-2H-pyran-4-carboxamide;
N-Methyl-4-({2-[(cis)-4-[4-fluoro-2-(trifluoromethyl)phenyl]cyclohexyl]ethyl}amino)oxane-4-carboxamide;
N-Methyl-4-({2-[(trans)-4-[4-fluoro-2-(trifluoromethyl)phenyl]cyclohexyl]ethyl}amino)oxane-4-carboxamide;
4-((2-((cis)-4-(3,4-difluoro-2-methylphenyl)cyclohexyl)ethyl)amino)tetrahydro-2H-pyran-4-carboxamide;
4-((2-((trans)-4-(3,4-difluoro-2-methylphenyl)cyclohexyl)ethyl)amino)tetrahydro-2H-pyran-4-carboxamide;
4-((2-((cis)-4-(5-fluoro-3-(trifluoromethyl)pyridin-2-yl)cyclohexyl)ethyl)amino)-N-methyltetrahydro-2H-pyran-4-carboxamide;
4-((2-((trans)-4-(5-fluoro-3-(trifluoromethyl)pyridin-2-yl)cyclohexyl)ethyl)amino)-N-methyltetrahydro-2H-pyran-4-carboxamide;
N-Ethyl-4-({2-[(cis)-4-[4-fluoro-2-(trifluoromethyl)phenyl]cyclohexyl]ethyl}amino)oxane-4-carboxamide;
(1S,3R)—N-{2-[4-(2-Chloro-4-fluorophenyl)cyclohexyl]ethyl}-3-fluorocyclopentan-1-amine;
3,3-Difluoro-N-{2-[(cis)-4-(2-chloro-4-fluorophenyl)cyclohexyl]ethyl}cyclopentan-1-amine;
N-(2-((cis)-4-(2-chloro-4-fluorophenyl)cyclohexyl)ethyl)-3-fluorotetrahydro-2H-pyran-4-amine;
N-(2-((cis)-4-(2-chloro-4-fluorophenyl)cyclohexyl)ethyl)-3-fluorotetrahydro-2H-pyran-4-amine;
N-(2-((cis)-4-(4-methylpyridin-3-yl)cyclohexyl)ethyl)tetrahydro-2H-pyran-4-amine;
N-(2-((trans)-4-(4-methylpyridin-3-yl)cyclohexyl)ethyl)tetrahydro-2H-pyran-4-amine;
4-((2-((cis)-4-(4-fluoro-2-methylphenyl)cyclohexyl)ethyl)amino)tetrahydro-2H-pyran-4-carboxamide;
N-{2-[(cis)-4-(2-Chloro-4-fluorophenyl)cyclohexyl]ethyl}oxan-4-amine;
4-((2-((cis)-4-(3-chloro-5-fluoropyridin-2-yl)cyclohexyl)ethyl)amino)-N-methyltetrahydro-2H-pyran-4-carboxamide;
4-((2-((trans)-4-(3-chloro-5-fluoropyridin-2-yl)cyclohexyl)ethyl)amino)-N-methyltetrahydro-2H-pyran-4-carboxamide;
N-{2-[(cis)-4-(2-Chloro-4-fluorophenyl)cyclohexyl]ethyl}cyclopentanamine;
2,2-Difluoro-N-{2-[(cis)-4-(2-chloro-4-fluorophenyl)cyclohexyl]ethyl}cyclopentan-1-amine;
[4-({2-[(cis)-4-(2-Chloro-4-fluorophenyl)cyclohexyl]ethyl}amino)oxan-4-yl]methanol;
N,N-Dimethyl-1-({2-[(cis)-4-(2-chloro-4-fluorophenyl)cyclohexyl]ethyl}amino)cyclopentane-1-carboxamide;
1-({2-[(cis)-4-(2-Chloro-4-fluorophenyl)cyclohexyl]ethyl}amino)cyclopentane-1-carboxamide;
4-({2-[(trans)-4-(2-Chloro-4-fluorophenyl)cyclohexyl]ethyl}amino)oxane-4-carboxamide;
N-Methyl-1-({2-[(cis)-4-(2-chloro-4-fluorophenyl)cyclohexyl]ethyl}amino)cyclopentane-1-carboxamide;
3-({2-[(cis)-4-(2-Chloro-4-fluorophenyl)cyclohexyl]ethyl}amino)oxane-3-carboxamide;
3-({2-[(cis)-4-(2-Chloro-4-fluorophenyl)cyclohexyl]ethyl}amino)oxolane-3-carboxamide;
N-(2-((cis)-4-(3-methylpyridin-4-yl)cyclohexyl)ethyl)tetrahydro-2H-pyran-4-amine;
N-(2-((trans)-4-(3-methylpyridin-4-yl)cyclohexyl)ethyl)tetrahydro-2H-pyran-4-amine;
N-(Cyclopropylmethyl)-1-({2-[(cis)-4-(2-chloro-4-fluorophenyl)cyclohexyl]ethyl}amino)cyclopentane-1-carboxamide;
N-Methyl-4-({2-[(cis)-4-(2-chloro-4-fluorophenyl)cyclohexyl]ethyl}amino)oxane-4-carboxamide;
N-Ethyl-4-({2-[(cis)-4-(2-chloro-4-fluorophenyl)cyclohexyl]ethyl}amino)oxane-4-carboxamide;
N-(2-((cis)-4-(3-chloro-5-fluoropyridin-2-yl)cyclohexyl)ethyl)tetrahydro-2H-pyran-4-amine;
N-(2-((trans)-4-(3-chloro-5-fluoropyridin-2-yl)cyclohexyl)ethyl)tetrahydro-2H-pyran-4-amine;
N-(2-((cis)-4-(3-methylpyridin-2-yl)cyclohexyl)ethyl)tetrahydro-2H-pyran-4-amine;
N-(2-((trans)-4-(3-methylpyridin-2-yl)cyclohexyl)ethyl)tetrahydro-2H-pyran-4-amine;
4-(Methoxymethyl)-N-{2-[(cis)-4-(2-chloro-4-fluorophenyl)cyclohexyl]ethyl}oxan-4-amine;
4-((2-((cis)-4-(3-chloro-5-fluoropyridin-4-yl)cyclohexyl)ethyl)amino)-N-methyltetrahydro-2H-pyran-4-carboxamide;
4-((2-((trans)-4-(3-chloro-5-fluoropyridin-4-yl)cyclohexyl)ethyl)amino)-N-methyltetrahydro-2H-pyran-4-carboxamide;
4-((2-((cis)-4-(3-chloro-5-fluoropyridin-2-yl)cyclohexyl)ethyl)amino)-N-ethyltetrahydro-2H-pyran-4-carboxamide;
4-((2-((trans)-4-(3-chloro-5-fluoropyridin-2-yl)cyclohexyl)ethyl)amino)-N-ethyltetrahydro-2H-pyran-4-carboxamide;

N-(2-((cis)-4-(3-methylpyrazin-2-yl)cyclohexyl)ethyl) tetrahydro-2H-pyran-4-amine;
N-(2-((trans)-4-(3-methylpyrazin-2-yl)cyclohexyl)ethyl) tetrahydro-2H-pyran-4-amine;
3-((cis)-4-(2-((tetrahydro-2H-pyran-4-yl)amino)ethyl)cyclohexyl)phenol;
3-((trans)-4-(2-((tetrahydro-2H-pyran-4-yl)amino)ethyl) cyclohexyl)phenol;
2-methyl-3-((cis)-4-(2-((tetrahydro-2H-pyran-4-yl) amino)ethyl)cyclohexyl)benzonitrile;
2-methyl-3-((trans)-4-(2-((tetrahydro-2H-pyran-4-yl) amino)ethyl)cyclohexyl)benzonitrile;
(cis)-4-({2-[(cis)-4-[4-Fluoro-2-(trifluoromethyl)phenyl] cyclohexyl]ethyl}amino)cyclohexane-1-carbonitrile;
N-{2-[4-(3-Methylpyridin-2-yl)cyclohexyl] ethyl}cyclopentanamine;
N-{2-[4-(2-Chloro-6-fluorophenyl)cyclohexyl] ethyl}cyclopentanamine;
N-{2-[4-(4-Chloro-2-fluorophenyl)cyclohexyl] ethyl}cyclopentanamine;
N-{2-[4-(4-Fluoro-2-methylphenyl)cyclohexyl] ethyl}cyclopentanamine;
N-{2-[4-(2-Chloro-5-fluorophenyl)cyclohexyl] ethyl}cyclopentanamine;
N-{2-[4-(2-Chlorophenyl)cyclohexyl]ethyl}oxan-4-amine;
N-{2-[4-(3-Methylpyridin-2-yl)cyclohexyl]ethyl}oxan-4-amine,
N-{2-[4-(4-Chloro-2-fluorophenyl)cyclohexyl] ethyl}oxan-4-amine;
N-{2-[4-(4-Fluoro-2-methylphenyl)cyclohexyl] ethyl}oxan-4-amine;
N-{2-[4-(2-Chloro-5-fluorophenyl)cyclohexyl] ethyl}oxan-4-amine;
N-{2-[4-(3-Methylpyridin-4-yl)cyclohexyl]ethyl}oxan-4-amine;
N-{2-[4-(2-Chlorophenyl)cyclohexyl]ethyl}-1-methylcyclopentan-1-amine;
N-{2-[4-(2-Chloro-3-fluorophenyl)cyclohexyl]ethyl}-1-methylcyclopentan-1-amine;
N-{2-[4-(2,4-Difluorophenyl)cyclohexyl]ethyl}-1-methylcyclopentan-1-amine;
N-{2-[4-(3-Chloro-5-fluoropyridin-2-yl)cyclohexyl] ethyl}-1-methylcyclopentan-1-amine;
N-{2-[4-(3-Chloropyridin-2-yl)cyclohexyl]ethyl}-1-methylcyclopentan-1-amine;
1-Methyl-N-{2-[4-(3-methylpyridin-2-yl)cyclohexyl] ethyl}cyclopentan-1-amine;
1-Methyl-N-{2-[4-(4-methylpyridin-3-yl)cyclohexyl] ethyl}cyclopentan-1-amine;
N-{2-[4-(2-Chloro-6-fluorophenyl)cyclohexyl]ethyl}-1-methylcyclopentan-1-amine;
1-({2-[4-(2-Chlorophenyl)cyclohexyl]ethyl}amino)cyclopentane-1-carboxamide;
1-({2-[4-(2-Chloro-3-fluorophenyl)cyclohexyl] ethyl}amino)cyclopentane-1-carboxamide;
1-({2-[4-(2,4-Difluorophenyl)cyclohexyl]ethyl}amino) cyclopentane-1-carboxamide;
1-({2-[4-(3-Chloropyridin-2-yl)cyclohexyl]ethyl}amino) cyclopentane-1-carboxamide;
1-({2-[4-(3-Methylpyridin-2-yl)cyclohexyl]ethyl}amino) cyclopentane-1-carboxamide;
1-({2-[4-(4-Methylpyridin-3-yl)cyclohexyl]ethyl}amino) cyclopentane-1-carboxamide;
N-{2-[4-(4-Fluoro-2-methylphenyl)cyclohexyl]ethyl}-1-methylcyclopentan-1-amine;
N-{2-[4-(2-Chloro-5-fluorophenyl)cyclohexyl]ethyl}-1-methylcyclopentan-1-amine;
1-Methyl-N-{2-[4(3-methylpyridin-4-yl)cyclohexyl] ethyl}cyclopentan-1-amine;
1-({2-[4-(2-Chloro-5-fluorophenyl)cyclohexyl] ethyl}amino)cyclopentane-1-carboxamide;
1-({2-[4-(3-Methylpyridin-4-yl)cyclohexyl]ethyl}amino) cyclopentane-1-carboxamide;
N-{2-[4-(2-Chloro-3-fluorophenyl)cyclohexyl] ethyl}cyclohexanamine;
N-{2-[4-(2,4-Difluorophenyl)cyclohexyl] ethyl}cyclohexanamine;
N-{2-[4-(3-Chloro-5-fluoropyridin-2-yl)cyclohexyl] ethyl}cyclohexanamine;
N-{2-[4-(3-Chloropyridin-2-yl)cyclohexyl] ethyl}cyclohexanamine;
N-{2-[4-(3-Methylpyridin-2-yl)cyclohexyl] ethyl}cyclohexanamine;
N-{2-[4-(2-Chloro-6-fluorophenyl)cyclohexyl] ethyl}cyclohexanamine;
N-{2-[4-(2-Chlorophenyl)cyclohexyl]ethyl}-4-methyl-oxan-4-amine;
N-{2-[4-(3-Chloro-5-fluoropyridin-2-yl)cyclohexyl] ethyl}-4-methyloxan-4-amine;
N-{2-[4-(3-Chloropyridin-2-yl)cyclohexyl]ethyl}-4-methyloxan-4-amine;
4-Methyl-N-{2-[4(3-methylpyridin-2-yl)cyclohexyl] ethyl}oxan-4-amine;
N-{2-[4-(4-Chloro-2-fluorophenyl)cyclohexyl] ethyl}cyclohexanamine;
N-{2-[4-(4-Fluoro-2-methylphenyl)cyclohexyl] ethyl}cyclohexanamine;
N-{2-[4-(2-Chloro-5-fluorophenyl)cyclohexyl] ethyl}cyclohexanamine;
N-{2-[4-(3-Methylpyridin-4-yl)cyclohexyl] ethyl}cyclohexanamine;
N-{2-[4-(4-Fluoro-2-methylphenyl)cyclohexyl]ethyl}-4-methyloxan-4-amine;
4-Methyl-N-{2-[4(3-methylpyridin-4-yl)cyclohexyl] ethyl}oxan-4-amine;
1-({2-[4-(3-Chloro-5-fluoropyridin-2-yl)cyclohexyl] ethyl}amino)-N-methylcyclopentane-1-carboxamide;
1-({2-[4-(3-Chloropyridin-2-yl)cyclohexyl] ethyl}amino)-N-methylcyclopentane-1-carboxamide;
N-{2-[4-(2-Chlorophenyl)cyclohexyl]ethyl}-4-(methoxymethyl)oxan-4-amine;
N-{2-[4-(2-Chloro-3-fluorophenyl)cyclohexyl]ethyl}-4-(methoxymethyl)oxan-4-amine;
N-{2-[4-(2,4-Difluorophenyl)cyclohexyl]ethyl}-4-(methoxymethyl)oxan-4-amine;
N-{2-[4-(3-Chloro-5-fluoropyridin-2-yl)cyclohexyl] ethyl}-4-(methoxymethyl)oxan-4-amine;
N-{2-[4-(3-Chloropyridin-2-yl)cyclohexyl]ethyl}-4-(methoxymethyl)oxan-4-amine;
4-(Methoxymethyl)-N-{2-[4-(4-methylpyridin-3-yl)cyclohexyl]ethyl}oxan-4-amine;
N-{2-[4-(2-Chloro-6-fluorophenyl)cyclohexyl]ethyl}-4-(methoxymethyl)oxan-4-amine;
1-({2-[4-(4-Chloro-2-fluorophenyl)cyclohexyl] ethyl}amino)-N-methylcyclopentane-1-carboxamide;
N-{2-[4-(2-Chloro-5-fluorophenyl)cyclohexyl]ethyl}-4-(methoxymethyl)oxan-4-amine;
(R)-4-((2-((cis)-4-(3-chloro-5-fluoropyridin-2-yl)cyclohexyl)ethyl)amino)piperidin-2-one;
(R)-4-((2-((trans)-4-(3-chloro-5-fluoropyridin-2-yl)cyclohexyl)ethyl)amino)piperidin-2-one;

(S)-4-((2-((cis)-4-(3-chloro-5-fluoropyridin-2-yl)cyclohexyl)ethyl)amino)piperidin-2-one;
(S)-4-((2-((trans)-4-(3-chloro-5-fluoropyridin-2-yl)cyclohexyl)ethyl)amino)piperidin-2-one;
1-Methanesulfonyl-N-{2-[(cis)-4-(2-chloro-4-fluorophenyl)cyclohexyl]ethyl}piperidin-4-amine;
1-[4-({2-[(cis)-4-(2-Chloro-4-fluorophenyl)cyclohexyl]ethyl}amino)piperidin-1-yl]ethan-1-one;
1-[3-({2-[(cis)-4-(2-Chloro-4-fluorophenyl)cyclohexyl]ethyl}amino)pyrrolidin-1-yl]ethan-1-one;
4-({2-[(cis)-4-(2-Chloro-4-fluorophenyl)cyclohexyl]ethyl}amino)piperidin-2-one;
1-Methyl-4-({2-[(cis)-4-(2-chloro-4-fluorophenyl)cyclohexyl]ethyl}amino)piperidin-2-one;
3-({2-[(cis)-4-(2-Chloro-4-fluorophenyl)cyclohexyl]ethyl}amino)pyrrolidin-2-one;
(4R)-4-({2-[(cis)-4-(2-Chloro-4-fluorophenyl)cyclohexyl]ethyl}amino)piperidin-2-one;
(4S)-4-({2-[(cis)-4-(2-Chloro-4-fluorophenyl)cyclohexyl]ethyl}amino)piperidin-2-one;
4-({2-[(trans)-4-(2-Chloro-4-fluorophenyl)cyclohexyl]ethyl}amino)piperidin-2-one;
4-({2-[4-(3-Chloro-5-fluoropyridin-2-yl)cyclohexyl]ethyl}amino)piperidine-1-carboxamide;
4-((2-((cis)-4-(3-chloro-5-fluoropyridin-2-yl)cyclohexyl)ethyl)amino)-4-methylpiperidin-2-one;
4-((2-((trans)-4-(3-chloro-5-fluoropyridin-2-yl)cyclohexyl)ethyl)amino)-4-methylpiperidin-2-one;
4-Methyl-4-({2-[(cis)-4-(2-chloro-4-fluorophenyl)cyclohexyl]ethyl}amino)piperidin-2-one;
4-(Methoxymethyl)-4-({2-[(cis)-4-(2-chloro-4-fluorophenyl)cyclohexyl]ethyl}amino)piperidin-2-one;
(R)-4-((2-((cis)-4-(4,5-difluoro-2-methylphenyl)cyclohexyl)ethyl)amino)piperidin-2-one;
(R)-4-((2-((trans)-4-(4,5-difluoro-2-methylphenyl)cyclohexyl)ethyl)amino)piperidin-2-one;
1-[4-({2-[4-(2-Chloro-3-fluorophenyl)cyclohexyl]ethyl}amino)piperidin-1-yl]ethan-1-one;
1-[4-({2-[4-(3-Chloro-5-fluoropyridin-2-yl)cyclohexyl]ethyl}amino)piperidin-1-yl]ethan-1-one;
1-[4-({2-[4-(3-Chloropyridin-2-yl)cyclohexyl]ethyl}amino)piperidin-1-yl]ethan-1-one;
1-[4-({2-[4-(3-Methylpyridin-2-yl)cyclohexyl]ethyl}amino)piperidin-1-yl]ethan-1-one;
1-[4-({2-[4-(4-Methylpyridin-3-yl)cyclohexyl]ethyl}amino)piperidin-1-yl]ethan-1-one;
1-[4-({2-[4-(4-Chloro-2-fluorophenyl)cyclohexyl]ethyl}amino)piperidin-1-yl]ethan-1-one;
1-[4-({2-[4-(4-Fluoro-2-methylphenyl)cyclohexyl]ethyl}amino)piperidin-1-yl]ethan-1-one;
1-[4-({2-[4-(2-Chloro-5-fluorophenyl)cyclohexyl]ethyl}amino)piperidin-1-yl]ethan-1-one;
N-{2-[4-(2-Chloro-3-fluorophenyl)cyclohexyl]ethyl}-1-methylpiperidin-4-amine;
N-{2-[4-(3-Chloro-5-fluoropyridin-2-yl)cyclohexyl]ethyl}-1-methylpiperidin-4-amine;
N-{2-[4-(3-Chloropyridin-2-yl)cyclohexyl]ethyl}-1-methylpiperidin-4-amine;
1-Methyl-N-{2-[4-(3-methylpyridin-2-yl)cyclohexyl]ethyl}piperidin-4-amine;
N-{2-[4-(2-Chloro-6-fluorophenyl)cyclohexyl]ethyl}-1-methylpiperidin-4-amine;
N-{2-[4-(4-Chloro-2-fluorophenyl)cyclohexyl]ethyl}-1-methylpiperidin-4-amine;
N-{2-[4-(4-Fluoro-2-methylphenyl)cyclohexyl]ethyl}-1-methylpiperidin-4-amine;
N-{2-[4-(2-Chloro-5-fluorophenyl)cyclohexyl]ethyl}-1-methylpiperidin-4-amine; and
1-Methyl-N-{2-[4-(3-methylpyridin-4-yl)cyclohexyl]ethyl}piperidin-4-amine.

21. A pharmaceutical composition comprising a compound, or pharmaceutically acceptable salt thereof, of claim 1, and a pharmaceutically acceptable carrier.

22. A method of treating a neurological disorder, comprising administering to a subject in need thereof an effective amount of a compound, or pharmaceutically acceptable salt thereof, of claim 1.

23. A method of treating a peripheral disorder, comprising administering to a subject in need thereof an effective amount of a compound, or pharmaceutically acceptable salt thereof, of claim 1.

24. A compound, or pharmaceutically acceptable salt thereof, selected from the group consisting of:
N-Methyl-4-({2-[(cis)-4-[4-fluoro-2-(trifluoromethyl)phenyl]cyclohexyl]ethyl}amino)oxane-4-carboxamide;
N-Methyl-4-({2-[(trans)-4-[4-fluoro-2-(trifluoromethyl)phenyl]cyclohexyl]ethyl}amino)oxane-4-carboxamide;
4-((2-((cis)-4-(4-fluoro-2-methylphenyl)cyclohexyl)ethyl)amino)tetrahydro-2H-pyran-4-carboxamide;
4-({2-[(cis)-4-(2-Chloro-4-fluorophenyl)cyclohexyl]ethyl}amino)oxane-4-carboxamide; and
4-({2-[(trans)-4-(2-Chloro-4-fluorophenyl)cyclohexyl]ethyl}amino)oxane-4-carboxamide.

25. A pharmaceutical composition comprising a compound, or pharmaceutically acceptable salt thereof, of claim 24, and a pharmaceutically acceptable carrier.

\* \* \* \* \*